(12) United States Patent
Liang et al.

(10) Patent No.: US 12,297,450 B2
(45) Date of Patent: May 13, 2025

(54) CRISPR-CAS13 SYSTEM AND USE THEREOF

(71) Applicants: GUANGZHOU REFORGENE MEDICINE CO., LTD., Guangdong (CN); ZHEJIANG SYNSORBIO TECHNOLOGY CO., LTD, Zhejiang (CN)

(72) Inventors: Junbin Liang, Guangdong (CN); Xingxiang Liang, Guangdong (CN); Yang Sun, Zhejiang (CN); Hui Xu, Guangdong (CN); Kaiwei Si, Guangdong (CN); Qiuting Li, Guangdong (CN); Zhiqin Peng, Guangdong (CN); Desheng Huangfu, Guangdong (CN)

(73) Assignees: GUANGZHOU REFORGENE MEDICINE CO., LTD., Guangzhou (CN); ZHEJIANG SYNSORBIO TECHNOLOGY CO., LTD, Shaoxing (CN)

( * ) Notice: Subject to any disclaimer, the term of this patent is extended or adjusted under 35 U.S.C. 154(b) by 0 days.

(21) Appl. No.: 18/755,750

(22) Filed: Jun. 27, 2024

(65) Prior Publication Data
US 2024/0392323 A1 Nov. 28, 2024

Related U.S. Application Data

(63) Continuation of application No. PCT/CN2023/115093, filed on Aug. 25, 2023.

(30) Foreign Application Priority Data

Aug. 26, 2022 (CN) .......................... 202211035342.8
Apr. 24, 2023 (CN) .......................... 202310457880.4

(51) Int. Cl.
*C12N 9/22* (2006.01)
*C12N 15/11* (2006.01)
*C12N 15/90* (2006.01)

(52) U.S. Cl.
CPC .............. *C12N 15/907* (2013.01); *C12N 9/22* (2013.01); *C12N 15/11* (2013.01); *C12N 2310/20* (2017.05); *C12N 2310/531* (2013.01)

(58) Field of Classification Search
None
See application file for complete search history.

(56) References Cited

U.S. PATENT DOCUMENTS

| | | | |
|---|---|---|---|
| 10,476,825 B2 | 11/2019 | Hsu et al. | |
| 2018/0274017 A1* | 9/2018 | Abudayyeh | C12N 9/22 |
| 2019/0062724 A1* | 2/2019 | Hsu | C12N 15/113 |
| 2022/0090088 A1 | 3/2022 | Anderson | |
| 2022/0186257 A1* | 6/2022 | Gao | C12N 9/22 |

FOREIGN PATENT DOCUMENTS

| | | |
|---|---|---|
| CN | 113234702 A | 8/2021 |
| CN | 113544267 A | 10/2021 |
| WO | 2016123230 A1 | 8/2016 |
| WO | 2020160150 A1 | 8/2020 |

OTHER PUBLICATIONS

Wu et al., CRISPR-Cas13 technology portfolio and alliance with other genetic tools. Biotechnology Advances (2022), 61: 108047, pp. 1-15 (Year: 2022).*
Zhang et al., Structural Basis for the RNA-Guided Ribonuclease Activity of CRISPR-Cas13d. Cell (2018), 175: 212-233 (Year: 2018).*
Shmakov et al., Discovery and functional characterization of diverse class 2 CRISPR-Cas systems. Molecular Cell (2015), 60: 385-397 (Year: 2015).*
Konerman et al., Transcriptome engineering with RNA-targeting type VI-D CRISPR effectors. Cell (2018), 173: 665-676 (Year: 2018).*
Graham and Hart, CRISPR/Cas9 gene editing therapies for cystic fibrosis. Expert Opinion on Biological Therapy (2021), 21: 767-780 (Year: 2021).*
NM_014495.4, Homo sapiens angiopoietin like 3 (ANGPTL3), mRNA, available Jul. 11, 2021, https://www.ncbi.nlm.nih.gov/nucleotide/NM_014495.4 [retrieved Sep. 30, 2024] (Year: 2021).*
Zhang et al., Structural basis for the RNA-guided ribonuclease activity of CRISPR-Cas13d. Cell (2018), 175:212-223 (Year: 2018).*
Dec. 13, 2023 International Search Report issued in International Patent Application No. PCT/CN2023/115093.
Dec. 13, 2023 Written Opinion of the International Searching Authority issued in International Patent Application No. PCT/CN2023/115093.
Michael Richter et al., Shifting the genomic gold standard for the prokaryotic species definition, Proc Natl Acad Sci USA. Nov. 10, 2009, vol. 106(45): 19126-19131.

(Continued)

*Primary Examiner* — Celine X Qian
*Assistant Examiner* — Catherine Konopka

(57) ABSTRACT

The present invention relates to a CRISPR-Cas13 system and use thereof, and also relates to a Cas13 protein, a fusion protein, and a guide polynucleotide. The Cas13 protein has at least 90% sequence identity compared to SEQ ID NO: 1. The fusion protein comprises the Cas13 protein fused to a protein domain and/or a polypeptide tag. The guide polynucleotide comprises a same-direction repetition sequence and a guide sequence that has been engineered to hybridize with the target RNA. The same-direction repetition sequence has at least 70% sequence identity to any of SEQ ID NOs: 3 and 80-87. The CRISPR-Cas13 system comprises the Cas13 protein that has at least 90% sequence identity to SEQ ID NO: 1, or a coding nucleic acid therefor, and the guide polynucleotide or a coding nucleic acid therefor.

27 Claims, 11 Drawing Sheets

Specification includes a Sequence Listing.

(56) References Cited

OTHER PUBLICATIONS

Cox et al., RNA editing with CRISPR-Cas13, Science. Nov. 24, 2017, 358(6366): 1019-1027.
Abudayyeh et al., A cytosine deaminase for programmable single-base RNA editing, Science. Jul. 26, 2019, 365 (6451): 382-386.
Konermann et al., Transcriptome Engineering with RNA-Targeting Type VI-D CRISPR Effectors, Cell. Apr. 19, 2018, 173(3): 665-676.
Konermann et al., Genome-scale transcriptional activation by an engineered CRISPR-Cas9 complex, Nature. Jan. 29, 2015, 517(7536): 583-588.
Hendel et al., Chemically modified guide RNAs enhance CRISPR-Cas genome editing in human primary cells, Nat Biotechnol. Sep. 2015, 33(9): 985-989.
Maeder et al., Development of a gene-editing approach to restore vision loss in Leber congenital amaurosis type 10, Nat Med. Feb. 2019, 25(2): 229-233.
Tabebordbar et al., Directed evolution of a family of AAV capsid variants enabling potent muscle-directed gene delivery across species, 2021, Cell 184, 4919-4938.
Gilmore et al., CRISPR-Cas9 In Vivo Gene Editing for Transthyretin Amyloidosis, The New England Journal of Medicine, Aug. 5, 2021, 385(6): 493-502.
Paunovska et al., Drug delivery systems for RNA therapeutics, Nat Rev Genet. May 2022, vol. 23(5): 265-280.
Banskota et al., Engineered virus-like particles for efficient in vivo delivery of therapeutic proteins, Cell. Jan. 20, 2022; 185(2): 250-2655.
Mangeot et al., Genome editing in primary cells and in vivo using viral-derived Nanoblades loaded with Cas9-sgRNA ribonucleoproteins, Nature Communications 10(1): 1-15.
Campbell et al., Gesicle-Mediated Delivery of CRISPR/Cas9 Ribonucleoprotein Complex for Inactivating the HIV Provirus, Mol Ther. Jan. 2019, vol. 27(1): 151-163.
Mangeot et al., Protein Transfer Into Human Cells by VSV-G-induced Nanovesicles, Mol Ther. Sep. 2011, vol. 19(9): 1656-1666.
Xie, F., MAG: type VI-D CRISPR-associated RNA-guided ribonuclease Cas13d [*Thermoguttaceae bacterium*], MBR0191107.1, NCBI_GenBanK, Apr. 21, 2021.
Yangmiao Ye, Structural biology study of CRISPR system-Cas13d effector protein, Master's thesis, Fujian Normal University.
Gupta et al., Cas13d: A New Molecular Scissor for Transcriptome Engineering, Frontiers in Cell and Developmental Biology, vol. 10, Mar. 31, 2022.
Cas13 protein published in GenBank, accession No. MBR0191107.1, https://www.ncbi.nlm.nih.gov/protein/MBR0191107.1/.

* cited by examiner (SEQ ID NO: 3)

```
CLUSTAL format alignment by MAFFT (v7.511)

DRrc        ggaagataactctacaaacctgtagggttctgagac (SEQ ID NO: 281)
DR-hf2      ggaagataactctacaaacctgtagagttctgagac (SEQ ID NO: 87)
DR2rc       ggaagatgactctacaaacctgtagggactgtgcgg (SEQ ID NO: 81)
            *******.*****************.*  ..  . .
```

(SEQ ID NO: 282)

```
                        SEQUENCE LISTING

Sequence total quantity: 284
SEQ ID NO: 1            moltype = AA  length = 893
FEATURE                 Location/Qualifiers
source                  1..893
                        mol_type = protein
                        organism = synthetic construct
SEQUENCE: 1
MSKDKKTKAK RMGVKALLAH GEDKLTMTTF GKGNRSKIEF TEGYHGRALE TPKHFGIRGF   60
EVRRIDENVD LCGDLEEGKT IEALLVNPSE KVGEDYLKLK GTLEKRFFGR EFPHDNIRIQ  120
LIYNILDIYK ILGMNVADIL YALGNMQDTE LDIDMFGQSL NNEDNLKECL KRMRPYMGYF  180
GDIFKISPKG ENIADREHNK KVLRCISVLR NATAHDKQDE YPWFKSSDIY ETKIFKADMW  240
KIIKDQYREK IKKVNKDFLS KNAVNMAILF DLLNARDVEQ KKQITDEFYR FTIRKDGKNL  300
GMNLVKIREI IIDRYASGLR DKKHDPHRQK INVIADFLIF RALSQNQGII DKTVSSLRLT  360
KDEEEKDHVY QNAAELVWGM VSNCLTPYFN DPKNKYILKY KDAKTPGDFE DWITSKISED  420
DGEPFVKVLS FLCNFLEGKE INELLTAYIH KFECIQDFLN VISSLGENVQ FQPRFALFNN  480
ASFAQNVAVQ LRILASIGKM KPDLTEAKRP LYKAAIRMLC PPEKWEKYTS DEWLEKNMLL  540
NSEDRKNDKK KKQVNPFRNF IAGNVIESRR FMYLVRYSKP KAVRAIMQNR SIVNYVLHRL  600
PSEQVHRYAS VFPENFADLE QEIDFLTKKL FEFSFEELLH EKDVILNNSR SHKPSLEIER  660
LKAITGLYLS VAYIAIKNIV KANARYYIAF AVFERDKELV KAKDARIQTK IPETDFPDYF  720
CLTQYYLDRD EEKKFPGDPR DKEAFFEHLR KTKRHFSKQW REWLNEKIAD AKSSQATGLL  780
LREARNDVEH LNVLRAIPDY IQDFRHGEKG ETAMNSYFEL YHYLMQRLML KNTELDLSHW  840
SGWIMRSGRP DRDLIQIAFV SLAYNLPRYR NLTKEHHFDD TVLQKIREKE SLD         893

SEQ ID NO: 2            moltype = AA  length = 966
FEATURE                 Location/Qualifiers
source                  1..966
                        mol_type = protein
                        organism = synthetic construct
SEQUENCE: 2
IEKKKSFAKG MGVKSTLVSG SKVYMTTFAE GSDARLEKIV EGDSIRSVNE GEAFSAEMAD   60
KNAGYKIGNA KFSHPKGYAV VANNPLYTGP VQQDMLGLKE TLEKRYFGES ADGNDNICIQ  120
VIHNILDIEK ILAEYITNAA YAVNNISGLD KDIIGFGKFS TVYTYDEFKD PEHHRAAFNN  180
NDKLINAIKA QYDEFDNFLD NPRLGYFGQA FFSKEGRNYI INYGNECYDI LALLSGLRHW  240
VVHNNEEESR ISRTWLYNLD KNLDNEYIST LNYLYDRITN ELTNSFSKNS AANVNYIAET  300
LGINPAEFAE QYFRFSIMKE QKNLGFNITK LREVMLDRKD MSEIRKNHKV FDSIRTKVYT  360
MMDFVIYRYY IEEDAKVAAA NKSLPDNEKS LSEKDIFVIN LRGSFNDDQK DALYYDEANR  420
IWRKLENIMH NIKEFRGNKT REYKKKDAPR LPRILPAGRD VSAFSKLMYA LTMFLDGKEI  480
NDLLTTLINK FDNIQSFLKV MPLIGVNAKF VEEYAFFKDS AKIADELRLI KSFARMGEPI  540
ADARRAMYID AIRILGTNLS YDELKALADT FSLDENGNKL KKGKHGMRNF IINNVISNKR  600
FHYLIRYGDP AHLHEIAKNE AVVKFVLGRI ADIQKKQGQN GKNQIDRYYE TCIGKDKGKS  660
VSEKVDALTK IITGMNYDQF DKKRSVIEDT GRENAEREKF KKIISLYLTV IYHILKNIVN  720
INARYVIGFH CVERDAQLYK EKGYDINLKK LEEKGFSSVT KLCAGIDETA PDKRKDVEKE  780
```

```
MAERAKESID SLESANPKLY ANYIKYSDEK KAEEFTRQIN REKAKTALNA YLRNTKWNVI  840
IREDLLRIDN KTCTLFRNKA VHLEVARYVH AYINDIAEVN SYFQLYHYIM QRIIMNERYE  900
KSSGKVSEYF DAVNDEKKYN DRLLKLLCVP FGYCIPRFKN LSIEALFDRN EAAKFDKEKK  960
KVSGNS                                                            966

SEQ ID NO: 3           moltype = RNA   length = 36
FEATURE                Location/Qualifiers
source                 1..36
                       mol_type = other RNA
                       organism = synthetic construct
SEQUENCE: 3
ggaagataac tctacaaacc tgtagggttc tgagac                            36

SEQ ID NO: 4           moltype = RNA   length = 30
FEATURE                Location/Qualifiers
source                 1..30
                       mol_type = other RNA
                       organism = synthetic construct
SEQUENCE: 4
tgccgttctt ctgcttgtcg gccatgatat                                   30

SEQ ID NO: 5           moltype = RNA   length = 26
FEATURE                Location/Qualifiers
source                 1..26
                       mol_type = other RNA
                       organism = synthetic construct
SEQUENCE: 5
agggcagaac cgatgctgat gaagac                                       26

SEQ ID NO: 6           moltype = RNA   length = 30
FEATURE                Location/Qualifiers
source                 1..30
                       mol_type = other RNA
                       organism = synthetic construct
SEQUENCE: 6
gtggttggag aactggatgt agatgggctg                                   30

SEQ ID NO: 7           moltype = RNA   length = 48
FEATURE                Location/Qualifiers
source                 1..48
                       mol_type = other RNA
                       organism = synthetic construct
SEQUENCE: 7
ccacgaccct ctttgtcttc actcgagtga agacaaagag ggtcgtgg               48

SEQ ID NO: 8           moltype = RNA   length = 48
FEATURE                Location/Qualifiers
source                 1..48
                       mol_type = other RNA
                       organism = synthetic construct
SEQUENCE: 8
cagcccatct acatccagtt cctcgaggaa ctggatgtag atgggctg               48

SEQ ID NO: 9           moltype = DNA   length = 2682
FEATURE                Location/Qualifiers
source                 1..2682
                       mol_type = other DNA
                       organism = synthetic construct
SEQUENCE: 9
atgagcaaag acaaaaaaac aaaagcgaaa cgaatgggag tcaaagccct gttggctcac    60
ggggaagata aactgacgat gaccacctt gggaaaggaa accgttcgaa gatcgagttt    120
acggaagggt atcacggccg agcgcttgag accccaaaac actttggaat acgcggcttt   180
gaggtaagga ggatcgatga aacgtcgat ctctgcgggg atctcgagga ggggaaaacg    240
atcgaggcct tgctggtcaa cccgtctgaa aaagtcgtaa aggactacct caagcttaag   300
gggacactgg aaaaacgttt cttcggccgt gaatttccgc atgacaacat ccggatccag   360
ctcatcctata atattctcga catttataag attttgggga tgaatgtcgc tgatattctt   420
tacgcgctgg gaaacatgca ggatacagag ctggacattg atatgtttgg acagtctttg   480
aacaatgaag acaaccttaa agaatgtctg aaacgaatgc ggcctattat gggctattta   540
ggagatattt tcaagatttc cccaaaaggc gagaacatag ccgatcggga acataacaaa   600
aaagttctgc gctgtatttc tgttctgcgc aacgctaccg cccatgacaa acaagacgaa   660
tatccgtggt tcaagagcag cgacatctac gaaacgaaaa ttttaaggc ggacatgtgg   720
aaaatcatca aggaccaata tcgggaaaag atcaagaaag tcaataagga ttttttatcg   780
aaaaacgcgc ttaacatggc catcctattt gaccttctga tgcccgtga tgtggaacag   840
aaaaagcaga tcacggtga attctatcgt ttcacgattc gaaaagacgg gaagaatctg   900
gggatgaatc tggttaagat ccgcgagata attattgatc gttacgccag tggcctccgt   960
gataaaaagc acgatcctca ccgcagaaa atcaatgtga tcgcggactt cctgattttc   1020
cgcgctcttt cgcaaaatca gggaatcatc gacaagaccg tttccagcct gcgcctcacg   1080
aaagacgaag aggaaaaaga ccacgtgtac cagaatgccg cggaactggt ctgggggatg   1140
gtcagtaatt gtttgacccc gtattttaac gaccctaaaa ataaatacat tcttaaatac   1200
```

```
aaagacgcca aaactcctgg tgacttcgag gattggatca ccagtaaaat ctcggaggat   1260
gacggggagc cgttcgtgaa agtgctttcg ttcctctgta atttcctgga agggaaggaa   1320
atcaacgagc tgctgaccgc ttacattcat aaattcgagt gtattcagga cttcttgaac   1380
gtgatttcca gtcttgggga aaacgttcag tttcagcctc gtttcgcgct gttcaacaat   1440
gccagtttcg cccaaaatgt tgcggtacag ttgcgtatcc tggcaagtat cgggaagatg   1500
aaacccgatt tgaccgaggc gaaacgcccg cttacaagg cagcgattcg gatgctttgt   1560
cctccagaga agtgggaaaa atacacctcg gatgagtggc ttgaaaaaaa tatgctcctc   1620
aattccgagg accgtaaaaa tgataaaaag aagaaacagg tcaacccttt ccggaatttc   1680
atcgcgggga atgtgatcga gtcacgtcgg tttatgtatc tggtccggta ttcaaagcg   1740
aaagcggttc gtgcgattat gcaaaaccgg agtatcgtga actatgttct tcacaggctt   1800
ccgtccgagc aggttcaccg gtacgccagc gtgtttcctg aaaatttcgc cgatctggaa   1860
caggaaattg acttcttgac aaagaaactt ttcgaattct cattcgagga actcctccat   1920
gaaaaggatg tgattttgaa taattccaga tctcacaaac cttccttaga gatcgaacgc   1980
cttaaagcca ttacagggct gtacctttcg gttgcctaca tcgccatcaa aaacatcgtg   2040
aaagccaacg cacggtatta catcgccttc gcggttttcg aacgtgacaa ggaactggtg   2100
aaagccaagg acgcacgaat ccagacgaag atccccgaga cagattttcc ggactatttc   2160
tgcctcacgc agtattacct tgaccgcgat gaggagaaaa aattcccggg tgaccgcgt   2220
gataaagagg cttttttcga acatctccgc aagacgaaag ggcatttctc aaaacagtga   2280
cgcgagtggc tgaatgagaa aattgcggac gcaaagagct cccagcaac cggccttttg   2340
ttgagagagg cccgaaacga cgtggaacat ttgaacgtcc tgcgcgcgat cccggattac   2400
atccaggatt tccgccatgg ggaaaaaggg gaaacggcaa tgaattcgta tttcgagctg   2460
taccattacc tcatgcagag gctgatgctc aaaaacaggt attggattt gtcccattgg   2520
agcggctgga tcatgcgttc cggtcggccg atcgggatt tgattcagat cgcgttcgtt   2580
tcattggctt acaatctgcc gcgctaccgt aatttgacga aggaaccaca tttcgatgat   2640
acggtattgc agaaaattcg tgagaaagag tccctagact aa                     2682

SEQ ID NO: 10           moltype = DNA   length = 8182
FEATURE                 Location/Qualifiers
source                  1..8182
                        mol_type = other DNA
                        organism = synthetic construct
SEQUENCE: 10
tggcgaatgg gacgcgccct gtagcggcgc attaagcgcg gcgggtgtgg tggttacgcg   60
cagcgtgacc gctacacttg ccagcgccct agcgcccgct cctttcgctt tcttcccttc   120
ctttctcgcc acgttcgccg gctttccccg tcaagctcta aatcggggc tcccttttagg   180
gttccgattt agtgctttac ggcacctcga ccccaaaaaa cttgattagg gtgatggttc   240
acgtagtggg ccatcgccct gatagacggt ttttcgccct tgacgttgg agtccacgtt   300
ctttaatagt ggactcttgt tccaaactgg aacaacactc aaccctatct cggtctattc   360
ttttgattta taagggattt tgccgatttc ggcctattgg ttaaaaatg agctgattta   420
acaaaaattt aacgcgaatt ttaacaaaat attaacgttt acaatttcag gtggcacttt   480
tcggggaaat gtgcgcggaa cccctatttg tttattttc taaatacatt caaatatgta   540
tccgctcatg aattaattct tagaaaaact catcgagcat caaatgaaac tgcaatttat   600
tcatatcagg attatcaata ccatattttt gaaaaagcg tttctgtaat gaaggagaaa   660
actcaccgag gcagttccat aggatggcaa gatcctggta tcggtctgcg attccgactc   720
gtccaacatc aatacaacct attaattcc cctcgtcaaa ataaggtta tcaagtgaga   780
aatcaccatg agtgacgact gaatccgtg agaatgcaa aagtttatgc atttctttcc   840
agacttgttc aacaggccag ccattacgct cgtcatcaaa atcactcga tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatgtc ggaagagca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataaac  1380
cccttgtatt actgtttatg taagcagaca gttttattgt tcatgaccaa atcccttaa   1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actcttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcaggggg cggagcctat ggaaaaacgc cagcaacgcg  2100
gcctttttac ggttcctggc ctttttgctg gccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt ttcctgtttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
```

```
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccag  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat tgattgcga gtgagatatt tatgccagcc agcagacgc agacgcgccg  4020
agacagaact taatgggccc gctaacgcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccgaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtgca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa agacaccgg  4560
catactctgc gacatcgtat aacgttactg gtttcacatt caccaccctg aattgactct  4620
cttccgggcg ctatcatgcc ataccgcgaa aggttttgcg ccattcgatg gtgtccggga  4680
tctcgacgct ctcccttatg cgactcctgc attaggaagc agcccagtag taggttgagg  4740
ccgttgagca ccgccgccgc aaggaatggt gcatgcaagg agatggcgcc caacagtccc  4800
ccggccacgg ggcctgccac catacccacg ccgaaacaag cgctcatgag cccgaagtgg  4860
cgagcccgat cttccccatc ggtgatgtcg gcgataagg cgccagcaac cgcacctgtg  4920
gcgccggtga tgccggccac gatgcgtccg cgtagagga tcgagatctc gatcccgcga  4980
aattaatacg actcactata ggggaattgt gagcggataa caattcccct ctagaaataa  5040
ttttgtttaa ctttaagaag gagatatacc atgggcagca gccatcatca tcatcatcac  5100
agcagcggcc tggtgccgcg cggcagccat atggctagca tgactggtgg acagcaaatg  5160
ggtcgcggat ccccggcagc taagaaaaag aaactggatg gcagcgtcga catgagcaag  5220
gacaagaaaa ccaaggccaa gagaatgggc gtgaaggccc tgctggccca cggcgaggac  5280
aagctgacca tgaccacctt cggcaagggc aacagaagca gatcgagtt caccgagggc  5340
taccacggca gagccctgga gacacccaag cacttcggca tcagaggctt cgaggtgaga  5400
agaatcgacg agaacgtgga cctgtgcggc gacctggagg agggcaagac catcgaggcc  5460
ctgctggtga accccagcga aaggtgggc gaggactacc tgaagctgaa gggcacccctg  5520
gagaagagat tcttcggcag agagttcccc cacgacaaca tcagaatcca gctgatctac  5580
aacatcctgg acatctacaa gatcctgggc ctgaacgtgg cgacatcct gtacgccctg  5640
ggcaacatgc aggacaccga gctggacatc gacatgttcg gccagagcct gaacaacgag  5700
gacaacctga aggagtgcct gaagagaatg aggccctaca tgggctactt cggcgacatc  5760
ttcaagatca gccccaaggg cgagaacatc gccgacagag agcacaacaa gaaggtgctg  5820
agatgcatca gcgtgctgag aaacgccacc gcccacgaca agcaggacga gtaccccctgg  5880
ttcaagagca gcgacatcta cgagacaaag atcttcaagg ccgacatgtg gaagatcatc  5940
aaggaccagt acagagagaa gatcaagaag gtgaacaagg acttcctgag caagaacgcc  6000
gtgaacatgg ccatcctgtt cgacctgctg aacgccagag acgtggagca gaagaagcag  6060
atcaccgacg agttctacag attcaccatc agaaaggacg gcaagaacct gggcatgaac  6120
ctggtgaaga tcagagagat catcatcgac agatacgcca gcggcctgag agacaagaag  6180
cacgacccccc acagacagaa gatcaacgtg atcgccgact tcctgatctt cagagccctg  6240
agccagaacc agggcatcat cgacaagacc gtgagcagcc tgagactgac caaggacgag  6300
gaggagaagg accacgtgta ccagaacgcc gccgagctgg tgtggggcat ggtgagcaac  6360
tgcctgacc cctacttcaa cgaccccaag aacaagtaca tcctgaagta caagacgcc  6420
aagacccccg cgacttcga ggactggatc accagcaaga tcagcgagga cgacggcgag  6480
cccttcgtga aggtgctgag cttcctgtgc aacttcctgg agggcaagga gatcaacgag  6540
ctgctgaccg cctacatcca aagttcgag tgcatccagg acttcctgaa cgtgatcagc  6600
agcctgggcg agaacgtgca gttccagccc agattcgccc tgttcaacaa cgccagctc  6660
gcccagaacg tggccgtgca gctgagaatc ctggccagca tcggcaagat gaagcccgac  6720
ctgaccgagg ccaagaggcc cctgtacaag gccgccatca aatgctgtg ccccccgag  6780
aagtgggaga agtacaccag cgacgagtgg ctggagaaga catgctgct gaacagcgag  6840
gacagaaaga acgacaagaa gaaggacgcag gtgaaccct tcagaaactt catcgccggc  6900
aacgtgatcg agagccaaag attcatgtac ctggtgagat acagcaaggc caaggcctg  6960
agagccatca tgcagaacag aagcatcgtg aactacgtgc tgcacagact gcccagcgag  7020
caggtgcaca gatacgccag cgtgttcccc gagaacttcg ccgacctgga gcaggagatc  7080
gacttcctga ccaagaagct gttcgagttc agcttcgagg agctgctgca cgagaaggac  7140
gtgatcctga acaacagcag aagccacaag cccagcctgg atcgagagag actgaaggcc  7200
atcaccgaga tgtacctgag cgtgcctcac atcaagaact gcaagggcca aggcctcaac  7260
gccagatact acatcgcctt cgccgtgttc gagagagaca aggactggtg gaaggccaag  7320
gacgccagaa tccagaccaa gatccccgag acagacttcc ccgactactt ctgcctgacc  7380
cagtactacc tggacagaga cgaggagaag aagttccccg cgaccccag agacaaggag  7440
gccttcttcg agcacctgag aaagaccaag agacacttca gcaagcagtg gagagagtgg  7500
ctgaacgaga agatcgccga cgccaagagc agccaggcca ccgcctgcct gctgagagag  7560
```

```
gccagaaacg acgtggagca cctgaacgtg ctgagagcca tccccgacta catccaggac 7620
ttcagacacg gcgagaaggg cgagacagcc atgaacagct acttcgagct gtaccactac 7680
ctgatgcaga gactgatgct gaagaacacc gagctggacc tgagccactg gagcggctgg 7740
atcatgagaa gcggcagacc cgacagagac ttgatccaga tcgccttcgt gagcctggcc 7800
tacaacctgc ccagatacag aaacctgacc aaggagcacc acttcgacga ccgtgctg 7860
cagaagatca gagagaagga gagcctggac acaggcggcg gccccggcgg cggcgccgcc 7920
gccggcagcg gcagccctaa gaaaaaacga aaagttggca gcggaagcaa aaggccggcg 7980
gccacgaaaa aggccggcca ggcaaaaaag aaaaagtaac tcgagcacca ccaccaccac 8040
cactgagatc cggctgctaa caaagcccga aggaagctga gttggctgc tgccaccgct 8100
gagcaataac tagcataacc ccttggggcc tctaaacgga tcttgagggg ttttttgctg 8160
aaaggaggaa ctatatccgg at                                         8182

SEQ ID NO: 11        moltype = AA    length = 982
FEATURE              Location/Qualifiers
source               1..982
                     mol_type = protein
                     organism = synthetic construct
SEQUENCE: 11
MGSSHHHHHH SSGLVPRGSH MASMTGGQQM GRGSPAAKKK KLDGSVDMSK DKKTKAKRMG   60
VKALLAHGED KLTMTTFGKG NRSKIEFTEG YHGRALETPK HFGIRGFEVR RIDENVDLCG  120
DLEEGKTIEA LLVNPSEKVG EDYLKLKGTL EKRFFGREFP HDNIRIQLIY NILDIYKILG  180
MNVADILYAL GNMQDTELDI DMFGQSLNNE DNLKECLKRM RPYMGYFGDI FKISPKGENI  240
ADREHNKKVL RCISVLRNAT AHDKQDEYPW FKSSDIYETK IFKADMWKII KDQYREKIKK  300
VNKDFLSKNA VNMAILFDLL NARDVEQKKQ ITDEFYRFTI RKDGKNLGMN LVKIREIIID  360
RYASGLRDKK HDPHRQKINV IADFLIFRAL SQNQGIIDKT VSSLRLTKDE EEKDHVYQNA  420
AELVWGMVSN CLTPYFNDPK NKYILKYKDA KTPGDFEDWI TSKISEDDGE PFVKVLSFLC  480
NFLEGKEINE LLTAYIHKFE CIQDFLNVIS SLGENVQFQP RFALFNNASF AQNVAVQLRI  540
LASIGKMKPD LTEAKRPLYK AAIRMLCPPE KWEKYTSDEW LEKNMLLNSE DRKNDKKKKQ  600
VNPFRNFIAG NVIESRRFMY LVRYSKPKAV RAIMQNRSIV NYVLHRLPSE QVHRYASVFP  660
ENFADLEQEI DFLTKKLFEF SFEELLHEKD VILNNSRSHK PSLEIERLKA ITGLYLSVAY  720
IAIKNIVKAN ARYYIAFAVF ERDKELVKAK DARIQTKIPE TDFPDYFCLT QYYLDRDEEK  780
KPPGDPRDKE AFFEHLRKTK RHFSKQWREW LNEKIADAKS SQATGLLLRE ARNDVEHLNV  840
LRAIPDYIQD FRHGEKGETA MNSYFELYHY LMQRLMLKNT ELDSHWSGW IMRSGRPDRD  900
LIQIAFVSLA YNLPRYRNLT KEHHFDDTVL QKIREKESLD TGGGPGGGAA AGSGSPKKKR  960
KVGSGSKRPA ATKKAGQAKK KK                                           982

SEQ ID NO: 12        moltype = DNA   length = 720
FEATURE              Location/Qualifiers
source               1..720
                     mol_type = other DNA
                     organism = synthetic construct
SEQUENCE: 12
atggtgagca agggcgagga gctgttcacc ggggtggtgc ccatcctggt cgagctggac   60
ggcgacgtaa acggccacaa gttcagcgtg tccggcgagg gcgagggcga tgccacctac  120
ggcaagctga ccctgaagtt catctgcacc accggcaagc tgcccgtgcc ctggcccacc  180
ctcgtgacca cctgacctac ggcgtgcagt gcttcagcc gctaccccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgay  540
gaccactacc agcagaacac ccccatcggc gacggccccg tgctgctgcc cgacaaccac  600
tacctgagca cccagtccgc cctgagcaaa gaccccaacg agaagcgcga tcacatggtc  660
ctgctggagt tcgtgaccgc cgccgggatc actctcggca tggacgagct gtacaagtaa  720

SEQ ID NO: 13        moltype = DNA   length = 4828
FEATURE              Location/Qualifiers
source               1..4828
                     mol_type = other DNA
                     organism = synthetic construct
SEQUENCE: 13
cctgcaggca gctgcgcgct cgctcgctca ctgaggccgc ccgggcgtcg gcgacctttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccca tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catggtgagc aagggcgagg   780
agctgttcac cggggtggtg cccatcctgg tcgagctgga cggcgacgta aacggccaca   840
agttcagcgt gtccggcgag ggcgagggcg atgccaccta cggcaagctg accctgaagt   900
tcatctgcac caccggcaag ctgcccgtgc cctggcccac cctcgtgacc accctgacct   960
acggcgtgca gtgcttcagc cgctaccccg accacatgaa gcagcacgac ttcttcaagt  1020
ccgccatgcc cgaaggctac gtccaggagc gcaccatctt cttcaaggac gacggcaact  1080
```

```
acaagacccg cgccgaggtg aagttcgagg gcgacaccct ggtgaaccgc atcgagctga    1140
agggcatcga cttcaaggag gacggcaaca tcctggggca caagctggag tacaactaca    1200
acagccacaa cgtctatatc atggccgaca agcagaagaa cggcatcaag gtgaacttca    1260
agatccgcca caacatcgag gacggcagcg tgcagctcgc cgaccactac cagcagaaca    1320
cccccatcgg cgacggcccc gtgctgctgc ccgacaacca ctacctgagc acccagtccg    1380
ccctgagcaa agaccccaac gagaagcgcg atcacatggt cctgctggag ttcgtgaccg    1440
ccgccgggat cactctcggc atggacgagc tgtacaagta aagcggccga attcctagag    1500
ctcgctgatc agcctcgact gtgccttcta gttgccagcc atctgttgtt tgcccctccc    1560
ccgtgccttc cttgacccty gaaggtgcca ctcccactgt cctttcctaa taaaatgagg    1620
aaattgcatc gcattgtctg agtaggtgtc attctattct ggggggtggg gtggggcagg    1680
acagcaaggg ggaggattgg gaagagaata gcaggcatgc tggggaggta ccgagggcct    1740
atttcccatg attccttcat atttgcatat acgatacaag gctgttagag agataattgg    1800
aattaatttg actgtaaaca caaagatatt agtacaaaat acgtgacgta gaaagtaata    1860
atttcttggg tagtttgcag ttttaaaatt atgttttaaa atggactatc atatgcttac    1920
cgtaacttga aagtatttcg atttcttggc tttatatatc ttgtggaaag gacgaaacac    1980
cggagaccac ggcaggtctc agttttagta ctctggaaac agaatctact aaaacaaggc    2040
aaaatgccgt gtttatctcg tcaacttgtt ggcgagattt ttgcggccgc aggaacccct    2100
agtgatggag ttggccactc cctctctgcg cgctcgctcg ctcactgagg ccgggcgacc    2160
aaaggtcgcc cgacgcccgg gctttgcccg gcggcctca gtgagcgagc gagcgcgcag    2220
ctgcctgcag gggcgcctga tgcggtattt tctccttacg catctgtgcg gtatttcaca    2280
ccgcatacgt caaagcaacc atagtacgcg ccctgtagcg gcgcattaag cgcggcgggt    2340
gtggtggtta cgcgcagcgt gaccgctaca cttgccagcg ccctagcgcc cgctcctttc    2400
gctttcttcc cttcctttct cgccacgttc gccggctttc cccgtcaagc tctaaatcgg    2460
gggctccctt tagggttccg atttagtgct ttacggcacc tcgaccccaa aaaacttgat    2520
ttgggtgatg gttcacgtag tgggccatcg ccctgataga cggtttttcg ccctttgacg    2580
ttggagtcca cgttctttaa tagtggactc ttgttccaaa ctggaacaac actcaaccct    2640
atctcgggct attcttttga tttataaggg attttgccga tttcggccta ttggttaaaa    2700
aatgagctga tttaacaaaa atttaacgcg aattttaaca aaatattaac gtttacaatt    2760
ttatggtgca ctctcagtac aatctgctct gatgccgcat agttaagcca gccccgacac    2820
ccgccaacac ccgctgacgc gccctgacgg gcttgtctgc tcccggcatc cgcttacaga    2880
caagctgtga ccgtctccgg gagctgcatg tgtcagaggt tttcaccgtc atcaccgaaa    2940
cgcgcgagac gaaagggcct cgtgatacgc ctatttttat aggttaatgt catgataata    3000
atggtttctt agacgtcagg tggcactttt cggggaaatg tgcgcggaac cctatttgt    3060
ttatttttct aaatacattc aaatatgtat ccgctcatga gacaataacc ctgataaatg    3120
cttcaataat attgaaaaag gaagagtatg agtattcaac atttccgtgt cgcccttatt    3180
ccctttttg cggcattttg ccttcctgtt tttgctcacc cagaaacgct ggtgaaagta    3240
aaagatgctg aagatcagtt gggtgcacga gtgggttaca tcgaactgga tctcaacagc    3300
ggtaagatcc ttgagagttt tcgccccgaa gaacgttttc caatgatgag cacttttaaa    3360
gttctgctat gtggcgcggt attatcccgt attgacgccg ggcaagagca actcggtcgc    3420
cgcatacact attctcagaa tgacttggtt gagtactcac cagtcacaga aaagcatctt    3480
acggatggca tgacagtaag agaattatgc agtgctgcca taaccatgag tgataacact    3540
gcggccaact tacttctgac aacgatcgga ggaccgaagg agctaaccgc ttttttgcac    3600
aacatggggg atcatgtaac tcgccttgat cgttgggaac cggagctgaa tgaagccata    3660
ccaaacgacg agcgtgacac cacgatgcct gtagcaatgg caacaacgtt gcgcaaacta    3720
ttaactggcg aactacttac tctagcttcc cggcaacaat taatagactg gatggaggcg    3780
gataaagttg caggaccact tctgcgctcg gcccttccgg ctggctggtt tattgctgat    3840
aaatctggag ccggtgagcg tggaagccgc ggtatcattg cagcactggg gccagatggt    3900
aagccctccc gtatcgtagt tatctacacg acggggagtc aggcaactat ggatgaacga    3960
aatagacaga tcgctgagat aggtgcctca ctgattaagc attggtaact gtcagaccaa    4020
gtttactcat atatacttta gattgattta aaacttcatt tttaatttaa aaggatctag    4080
gtgaagatcc ttttgataa tctcatgacc aaaatccctt aacgtgagtt ttcgttccac    4140
tgagcgtcag accccgtaga aaagatcaaa ggatcttctt gagatccttt ttttctgcgc    4200
gtaatctgct gcttgcaaac aaaaaaacca ccgctaccag cggtggtttg tttgccggat    4260
caagagctac caactctttt tccgaaggta actggcttca gcagagcgca gataccaaat    4320
actgtccttc tagtgtagcc gtagttaggc caccacttca agaactctgt agcaccgcct    4380
acatacctcg ctctgctaat cctgttacca gtggctgctg ccagtggcga taagtcgtgt    4440
cttaccgggt tggactcaag acgatagtta ccggataagg cgcagcggtc gggctgaacg    4500
gggggttcgt gcacacagcc cagcttggag cgaacgacct acaccgaact gagatacca    4560
cagcgtgagc tatgagaaag cgccacgctt cccgaaggga gaaaggcgga caggtatccg    4620
gtaagcggca gggtcggaac aggagagcgc acgaggggag ttccagggg aaacgcctgg    4680
tatctttata gtcctgtcgg gtttcgccac ctctgacttg agcgtcgatt tttgtgatgc    4740
tcgtcagggg gcggagcct atggaaaaac gccagcaacg cggcctttt acggttcctg    4800
gccttttgct ggccttttgc tcacatgt                                      4828
SEQ ID NO: 14           moltype = DNA   length = 6803
FEATURE                 Location/Qualifiers
source                  1..6803
                        mol_type = other DNA
                        organism = synthetic construct
SEQUENCE: 14
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact    120
aggggttcct gcggcctcta gactcgaggc gttgacattg attattgact agttattaat    180
agtaatcaat tacggggtca ttagttcata gcccatatat ggagttccgc gttacataac    240
ttacggtaaa tggcccgcct ggctgaccgc ccaacgaccc ccgcccattg acgtcaataa    300
tgacgtatgt tcccatagta acgccaatag ggactttcca ttgacgtcaa tgggtggagt    360
atttacggta aactgcccac ttggcagtac atcaagtgta tcatatgcca agtacgcccc    420
ctattgacgt caatgacggt aaatggcccg cctggcatta tgcccagtac atgaccttat    480
gggactttcc tacttggcag tacatctacg tattagtcat cgctattacc atggtgatgc    540
```

```
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgagca aggacaagaa aaccaaggcc aagagaatgt   840
gcgtgaaggc cctgctggcc cacgcgagg  acaagctgac catgaccacc ttcggcaagg   900
gcaacagaag caagatcgag ttcaccgagg ctaccacgg  cagagccctg agacaccca    960
agcacttcgg catcagaggc ttcgaggtga agaatcga  cgagaacgtg gacctgtgcg  1020
gcgacctgga ggagggcaag accatccgagg ccctgctggt gaaccccagc gagaaggtgg  1080
gcgaggacta cctgaagctg aagggcaccc tggagaagaa attcttcggc agagagttcc  1140
cccacgacaa catcagaatc cagctgatct acaacatcct ggacatctac aagatcctgg  1200
gcatgaacgt ggccgacatc ctgtacgccc tgggcaacat gcaggacacc gagctggaca  1260
tcgacatgtt cggccagagc ctgaacaacg gacaacctc aaggagtgc ctgaagagaa    1320
tgaggcccta catgggctac ttcggcgaca tcttcaagat cagccccaag ggcgagaaca  1380
tcgccgacag agagcacaac aagaaggtgc tgagatgcat cagcgtgctg agaaacgcca  1440
ccgcccacga caagcaggac gagtaccct ggttcaagag cagcgacatc tacgagacaa   1500
agatcttcaa ggccgacatg tggaagatca tcaaggacca gtacagagag aagatcaaga  1560
aggtgaacaa ggacttcctg agcaagaacg ccgtgaacat ggccatcctg ttcgacctgc  1620
tgaacgccag agacgtggag cagaagaagc agatcaccga cgagttctac agattccacca 1680
tcagaaagga cggcaagaac ctgggcatga acctggtgaa gatcagagag atcatcatcg  1740
acagatacgc cagcggcctg agagacaaga agcacgaccc ccagacagca agatcaacg    1800
tgatcgccga cttcctgatc ttcagagccc tgagccagaa ccagggcatc atcgacaaga  1860
ccgtgagcag cctgagactg accaaggacg aggaggaga ggaccacgtg taccagaacg   1920
ccgccgagct ggtgtgggc atggtgagca actgctgac ccctacttc aacgaccca     1980
agaacaagta catcctgaag tacaaggacg ccaagacccc cggcgacttc gaggactgga  2040
tcaccagcaa gatcagcgag gacgacgcg agcccttcgt gaaggtgctg agcttcctgt    2100
gcaacttcct ggagggcaag gagatcaacg agctgctgac cgcctacatc cacaagttcg  2160
agtgcatcca ggacttcctg aacgtgatca gcagcctgac cgagaacgtg cagttccagc  2220
ccagattcgc cctgttcaac aacgccagct tcgcccagaa cgtggccgtg cagctgagaa  2280
tcctggccag catcggcaga atgaagcccg acctgaccga ggccaagagg cccctgtaca  2340
aggccgccat cagaatgctg tgcccccccg agaagtggga gaagtacacc agcgacgagt  2400
ggctggagaa gaacatgctg ctgaacagca ggacagaaa gaacgacaag aagaagaagc   2460
aggtgaaccc cttcagaaac ttcatcgccg gcaacgtgat cgagagcaga agattcatgt  2520
acctggtgag atacagcaag cccaaggccg tgagagccat catgcagaac agaagcatcg  2580
tgaactacgt gctgcacaga ctgccagcg agcaggtgca cagatacgcc agcgtgttcc   2640
ccgagaactt cgccgacctg gagcaggaga tcgacttcct gaccaagaag ctgttcgagt  2700
tcagcttcga ggagctgctg cacgagaagg acgtgatcct gaacaacagc agaagccaca  2760
agcccagcct ggagatcgag agactgaagg ccatcaccgg cctgtacctg agcgtggcct  2820
acatccgcat caagaacatc gtgaaggcca acgccagata ctacatcgcc ttcgccgtgt  2880
tcgagagaga caaggagctg gtgaaggcca aggacgccag aatccagacc aagatccccg  2940
agacagactt ccccgactac ttctgcctga cccagtacta cctggacaga gacgaggaga  3000
agaagttccc cggcgacccc agagacaagg aggccttctt cgagcacctg agaaagacca  3060
agagacactt cagcaagcag tggagagagt ggctgaacga gaagatcgcc gacgccagaa  3120
gcagccaggc caccggcctg ctgctgagag aggccagaaa cgacgtggag cacctgaacg  3180
tgctgagagc catccccgac tacatccagg acttcagaca cggcgagaag ggcgagacag  3240
ccatgaacag ctacttcgag ctgtaccact acctgatgca gagactgatg ctgaagaaca  3300
ccgagctgga cctgagccac tggagcggct ggatcatgaa aagcggcaga cccgacagg   3360
acttgatcca gatcgccttc gtgagcctgg cctacaacct gcccagatac agaaacctga  3420
ccaaggagca ccacttcgac gacaccgtgc tgcagaagat cagagagaag gagagcctgg  3480
acacaggcgg cggccccggc ggcggcgccg ccgccggcag cggcagccct aagaaaaaac  3540
gaaaagttgg cagcggaagc aaaaggccgg cggccacgaa aaaggccggc caggcaaaaa  3600
agaaaaagct cgagtaccca tacgatgttc cagattacgc ttgagaattc cccttgagca  3660
tctgacttct ggctaataaa ggaaatttat tttcattgca atagtgtgtt ggaattttttt  3720
gtgtctctca ggtaccgagg gcctatttcc catgattcct tcatatttgc atatacgata  3780
caaggctgtt agagagataa ttggaattaa tttgactgta aacacaaaga tattagtaca  3840
aaatacgtga cgtagaaagt aataattct  tgggtagttt gcagttttaa aattatgttt   3900
taaaatggac tatcatatgc ttaccgtaac ttgaaagtat ttcgatttct ggctttata    3960
tatcttgtgt aaaggacgaa acaccggaag ataactctac aaacctgtag ggttctgaga  4020
ctgccgttct tctgcttgtc ggccatgata ttttttttgc gccgcaggaa cccctagtga  4080
tggagttggc cactccctct ctgcgcgctc gctcgctcac tgaggccggg cgaccaaagg  4140
tcgcccgacg cccgggcttt gcccggcgg cctcagtgac cgagcgagcg cgcagctgcc   4200
tgcaggggcg cctgatgcgg tattttctcc ttacgcatct gtgcggtatt tcacaccgca  4260
tacgtcaaag caaccatagt acgcgccctg tagcggcgca ttaagcgcgg cgggtgtggt  4320
ggttacgcgc agcgtgaccg ctacacttgc cagcgcctta cgcccgctc ctttcgcttt    4380
cttccctcc ttcgccag cgttcgccgc ctttccccgt caagctctaa atcggggggct    4440
cccttaggg ttccgattta gtgctttacg gcacctcgac cccaaaaaac ttgattggg    4500
tgatggttca cgtagtgggc catcgccctg atagacggtt tttcgccctt tgacgttgga  4560
gtccacgttc tttaatagtg gactcttgtt ccaaactgga caacactca actctatctc    4620
gggctattct tttgatttat aagggattt  gccgatttcg gtctattggt taaaaaatga   4680
gctgatttaa caaaaattta acgcgaattt taacaaaata ttaacgttta cattttatg    4740
gtgcactctc agtacaatct gctctgatgc cgcatagtta agccagcccc gacacccgcc  4800
aacacccgct gacgcgccct gacgggcttg tctgctcccg gcatccgctt acagacaagc  4860
tgtgaccgtc tccgggagct gcatgtgtca gaggttttca ccgtcatcac cgaaacgcgc  4920
gagacgaaag ggcctcgtga tacgcctatt tttataggtt aatgtcatga taataatggt  4980
ttcttagacg tcaggtggca cttttcgggg aaatgtgcgc ggaacccta tttgtttatt    5040
tttctaaata cattcaaata tgtatccgct catgagacaa taaccctgat aaatgcttca  5100
ataatattga aaaggaagag gtatgagtat tcaacatttc cgtgtcgccc ttattcccctt  5160
ttttgcggca ttttgccttc ctgtttttgc tcacccagaa acgctggtga agtaaaaga   5220
tgctgaagat cagttgggtg cacgagtggg ttacatcgaa ctggatctca acagcggtaa  5280
```

```
gatccttgag agttttcgcc ccgaagaacg ttttccaatg atgagcactt ttaaagttct   5340
gctatgtggc gcggtattat cccgtattga cgccgggcaa gagcaactcg gtcgccgcat   5400
acactattct cagaatgact tggttgagta ctcaccagtc acagaaaagc atcttacgga   5460
tggcatgaca gtaagagaat tatgcagtgc tgccataacc atgagtgata acactgcggc   5520
caacttactt ctgacaacga tcggaggacc gaaggagcta accgcttttt tgcacaacat   5580
gggggatcat gtaactcgcc ttgatcgttg ggaaccggag ctgaatgaag ccataccaaa   5640
cgacgagcgt gacaccacga tgcctgtagc aatggcaaca acgttgcgca aactattaac   5700
tggcgaacta cttactctag cttcccggca acaattaata gactggatgg aggcggataa   5760
agttgcagga ccacttctgc gctcggccct tccggctggc tggtttattg ctgataaatc   5820
tggagccggt gagcgtggaa gccgcggtat cattgcagca ctggggccag atggtaagcc   5880
ctcccgtatc gtagttatct acacgacggg gagtcaggca actatggatg aacgaaatag   5940
acagatcgct gagataggtg cctcactgat taagcattgg taactgtcag accaagttta   6000
ctcatatata ctttagattg atttaaaact tcattttttaa tttaaaagga tctaggtgaa   6060
gatccttttt gataatctca tgaccaaaat cccttaacgt gagttttcgt tccactgagc   6120
gtcagacccc gtagaaaaga tcaaaggatc ttcttgagat cctttttttc tgcgcgtaat   6180
ctgctgcttg caaacaaaaa aaccaccgct accagcggtg gtttgtttgc cggatcaaga   6240
gctaccaact cttttttccga aggtaactgg cttcagcaga gcgcagatac caaatactgt   6300
tcttctagtg tagccgtagt taggccacca cttcaagaac tctgtagcac cgcctacata   6360
cctcgctctg ctaatcctgt taccagtggc tgctgccagt ggcgataagt cgtgtcttac   6420
cgggttggac tcaagacgat agttaccgga taaggcgcag cggtcgggct gaacggggg    6480
ttcgtgcaca cagcccagct tggagcgaac gacctacacc gaactgagat acctacagcg   6540
tgagctatga gaaagcgcca cgcttcccga agggagaaag gcggacaggt atccggtaag   6600
cggcagggtc ggaacaggag agcgcacgag ggagcttcca gggggaaacg cctggtatct   6660
ttatagtcct gtcgggtttc gccacctctg acttgagcgt cgatttttgt gatgctcgtc   6720
aggggggcgg agcctatgga aaaacgccag caacgcggcc ttttttacggt tcctggcctt   6780
ttgctggcct tttgctcaca tgt                                          6803

SEQ ID NO: 15           moltype = DNA   length = 6793
FEATURE                 Location/Qualifiers
source                  1..6793
                        mol_type = other DNA
                        organism = synthetic construct
SEQUENCE: 15
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgagca aggacaagaa aaccaaggcc aagagaaatgg   840
gcgtgaaggc cctgctggcc cacggcgagg acaagctgac catgaccacc ttcggcaagg   900
gcaacagaag caagatcgag ttcaccgagg ctaccacgg cagagccctg agacaccca    960
agcacttcgg catcagaggc ttcgaggtga aagaatcga cgagaacgtg gacctgtgcg   1020
cgacctgga ggagggcaag accatcgagg ccctgctgt gaaccccag gagaaggtgg   1080
gcgaggacta cctgaagctg aagggcaccc tggagaagag attcttcggc agagagttcc   1140
cccacgacaa catcagaatc cagctgatct acaacatcct ggacatctac aagatcctgg   1200
gcatgaacgt ggccgacatc ctgtacgccc tgggcaacat gcaggacacc gagctggaca   1260
tcgacatgtt cggccagagc tgaacaacg aggacaacct gaaggagtgc ctgaagagaa   1320
tgaggcccta catgggctac ttcggcgaca tcttcaagat cagccccaag ggcgagaaca   1380
tcgccgacag agagcacaac aagaaggtgc tgagatgcat cagcgtgctg agaaacgcca   1440
ccgcccacga caagcaggac gagtacccct ggttcaagag cagcgacatc tacgagcaaa   1500
agatcttcaa ggccgacatg tggaagatca tcaaggacca gtacaaggac aagatcaaga   1560
aggtgaacaa ggacttcctg agcaagaacg ccgtgaacat ggccatcctg ttcgacctgc   1620
tgaacgccag agacgtggag cagaagaagc agatcaccga cgagttctac agattcacca   1680
tcagaaagga cggcaagaac ctgggcatga acctggtgaa gatcagagag atcatcatcg   1740
acagatacgc cagcggcctg agagacaaga gcacgaccc ccacgacag aagatcaacg   1800
tgatcgccga cttcctgatc ttcagagccc tgagccagaa ccagggcatc atcgacaaga   1860
ccgtgagcag cctgagactg accaaggacg aggaggagaa ggaccacgtg taccagaacg   1920
ccgccgagct ggtgtgggc atggtgagca actgctgac ccctacttc aacgacccca   1980
agaacaagta catcctgaag tacaaggacg ccaagacccc cggcgacttc gaggactgga   2040
tcaccagcaa gatcagcgag gacgccgcg agccccttcgt gaaggtgctg agcttcctgt   2100
gcaacttcct ggagggcaag gagatcaacg agctgctgac cctctacatc cacaagttgt   2160
agtgcatcca ggacttcctg aacgtgatca gcagcctggg cgagaacgtg cagttccagc   2220
ccagattcgc cctgttcaac aacgccagct cgcccagaa cgtggccgtg cagctgagaa   2280
tcctggccag catcggcaag atgaagccc acctgaccga ggccaagagg cccctgtaca   2340
aggccgccca gaatgctgt gccccccg agaagtggga gaagtacacc agcgacgagt   2400
ggctgaagaa gaacatgctg ctgaacgcg aggacaagaa aagaagac   2460
aggtgaaccc cttcagaaac ttcatcgccg gcaacgtgat cgagagcaga agattcatgt   2520
acctggtgag atacagcaag cccaaggcg tgagagccat catgcagaac agaagcatcg   2580
tgaactacgt gctgcacaga ctgccagcg gcaggtgca cagatacgcc agcgtgttcc   2640
ccgagaactt cgccgacctg gagcaggaga tcgacttcct gaccaagaag ctgttcgagt   2700
tcagcttcga ggagctgctg cacgagaagg acgtgatcct gaacaacagc agaagccaca   2760
```

```
agcccagcct ggagatcgag agactgaagg ccatcaccgg cctgtacctg agcgtggcct   2820
acatcgccat caagaacatc gtgaaggcca acgccagata ctacatcgcc ttcgccgtgt   2880
tcgagagaga caaggagctg gtgaaggcca aggacgccag aatccagacc aagatccccg   2940
agacagactt ccccgactac ttctgcctga cccagtacta cctggacaga gacgaggaga   3000
agaagttccc cggcgacccc agagacaagg aggccttcct cgagcacctg agaaagacca   3060
agagacactt cagcaagcag tggagagagt ggctgaacga gaagatcgcc gacgccaaga   3120
gcagccaggc caccggcctg ctgctgagag aggccagaaa cgacgtggag cacctgaacg   3180
tgctgagagc catccccgac tacatccagg acttcagaca cggcgagaag ggcgagacag   3240
ccatgaacag ctacttcgag ctgtaccact acctgatgca gagactgatg ctgaagaaca   3300
ccgagctgga cctgagccac tggagcggct ggatcatgag aagcggcaga cccgacagag   3360
acttgatcca gatcgccttc gtgagcctgg cctacaacct gcccagatac agaaacctga   3420
ccaaggagca ccacttcgac gacaccgtgc tgcagaagat cagagagaag gagagcctgg   3480
acacaggcgg cggccccggc ggcggcgccg ccgccggcag cggcagccct aagaaaaaac   3540
gaaaagttgg cagcggaagc aaaaggccgg cggccacgaa aaaggccggc caggcaaaaa   3600
agaaaaagct cgagtaccca tacgatgttc cagattacgc ttgagaattc cccttgagca   3660
tctgacttct ggctaataaa ggaaatttat tttcattgca atagtgtgtt ggaatttttt   3720
gtgtctctca ggtaccgagg gcctatttcc catgattcct tcatatttgc atatacgata   3780
caaggctgtt agagagataa ttggaattaa tttgactgta aacacaaaga tattagtaca   3840
aaatacgtga cgtagaaagt aataatttct tgggtagttt gcagttttaa aattatgttt   3900
taaaatggac tatcatatgc ttaccgtaac ttgaaagtat ttcgatttct ggctttata    3960
tatcttgtgg aaaggacgaa acaccggaag ataactctac aaacctgtag ggttctgaga   4020
cggagaccac ggcaggtctc atttttttgcg gccgcaggaa cccctagtga tggagttggc   4080
cactccctct ctgcgcgctc gctcgctcac tgaggccggg cgaccaaagg tcgcccgacg   4140
cccgggcttt gcccgggcgg cctcagtgag cgagcgagcg cgcagctgcc tgcaggggcg   4200
cctgatgcgg tatttctcc ttacgcatct gtgcggtatt tcacaccgca tacgtcaaag   4260
caaccatagt acgcgccctg tagcggcgca ttaagcgcgg cgggtgtggt ggttacgcgc   4320
agcgtgaccg ctacacttgc cagcgcctta gcgcccgctc ctttcgcttt cttcccttcc   4380
tttctcgcca cgttcgccgg ctttccccgt caagctctaa atcgggggct ccctttaggg   4440
ttccgattta gtgctttacg gcacctcgac cccaaaaaac ttgatttggg tgatggttca   4500
cgtagtgggc catcgccctg atagacggtt tttcgccctt tgacgttgga gtccacgttc   4560
tttaatagtg gactcttgtt ccaaactgga acaacactca actctatctc gggctattct   4620
tttgatttat aagggatttt gccgatttcg gtctattggt taaaaaatga gctgatttaa   4680
caaaaattta acgcgaattt taacaaaata ttaacgttta aattttatg gtgcactctc   4740
agtacaatct gctctgatgc cgcatagtta agccagcccc gacacccgcc aacacccgct   4800
gacgcgccct gacgggcttg tctgctcccg gcatccgctt acagacaagc tgtgaccgtc   4860
tccgggagct gcatgtgtca gaggttttca ccgtcatcac cgaaacgcgc gagacgaaag   4920
ggcctcgtga tacgcctatt tttataggtt aatgtcatga taataatggt ttcttagacg   4980
tcaggtggca cttttcgggg aaatgtgcgc ggaaccccta tttgtttatt tttctaaata   5040
cattcaaata tgtatccgct catgagacaa taaccctgat aaatgcttca ataatattga   5100
aaaaggaaga gtatgagtat tcaacatttc cgtgtcgccc ttattccctt ttttgcggca   5160
ttttgccttc ctgtttttgc tcacccagaa acgctggtga agtaaaaga tgctgaagat   5220
cagttgggtg cacgagtggg ttacatcgaa ctggatctca acagcggtaa gatccttgag   5280
agttttcgcc ccgaagaacg ttttccaatg atgagcactt ttaaagttct gctatgtggc   5340
gcggtattat cccgtattga cgccgggcaa gagcaactcg gtcgccgcat acactattct   5400
cagaatgact tggttgagta ctcaccagtc acagaaaagc atcttacgga tggcatgaca   5460
gtaagagaat tatgcagtgc tgccataacc atgagtgata cactgcggc caacttactt   5520
ctgacaacga tcggaggacc gaaggagcta accgcttttt tgcacaacat ggggatcat   5580
gtaactcgcc ttgatcgttg gaaccggag ctgaatgaag ccataccaaa cgacgagcgt   5640
gacaccacga tgcctgtagc aatggcaaca acgttgcgca aactattaac tggcgaacta   5700
cttactctag cttcccggca acaattaata gactggatgg aggcggataa agttgcagga   5760
ccacttctgc gctcggccct tccggctggc tggttttatt ctgataaatc tggagccggt   5820
gagcgtggaa gccgcggtat cattgcagca ctggggccag atggtaagcc ctcccgtatc   5880
gtagttatct acacgacggg gagtcaggca actatggatg aacgaaatag acagatcgct   5940
gagataggtg cctcactgat taagcattgg taactgtcag accaagttta ctcatatata   6000
ctttagattg atttaaaact tcatttttaa tttaaaagga tctaggtgaa gatcctttg    6060
gataatctca tgaccaaaat cccttaacgt gagttttcgt tccactgagc gtcagacccc   6120
gtagaaaaga tcaaaggatc ttcttgagat cctttttttc tgcgcgtaat ctgctgcttg   6180
caaacaaaaa aaccaccgct accagcggtg gtttgtttgc cggatcaaga gctaccaact   6240
cttttccga aggtaactgg cttcagcaga gcgcagatac caaatactgt tcttctagtg   6300
tagccgtagt taggccacca cttcaagaac tctgtagcac cgcctacata cctcgctctg   6360
ctaatcctgt taccagtggc tgctgccagt ggcgataagt cgtgtcttac cgggttggac   6420
tcaagacgat agttaccgga taaggcgcag cggtcgggct gaacggggg ttcgtgcaca   6480
cagcccagct tggagcgaac gacctacacc gaactgagat acctacagcg tgagctatga   6540
gaaagcgcca cgcttcccga agggagaaag gcggacaggt atccggtaag cggcagggtc   6600
ggaacaggag agcgcacgag ggagcttcca gggggaaacg cctggtatct ttatagtcct   6660
gtcgggtttc gccaccctg acttgagcgt cgatttttgt gatgctcgtc aggggggcgg   6720
agcctatgga aaacgccag caacgcggcc tttttacggt tcctggcctt ttgctggcct   6780
tttgctcaca tgt                                                      6793

SEQ ID NO: 16         moltype = DNA   length = 9363
FEATURE               Location/Qualifiers
source                1..9363
                      mol_type = other DNA
                      organism = synthetic construct
SEQUENCE: 16
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt gcgctgcttc gcgatgtacg ggccagatat acgcgttgac   240
```

```
attgattatt gactagttat taatagtaat caattacggg gtcattagtt catagcccat    300
atatggagtt ccgcgttaca taacttacgg taaatggccc gcctggctga ccgcccaacg    360
accccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taccagatct gagcctggga gctctctggc    840
taactaggga acccactgct taagcctcaa taaagcttgc cttgagtgct tcaagtagtg    900
tgtgcccgtc tgttgtgtga ctctggtaac tagagatccc tcagaccctt ttagtcagtg    960
tggaaaatct ctagcagtgg cgcccgaaca gggacttgaa agcgaaaggg aaaccagagg   1020
agctctctcg acgcaggact cggcttgctg aagcgcgcac gcaagaggcg aggggcggc   1080
gactggtgag tacgccaaaa attttgacta gcggaggcta agaagagaga gatgggtgcg   1140
agagcgtcag tattaagcgg gggagaatta gatcgcgatg ggaaaaaatt cggttaaggc   1200
cagggggaaa gaaaaaatat aaataaacat atagtatggg caagcaggga gctagaacga   1260
ttcgcagtta atcctggcct gttagaaaca tcagaaggct gtagacaaat actgggacag   1320
ctacaaccat cccttcagac aggatcagaa gaacttagat cattatataa tacagtagca   1380
accctctatt gtgtgcatca aaggatagag ataaaagaca ccaaggaagc tttagacaag   1440
atagaggaag agcaaaacaa aagtaagacc accgcacagc aagcggccgg ccgcgctgat   1500
cttcagacct ggaggaggag atatgaggga caattggaga agtgaattat ataaatataa   1560
agtagtaaaa attgaaccat taggagtagc acccaccaag gcaaagaaa gagtggtgca   1620
gagagaaaaa agagcagtgg gaataggagc tttgttcctt gggttcttgg gagcagcagg   1680
aagcactatg ggcgcagcgt caatgacgct gacggtacag gccagacaat tattgtctgg   1740
tatagtgcag cagcagaaca atttgctgag ggctattgag gcgcaacagc atctgttgca   1800
actcacagtc tggggcatca agcagctcca ggcaagaatc ctggctgtgg aaagatacct   1860
aaaggatcaa cagctcctgg ggatttgggg ttgctctgga aaactcattt gcaccactgc   1920
tgtgccttgg aatgctagtt ggagtaataa atctctggaa cagatttgga atcacacgac   1980
ctggatggag tgggacagag aaattaacaa ttacacaagc ttaatacact ccttaattga   2040
agaatcgcaa aaccagcaag aaaagaatga acaagaatta ttggaattag ataaatgggc   2100
aagtttgtgg aattggttta acataacaaa ttggctgtgg tatataaaat tattcataat   2160
gatagtagga ggcttggtag gtttaagaat agttttgct gtactttcta tagtgaatag   2220
agttaggcag ggatattcac cattatcgtt tcagacccac ctcccaaccc cgagggggacc   2280
cgacaggccc gaaggaatag aagaagaagg tggagagaga gacagagaca gatccattcg   2340
attagtgaac ggatcggcac tgcgtgcgcc aattctgcag acaaatggca gtattcatcc   2400
acaattttaa aagaaaaggg gggattgggg ggtacagtgc aggggaaaga atagtagaca   2460
taatagcaac agacatacaa actaaagaat tacaaaaaca aattacaaaa attcaaaatt   2520
ttcgggttta ttacagggac agcagagatc cagtttggtt agtaccgggc ccgctctagc   2580
gtcgaggagc ttggcccatt gcatacgttg tatccatatc ataatatgta catttatatt   2640
ggctcatgtc caacattacc gccatgttga cattgattat tgactagtta ttaatagtaa   2700
tcaattacgg ggtcattagt tcatagccca tatatggagt tccgcgttac ataacttacg   2760
gtaaatggcc cgcctggctg accgcccaac gacccccgcc cattgacgtc aataatgacg   2820
tatgttccca tagtaacgcc aatagggact ttccattgac gtcaatgggt ggagtattta   2880
cggtaaactg cccacttggc agtacatcaa gtgtatcata tgccaagtac gccccctatt   2940
gacgtcaatg acggtaaatg gcccgcctgg cattatgccc agtacatgac cttatgggac   3000
tttcctactt ggcagtacat ctacgtatta gtcatcgcta ttaccatggt gatgcggttt   3060
tggcagtaca tcaatgggcg tggatagcgg tttgactcac ggggatttcc aagtctccac   3120
cccattgacg tcaatgggag tttgttttgg caccaaaatc aacgggactt tccaaaatgt   3180
cgtaacaact ccgccccatt gacgcaaatg gcggtaggc gtgtacggtg ggaggtctat   3240
ataagcagag ctcgtttagt gaaccgtcag atcgcctgga gacgccatcc acgctgtttt   3300
gacctccata gaagacaccg ggaccgatcc agcctccgcg gccccgaatt cgccaccatg   3360
gccagcgagt tcaagaagaa gctcttctgg agggcagtgg tggccgagtt cctgccacg   3420
accctctttg tcttcatcag catccggttct gccctgggct tcaaatacc ggtggggaac   3480
aaccagacgg cggtccagga caacgtgaag gtgtcgctgg ccttcgggtc gagcatcgct   3540
acgctggcgc agagtgtggg ccacatcagc ggcgcccacc tcaaccggc tgtcacactg   3600
gggctgctgc tcagctgcca gatcagcatc ttccgtgccc tcatgtacat catcgcccag   3660
tgcgtggggg ccatcgtcgc caccgccatc ctctcaggca tcacctcctc cctgactggg   3720
aactcgcttg gccgcaatga cctggctgat ggtgtgaact cggcccaggg cctgggcatc   3780
gagatcatcg ggaccctcca gctggtgcta tgcgtcgtgg ctactaccga ccggaggcgc   3840
cgtgaccttg gtggctcagc ccccttgcc atcggcctct ctgtagccct tggacacctc   3900
ctggctattg actacactgg ctgtgggatt aaccctgctc ggtcctttgg ctccgcggtg   3960
atcacacaca acttcagcaa ccactggatt tctgggtgtg ggccattcat cggggagcc   4020
ctggctgtac tcatctacga cttcatcctg cccccacga gcagtgacct cacagaccgg   4080
gtgaaggtgt ggaccagcgg ccaggtggag gagtatgacc tggatgccga cgacatcaac   4140
tccagggtgg agatgaagcc caaataccca tacgatgttc cagattacgc tggatccgct   4200
agcggcagtg gagagggcag aggaagtctg ctaacatgcg gtgacgtcga ggagaatcct   4260
ggcccagtga gcaagggcga ggagctgttc accggggtgg tgcccatcct ggtcgagctg   4320
gacggcgacg taaacggcca caagttcagc gtgtccggcg agggcgaggg cgatgccaca   4380
tacggcaagc tgaccctgaa gttcatctgc accaccggca agctgcccgt gcccctgccc   4440
accctcgtga ccaccctgac ctacggcgtg cagtgcttca gccgctaccc cgaccacatg   4500
aagcagcacg acttcttcaa gtccgccatg cccgaaggct acgtccagga gcgcaccatc   4560
ttcttcaagg acgacggcaa ctacaagacc cgcgccgagg tgaagttcga gggcgacacc   4620
ctggtgaacc gcatcgagct gaagggcatc gacttcaagg aggacggcaa catcctgggc   4680
cacaagctgg agtacaacta caacagccac aacgtctata tcatggccga caagcagaag   4740
aacggcatca aggtgaactt caagatccgc cacaacatcg aggacggcag cgtgcagctc   4800
gccgaccact accagcagaa cacccccatc ggcgacggcc ccgtgctgct gcccgacaac   4860
cactacctga gcacccagtc cgccctgagc aaagacccca acgagaagcg cgatcacatg   4920
gtcctgctgg agttcgtgac cgccgccggg atcactctcg gcatggacga gctgtacaag   4980
```

```
taaggatcct aggcggccgc gcatgccctg caggtgatct atcgatcggc cggcccctct 5040
ccctccccc ccccctaacg ttactggccg aagccgcttg gaataaggcc ggtgtgcgtt 5100
tgtctatatg ttattttcca ccatattgcc gtcttttggc aatgtgaggg cccggaaacc 5160
tggccctgtc ttcttgacga gcattcctag gggtctttcc cctctcgcca aaggaatgca 5220
aggtctgttg aatgtcgtga aggaagcagt tcctctggaa gcttcttgaa gacaaacaac 5280
gtctgtagcg accctttgca ggcagcggaa ccccccacct ggcgacaggt gcctctgcgg 5340
ccaaaagcca cgtgtataag atacacctgc aaaggcggca caaccccagt gccacgttgt 5400
gagttggata gttgtggaaa gagtcaaatg gctctcctca agcgtattca acaaggggct 5460
gaaggatgcc cagaaggtac cccattgtat gggatctgat ctggggcctc ggtacacatg 5520
ctttacatgt gtttagtcga ggttaaaaaa acgtctaggc ccccgaacc acggggacgt 5580
ggttttcctt tgaaaaacac gatgataata tggccacaac cgggccggat atcacgcgtg 5640
atctgatcag cacgtgttga caattaatca tcggcatagt atatcggcat agtataatac 5700
gacaaggtga ggaactaaac catggccaag cctttgtctc aagaagaatc caccctcatt 5760
gaaagagcaa cggctacaat caacagcatc cccatctctg aagactacag cgtcgccagc 5820
gcagctctct ctagcgacgg ccgcatcttc actggtgtca atgtatatca ttttactggg 5880
ggaccttgtg cagaactcgt ggtgctgggc actgctgctg ctgcggcagc tggcaacctg 5940
acttgtatcg tcgcgatcgg aaatgagaac aggggcatct tgagccctg cggacggtgc 6000
cgacaggtgc ttctcgatct gcatcctggg atcaaagcca tagtgaagga cagtgatgga 6060
cagccgacgg cagttgggat tcgtgaattg ctgccctctg gttatgtgtg ggagggctaa 6120
gcaatgcata catgtgttta aacctcgact taattaagtc gagggtcgac ggtatcgata 6180
agctcgcttc acgagatcat gtttaagggt tccggttcca ctaggtacaa ttcgatatca 6240
agcttatcga taatcaacct ctggattaca aaatttgtga aagattgact ggtattctta 6300
actatgttgc tccttttacg ctatgtggat acgctgcttt aatgcctttg tatcatgcta 6360
ttgcttcccg tatggctttc attttctcct ccttgtataa atcctggttg ctgtctcttt 6420
atgaggagtt gtgccccgtt gtcaggcaac gtggcgtggt gtgcactgtg tttgctgacg 6480
caaccccac tggttgggc attgccacca cctgtcagtc cctttccggg acttttcgctt 6540
tccccctccc tattgccacg gcggaactca tcgccgcctg ccttgcccgc tgctggacag 6600
gggctcggct gttgggcact gacaattccg tggtgttgtc ggggaaatca tcgtcctttc 6660
cttggctgct cgcctgtgtt gccacctgga ttctgcgcgg gacgtccttc tgctacgtcc 6720
cttcgccct caatccagcg gaccttcctt ccgcgcggcct gctgccggcct ctgcggcctc 6780
ttccgcgtct tcgccttcgc cctcagacga gtcggatctc cctttgggcc gcctcccgc 6840
atcgataccg tcgacctcga tcgagaccta gaaaaacatg gagcaatcac aagtagcaat 6900
acagcagcta ccaatgctga ttgtgcctgg ctagaagcac aagaggagga ggaggtgggt 6960
tttccagtca cacctcaggt acctttaaga ccaatgactt acaaggcagc tgtagatctt 7020
agccactttt taaaagaaaa gggggggactg gaagggctaa ttcactccca acgaagacaa 7080
gatatccttg atctgtggat ctaccacaca caaggctact tccctgattg gcagaactac 7140
acaccagggc cagggatcag atatccactg acctttggat ggtgctacaa gctagtacca 7200
gttgagcaag agaaggtaga agaagccaat gaaggagaga acacccgctt gttacacctc 7260
gtgagcctgc atgggatgga tgacccggag agagaagtat tagagtggag gtttgacagc 7320
cgcctagcat ttcatcacat ggcccgagag ctgcatccgg actgtactgg gtctctctgg 7380
ttagaccaga tctgagcctg ggagctctct ggctaactag gaacccact gcttaagcct 7440
caataaagct tgccttgagt gcttcaagta gtgtgtgccc gtctgttgtg tgactctggt 7500
aactagagat ccctcagacc cttttagtca gtgtggaaaa tctctagcag catgtgagca 7560
aaaggccagc aaaaggccag gaaccgtaaa aaggccgcgt tgctggcgtt tttccatagg 7620
ctccgccccc ctgacgagca tcacaaaaat cgacgctcaa gtcagaggtg gcgaaacccg 7680
acaggactat aaagatacca ggcgtttccc cctggaagct ccctcgtgcg ctctcctgtt 7740
ccgaccctgc cgcttaccgg atacctgtcc gcctttctcc cttcgggaag cgtggcgctt 7800
tctcatagct cacgctgtag gtatctcagt tcggtgtagg tcgttcgctc caagctgggc 7860
tgtgtgcacg aaccccccgt tcagcccgac cgctgcgcct tatccggtaa ctatcgtctt 7920
gagtccaacc cggtaagaca cgacttatcg ccactggcag cagccactgg taacaggatt 7980
agcagagcga ggtatgtagg cggtgctaca gagttcttga agtggtggcc taactacggc 8040
tacactagaa gaacagtatt tggtatctgc gctctgctga agccagttac cttcggaaaa 8100
agagttggta gctcttgatc cggcaaacaa accaccgctg gtagcggtgg ttttttgtt 8160
tgcaagcagc agattacgcg cagaaaaaaa ggatctcaag aagatccttt gatcttttct 8220
acggggtctg acgctcagtg gaacgaaaac tcacgttaag ggattttggt catgagatta 8280
tcaaaaagga tcttcaccta gatccttta aattaaaaat gaagttttaa atcaatctaa 8340
agtatatatg agtaaacttg gtctgacagt taccaatgct taatcagtga ggcacctatc 8400
tcagcgatct gtctatttcg ttcatccata gttgcctgac tccccgtcgt gtagataact 8460
acgatacggg agggcttacc atctggcccc agtgctgcaa tgataccgcg agacccacgc 8520
tcaccggctc cagatttatc agcaataaac cagccagccg gaagggccga gcgcagaagt 8580
ggtcctgcaa ctttatccgc ctccatccag tctattaatt gttgccggga agctagagta 8640
agtagttcgc cagttaatag tttgcgcaac gttgttgcca ttgctacagg catcgtggtg 8700
tcacgctcgt cgtttggtat ggcttcattc agctccggtt cccaacgatc aaggcgagtt 8760
acatgatccc ccatgttgtg caaaaaagcg gttagctcct tcggtcctcc gatcgttgtc 8820
agaagtaagt tggccgcagt gttatcactc atggttatgg cagcactgca taattctctt 8880
actgtcatgc catccgtaag atgcttttct gtgactggtg agtactcaac caagtcattc 8940
tgagaatagt gtatgcggcg accgagttgc tcttgcccgg cgtcaatacg ggataatacc 9000
gcgccacata gcagaacttt aaaagtgctc atcattggaa aacgttcttc ggggcgaaaa 9060
ctctcaagga tcttaccgct gttgagatcc agttcgatgt aacccactcg tgcacccaac 9120
tgatcttcag catcttttac tttcaccagc gtttctgggt gagcaaaaac aggaaggcaa 9180
aatgccgcaa aaaagggaat aagggcgaca cggaaatgtt gaatactcat actcttcctt 9240
tttcaatatt attgaagcat ttatcagggt tattgtctca tgagcggata catatttgaa 9300
tgtatttaga aaaataaaca aataggggtt ccgcgcacat ttccccgaaa agtgccacct 9360
gac                                                                9363

SEQ ID NO: 17       moltype = DNA  length = 7110
FEATURE             Location/Qualifiers
source              1..7110
                    mol_type = other DNA
```

```
SEQUENCE: 17
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggcctcta gactcgaggc gttgacattg attattgact agttattaat  180
agtaatcaat tacggggtca ttagttcata gcccatatat ggagttccgc gttacataac  240
ttacggtaaa tggcccgcct ggctgaccgc ccaacgaccc ccgcccattg acgtcaataa  300
tgacgtatgt tcccatagta acgccaatag ggactttcca ttgacgtcaa tgggtggagt  360
atttacggta aactgcccac ttggcagtac atcaagtgta tcatatgcca agtacgcccc  420
ctattgacgt caatgacggt aaatggcccg cctggcatta tgcccagtac atgaccttat  480
gggactttcc tacttggcag tacatctacg tattagtcat cgctattacc atggtgatgc  540
ggttttggca gtacatcaat gggcgtggat agcggtttga ctcacgggga tttccaagtc  600
tccaccccat tgacgtcaat gggagtttgt tttggcacca aaatcaacgg gactttccaa  660
aatgtcgtaa caactccgcc ccattgacgc aaatgggcgg taggcgtgta cggtgggagg  720
tctatataag cagagctctc tggctaacta ccggtgccac catgagcccc aagaagaaga  780
gaaaggtgga ggccagcatc gaaaaaaaaa agtccttcgc caagggcatg ggcgtgaagt  840
ccacactcgt gtccggctcc aaagtgtaca tgacaacctt cgccgaaggc agcgacgcca  900
ggctcgaaaa gatcgtggag ggcgacagca tcaggagccg gaatgagggc gaggccttca  960
gcgctgaaat ggccgataaa aacgccggct ataagatcgg caacgccaaa ttcagccatc 1020
ctaagggcta cgccgtggtg gctaacaacc ctctgtatac aggacccgtc cagcaggata 1080
tgctcggcct gaaggaaact ctggaaagaa ggtacttcgg cgagagcgct gatggcaatg 1140
acaatatttg tatccaggtg atccataaca tcctggacat tgaaaaaaatc ctcgccgaat 1200
acattaccaa cgccgcctac gccgtcaaca atatctccgg cctggataag gacattattg 1260
gattcggcaa gttctccaca gtgtatacct acgacgaatt caaagacccc gagcaccata 1320
gggccgcttt caacaataac gataagctca tcaacgccat caaggcccag tatgacgagt 1380
tcgacaactt cctcgataac cccagactcg gctatttcgg ccaggccttt ttcagcaagg 1440
agggcagaaa ttacatcatc aattacggca acgaatgcta tgacattctg gccctcctga 1500
gcggactgag gcactgggtg gtccataaca cgaagaaga gtccaggatc tccaggacct 1560
ggctctacaa cctcgataag aacctcgaca acgaatacat ctccaccctc aactacctct 1620
acgacaggat caccaatgag ctgaccaact ccttctccaa gaactccgcc gccaacgtga 1680
actatattgc cgaaactctg ggaatcaacc ctgccgaatt cgccgaacaa tatttcagat 1740
tcagcattat gaaagagcag aaaaacctcg gattcaatat caccaagctc agggaagtga 1800
tgctggacag gaaggatatg tccgagatca ggaaaaatca taaggtgttc gactccatca 1860
ggaccaaggt ctacaccatg tggacttttg tgatttatag gtattacatc gaagaggatg 1920
ccaaggtggc tgccgccaat aagtccctcc ccgataatga gaagtccctg agcgagaagg 1980
atatctttgt gattaacctg aggggctcct tcaacgacga ccagaaggat gccctctact 2040
acgatgaagc taatagaatt tggagaaagc tcgaaaatat catgcacaac atcaaggaat 2100
ttaggggaaa caagacaaga gagtataaga agaaggacgc ccctagactg cccagaatcc 2160
tgcccgctgg ccgtgatgtt tccgccttca gcaaactcat gtatgcctcg accatgttcc 2220
tggatgccaa ggagatcaac gacctcctga ccaccctgat taataaattc gataacatcc 2280
agagcttcct gaaggtgatg cctctcatcg gagtcaacgc taagttcgtg gaggaatacg 2340
ccttttttcaa agactccgcc aagatcgccg atgagctgag gctgatcaag tccttcgcta 2400
gaatgggaga acctattgcc gatgccagga gggccatgta tatcgacgcc atccgtattt 2460
taggaaccaa cctgtcctat gatgagctca aggcctcgc cgacacctttt ccctggacg 2520
agaacggaaa caagctcaag aaaggcaagc acggcatgga aaatttcatt attaataacg 2580
tgatcagcaa taaaaggttc cactacctga tcagatacgt gatcctgcc cacctccatg 2640
agatcgccaa aaacgaggcc gtggtgaagt tcgtgctcga caggatgctg gacatccaga 2700
aaaaacaggg ccagaacggc aagaaccaga tcgacaggta ctacgaaact tgtatcggaa 2760
aggataaggg caagagcgtg agcgaaaagg tggacgctct cacaaagatc atcaccggaa 2820
tgaactacga ccaattcgac aagaaaagga gcgtcattga ggacaccggc agggaaaacg 2880
ccgagaggga gaagtttaaa aagatcatca gcctgtacct caccgtgatc taccacatcc 2940
tcaagaatat tgtcaatatc aacgccaggt acgtcatcgg attccattgc gtcgagcgtg 3000
atgctcaact gtacaaggag aaaggctacg acatcaatct caagaaactg gaagagaagg 3060
gattcagctc cgtcaccaag ctctgcgctg cattgatgaa actgccccc gataagaaa  3120
aggacgtgga aaaggagatg gctgaaagag ccaaggagga cattgacagc ctcgagagcg 3180
ccaacccccaa gctgtatgcc aattacatca aatacagcga cgagaagaaa gccgaggagt 3240
tcaccaggca gattaacagg gagaaggcca aaccgccct gaacgcctac ctgaggaaca 3300
ccaagtggaa tgtgatcatc agggaggacc tcctgagaat tgacaacaag acatgtaccc 3360
tgttcagaaa caaggccgtc cacctggaa tggccagtga tgtccacgcc tatatcaacg 3420
acattgccaa ggtcaattcc tacttccaac tgtaccatta catcatgcag agaattatca 3480
tgaatgagag gtacgagaaa gcagcggaa aggtgtccga gtacttcgac gctgtgaatg 3540
acgaagaa gtcaacgat aggctcctga aactgctgtg tgtgccttcc ggctactgta 3600
tccccaggtt taagaacctg agcatcgagg ccctgttcga taggaacgag gccgccaagt 3660
tcgacaagga gaaaagaag gtgtccggca attccgagtc cggacctaag aaaaagaggg 3720
aggtggcggc cgcttaccca tacgatgttc cagattacgc ttgaggtacc ctagagctcg 3780
ctgatcagcc tcgactgtgc cttctagttg ccagccatct gttgtttgcc cctcccccgt 3840
gccttccttg accctggaag gtgccactcc cactgtcctt tcctaataaa atgaggaaat 3900
tgcatcgcat tgtctgagta ggtgtcattc tattctgggg gtgggggtgg ggcaggacag 3960
caaggggag gattgggaag agaatcagc gcatgctgg gagagggcct atttcccatg 4020
attccttcat atttgcatat acgatacaag gctgttagag agataattgg aattaatttg 4080
actgtaaaca caaagatatt agtacaaaat acgtgacgta gaaagtaata atttcttggg 4140
tagtttgcag ttttaaatt atgttttaaa atggactatc atatgcttac cgtaacttga 4200
aagtatttcg atttcttggc tttatatatc ttgtggaaag gacgaaacac cgcaagtaaa 4260
cccctaccac ctggtcgggg tttgaaacag ggcaaaaccg atgctgatga agaccaagta 4320
aaccctaccc aactggtcgg ggtttgaaac ttttttccc gggaatggcc gcaggaaccc 4380
ctagtgatgg agttggccac tccctctctg cgcgctcgct cgctcactga ggccgggcga 4440
ccaaaggtcg cccgacgccc gggctttgcc cggcggcct cagtgagcga gcgagcgcgc 4500
agctgcctga gggggcgcct gatgcggtat tttctcctta cgcatctgtg cggtatttca 4560
caccgcatac gtcaaagcaa ccatagtacg cgccctgtag cggcgcatta agcgcggcgg 4620
```

```
gtgtggtggt tacgcgcagc gtgaccgcta cacttgccag cgccctagcg cccgctcctt    4680
tcgctttctt cccttcctttc ctcgccacgt tcgccggctt tccccgtcaa gctctaaatc    4740
gggggctccc tttagggttc cgatttagtg ctttacggca cctcgacccc aaaaaacttg    4800
atttgggtga tggttcacgt agtgggccat cgccctgata gacggttttt cgcccttgta    4860
cgttggagtc cacgttcttt aatagtggac tcttgttcca aactggaaca acactcaacc    4920
ctatctcggg ctattcttttt gatttataag ggattttgcc gatttcggcc tattggttaa    4980
aaaatgagct gatttaacaa aaatttaacg cgaattttaa caaaatatta acgtttacaa    5040
ttttatggtg cactctcagt acaatctgct ctgatgccgc atagttaagc cagcccgac     5100
acccgccaac acccgctgac gcgccctgac gggcttgtct gctcccggca tccgcttaca    5160
gacaagctgt gaccgtctcc gggagctgca tgtgtcagag gttttcaccg tcatccaccga   5220
aacgcgcgag acgaaagggc ctcgtgatac gcctattttt ataggttaat gtcatgataa    5280
taatggtttc ttagacgtca ggtggcactt tcggggaaaa tgtgcgcgga accctatttt    5340
gtttatttttt ctaaatacat tcaaatatgt atccgctcat gagacaataa ccctgataaa   5400
tgcttcaata atattgaaaa aggaagagta tgagtattca acatttccgt gtcgcccta     5460
ttcccttttt tgcggcattt tgccttcctg ttttttgctca cccagaaacg ctggtgaaag    5520
taaaagatgc tgaagatcag ttgggtgcac gagtgggtta catcgaactg gatctcaaca    5580
gcggtaagat ccttgagagt tttcgccccg aagaacgttt tccaatgatg agcactttta    5640
aagttctgct atgtggcgcg gtattatccc gtattgacgc cgggcaagag caactcggtc    5700
gccgcataca ctattctcag aatgacttgg ttgagtactc accagtcaca gaaaagcatc    5760
ttacggatgg catgacagta agagaattat gcagtgctgc cataaccatg agtgataaca    5820
ctgcggccaa cttacttctg acaacgatcg gaggaccgaa ggagctaacc gcttttttgc    5880
acaacatggg ggatcatgta actcgccttg atcgttggga accggagctg aatgaagcca    5940
taccaaacga cgagcgtgac accacgatgc ctgtagcaat ggcaacaacg ttgcgcaaac    6000
tattaactgg cgaactactt actctagctt cccggcaaca attaatagac tggatggagg    6060
cggataaagt tgcaggacca cttctgcgct cggcccttcc ggctggctgg tttattgctg    6120
ataaatctgg agccggtgag cgtggaagcc gcggtatcat tgcagcactg gggccagatg    6180
gtaagccctc ccgtatcgta gttatctaca cgacggggag tcaggcaact atggatgaac    6240
gaaatagaca gatcgctgag ataggtgcct cactgattaa gcattggtaa ctgtcagacc    6300
aagtttactc atatatactt tagattgatt taaaacttca ttttttaattt aaaaggatct    6360
aggtgaagat ccttttttgat aatctcatga ccaaaatccc ttaacgtgag ttttcgttcc    6420
actgagcgtc agaccccgta gaaaagatca aaggatcttc ttgagatcct ttttttctgc    6480
gcgtaatctg ctgcttgcaa acaaaaaaac caccgctacc agcggtggtt tgtttgccgg    6540
atcaagagct accaactctt tttccgaagg taactggctt cagcagagcg cagataccaa    6600
atactgtcct tctagtgtag ccgtagttag gccaccactt caagaactct gtagcaccgc    6660
ctacatacct cgctctgcta atcctgttac cagtggctgc tgccagtggc gataagtcgt    6720
gtcttaccgg gttggactca agacgatagt taccggataa ggcgcagcgg tcgggctgaa    6780
cggggggttc gtgcacacag cccagcttgg agcgaacgac ctacaccgaa ctgagatacc    6840
tacagcgtga gctatgagaa agcgccacgc ttcccgaagg gagaaaggcg gacaggtatc    6900
cggtaagcgg cagggtcgga acaggagagc gcacgaggga gcttccaggg ggaaacgcct    6960
ggtatcttta tagtcctgtc gggtttcgcc acctctgact tgagcgtcga ttttttgtgat   7020
gctcgtcagg ggggcggagc ctatggaaaa acgccagcaa cgcggccttt ttacgttcc     7080
tggccttttg ctggccttttt gctcacatgt                                    7110
```

```
SEQ ID NO: 18           moltype = DNA   length = 7114
FEATURE                 Location/Qualifiers
source                  1..7114
                        mol_type = other DNA
                        organism = synthetic construct
SEQUENCE: 18
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcatt    120
aggggttcct gcggcctcta gactcgaggc gttgacattg attattgact agttattaat    180
agtaatcaat tacggggtca ttagttcata gcccatatat ggagttccgc gttacataac    240
ttacggtaaa tggcccgcct ggctgaccgc ccaacgaccc ccgcccattg acgtcaataa    300
tgacgtatgt tcccatagta acgccaatag ggactttcca ttgacgtcaa tgggtggagt    360
atttacggta aactgcccac ttggcagtac atcaagtgta tcatatgcca agtacgcccc    420
ctattgacgt caatgacggt aaatggcccg cctggcatta tgcccagtac atgaccttat    480
gggactttcc tacttggcag tacatctacg tattagtcat cgctattacc atggtgatgc    540
ggttttggca gtacatcaat gggcgtggat agcggtttga ctcacgggga tttccaagtc    600
tccaccccat tgacgtcaat gggagtttgt tttggcacca aaatcaacgg gactttccaa    660
aatgtcgtaa caactccgcc ccattgacgc aaatgggcgg taggcgtgta cggtgggagg    720
tctatataag cagagctctc tggctaacta ccggtgccac catgagcccc aagaagaaga    780
gaaaggtgga ggccagcatc gaaaaaaaaa agtccttcgc caagggcatg ggcgtgaagt    840
ccacactcgt gtccggcttc aaagtgtaca gacaacctt cgccgaaggc agcgacgtca    900
ggctggaaaa gatcgtggag ggcgacagca tcaggagcgc gaatgagggc gaggccttca    960
gcgctgaaat ggcgataaa acgccggct ataagatcgg caacgccaaa ttcagccatc    1020
ctaagggcta cgccgtggtg ctaacaacc ctctgtatac aggacccgtc cagcaggata    1080
tgctcggctt gaaggaaact ctggaaaaga ggtacttcgg cgagagcgct gatgcaatg    1140
acaatatttg tatccaggtg atccataaca tcctggacat tgaaaaatct ctcgccgaat    1200
acattaccaa cgccgcctac gccgtcaaca atatctccgg cctggataag gacattattg    1260
gattcggcaa gttctccaca gtgtatacct acgacgaatt caaagacccc gagcaccata    1320
gggccgcttt caacaataac gataagctca tcaacgccat caaggcccag tatgacgagt    1380
tcgacaactt cctcgataaa cccagactcg gctatttcgg ccaggccttt ttcagcaagg    1440
aggggcagaaa ttacatcatc aattacggaa acgtagtgtc tgcattctg gccctcctga    1500
gcggactgag gcactgggtg gtccataaca acgaagaaga gtccaggatc tccaggacct    1560
ggctctacaa cctcgataag aacctcgaca cgaatacat ctccaccctc aactacctct    1620
acgacaggat caccaatgag ctgaccaact cctctcccaa gaactccgcc gccaacgtga    1680
actatattgc cgaaactctg ggaatcaacc ctgccgaatt cgccgaacaa tatttcagat    1740
tcagcattat gaaagagcag aaaaaccctcg gattcaatat caccaagctc agggaagtga    1800
```

```
tgctggacag gaaggatatg tccgagatca ggaaaaatca taaggtgttc gactccatca  1860
ggaccaaggt ctacaccatg atggactttg tgatttatag gtattacatc gaagaggatg  1920
ccaaggtggc tgccgccaat aagtccctcc ccgataatga gaagtccctg agcgagaagg  1980
atatctttgt gattaacctg aggggctcct tcaacgacga ccagaaggat gccctctact  2040
acgatgaagc taatagaatt tggagaaagc tcgaaaatat catgcacaac atcaaggaat  2100
ttagggaaaa caagacaaga gagtataaga agaaggacgc ccctagactg cccagaatcc  2160
tgcccgctgg ccgtgatgtt tccgccttca gcaaactcat gtatgccctg accatgttcc  2220
tggatggcaa ggagatcaac gacctcctga ccacccctgat taataaattc gataacatcc  2280
agagcttcct gaaggtgatg cctctcatcg gagtcaacgc taagttcgtg gaggaatacg  2340
ccttttttcaa agactccgcc aagatcgccg atgagctgga gctgatcaag tccttcgcta  2400
gaatgggaga acctattgcc gatgccagga gggccatgta tatcgacgcc atccgtatt  2460
taggaaccaa cctgtcctat gatgagctca aggccctcgc cgacaccttt tccctggacg  2520
agaacggaaa caagctcaag aaaggcaagc acggcatgag aaatttcatt attaataacg  2580
tgatcagcaa taaaaggttc cactacctga tcagatacgg tgatcctgcc cacctccatg  2640
agatcgccaa aaacgaggcc gtggtgaagt tcgtgctcgg caggatcgct gacatccaga  2700
aaaaacaggg ccagaacggc aagaaccaga tcgacaggta ctacgaaact tgtatcggaa  2760
aggataaggg caagagcgtg agcgaaaagg tggacgctct cacaaagatc atcaccggaa  2820
tgaactacga ccaattcgac aagaaaagga gcgtcattga ggacaccggc agggaaaacg  2880
ccgagaggga gaagtttaaa aagatcatca gcctgtacct caccgtgatc taccacatcc  2940
tcaagaatat tgtcaatatc aacgccaggt acgtcatcgg attccattgc gtcgagcgtg  3000
atgctcaact gtacaaggag aaaggctacg acatcaatct caagaaactg gaagagaagg  3060
gattcagctc cgtcaccaag ctctgcgctg gcattgataa ctgccccgc gataagagaa  3120
aggacgtgga aaaggagatg gctgaaagag ccaaggagag cattgacagc ctcgagagcg  3180
ccaaccccaa gctgtatgcc aattacatca aatacagcga cgagaagaaa gccgaggagt  3240
tcaccaggca gattaacagg gagaaggcca aaaccgccct gaacgcctac ctgaggaaca  3300
ccaagtgcaa tgtgatcatc agggaggacc tcctgagaat tgacaacaag acatgtaccc  3360
tgttcagaaa caaggccgtc cacctggaag tggccaggta tgtccacgcc tatatcaacg  3420
acattgccga ggtcaattcc tacttccaac tgtaccatta catcatgcag agaattatca  3480
tgaatgagag gtacgagaaa agcagcggaa aggtgtccga gtacttcgac gctgtgaatg  3540
acgagaagaa gtacaacgat aggctcctga aactgctgtg tgtgcctttc ggctactgta  3600
tccccaggtt taagaacctg agcatcgagg ccctgttcga taggaacgag gccgccaagt  3660
tcgacaagga gaaaagaag gtgtccggca ttccggatc cggacctaag aaaagagga  3720
aggtggcggc cgcttaccca tacgatgttc cagattacgc ttgaggtacc ctagagctcg  3780
ctgatcagcc tcgactgtgc cttctagttg ccagccatct gttgtttgcc cctcccccgt  3840
gccttccttg accctggaag gtgccactcc cactgtcctt tcctaataaa atgaggaaat  3900
tgcatcgcat tgtctgagta ggtgtcattc tattctgggg ggtggggtgg ggcaggacag  3960
caaggggga g gattgggaag agaatagcag gcatgctggg gagagggcct atttcccatg  4020
attccttcat atttgcatat acgatacaag gctgttagag agataattgg aattaatttg  4080
actgtaaaca caaagatatt agtacaaaat acgtgacgta gaaagtaata atttcttggg  4140
tagtttgcag ttttaaaatt atgttttaaa atggactatc atatgcttac cgtaacttga  4200
aagtatttcg atttcttggc tttatatatc ttgtggaaag gacgaaacac cgcaagtaaa  4260
cccctaccaa ctggtcgggg tttgaaacgt ggttggagaa ctggatgtag atgggctgca  4320
agtaaacccc taccaactgg tcggggtttg aaacttttt cccgggaat ggccgcagga  4380
accccctagtg atggagttgg ccactccctc tctgcgcgct cgctcgctca ctgaggccgg  4440
gcgaccaaag tcgcccgac gcccgggctt gcccgggcg gcctcagtga gcgagcgagc  4500
gcgcagctgc ctgcaggggc gcctgatgcg gtattttctc cttacgcatc tgtgcggtat  4560
ttcacaccgc atacgtcaaa gcaaccatag tacgcgccct gtagcggcgc attaagcgcg  4620
gcgggtgtgg tggttacgcg cagcgtgacc gctacacttg ccagcgccct agcgcccgct  4680
cctttcgctt tcttcccttc ctttctcgcc acgttcgccg gctttccccg tcaagctcta  4740
aatcggggc tccctttagg gttccgattt agtgctttac ggcacctcga ccccaaaaaa  4800
cttgatttgg gtgatggttc acgtagtggg ccatcgccct gatagacgtt ttttcgcct  4860
ttgacgttgg agtccacgtt ctttaatagt ggactcttgt tccaaactgg aacaacactc  4920
aaccctatct cgggctattc ttttgattta tgggattt tgccgatttc ggcctattgg  4980
ttaaaaaatg agctgattta acaaaattt acgcgaatt ttaacaaaat attaacgttt  5040
acaattttat ggtgcactct cagtacaatc tgctctgatg ccgcatagtt aagccagccc  5100
cgacacccgc caacacccgc tgacgcgccc tgacgggctt gtctgctccc ggcatccgct  5160
tacagacaag ctgtgaccgt ctccgggagc tgcatgtgtc agaggttttc accgtcatca  5220
ccgaaacgcg cgagacgaaa gggcctcgtg atacgcctat ttttataggt taatgtcatg  5280
ataataatgg tttcttagac gtcaggtggc acttttcggg gaaatgtgcg cggaaccct  5340
atttgttat ttttctaaat acattcaaat atgtatccgc tcatgagaca ataaccctga  5400
taaatgcttc aataatattg aaaaaggaag agtatgagta ttcaacattt ccgtgtcgcc  5460
cttattcct tttttgcggc attttgcctt cctgtttttg ctcacccaga aacgctggtg  5520
aaagtaaaag atgctgaaga tcagttgggt gcacgagtgg gttacatcga actggatctc  5580
aacagcggta agatcctga gttttcgc cccgaagaac gttttccaat gatgagcact  5640
tttaaagttc tgctatgtgg cgcggtatta tcccgtattg acgccgggca agagcaactc  5700
ggtcgccgca tacactattc tcagaatgac ttggttgagt actcaccagt cacagaaaag  5760
catcttacgg atggcatgac agtaagagaa ttatgcagtg ctgccataac catgagtgat  5820
aacactgcgg ccaacttact tctgacaacg atcggaggac cgaaggagct aaccgctttt  5880
ttgcacaaca tgggggatca tgtaactcgc cttgatcgtt gggaaccgga gctgaatgaa  5940
gccataccaa acgacgagcg tgacaccacg atgcctgtag caatggcaac aacgttgcgc  6000
aaactattaa ctggcgaact acttactcta gcttcccggc aacaattaat agactggatg  6060
gaggcggata aagttgcagg accacttctg cgctcggccc ttccggctgg ctggtttatt  6120
gctgataaat ctggagccgg tgagcgtgga agccgcggta tcattgcagc actggggcca  6180
gatggtaagc cctcccgtat cgtagttatc tacacgacgg ggagtcaggc aactatggat  6240
gaacgaaata gacagatcgc tgagataggt gcctcactga ttaagcattg gtaactgtca  6300
gaccaagttt actcatatat actttagatt gatttaaaac ttcattttta atttaaaagg  6360
atctaggtga agatcctttt tgataatctc atgaccaaaa tcccttaacg tgagttttcg  6420
ttccactgag cgtcagaccc cgtagaaaag atcaaaggat cttcttgaga tccttttttt  6480
ctgcgcgtaa tctgctgctt gcaaacaaaa aaaccaccgc taccagcggt ggtttgtttg  6540
```

```
ccggatcaag agctaccaac tctttttccg aaggtaactg gcttcagcag agcgcagata 6600
ccaaatactg tccttctagt gtagccgtag ttaggccacc acttcaagaa ctctgtagca 6660
ccgcctacat acctcgctct gctaatcctg ttaccagtgg ctgctgccag tggcgataag 6720
tcgtgtctta ccgggttgga ctcaagacga tagttaccgg ataaggcgca gcggtcgggc 6780
tgaacggggg gttcgtgcac acagcccagc ttggagcgaa cgacctacac cgaactgaga 6840
tacctacagc gtgagctatg agaaagcgcc acgcttcccg aagggagaaa ggcggacagg 6900
tatccggtaa gcggcagggt cggaacagga gagcgcacga gggagcttcc aggggggaaac 6960
gcctggtatc tttatagtcc tgtcgggttt cgccacctct gacttgagcg tcgatttttg 7020
tgatgctcgt caggggggcg gagcctatgg aaaaacgcca gcaacgcggc cttttttacgg 7080
ttcctggcct tttgctggcc ttttgctcac atgt 7114
```

```
SEQ ID NO: 19          moltype = DNA   length = 4780
FEATURE                Location/Qualifiers
source                 1..4780
                       mol_type = other DNA
                       organism = synthetic construct
SEQUENCE: 19
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgaggc gttgacattg attattgact agttattaat 180
agtaatcaat tacgggtgtca ttagttcata gcccatatat ggagttccgc gttacataac 240
ttacggtaaa tggcccgcct ggctgaccgc ccaacgaccc cgcccattg acgtcaataa 300
tgacgtatgt tcccatagta acgccaatag ggactttcca ttgacgtcaa tgggtggagt 360
atttacggta aactgcccac ttggcagtac atcaagtgta tcatatgcca agtacgcccc 420
ctattgacgt caatgacggt aaatggcccg cctggcatta tgcccagtac atgaccttat 480
gggactttcc tacttggcag tacatctacg tattagtcat cgctattacc atggtgatgc 540
ggttttggca gtacatcaat gggcgtggat agcggtttga ctcacgggga tttccaagtc 600
tccaccccat tgacgtcaat gggagtttgt tttggcacca aaatcaacgg gactttccaa 660
aatgtcgtaa caactccgcc ccattgacgc aaatgggcgg taggcgtgta cggtgggagg 720
tctatataag cagagctctc tggctaacta ccggtgccac catggtgagc aagggcgagg 780
agctgttcac cggggtggtg cccatcctgg tcgagctgga cggcgacgta aacggccaca 840
agttcagcgt gtccggcgag ggcgagggcg atgccaccta cggcaagctg accctgaagt 900
tcatctgcac caccggcaag ctgcccgtgc cctggcccac cctcgtgacc accctgacct 960
acggcgtgca gtgcttcagc cgctaccccg accacatgaa gcagcacgac ttcttcaagt 1020
ccgccatgcc cgaaggctac gtccaggagc gcaccatctt cttcaaggac gacggcaact 1080
acaagacccg cgccgaggtg aagttcgagg gcgacaccct ggtgaaccgc atcgagctga 1140
agggcatcga cttcaaggag gacggcaaca tcctggggca caagctggag tacaactaca 1200
acagccacaa cgtctatatc atggccgaca agcagaagaa cggcatcaag gtgaacttca 1260
agatccgcca caacatcgag gacggcagcg tgcagctcgc cgaccactac cagcagaaca 1320
cccccatcgg cgacggcccc gtgctgctgc ccgacaacca ctacctgagc acccagtccg 1380
ccctgagcaa agaccccaac gagaagcgcg atcacatggt cctgctggag ttcgtgaccg 1440
ccgccgggat cactctcggc atggacgagc tgtacaagta aagcggccga attcctagag 1500
ctcgctgatc agcctcgact gtgccttcta gttgccaagc atctgttgtt tgccctccc 1560
ccgtgccttc cttgaccctg gaaggtgcca ctcccactgt cctttcctaa taaaatgagg 1620
aaattgcatc gcattgtctg agtaggtgtc attctattct ggggggtggg gtggggcagg 1680
acagcaaggg gaggattgg gaagagaata gcaggcatgc tggggaggta ccgagggcct 1740
atttccatg attccttcat attttgcatat acgatacaag tcgttagag agataattgg 1800
aattaatttg actgtaaaca caaagatatt agtacaaaat acgtgacgta gaaagtaata 1860
atttcttggg tagtttgcag ttttaaaatt atgttttaaa atggactatc atatgcttac 1920
cgtaacttga aagtatttcg atttcttggc tttatatatc ttgtggaaag gacgaaacac 1980
cgccacgacc ctctttgtct tcactcgagt gaagacaaag agggtcgtgg tttttttgcc 2040
gcaggaaccc ctagtgatga agttggccac tccctctctg cgcgctcgct cgctcactga 2100
ggccgggcga ccaaaggtcg cccgacgccc gggctttgcc cgggcggcct cagtgagcga 2160
gcgagcgcgc agctgcctgc aggggcgcct gatgcggtat tttctcctta cgcatctgtg 2220
cggtatttca caccgcatac gtcaaagcaa ccatagtacg cgccctgtag cggcgcatta 2280
agcgcggcgg gtgtggtggt tacgcgcagc gtgaccgcta cacttgccag cgccctagcg 2340
cccgctcctt tcgctttctt cccttccttt ctcgccacgt tcgccggctt tccccgtcaa 2400
gctctaaatc gggggctccc tttagggttc cgatttagtg ctttacggca cctcgacccc 2460
aaaaaacttg atttgggtga tggttcacgt agtgggccat cgccctgata cggcgttttt 2520
cgccctttga cgttggagtc cacgttcttt aatagtggac tcttgttcca aactggaaca 2580
acactcaacc ctatctcggg ctattctttt gatttataag gattttgccg gatttcggcc 2640
tattggttaa aaaatgagct gatttaacaa aaatttaacg cgaattttaa caaaatatta 2700
acgtttacaa ttttatggtg cactctcagt acaatctgct ctgatgccgc atagttaagc 2760
cagccccgac acccgccaac acccgctgac gcgccctgac gggcttgtct gctcccggca 2820
tccgcttaca gacaagctgt gaccgtctcc gggagctgca tgtgtcagag gttttcaccg 2880
tcatcaccga aacgcgcgag acgaaagggc ctcgtgatac gcctatttt ataggttaat 2940
gtcatgataa taatggtttc ttagacgtca ggtggcactt ttcggggaaa tgtgcgcgga 3000
acccctattt gtttattttt ctaaatacat tcaaatatgt atccgctcat gagacaataa 3060
ccctgataaa tgcttcaata atattgaaaa aggaagagta tgagtattca acatttccgt 3120
gtcgccctta ttccctttt tgcggcattt tgccttcctg tttttgctca cccagaaacg 3180
ctggtgaaag taaaagatgc tgaagatcag ttgggtgcac gagtgggtta catcgaactg 3240
gatctcaaca gcggtaagat ccttgagagt tttcgccccg aagaacgttt tccaatgatg 3300
agcactttta aagttctgct atgtggcgcg gtattatccc gtattgacgc cgggcaagag 3360
caactcggtc gccgcataca ctattctcag aatgacttgg ttgagtactc accagtcaca 3420
gaaaagcatc ttacgcatgg catgacagta agagaattat gcagtgctgc cataaccatg 3480
agtgataaca ctgcggccaa cttacttctg acaacgatcg gaggaccgaa ggagctaacc 3540
gcttttttgc acaacatggg ggatcatgta actcgccttg atcgttggga accggagctg 3600
aatgaagcca taccaaacga cgagcgtgac accacgatgc ctgtagcaat ggcaacaacg 3660
ttgcgcaaac tattaactgg cgaactactt actctagctt cccggcaaca attaatagac 3720
```

```
tggatggagg cggataaagt tgcaggacca cttctgcgct cggcccttcc ggctggctgg   3780
tttattgctg ataaatctgg agccggtgag cgtggaagcc gcggtatcat tgcagcactg   3840
gggccagatg gtaagccctc ccgtatcgta gttatctaca cgacggggag tcaggcaact   3900
atggatgaac gaaatagaca gatcgctgag ataggtgcct cactgattaa gcattggtaa   3960
ctgtcagacc aagtttactc atatatactt tagattgatt taaaacttca tttttaattt   4020
aaaaggatct aggtgaagat cctttttgat aatctcatga ccaaaatccc ttaacgtgag   4080
ttttcgttcc actgagcgtc agaccccgta gaaaagatca aaggatcttc ttgagatcct   4140
ttttttctgc gcgtaatctg ctgcttgcaa acaaaaaaac caccgctacc agcggtggtt   4200
tgtttgccgg atcaagagct accaactctt tttccgaagg taactggctt cagcagagcg   4260
cagataccaa atactgtcct tctagtgtag ccgtagttag gccaccactt caagaactct   4320
gtagcaccgc ctacatacct cgctctgcta atcctgttac cagtggctgc tgccagtggc   4380
gataagtcgt gtcttaccgg gttggactca agacgatagt taccggataa ggcgcagcgg   4440
tcgggctgaa cggggggttc gtgcacacag cccagcttgg agcgaacgac ctacaccgaa   4500
ctgagatacc tacagcgtga gctatgagaa agcgccacgc ttcccgaagg gagaaaggcg   4560
gacaggtatc cggtaagcgg cagggtcgga acaggagagc gcacgaggga gcttccaggg   4620
ggaaacgcct ggtatcttta tagtcctgtc gggtttcgcc acctctgact tgagcgtcga   4680
tttttgtgat gctcgtcagg ggggcggagc ctatggaaaa acgccagcaa cgcggccttt   4740
ttacggttcc tggccttttg ctggcctttt gctcacatgt                         4780

SEQ ID NO: 20         moltype = DNA   length = 4780
FEATURE               Location/Qualifiers
source                1..4780
                      mol_type = other DNA
                      organism = synthetic construct
SEQUENCE: 20
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcgccctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa    300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catggtgagc aagggcgagg   780
agctgttcac cggggtggtg cccatcctgt cgagctgga cggcgacgta aacgccaca    840
agttcagcgt gtccggcgag ggcgagggcg atgccaccta cggcaagctg accctgaagt   900
tcatctgcac caccggcaag ctgcccgtgc cctggcccac cctcgtgacc accctgacct   960
acggcgtgca gtgcttcagc cgctaccccg accacatgaa gcagcacgac ttcttcaagt   1020
ccgccatgcc cgaaggctac gtccaggagc gcaccatctt cttcaaggac gacggcaact   1080
acaagacccg cgccgaggtg aagttcgagg gcgacaccct ggtgaaccgc atcgagctga   1140
agggcatcga cttcaaggag gacggcaaca tcctggggca caagctggag tacaactaca   1200
acagccacaa cgtctatatc atggccgaca agcagaagaa cggcatcaag gtgaacttca   1260
agatccgcca caacatcgag gacggcagcg tgcagctcgc cgaccactac cagcagaaca   1320
cccccatcgg cgacggcccc gtgctgctgc ccgacaacca ctacctgagc acccagtccg   1380
ccctgagcaa agaccccaac gagaagcgcg atcacatggt cctgctggag ttcgtgaccg   1440
ccgccgggat cactctcggc atggacgagc tgtacaagta aagcggccga attcctagag   1500
ctcgctgatc agcctcgact gtgccttcta gttgccagcc atctgttgtt tgcccctccc   1560
ccgtgccttc cttgaccctg gaaggtgcca ctcccactgt cctttcctaa taaaatgagg   1620
aaattgcatc gcattgtctg agtaggtgtc attctattct ggggggtggg gtggggcagg   1680
acagcaaggg ggaggattgg gaagagaata gcaggcatgc tggggaggta ccgagggcct   1740
atttcccatg attccttcat atttgcatat acgatacaag gctgttagag agataattga   1800
aattaatttg actgtaaaca caaagatatt agtacaaat acgtgacgta gaaagtaata    1860
atttcttggg tagtttgcag ttttaaaatt atgttttaaa atggactatc atatgcttac   1920
cgtaacttga agtatttcg atttcttggc tttatatatc ttgtggaaag gacgaaacac    1980
cgcagcccat ctacatccag ttcctgcgagg aactggatgt agatgggctg ttttttggcc   2040
gcaggaaccc ctagtgatgg agttggccac tccctctctg cgcgctcgct cgctcactga   2100
ggccgggcga ccaaaggtcg cccgacgccc gggctttgcc cggcggcct cagtgagcga   2160
gcgagcgcgc agctgcctgc aggggcgcct gatgcggtat tttctcctta cgcatctgtg   2220
cggtatttca caccgcatac gtcaaagcaa ccatagtacg cgcctgtag cggcgcatta    2280
agcgcggcgg gtgtggtggt tacgcgcagc gtgaccgcta catgccgag cgcctagcg    2340
cccgctcctt tcgctttctt cccttccttt ctcgccacgt tcgccggctt tccccgtcaa   2400
gctctaaatc gggggctccc tttagggttc cgatttagtg ctttacggca cctcgacccc   2460
aaaaaacttg atttgggtga tggttcacgt agtgggccat cgccctgata acggttttt    2520
cgcccttga cgttggagtc cacgttcttt aatagtggac tcttgttcca aactggaaca   2580
acactcaacc ctatctcggg ctattctttt gatttataag ggattttgcc gatttcggcc   2640
tattggttaa aaaatgagct gatttaacaa aatttaacg cgaattttaa caaaatatta    2700
acgtttacaa ttttatggtg cactctcagt acaatctgct ctgatgccgc atagttaagc   2760
cagccccgac acccgccaac acccgctgac gcgccctgac gggcttgtct gctcccggca   2820
tccgcttaca gacaagctgt gaccgtctcc gggagctgca tgtgtcagag gttttcaccg   2880
tcatcaccga aacgcgcgag acgaaagggc ctcgtgatac gcctattttt ataggttaat   2940
gtcatgataa taatggtttc ttagacgtca ggtggcactt ttcggggaaa tgtgcgcgga   3000
acccctattt gtttattttt ctaaatacat tcaaatatgt atccgctcat gagacaataa   3060
ccctgataaa tgcttcaata atattgaaaa aggaagagta tgagtattca acatttccgt   3120
gtcgccctta ttcccttttt tgcggcattt tgccttcctg ttttgctca cccagaaacg   3180
ctggtgaaag taaaagatgc tgaagatcag ttgggtgcac gagtgggtta catcgaactg   3240
```

```
gatctcaaca gcggtaagat ccttgagagt tttcgccccg aagaacgttt tccaatgatg    3300
agcactttta aagttctgct atgtggcgcg gtattatccc gtattgacgc cgggcaagag    3360
caactcggtc gccgcataca ctattctcag aatgacttgg ttgagtactc accagtcaca    3420
gaaaagcatc ttacgatgg catgacagta agagaattat gcagtgctgc cataaccatg    3480
agtgataaca ctgcggccaa cttacttctg acaacgatcg gaggaccgaa ggagctaacc    3540
gcttttttgc acaacatggg ggatcatgta actcgccttg atcgttggga accggagctg    3600
aatgaagcca taccaaacga cgagcgtgac accacgatgc ctgtagcaat ggcaacaacg    3660
ttgcgcaaac tattaactgg cgaactactt actctagctt cccggcaaca attaatagac    3720
tggatggagg cggataaagt tgcaggacca ctttctgcgct cggcccttcc ggctggctgg    3780
tttattgctg ataaatctgg agccggtgag cgtggaagcc gcggtatcat tgcagcactg    3840
gggccagatg gtaagccctc ccgtatcgta gttatctaca cgacggggag tcaggcaact    3900
atggatgaac gaaatagaca gatcgctgag ataggtgcct cactgattaa gcattggtaa    3960
ctgtcagacc aagtttactc atatatactt tagattgatt taaaacttca tttttaattt    4020
aaaaggatct aggtgaagat ccttttttgat aatctcatga ccaaaatccc ttaacgtgag    4080
ttttcgttcc actgagcgtc agaccccgta gaaaagatca aaggatcttc ttgagatcct    4140
ttttttctgc gcgtaatctg ctgcttgcaa acaaaaaaac caccgctacc agcggtggtt    4200
tgtttgccgg atcaagagct accaactctt tttccgaagg taactggctt cagcagagcg    4260
cagataccaa atactgtcct tctagtgtag ccgtagttag gccaccactt caagaactct    4320
gtagcaccgc ctacatacct cgctctgcta atcctgttac cagtggctgc tgccagtggc    4380
gataagtcgt gtcttaccgg gttggactca agacgatagt taccggataa ggcgcagcgg    4440
tcgggctgaa cggggggttc gtgcacacag cccagcttgg agcgaacgac ctacaccgaa    4500
ctgagatacc tacagcgtga gctatgagaa agcgccacgc ttcccgaagg gagaaaggcg    4560
gacaggtatc cggtaagcgg cagggtcgga acaggagagc gcacgaggga gcttccaggg    4620
ggaaacgcct ggtatcttta tagtcctgtc gggtttcgcc acctctgact tgagcgtcga    4680
tttttgtgat gctcgtcagg ggggcggagc ctatggaaaa acgccagcaa cgcggccttt    4740
ttacggttcc tggccttttg ctggcctttt gctcacatgt                          4780

SEQ ID NO: 21        moltype = DNA  length = 7108
FEATURE              Location/Qualifiers
source               1..7108
                     mol_type = other DNA
                     organism = synthetic construct
SEQUENCE: 21
cctgcaggca gctgcgcgct cgctcgctca ctgaggccgc ccgggcgtcg ggcgaccttt     60
ggtcgcccgg cctcagtgag cgagcgagcg cgcagagagg gagtgggccaa ctccatcact    120
aggggttcct gcggcctcta gactcgaggc gttgacattg attattgact agttattaat    180
agtaatcaat tacggggtca ttagttcata gcccatatat ggagttccgc gttacataac    240
ttacggtaaa tggcccgcct ggctgaccgc ccaacgaccc ccgcccattg acgtcaataa    300
tgacgtatgt tcccatagta acgccaatag ggactttcca ttgacgtcaa tgggtggagt    360
atttacggta aactgcccac ttggcagtac atcaagtgta tcatatgcca agtacgcccc    420
ctattgacgt caatgacggt aaatggcccg cctggcatta tgcccagtac atgaccttat    480
gggactttcc tacttggcag tacatctacg tattagtcat cgctattacc atggtgatgc    540
ggttttggca gtacatcaat gggcgtggat agcggtttga ctcacgggga tttccaagtc    600
tccaccccat tgacgtcaat gggagtttgt tttggcacca aaatcaacgg gactttccaa    660
aatgtcgtaa caactccgcc ccattgacgc aaatgggcgg taggcgtgta cggtgggagg    720
tctatataag cagagctctc tggctaacta ccggtgccac catgagcccc aagaagaaga    780
gaaaggtgga ggccagcatc gaaaaaaaaa agtccttcgg cggcgtgaagt gcgtgaagtt    840
ccacactcgt gtccggctcc aaagtgtaca tgacaacctt cgccgaagtc agcgacgcca    900
ggctggaaaa gatcgtggag ggcgacagca tcaggagcgt gaatgagggc gaggccttca    960
gcgctgaaat ggccgataaa aacgccggct ataagatcgg caacgccaaa ttcagccatc   1020
ctaaggcta cgccgtggtg gctaacaacc ctctgtatac aggacccgtc cagcaggata   1080
tgctcggcct gaaggaaact ctggaaaaga ggtacttcgg cgagagcgct gatggcaatg   1140
acaatatttg tatccaggtg atccataaca tcctggacat tgaaaaaatc ctcgccgaat   1200
acattaccaa cgccgcctac gccgtcaaca atatctccgg cctggataag gacattattg   1260
gattcggcaa gttctccaca gtgtatacct acgacgaatt caaagacccc gagcaccata   1320
gggccgcttt caacaataac gataagctca tcaacgccaa caaggcccag tatgacgagt   1380
cgacaactt cctcgataac cccagactcg gctatttcgg ccaggccttt ttcagcaagg   1440
agggcagaaa ttacatcatc aattacggca acgaatgcta tgacattctg gccctcctga   1500
gcggactgag gcactgggtg gtccataaca acgaagaaga gtccaggatc tccaggacct   1560
ggctctacaa cctcgataag aacctcgaca acgaatacat ctccaccctc aactacctct   1620
acgacaggat caccaatgag ctgaccaact ccttctccaa gaactccgcc gccaacgtga   1680
actatattgc cgaaactctg ggaatcaacc ctgccgaatt cgccgaacaa tatttccagat  1740
tcagcattat gaaagagcag aaaaacctcg gattcaatat caccaagctc agggaagtga   1800
tgctggacag gaaggatatg tccgagatca ggaaaaatca taaggtgttc gactccatca   1860
ggaccaaggt ctacaccatg atggactttg tgatttatag gtattacatc gaagaggatg   1920
ccaaggtggc tgccgccaat aagtccctcc ccgataatga aagtccctg agcgagaagg   1980
atatctttgt gattaacctg aggggctcct tcaacgacga ccagaaggat gccctctact   2040
acgatgaagc taatagaatt tggagaaagc tcgaaaatat catgcacaac atcaaggaat   2100
ttaggggaaa caagacaaga gagtataaga agaaggacgc ccctagactg cccagaatcc   2160
tgcccgctgg ccgtgatgtt tccgccttca gcaaactcat gtatgccctg accatgttcc   2220
tggatgcaa ggagatcaac gacctcctga ccacccctga taataaattc gataacatcc   2280
agagcttcct gaaggtgatg cctctcatcg gagtcaacgc taagttcgtg gaggaatacg   2340
ccttttcaa agactccgcc aagatcgccg atgctgag gctgatcaag tccttcgcta   2400
gaatggaga acctattgcc gatgccagga gggcattgta tatcgacaac atccgtatttt   2460
taggaaccaa cctgtcctat gatgagctca aggccctcgc cgacaccttt tccctggacg   2520
agaacgaaa caagctcaag aaaggcaagc acggcatgaa aatttcatt attaataacg   2580
tgatcagcaa taaaaggttc cactacctga tcagatacgg tgatcctgcc cacctccatg   2640
agatcgccaa aacgaggcc gtggtgaagt tcgtgctcgg caggatcgct gacatccaga   2700
aaaaacaggg ccagaacggc aagaaccaga tcgacaggta ctacgaaact tgtatcggaa   2760
```

```
aggataaggg caagagcgtg agcgaaaagg tggacgctct cacaaagatc atcaccggaa   2820
tgaactacga ccaattcgac aagaaaagga gcgtcattga ggacaccggc agggaaaacg   2880
ccgagaggga gaagtttaaa aagatcatca gcctgtacct caccgtgatc taccacatcc   2940
tcaagaatat tgtcaatatc aacgccaggt acgtcatcgg attccattgc gtcgagcgtg   3000
atgctcaact gtacaaggag aaaggctacg acatcaatct caagaaactg gaagagaagg   3060
gattcagctc cgtcaccaag ctctgcgctg gcattgatga aactgccccc gataagagaa   3120
aggacgtgga aaaggagatg gctgaaagag ccaaggagag cattgacagc ctcgagagcg   3180
ccaaccccaa gctgtatgcc aattacatca aatacagcga cgagaagaaa gccgaggagt   3240
tcaccaggca gattaacagg gagaaggcca aaaccgccct gaacgcctac ctgaggaaca   3300
ccaagtggaa tgtgatcatc agggaggacc tcctgagaat tgacaacaag acatgtaccc   3360
tgttcagaaa caaggccgtc cacctggaag tggccaggta tgtccacgcc tatatcaacg   3420
acattgccga ggtcaattcc tacttccaac tgtaccatta catcatgcag agaattatca   3480
tgaatgagag gtacgagaaa agcagcgaaa aggtgtccga gtacttcgac gctgtgaatg   3540
acgagaagaa gtacaacgat aggctcctga aactgctgta tgtgcctttc ggctactgta   3600
tccccaggtt taagaacctg agcatcgagg ccctgttcga taggaacgag gccgccaagt   3660
tcgacaagga gaaaaagaag gtgtccggca attccggatc cggacctaag aaaaagagga   3720
aggtggcggc cgcttaccca tacgatgttc cagattacgc ttgaggtacc ctagagctcg   3780
ctgatcagcc tcgactgtgc cttctagttg ccagccatct gttgtttgcc cctcccccgt   3840
gccttccttg accctggaag gtgccactcc cactgtcctt tcctaataaa atgaggaaat   3900
tgcatcgcat tgtctgagta ggtgtcattc tattctgggg ggtggggtgg ggcaggacag   3960
caaggggga gattgggaag agaatagcag gcatgctggg gagagggcct atttcccatg   4020
attccttcat atttgcatat acgatacaag gctgttagag atgaattgg aattaatttg   4080
actgtaaaca caaagatatt agtacaaaat acgtgacgta gaaagtaata atttcttggg   4140
tagtttgcag ttttaaaatt atgttttaaa atggactatc atatgcttac cgtaacttga   4200
aagtatttcg atttcttggc tttatatatc ttgtggaaag gacgaaacac cgcaagtaaa   4260
cccctaccaa ctggtcgggg tttgaaacga tcaacattaa atgtgagcga gtcaagtaaa   4320
cccctaccaa ctggtcgggg tttgaaactt ttttttcccgg gaatggccgc aggaacccct   4380
agtgatggag ttggccactc cctctctgcg cgctcgctcg ctcactgagg ccgggcgacc   4440
aaaggtcgcc cgacgcccgg gctttgcccg ggcggcctca gtgagcgagc gagcgcgcag   4500
ctgcctgcga gggcgcctga tgcggtattt tctccttacg catctgtgcg gtatttcaca   4560
ccgcatacgt caaagcaacc atagtacgcg ccctgtagcg cgcattaag cgcggcgggt   4620
gtggtggtta cgcgcagcgt gaccgctaca cttgccagcg ccctagcgcc cgctcctttc   4680
gctttcttcc cttcctttct cgccacgttc gccggctttc cccgtcaagc tctaaatcgg   4740
gggctccctt taggtttccg atttagtgct ttacggcacc tcgacccaa aaaacttgat   4800
ttgggtgatg gttcacgtag tgggccatcg ccctgataga cggttttcg ccctttgacg   4860
ttggagtcca cgttctttaa tagtggactc ttgttccaaa ctggaacaac actcaaccct   4920
atctcgggct attcttttga tttataaggg attttgccga tttcggccta ttggttaaaa   4980
aatgagctga tttaacaaaa atttaacgcg aattttaaca aaatattaac gtttacaatt   5040
ttatggtgca ctctcagtac aatctgctct gatgccgcat agttaagcca gccccgacac   5100
ccgccaacac ccgctgacgc gccctgacgg gcttgtctgc tcccggcatc cgcttacaga   5160
caagctgtga ccgtctccgg gagctgcatg tgtcagaggt tttcaccgtc atcaccgaaa   5220
cgcgcgagac gaaagggcct cgtgatacgc ctatttttat aggttaatgt catgataata   5280
atggtttctt agacgtcagg tggcacttt cggggaaatg tgcgcggaac ccctatttgt   5340
ttatttttct aaatacattc aaatatgtat ccgctcatga caataaaccc ctgataaatgt   5400
cttcaataat attgaaaaag gaagagtatg agtattcaac atttccgtgt cgcccttatt   5460
cccttttttg cggcattttg ccttcctgtt tttgctcacc cagaaacgct ggtgaaagta   5520
aaagatgctg aagatcagtt gggtgcacga gtgggttaca tcgaactgga tctcaacagc   5580
ggtaagatcc ttgagagttt tcgccccgaa gaacgttttc caatgatgag cacttttaaa   5640
gttctgctat gtggcgcggt attatcccgt attgacgccg ggcaagagca actcggtcgc   5700
cgcatacact attctcagaa tgacttggtt gagtactcac cagtcacaga aaagcatctt   5760
acggatggca tgacagtaag agaattatgc agtgctgcca taaccatgag tgataacact   5820
gcggccaact tacttctgac aacgatcgga ggaccgaagg agctaaccgc ttttttgcac   5880
aacatggggg atcatgtaac tcgccttgat cgttgggaac cggagctgaa tgaagccata   5940
ccaaacgacg agcgtgacac cacgatgcct gtagcaatgg caacaacgtt gcgcaaacta   6000
ttaactggcg aactacttac tctagcttcc cggcaacaat taatagactg gatggaggcg   6060
gataaagttg caggaccact tctgcgctcg gcccttccgg ctggctggtt tattgctgat   6120
aaatctggag ccggtgagcg tggaagccgc ggtatcattg cagcactggg gccagatggt   6180
aagccctccc gtatcgtagt tatctacacg acggggagtc aggcaactat ggatgaacga   6240
aatagacaga tcgctgagat aggtgcctca ctgattaagc attggtaact gtcagaccaa   6300
gtttactcat atatacttta gattgattta aaacttcatt tttaatttaa aaggatctag   6360
gtgaagatcc tttttgataa tctcatgacc aaaatccctt aacgtgagtt ttcgttccac   6420
tgagcgtcag accccgtaga aaagatcaaa ggatcttctt gagatccttt ttttctgcgc   6480
gtaatctgct gcttgcaaac aaaaaaacca ccgctaccag cggtggtttg tttgccggat   6540
caagagctac caactctttt tccgaaggta actggcttca gcagagcgca gataccaaat   6600
actgtccttc tagtgtagcc gtagttaggc caccacttca agaactctgt agcaccgcct   6660
acatacctcg ctctgctaat cctgttacca gtggctgctg ccagtggcga taagtcgtgt   6720
cttaccgggt tggactcaag acgatagtta ccggataagg cgcagcggtc gggctgaacg   6780
gggggttcgt gcacacagcc cagcttggag cgaacgacct acaccgaact gagataccta   6840
cagcgtgagc tatgagaaag cgccacgctt cccgaaggga gaaaggcgga caggtatccg   6900
gtaagcggca gggtcggaac aggagagcgc acgagggagc ttccagggg aaacgcctgg   6960
tatctttata gtcctgtcgg gtttcgccac ctctgacttg agcgtcgatt tttgtgatgc   7020
tcgtcagggg gcggagcct atggaaaaac gccagcaacg cggccttttt acggttcctg   7080
gccttttgct ggccttttgc tcacatgt                                       7108

SEQ ID NO: 22        moltype = DNA  length = 34
FEATURE              Location/Qualifiers
source               1..34
                     mol_type = other DNA
                     organism = synthetic construct
```

-continued

| | | |
|---|---|---|
| SEQUENCE: 22<br>agacgtggtt ggagaactgg atgtagatgg gctg | | 34 |
| SEQ ID NO: 23<br>FEATURE<br>source | moltype = DNA length = 34<br>Location/Qualifiers<br>1..34<br>mol_type = other DNA<br>organism = synthetic construct | |
| SEQUENCE: 23<br>aaaacagccc atctacatcc agttctccaa ccac | | 34 |
| SEQ ID NO: 24<br>FEATURE<br>source | moltype = DNA length = 30<br>Location/Qualifiers<br>1..30<br>mol_type = other DNA<br>organism = synthetic construct | |
| SEQUENCE: 24<br>agacagggca gaaccgatgc tgatgaagac | | 30 |
| SEQ ID NO: 25<br>FEATURE<br>source | moltype = DNA length = 30<br>Location/Qualifiers<br>1..30<br>mol_type = other DNA<br>organism = synthetic construct | |
| SEQUENCE: 25<br>aaaagtcttc atcagcatcg gttctgccct | | 30 |
| SEQ ID NO: 26<br>FEATURE<br>source | moltype = DNA length = 22<br>Location/Qualifiers<br>1..22<br>mol_type = other DNA<br>organism = synthetic construct | |
| SEQUENCE: 26<br>attgtcccag atatagccgt tg | | 22 |
| SEQ ID NO: 27<br>FEATURE<br>source | moltype = DNA length = 20<br>Location/Qualifiers<br>1..20<br>mol_type = other DNA<br>organism = synthetic construct | |
| SEQUENCE: 27<br>gctgtcattt ccgtttgctg | | 20 |
| SEQ ID NO: 28<br>FEATURE<br>source | moltype = DNA length = 20<br>Location/Qualifiers<br>1..20<br>mol_type = other DNA<br>organism = synthetic construct | |
| SEQUENCE: 28<br>gctcttctgg agggcagtgg | | 20 |
| SEQ ID NO: 29<br>FEATURE<br>source | moltype = DNA length = 21<br>Location/Qualifiers<br>1..21<br>mol_type = other DNA<br>organism = synthetic construct | |
| SEQUENCE: 29<br>cagtgtgaca gccgggttga g | | 21 |
| SEQ ID NO: 30<br>FEATURE<br>source | moltype = DNA length = 20<br>Location/Qualifiers<br>1..20<br>mol_type = other DNA<br>organism = synthetic construct | |
| SEQUENCE: 30<br>ccatggggaa ggtgaaggtc | | 20 |
| SEQ ID NO: 31<br>FEATURE<br>source | moltype = DNA length = 21<br>Location/Qualifiers<br>1..21<br>mol_type = other DNA<br>organism = synthetic construct | |
| SEQUENCE: 31<br>gaagggtca ttgatggcaa c | | 21 |
| SEQ ID NO: 32<br>FEATURE<br>source | moltype = AA length = 928<br>Location/Qualifiers<br>1..928<br>mol_type = protein | |

```
                    organism = synthetic construct
SEQUENCE: 32
MSKDKKTKAK RMGVKALLAH GEDKLTMTTF GKGNRSKIEF TEGYHGRALE TPKHFGKRGF      60
EVRKIDENVD LYGDLEEGKT IEALLINPSE KVGEDYLKLK GTLEKRFFGR EFPHDNIRIQ     120
LIYNILDIYK ILGMNVADIL YALGNMQDTE LDIDMFGQSL NNPEKAKDVV QRMKPYMGFF     180
GGIFRTQKKE DRKKDSNLSE EEKEEKKKKQ EELLQKDLQH NMDVARCISA LRHATAHNKP     240
ATAHDKQDEY PWFKSSDIYE TKIFKAGMWS VIEADYKKKI QDVNKQFFSK NKVNLAILFD     300
LLDVRDVKQK KRISDEFYRF TIRKDGKNLG MNLVKIREII IDRYASGLRD KKHDPHRQKI     360
NVIADFLIFR ALSQNQGIID KTVSSLRLTK DEEEKDHVYQ NAAELVWGMV SNCLTPYFND     420
PKNKYILKYK DAKTPGDFED WITSKISEDD GEPFVKVLSF LCNFLEGKEI NELLTAYIHK     480
FECIQDFLNV ISSLGENVQF QPRFALFNNA SFAQNVAVQL RILASIGKMK PDLTEAKRPL     540
YKAAIRMLCP PEKWEKYTSD EWLEKNMLLN SEDRKNDKKK KQVNPFRNFI AGNVIESRRF     600
MYLVRYSKPK AVRAIMQNRS IVNYVLHRLP SEQIKTYSRV FPEDFSDTEA EIDFLVNKLS     660
EFSFETFISN QQTILNNSKR GFSPNRRETA EEIERLKAIT GLYLSVAYIA IKNIVKANAR     720
YYIAFAVFER DKELVKAKDA RIQTTIPNTK FTNYFCLTQY YLDRDEEKKF PGDPRDKEAF     780
FEHLRKTKRH FSKQWREWLN EKIADAKSSQ ATGLLLREAR NDVEHLNVLR AIPDYIQDFR     840
HGEKGETAMN SYFELYHYLM QRLMLKNTEL DLSHWSGWIM RSGRPDRDLI QIAFVSLAYN     900
LPRYRNLTKE HHFDDTVLQK IREKESLD                                       928

SEQ ID NO: 33              moltype = RNA   length = 36
FEATURE                    Location/Qualifiers
source                     1..36
                           mol_type = other RNA
                           organism = synthetic construct
SEQUENCE: 33
ggtcaacagt gtgggaatt acccgcactc tacaac                                 36

SEQ ID NO: 34              moltype = AA    length = 891
FEATURE                    Location/Qualifiers
source                     1..891
                           mol_type = protein
                           organism = synthetic construct
SEQUENCE: 34
MSKDKKTKAK RMGVKALLAH GEDKLTMTTF GKGNRSQIEF TEGYHGRALE TPKRFGKRGF      60
EVRKIDENVD LYGDLDEGKT IEALLVNPSE NVGEDYLKLK STLENYFFGR EFPHDNIRIQ     120
LIYNILDIYK ILGMNVADIL YTLGNLQDAE GDIDLFGKSL NNEDNIKESL NRMRPYMGYF     180
GEVFKKDNRE HNKKVLRCIS ALRNATAHGK QDEYPWFKSS DIYEKTIFKA DKWRIIEDQY     240
REKIRKVNNE FFSKNKVNLA ILFDLLHARD VEPKKQIADE FYRFTIRKDG KNLGMNLVKI     300
REKIIDRFAR DLRDKKHDPH RQKIHVIADF LIFRALSQNQ EVIDKTVSRL RLTKDEEEKD     360
RVYQNAAELV WGMVSNCLSP YFKDPKKYII QYKSGGKIKI FDDWITSKIS AKDGEPFVKV     420
LSFLCNFLEG KEINELLTAY IHKFECIQDF LKVISSLGER AQFQPRFDLF NKPDFAQNVA     480
VQLRILASIG KMKPDLTEAK RPLYKAAIQM LCPPEKWEKY TSDEWLEENM LLNSEDRQNK     540
EKREKVNPFR NFIAGNVIES RRFMYLVRYS KPKAVRALMK NRSVVNYVLH RLPPEQIKTY     600
SRVFPDDFND TEAEIDFLVN KLSEFSFETF ITSRQTILAN SKRGFSPNRR ETAEEIERLK     660
AITGLYLSVA YIAIKNIVKA NARYYIAFAV FERDKELVKA KDARIQTTIP NTTYTNYFCL     720
TQYYLDRDEE KKFQGDPRDK EAFFEHLRKK KTHFSKQWRE WLNEKIADAK SAQETGLLLT     780
EARNDVEHLN VLRAIPDYIQ DFRHGDKGET PMNSYFELYH YLLQRLMLKN RLLDLSSWRS     840
WIERSGRPDR DLIQIAFVSL AYNLPRYRNL TKEHHFDDTV LQKIRERKSL D              891

SEQ ID NO: 35              moltype = RNA   length = 34
FEATURE                    Location/Qualifiers
source                     1..34
                           mol_type = other RNA
                           organism = synthetic construct
SEQUENCE: 35
agtctcagaa ccctacaggt ttgtagagtt atct                                  34

SEQ ID NO: 36              moltype = DNA   length = 6898
FEATURE                    Location/Qualifiers
source                     1..6898
                           mol_type = other DNA
                           organism = synthetic construct
SEQUENCE: 36
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct gcggcctcta gactcgaggc gttgacattg attattgact agttattaat     180
agtaatcaat tacggggtca ttagttcata gcccatatat ggagttccgc gttacataac     240
ttacggtaaa tggcccgcct ggctgaccgc ccaacgaccc ccgcccattg acgtcaataa     300
tgacgtatgt tcccatagta acgccaatag ggactttcca ttgacgtcaa tgggtggagt     360
atttacggta aactgcccac ttggcagtac atcaagtgta tcatatgcca agtacgcccc     420
ctattgacgt caatgacggt aaatggcccg cctggcatta tgcccagtac atgaccttat     480
gggactttcc tacttggcag tacatctacg tattagtcat cgctattacc atggtgatgc     540
ggttttggca gtacatcaat gggcgtggat agcggtttga ctcacgggga tttccaagtc     600
tccaccccat tgacgtcaat gggagtttgt tttggcacca aaatcaacgg gactttccaa     660
aatgtcgtaa caactccgcc ccattgacgc aaatgggcgg taggcgtgta cggtgggagg     720
tctatataag cagagctctc tggctaacta ccggtgccac catgccggca gctaagaaaa     780
agaaactgga tggcagcgtc gacatgagca aggataagaa aaccaaagcc aagaggatgg     840
gtgtgaaagc cctgctggcc cacggagagg acaagctgac aatgaccaca ttcggaaagg     900
gcaatagatc caaaatcgag ttcacagagg ataccacgg cagggccctg aaaccccca     960
```

```
agcactttgg caagagggga ttcgaggtcc ggaagatcga tgagaatgtt gacctgtacg    1020
gggacctcga ggagggcaaa accattgaag ccctgctcat taatcctagc gagaaggtgg    1080
gcgaggacta cctcaagctg aaggggactc tcgagaaacg gttttttggg cgcgaatttc    1140
cacatgacaa tatcagaatc cagctgatct acaaacatcct ggacatctac aaaatactgg    1200
gcatgaacgt cgccgacatc ctgtacgctc tgggcaatat gcaggacaca gagctggaca    1260
ttgatatgtt cggccagtct ctgaataatc ctgagaaggc caaagatgtg gtgcagagga    1320
tgaagcctta catgggcttt tttggcggca tcttcagaac ccagaagaag gaggaccgga    1380
agaaggacag caatctcagc gaggaggaga aggaggagaa gaagaagaag caggaagagc    1440
tgctgcagaa ggacctgcag cacaaacatgg atgtcgccag atgtattagc gcactgagac    1500
atgccaccgc ccacaataag ccagccactg cccacgataa gcaggacgaa taccccctggt    1560
tcaagagcag cgacatttat gagacaaaga ttttcaaagc aggcatgtgg tcagtgatcg    1620
aggctgatta taagaagaag atccaggatg ttaataaaca gttcttcagc aagaataagg    1680
tgaacctggc catcctcttt gacctgctgg acgtacgtga tgtgaagcaa aaaaagcgga    1740
tcagcgatga gttctaccgt tttaccatca ggaaggacgg gaaaaacctg ggcgtccaact    1800
tcgtgaaaat tagagagatc attatcgacc gctacgccag cgggctgcgc gataagaaac    1860
atgatcccca cagacagaaa atcaacgtaa ttgcagactt cctgattttc cgggccctgt    1920
cacagaaacca ggggatcata gataagactg tgtctagtct gcggctgacc aaggacgagg    1980
aggagaagga ccatgtgtat cagaatgcag ccgaactggt gtgggggatg gtgtccaact    2040
gcctgacccc atacttcaat gatcccaaga ataaatacat cctgaaatac aaagacgcca    2100
agactcccgg ggatttcgag gattggatca ccagcaaaat cagtgaggac gatggggagc    2160
ctttttgtgaa ggtgctgagc tttctgtgta atttcttaga gggaaaggaa attaacgagc    2220
tgcttaccgc ctacatccat aaaattcgaat gtatccagga ttttctgaac gtgatatctt    2280
cactgggcga gaacgtccag tttcagccca gatttgccct gtttaataat gctagcttcg    2340
ctcagaacgt tgccgtccag ctgaggattt tggccagcat cggcaagatg aagcctgatc    2400
tgaccgaggc caaaaggccc ctgtacaaag cagccatcag aatgctgtgc ccccccgaga    2460
agtgggaaga gtacaccagt gatgaatggc tggagaagaa catgctgctg aatagcgagg    2520
acagaaagaa cgacaagaaa aagaaacagg tgaaccctt caggaatttt attgcaggga    2580
acgttatcga gtctcgccgc tttatgtatc tggtgaggta cagcaagcca aaggccgtgc    2640
gggccatcat gcagaacagg tcaatcgtga actacgtgct ccaccggctg ccttcagagc    2700
agatcaaaac ttactcccgt gtgttccccg aggaattctc cgacaccgag gccgaaatcg    2760
actttctcgt gaataaactg agtgaatttt catttgaaac cttcatctcc aaccagcaga    2820
caattctgaa caactccaag agaggcttta gccccaatag acgggaaacg gccgaggaga    2880
ttgaacggct gaaggccatt accggcctgt acctctcagt ggcctatatc gccatcaaaa    2940
acatcgtgaa ggcaacgct aggtactata ttgcattcgc cgtgttcgaa agagataagg    3000
agctgctgaa agccaaggac gcccgcatac agaccactat ccctaacaca aaatttacta    3060
actattttg tctgactcag tactatctgg accgcgacga agagaagaag ttcctggccg    3120
acccccgcga caaggaggcc ttctttgaac atctgaggaa aactaagcgg cactttagta    3180
aacagtggag agagtggctg aacgagaaga tcgccgacgc caagagcagc caggccaccg    3240
ggctgctgct gcgggaggca agaaatgatg tggaacacct gaatgtgctg aagctatcc    3300
ccgactacat ccaggacttt cgccacggag agaagggcga gacagccatg aatagctact    3360
tcgagctgta tcactacctg atgcagaggc tgatgcttaa gaacaccgag ctggacctga    3420
gccactggag cggctggatc atgaggtccg gtcgacctga cagggatctg atacagattg    3480
ctttcgtgtc cctggcatac aatctgccac ggtacagaaa tctgaccaaa gacatcact    3540
tcgatgacac cgtgcttcag aagatcaggg agaaagagag cctggataca ggcggcggcc    3600
ccggcggcgg cgccgccgcc ggcagcggca gccctaagaa aaaacgaaaa gttggcagcg    3660
gaagcaaaag gccggcggcc acgaaaaagg ccggccaggc aaaaaagaaa aagctcgagt    3720
acccatcga tgttccagat tacgcttgag aattccctt gagcatctga cttctggcta    3780
ataaggaaaa tttatttta ttgcaatagt gtgttggaat ttttttgtgtc tctcaggtac    3840
cgagggccta tttcccatga ttccttcata tttgcatata cgatacaagg ctgttagaga    3900
gataattgga attaatttga ctgtaaacac aaagatatta gtacaaaata cgtgacgtag    3960
aaagtaataa tttcttgggt agtttgcagt tttaaaatta tgttttaaaa tggactatca    4020
tatgcttacc gtaacttgaa agtatttcga tttcttggct ttatatatct tgtgaaaggt    4080
acgaaacacc ggtcaacagt gtggggaatt cccgcactc tacaacggag accacggcag    4140
gtctcatttt ttgcggccgc aggaacccct agtgatggag ttggcactc cctctctgcg    4200
cgctcgctcg ctcactgagg ccgggcgacc aaagtgcgc cgacgcccgg gctttgcccg    4260
ggcggcctca gtgagcgagc gagcgcgcag ctgcctgcag gggcgcctga tgcggtattt    4320
tctccttacg catctgtgcg gtatttcaca ccgcatacgt caaagcaacc atagtacgcg    4380
ccctgtagcg cgcattaag cgcggcgggt gtggtggtta cgcgcagcgt gaccgctaca    4440
cttgccagcg ccttagcgcc cgctccttc gctttcttcc cttccttttct cgccacgttc    4500
gccggctttc cccgtcaagc tctaaatcgg gggctccctt tagggttccg atttagtgct    4560
ttacggcacc tcgaccccaa aaaacttgat ttgggtgatg gttcacgtag tgggccatcg    4620
ccctgataga cggtttttcg ccctttgacg ttggagtcca cgttctttaa tagtggactc    4680
ttgttccaaa ctggaacaac actcaactct atctcgggct attctttga tttataaggg    4740
attttgccga tttcggtcta ttggttaaaa aatgagctga tttaacaaaa atttaacgcg    4800
aattttaaca aaatattaac gtttacaatt ttatggtgca ctctcagtac aatctgctct    4860
gatgccgcat agttaagcca gccccgacac ccgccaacac ccgctgacgc gccctgacgg    4920
gcttgtctgc tcccggcatc cgcttacaga caagctgtga ccgtctccgg agctgcatg    4980
tgtcagaggt tttcaccgtc atcaccgaaa cgcgcgagac gaaagggcct cgtgatacgc    5040
ctatttttat aggttaatgt catgataata atggtttctt agacgtcagg tggcactttt    5100
cggggaaatg tgcgcggaac ccctatttgt ttatttttct aaatacattc aaatatgtat    5160
ccgctcatga caataaacc ctgataaatg cttcaataat attgaaaaag gaagagtatg    5220
agtattcaac atttccgtgt cgcccttatt cccttttttg cggcattttg ccttcctgtt    5280
tttgctcacc cagaaacgct ggtgaaagta aaagatgctg aagatcagtt gggtgcacga    5340
gtgggttaca tcgaactgga tctcaacagc ggtaagatcc ttgagagttt tcgccccga    5400
gaacgttttc caatgatgag cacttttaaa gttctgctat gtggcgcggt attatcccgt    5460
attgacgccg gcaagagca actcggtcgc cgcatacact attctcagaa tgacttggtt    5520
gagtactcac cagtcacaga aaagcatctt acggatggca tgacagtaag agaattatgc    5580
agtgctgcca taaccatgag tgataacact gcggccaact tacttctgac aacgatcgga    5640
ggaccgaagg agctaaccgc ttttttgcac aacatggggg atcatgtaac tcgccttgat    5700
```

-continued

```
cgttgggaac cggagctgaa tgaagccata ccaaacgacg agcgtgcaca cacgatgcct   5760
gtagcaatgg caacaacgtt gcgcaaacta ttaactggcg aactactTac tctagcttcc   5820
cggcaacaat taatagactg gatggaggcg gataaagttg caggaccact tctgcgctcg   5880
gcccttccgg ctggctggtt tattgctgat aaatctggag ccggtgagcg tggaagccgc   5940
ggtatcattg cagcactggg gccagatggt aagccctccc gtatcgtagt tatctcacacg   6000
acggggagtc aggcaactat ggatgaacga aatagacaga tcgctgagat aggtgcctca   6060
ctgattaagc attggtaact gtcagaccaa gtttactcat atatacttta gattgattta   6120
aaacttcatt tttaatttaa aaggatctag gtgaagatcc ttttTgataa tctcatgacc   6180
aaaatccctt aacgtgagtt ttcgttccac tgagcgtcag accccgtaga aaagatcaaa   6240
ggatcttctt gagatccttt ttttctgcgc gtaatctgct gcttgcaaac aaaaaaacca   6300
ccgctaccag cggtggtttg tttgccggat caagagctac caactctttt tccgaaggta   6360
actggcttca gcagagcgca gataccaaat actgttcttc tagtgtagcc gtagttaggc   6420
caccacttca agaactctgt agcaccgcct acatacctcg ctctgctaat cctgttacca   6480
gtggctgctg ccagtggcga taagtcgtgt cttaccgggt tggactcaag acgatagtta   6540
ccggataagg cgcagcggtc gggctgaacg gggggttcgt gcacacagcc cagcttggag   6600
cgaacgacct acaccgaact gagatacccta cagcgtgagc tatgagaaag cgccacgctt   6660
cccgaaggga gaaaggcgga caggtatccg gtaagcggca gggtcggaac aggagagcgc   6720
acgagggagc ttccaggggg aaacgcctgg tatctttata gtcctgtcgg gtttcgccac   6780
ctctgacttg agcgtcgatt tttgtgatgc tcgtcagggg ggcggagcct atggaaaaac   6840
gccagcaacg cggccttttt acggttcctg gccttttgct ggccttttgc tcacatgt     6898

SEQ ID NO: 37             moltype = DNA  length = 6786
FEATURE                   Location/Qualifiers
source                    1..6786
                          mol_type = other DNA
                          organism = synthetic construct
SEQUENCE: 37
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcacg   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgtcca aggacaagaa aaccaaggcc aagcggatgt   840
gcgtgaaagc actgctggcc catggcgagg ataagctcac catgaccact tttggtaagg   900
gaaataggtc ccagatcgag tttacagaag gctatcacgg ccgagccctg gagacaccca   960
aaagattcgg caagaggggg tttgaggtga aaagatcga tgaaaacgtc gacctgtatg   1020
gtgacctgga cgagggcaag actattgagg ccctgctggt gaaccctcc gagaacgttg   1080
gagaggacta tctgaaactg aaaagcacac tggagaacta ttttttcggt cgcgagttcc   1140
ctcatgacaa tatccgcatc cagctgatct acaacatcta ggatatctat aagatcctga   1200
ggatgaacgt ggctgacatc ctctacaccc tgggcaatct gcaggacgat gaaggagata   1260
tcgatctgtt cggggaagtcc ctcaacaacg aggacaacat taagaaagt ctgaatagaa   1320
tgaggcccta catgggctac ttttggggag tgttaaaaaa ggacaataga gaacataaca   1380
agaaagtgct ccggtgcatc tccgctctgc gcaacgcac agcccacgc aaacaggatg   1440
aatatccttg gttcaagagc agcgatatct atgaaaagac tatcttcaaa gccgacaagt   1500
ggcggatcat cgaggaccag tacagagaaa agattaggaa ggtgaacaac gagttttca   1560
gcaaaaacaa agtcaatctg ctatcctct tcgatcttct gcacgccaga gatgtggaac   1620
ctaagaacaa gattgccgat gaattttaca ggttcaccat cagaaaggat ggcaaaaatc   1680
tgggatgaa cctggtgaag atcagggaga aaatcatcga tcggtttgcc cgcgatctgc   1740
gagacaagaa acacgaccca cacagacaga aaattcacgt gatcgccgat ttcctgattt   1800
tcagggccct gagtcagaat caggaagtga tcgacaaaac agtcagccgg ctgaggctga   1860
ccaaggatga agaggagaaa gataagtgt accagaacgc cgccgagctc gtgtgggaa   1920
tggtgtccaa ctgtctgagc ccatatttca aagaccctaa gaaatacatc atccagtata   1980
agtccgcgg aaaaatcaaa atcttcgacg actggatcac ctctaagatt tccgccaaag   2040
atggcgagcc atttgtgaag gtgctgtcct ttctctgcaa tttcctggag ggcaaggaga   2100
tcaacgagct gctgaccgcc tacatccaca gttcgagtg catccaggat tttctgaaag   2160
tcattccag cctgggcgaa agggccagt ttcagctcg tgatctg ttcaataagc   2220
ctgactttgc acagaacgtg gccgtgcagc tgcgcatcct cgccagtatt gggaaaatga   2280
agcccgatct gactgaggcc aaaaggcctc tctacaaagc tgccatccag atgctctgcc   2340
ctcctgagaa atgggagaaa tacacaagcg acgagtggct ggaggagaac atgctgctga   2400
actccgagga taggcagaat aaggagaagc gagagaaggt caatccctt cggaaattca   2460
tcgccggcaa tgtgattgag agccgccgat ttatgtcacct tccaagccca   2520
aggcagttcg ggctctgatg aaaaatagat cagtggtgaa ctacgtgctg cacaggctgc   2580
ctccagagca gatcaagacc tactccaggg tgttccctga tgacttcaat gatactgaag   2640
ctgagatcga tttcctggtg aacaagctca gcgaattttc cttcgagaca ttcatccaca   2700
gcagacagac cattctggca aattccaaga gggggttttc tcctaaccgg cgggagcag   2760
ccgagggagat cgaaaggctg aaagccatca gggcctgcta cctacattg   2820
ctatcaaaaa tatcgtgaaa gcaaatgccc gatactacat agccttcgcc gtgttcgagc   2880
gggcaaggga gctcgtgaaa gccaaggacg ccaggatcca gactaccatc cccaatacaa   2940
cctacactaa ttacttctgc ctgactcagt actacctggac ccgtgacgag gagaaaaagt   3000
tcagggcga ccctcgggat aaggaggctt ctttgaaca tctccgtaag aagaaaaacac   3060
actttagcaa gcagtggcgg gagtggctga atgagaagat cgctgatgcc aagtccgccc   3120
```

```
aggaaaccgg cctgctgctg accgaggcca ggaatgacgt ggaacacctg aatgtgctgc 3180
gggccattcc cgattatatc caggacttca ggcacggaga taaggggaa actcctatga  3240
acagctactt cgagctgtat cattacctgc tgcagaggct catgctgaaa aatcggctgc  3300
tcgacctgtc tagctggcgc tcctggatcg agaggtctgg ccgacctgat cgcgacctga  3360
ttcagatcgc atttgtgagc ctggcttata atctgcctag atatcggaat ctgaccaagg  3420
agcaccactt tgatgatacc gtgctgcaga agattagaga aggaagagc ctggacacag   3480
gcggcggccc cggcggcggc gccgccgccg cagcggcag ccctaagaaa aaacgaaaag   3540
ttggcagcgg aagcaaaagg ccggcggcca cgaaaaaggc cggccaggca aaaagaaaa   3600
agctcgagta cccatacgat gttccagatt acgcttgaga attcccttg agcatctgac   3660
ttctggctaa taaaggaaat ttattttcat tgcaatagtg tgttggaatt ttttgtgtct   3720
ctcaggtacc gagggcctat ttcccatgat tccttcatat ttgcatatac gatacaaggc   3780
tgttagagag ataattggaa ttaatttgac tgtaaacaca aagatattag tacaaaatac   3840
gtgacgtaga aagtaataat ttcttgggta gtttgcagtt ttaaaattat gttttaaaat   3900
ggactatcat atgcttaccg taacttgaaa gtatttcgat ttcttggctt tatatatctt   3960
gtggaaagga cgaaacaccg agtctcagaa ccctacaggt ttgtagagtt atctggagac   4020
cacggcaggt ctcatttttt gcggccgcag gaacccctag tgatggagtt ggccactccc   4080
tctctgcgcg ctcgctcgct cactgaggcc gggcgaccaa aggtcgcccg acgcccggc    4140
tttgcccggg cggcctcagt gagcgagcga gcgcgcagct gcctgcaggg gcgcctgatg   4200
cggtattttc tccttacgca tctgtgcggt atttcacacc gcatacgtca aagcaaccat   4260
agtacgcgcc ctgtagcggc gcattaagcg cggcgggtgt ggtggttacg cgcagcgtga   4320
ccgctacact tgccagcgcc ttagcgcccg ctcctttcgc tttcttccct tccttttctcg   4380
ccacgttcgc cggctttccc cgtcaagctc taaatcgggg ctccctttta gggttccgat   4440
ttagtgcttt acggcacctc gaccccaaaa aacttgattt gggtgatggt tcacgtagtg   4500
ggccatcgcc ctgatagacg gttttcgcc ctttgacgtt ggagtccacg ttctttaata    4560
gtggactctt gttccaaact ggaacaacac tcaactctat ctcgggctat tcttttgatt   4620
tataaggat tttgccgatt tcggtctatt ggttaaaaaa tgagctgatt taacaaaaat    4680
ttaacgcgaa ttttaacaaa atattaacgt ttacaatttt atggtgcact ctcagtacaa   4740
tctgctctga tgccgcatag ttaagccagc cccgacaccc gccaacaccc gctgacgcgc   4800
cctgacgggc ttgtctgctc ccggcatccg cttacagaca agctgtgacc gtctccggga   4860
gctgcatgtg tcagaggttt tcaccgtcat caccgaaacg cgcgagacga aagggcctcg   4920
tgatacgcct atttttatag gttaatgtca tgataataat ggtttcttag acgtcaggtg   4980
gcacttttcg gggaaatgtg cgcggaaccc ctatttgttt atttttctaa atacattcaa   5040
atatgtatcc gctcatgaga caataaccct gataaatgct tcaataatat tgaaaaagga   5100
agagtatgag tattcaacat ttccgtgtcg ccctttattcc cttttttgcg gcattttgcc   5160
ttcctgtttt tgctcaccca gaaacgctgg tgaaagtaaa agatgctgaa gatcagttgg   5220
gtgcacgagt gggttacatc gaactggatc tcaacagcgg taagatcctt gagagttttc   5280
gccccgaaga acgttttcca atgatgagca cttttaaagt tctgctatgt ggcgcggtat   5340
tatcccgtat tgacgccggg caagagcaac tcggtcgccg catacactat tctcagaatg   5400
acttggttga gtactcacca gtcacagaaa agcatcttac ggatggcatg acagtaagag   5460
aattatgcag tgctgccata accatgagtg ataacactgc ggccaactta cttctgacaa   5520
cgatcggagg accgaaggag ctaaccgctt ttttgcacaa catgggggat catgtaactc   5580
gccttgatcg ttgggaaccg gagctgaatg aagccatacc aaacgacgag cgtgacacca   5640
cgatgcctgt agcaatggca acaacgttgc gcaaactatt aactggcgaa ctacttactc   5700
tagcttcccg gcaacaatta atagactgga tggaggcgga taaagttgca ggaccacttc   5760
tgcgctcggc ccttccggct ggctggttta ttgctgataa atctggagcc ggtgagcgtg   5820
gaagccgcg tatcattgca gcactgggc cagatggtaa gccctcccgt atcgtagtta   5880
tctacacgac ggggagtcag gcaactatgg atgaacgaaa tagacagatc gctgagatag   5940
gtgcctcact gattaagcat tggtaactgt cagaccaagt ttactcatat atactttaga   6000
ttgatttaaa acttcatttt taattaaaag gatctaggt gaagatcctt tttgataatc   6060
tcatgaccaa aatcccttaa cgtgagtttt cgttccactg agcgtcagac cccgtagaaa   6120
agatcaaagg atcttcttga gatccttttt tctgcgcgt aatctgctgc ttgcaaacaa   6180
aaaaaccacc gctaccagcg gtggtttgtt tgccggatca agagctacca actctttttc   6240
cgaaggtaac tggcttcagc agagcgcaga taccaaatac tgttcttcta gtgtagccgt   6300
agttaggcca ccacttcaag aactctgtag caccgcctac atacctcgct ctgctaatcc   6360
tgttaccagt ggctgctgcc agtggcgata gtcgtgtct taccgggttg gactcaagac   6420
gatagttacc ggataaggcg cagcggtcgg gctgaacggg gggttcgtgc acacagccca   6480
gcttggagcg aacgacctac accgaactga gatacctaca gcgtgagcta tgagaaagcg   6540
ccacgcttcc cgaagggaga aaggcggaca ggtatccgt aagcggcagg gtcggaacag    6600
gagagcgcac gagggagctt ccaggggaa acgcctggta tctttatagt cctgtcgggt    6660
ttcgccacct ctgacttgag cgtcgatttt tgtgatgctc gtcaggggg cggagcctat    6720
ggaaaaacgc cagcaacgcg gcctttttac ggttcctggc cttttgctgg ccttttgctc   6780
acatgt                                                              6786

SEQ ID NO: 38          moltype = DNA  length = 34
FEATURE                Location/Qualifiers
source                 1..34
                       mol_type = other DNA
                       organism = synthetic construct
SEQUENCE: 38
caacgtggtt ggagaactgg atgtagatgg gctg                               34

SEQ ID NO: 39          moltype = DNA  length = 34
FEATURE                Location/Qualifiers
source                 1..34
                       mol_type = other DNA
                       organism = synthetic construct
SEQUENCE: 39
atctgtggtt ggagaactgg atgtagatgg gctg                               34
```

-continued

```
SEQ ID NO: 40           moltype = RNA  length = 21
FEATURE                 Location/Qualifiers
source                  1..21
                        mol_type = other RNA
                        organism = synthetic construct
SEQUENCE: 40
gcccatctac atccagttct c                                                  21

SEQ ID NO: 41           moltype = RNA  length = 21
FEATURE                 Location/Qualifiers
source                  1..21
                        mol_type = other RNA
                        organism = synthetic construct
SEQUENCE: 41
cagcccatct acatccagtt c                                                  21

SEQ ID NO: 42           moltype = RNA  length = 30
FEATURE                 Location/Qualifiers
source                  1..30
                        mol_type = other RNA
                        organism = synthetic construct
SEQUENCE: 42
catgaaaaac ttgagagttg ctgggtctga                                         30

SEQ ID NO: 43           moltype = RNA  length = 30
FEATURE                 Location/Qualifiers
source                  1..30
                        mol_type = other RNA
                        organism = synthetic construct
SEQUENCE: 43
gaattaagtt agttagttgc tcttctaaat                                         30

SEQ ID NO: 44           moltype = RNA  length = 30
FEATURE                 Location/Qualifiers
source                  1..30
                        mol_type = other RNA
                        organism = synthetic construct
SEQUENCE: 44
cgatgttgaa ttaatgtcca tggactacct                                         30

SEQ ID NO: 45           moltype = RNA  length = 30
FEATURE                 Location/Qualifiers
source                  1..30
                        mol_type = other RNA
                        organism = synthetic construct
SEQUENCE: 45
gatagagaaa tttctgtggg ttcttgaata                                         30

SEQ ID NO: 46           moltype = RNA  length = 30
FEATURE                 Location/Qualifiers
source                  1..30
                        mol_type = other RNA
                        organism = synthetic construct
SEQUENCE: 46
ctggagaagg tctttgatgc tattatcttg                                         30

SEQ ID NO: 47           moltype = RNA  length = 30
FEATURE                 Location/Qualifiers
source                  1..30
                        mol_type = other RNA
                        organism = synthetic construct
SEQUENCE: 47
cactatggag tatatcttct ctaggcccaa                                         30

SEQ ID NO: 48           moltype = RNA  length = 30
FEATURE                 Location/Qualifiers
source                  1..30
                        mol_type = other RNA
                        organism = synthetic construct
SEQUENCE: 48
ccacactcat catgccacca ccagcctcct                                         30

SEQ ID NO: 49           moltype = RNA  length = 30
FEATURE                 Location/Qualifiers
source                  1..30
                        mol_type = other RNA
                        organism = synthetic construct
SEQUENCE: 49
gaccatctaa aattgattcc cacatcacaa                                         30
```

```
SEQ ID NO: 50          moltype = DNA   length = 21
FEATURE                Location/Qualifiers
source                 1..21
                       mol_type = other DNA
                       organism = synthetic construct
SEQUENCE: 50
ccagaacacc cagaagtaac t                                              21

SEQ ID NO: 51          moltype = DNA   length = 24
FEATURE                Location/Qualifiers
source                 1..24
                       mol_type = other DNA
                       organism = synthetic construct
SEQUENCE: 51
tctgtgggtt cttgaatact agtc                                           24

SEQ ID NO: 52          moltype = DNA   length = 9915
FEATURE                Location/Qualifiers
source                 1..9915
                       mol_type = other DNA
                       organism = synthetic construct
SEQUENCE: 52
gtcgacggat cgggagatct cccgatcccc tatggtgcac tctcagtaca atctgctctg    60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt cgctgcttc gcgatgtacg ggccagatat acgcgttgac    240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg cccctattg acgtcaatga cggtaaatgg cccgcctggc    540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca gtctccacc ccattgacgt caatgggagt ttgttttggc    720
accaaaatca acgggacttt ccaaaatgtc gtaacaactc cgccccattg acgcaaatgg   780
gcggtaggcg tgtacggtgg gaggtctata taccagatct gagcctggga gctctctggc   840
taactaggga acccactgct taagcctcaa taaagcttgc cttgagtgct tcaagtagtg   900
tgtgcccgtc tgttgtgtga ctctggtaac tagagatccc tcagaccctt ttagtcagtg   960
tggaaaatct ctagcagtgg cgcccgaaca gggacttgaa agcgaaaggg aaaccagagg  1020
agctctctcg acgcaggact cggcttgctg aagcgcgcac ggcaagaggc gaggggcggc  1080
gactggtgag tacgccaaaa attttgacta gcggaggcta aaggagaga gatgggtgcg   1140
agagcgtcag tattaagcgg gggagaatta gatcgcgatg ggaaaaaatt cggttaaggc  1200
cagggggaaa gaaaaaatat aaataaacat atagtatggg caagcaggga gctagaacga  1260
ttcgcagtta atcctggcct gttagaaaca tcagaaggct gtagacaaat actgggacag  1320
ctacaaccat cccttcagac aggatcagaa gaacttagat cattatataa tacagtagca  1380
accctctatt gtgtgcatca aaggatagag ataaaagaca ttgaagaagc tttagacaag  1440
atagaggaag agcaaacaa aagtaagacc accgcacagc aagcggccgg ccgcgctgat   1500
cttcagacct ggaggaggag atatgaggga caattggaga agtgaattat ataaatataa  1560
agtagtaaaa attgaaccat taggagtagc acccaccaag gcaaagagaa gagtggtgca  1620
gagagaaaaa agagcagtgg gaataggagc tttgttcctt gggttcttgg gagcagcagg  1680
aagcactatg ggcgcagcgt caatgacgct gacggtacag gccagacaat tattgtctgt  1740
tatagtgcag cagcagaaca atttgctgag ggctattgag gcgcaacagc atctgttgca  1800
actcacagtc tggggcatca agcagctcca ggcaagaatc ctggctgtgg aaagatacct  1860
aaaggatcaa cagctcctgg ggatttgggg ttgctctgga aaactcattt gcaccactgc  1920
tgtgccttgg aatgctagtt ggagtaataa atctctgaa cagatttgga atcacacgac    1980
ctggatggag tgggacagag aaattaacaa ttacacaagc ttaatacact ccttaattga  2040
agaatcgcaa aaccagcaag aaaagaatga acaagaatta ttggaattag ataaatgggc  2100
aagtttgtgg aattggttta acataacaaa ttggctgtgg tatataaaat tattcataat  2160
gatagtagga ggcttggtag gtttaagaat agtttttgct gtactttcta tagtgaatag  2220
agttaggcag ggatattcac cattatcgtt tcagacccac ctcccaaccc cgaggggacc  2280
cgacaggccc gaaggaatag aagaagaagg tggagagaga cagagacag gatccattcg   2340
attagtgaac ggatcggcac tgcgtgcgcc aattctgcag acaaatgca gtattcatcc    2400
acaattttaa agaaaagggg ggattgggg gtacagtgc aggggaaaga atagtagaca    2460
taatagcaac agacatacaa actaaagaat tacaaaaca aattcaaaatt                2520
ttcgggttta ttacagggac agcagagatc cagtttggtt agtaccgggc ccgctctagc  2580
gtcgaggagc ttgcccatt gcatacgttg tatccatatc ataatatgta catttatatt    2640
ggctcatgtc caacattacc gccatgttga cattgattat tgactagtta ttaatagtaa  2700
tcaattacgg ggtcattagt tcatagccca tatatggagt tccgcgttac ataacttacg  2760
gtaaatggcc cgcctggctg accgcccaac gacccccgcc cattgacgtc aataatgacg  2820
tatgttccca tagtaacgcc aatagggact ttccattgac gtcaatgggt ggagtattta  2880
cggtaaactg cccacttggc agtacatcaa gtgtatcata tgccaagtac gccccctatt  2940
gacgtcaatg acggtaaatg gcccgcctgg cattatgccc agtacatgac cttatgggac  3000
tttcctactt ggcagtacat ctacgtatta gtcatcgcta ttaccatggt gatgcggttt  3060
tggcagtaca tcaatgggcg tggatagcgg tttgactcac ggggatttcc aagtctccac  3120
cccattgacg tcaatgggag tttgttttgg caccaaaatc aacgggactt tccaaaatgt  3180
cgtaacaact ccgccccatt gacgcaaatg gcggtaggc gtgtacggtg ggaggtctat    3240
ataagcagag ctcgtttagt gaaccgtcag atcgcctgga gacgccatcc acgctgtttt  3300
gacctccata agacaccg ggaccgatcc agcctccgcg gccccgaatt cgccaccatg     3360
```

```
gccatgttca caattaagct ccttcttttt attgttcctc tagttatttc ctccagaatt  3420
gatcaagaca attcatcatt tgattctcta tctccagagc caaaatcaag atttgctatg  3480
ttagacgatg taaaaatttt agccaatggc ctccttcagt tgggacatgg tcttaaagac  3540
tttgtccata agacgaaggg ccaaattaat gacatatttc aaaaactcaa catatttgat  3600
cagtcttttt atgatctatc gctgcaaacc agtgaaatca aagaagaaga aaaggaactg  3660
agaagaacta catataaact acaagtcaaa aatgaagagg taaagaatat gtcacttgaa  3720
ctcaactcaa aacttgaaag cctcctagaa gaaaaaattc tacttcaaca aaaagtgaaa  3780
tatttagaag agcaactaac taacttaatt caaaatcaac ctgaaactcc agaacaccca  3840
gaagtaactt cacttaaaac ttttgtagaa aaacaagata atagcatcaa agaccttctc  3900
cagaccgtgg aagaccaata taaacaatta aaccaacagc atagtcaaat aaaagaaata  3960
gaaaatcagc tcagaaggac tagtattcaa gaacccacag aaatttctct atcttccaag  4020
ccaagagcac caagaactac tccctttctt cagttgaatg aaataagaaa tgtaaaacat  4080
gatggcattc ctgctgaatg taccaccatt tataacagag gtgaacatac aagtggcatg  4140
tatgccatca gacccagcaa ctctcaagtt tttcatgtct actgtgatgt tatatcaggt  4200
agtccatgga cattaattca acatcgaata gatggatcac aaaacttcaa tgaaacgtgg  4260
gagaactaca aatatggttt tgggaggctt gatggagaat tttggttggg cctagagaag  4320
atatactcca tagtgaagca atctaattat gttttacgaa ttgagttgga agactggaaa  4380
gacaacaaac attatattga atattctttt tacttgggaa atcacgaaac caactatacg  4440
ctacatctag ttgcgattac tggcaatgtc cccaatgcaa tcccggaaaa caaagatttg  4500
gtgttttcta cttgggatca caaagcaaaa ggacacttca actgtccaga gggttattca  4560
ggaggctggt ggtggcatga tgagtgtgga gaaaacaacc taaatggtaa atataacaaa  4620
ccaagagcaa aatctaagcc agagaggaga agaggattat cttggaagtc tcaaaatgga  4680
aggttatact ctataaaatc aaccaaaatg ttgatccatc caacagattc agaaagcttt  4740
gaaggatccg ctagcggcag tggagagggc agaggaagtc tgctaacatg cggtgacgtc  4800
gaggagaatc ctgcccagt gagcaagggc gaggagctgt tcaccgggggt ggtgcccatc  4860
ctggtcgagc tggacggcga cgtaaacggc cacaagttca gcgtgtccgg cgagggcgag  4920
ggcgatgcca cctacggcaa gctgaccctg aagttcatct gcaccaccgg caagctgccc  4980
gtgccctggc ccaccctcgt gaccaccctg acctacggcg tgcagtgctt cagccgctac  5040
cccgaccaca tgaagcagca cgacttcttc aagtccgcca tgcccgaagg ctacgtccag  5100
gagcgcacca tcttcttcaa ggacgacggc aactacaaga cccgcgccga ggtgaagttc  5160
gagggcgaca cccttggtgaa ccgcatcgag ctgaagggca tcgacttcaa ggaggacggc  5220
aacatcctgg ggcacaagct ggagtacaac tacaacagcc acaacgtcta tatcatggcc  5280
gacaagcaga gaacggcat caaggtgaac ttcaagatcc gccacaacat cgaggacggc  5340
agcgtgcagc tcgccgacca ctaccagcag aacacccca tcggcgacgg ccccgtgctg  5400
ctgcccgaca accactacct gagcacccag tccgccctga gcaaagaccc caacgagaag  5460
cgcgatcaca tggtcctgct ggagttcgtg accgccgccg ggatcactct cggcatggac  5520
gagctgtaca agtaaggatc ctaggcgcc gcgcatgccc tgcaggtgat ctatcgatcg  5580
gccggcccct ctccctcccc ccccccctaa cgttactggc cgaagccgct tggaataagg  5640
ccggtgtgcg tttgtctata tgttattttc caccatattg ccgtcttttg gcaatgtgag  5700
ggcccggaaa cctggccctg tcttcttgac gagcattcct aggggtcttt ccctctcgc  5760
caaaggaatg caaggtctgt tgaatgtcgt gaaggaagca gttcctctgg aagcttcttg  5820
aagacaaaca acgtctgtag cgacccttg caggcagcgg aaccccccac ctggcgacag  5880
tgcctctgc ggccaaaagc cacgtgtata agatacacct gcaaaggcgg cacaacccca  5940
gtgccacgtt gtgagttgga tagttgtgga aagagtcaaa tggctctcct caagcgtatt  6000
caacaagggg ctgaaggatg cccagaaggt accccattgt atgggatctg atctggggcc  6060
tcggtacaca tgctttacat gtgtttagtc gaggttaaaa aaacgtctag gccccccgaa  6120
ccacgggac gtggttttcc tttgaaaaac acgatgataa tatggccaca accgggccgg  6180
atatcacgcg tgatctgatc agcacgtgtt gacaattaat catcggcata gtatatcggc  6240
atagtataat acgacaaggt gaggaactaa accatgccca agcctttgtc tcaagaagaa  6300
tccaccctca ttgaaagagc aacggctaca atcaacagca tccccatctc tgaagactac  6360
agcgtcgcca gcgcagctct ctctagcgca ggccgcatct tcactggtgt caatgtatat  6420
cattttactg ggggaccttg tgcagaactc gtggtgctgg gcactgctgc tgctgcggca  6480
gctggcaacc tgacttgtat cgtcgcgatc ggaaatgaga acaggggcat cttgagcccc  6540
tgcggacggt gccgacaggt gcttctcgat ctgcatcctg ggatcaaagc catagtgaag  6600
gacagtgatg gacagccgac ggcagttggg attcgtgaat tgctgccctc tggttatgtg  6660
tgggagggct aagcaatgca tacatgtgtt taaacctcga cttaattaag tcgagggtcg  6720
acggtatcga taagctcgct tcacgagatc atgtttaagg gttccggttc cactaggtac  6780
aattcgatat caagcttatc gataatcaac ctctggatta caaaatttgt gaaagattga  6840
ctggtattct taactatgtt gctcctttta cgctatgtgg atacgctgct ttaatgcctt  6900
tgtatcatgc tattgcttcc cgtatggctt tcattttctc ctccttgtat aaatcctggt  6960
tgctgtctct ttatgaggag ttgtggcccg ttgtcaggca acgtggcgtg gtgtgcactg  7020
tgtttgctga cgcaacccc actggttggg gcattgccac cacctgtcag ctcctttccg  7080
ggactttcgc tttccccctc cctattgcca cggcggaact catcgccgcc tgccttgccc  7140
gctgctggac aggggctcgg ctgttgggca ctgacaattc cgtggtgttg tcggggaaat  7200
catcgtcctt tccttggctg ctcgcctgtg ttgccacctg gattctgcgc gggacgtcct  7260
tctgctacgt cccttcggcc ctcaatccag cggaccttcc ttcccgcggc ctgctgccgg  7320
ctctgcggcc tcttccgcgt cttcgccttc gccctcagac gagtcggatc tccctttggg  7380
ccgcctcccc gcatcgatac cgtcgacctc gatcgagacc tagaaaaaca tggagcaatc  7440
acaagtagca atacagcagc taccaatgct gattgtgcct ggctagaagc acaagaggag  7500
gaggaggtgg gttttccagt cacacctcag gtacctttaa gaccaatgac ttacaaggca  7560
gctgtagatc ttagccactt tttaaaagaa aaggggggac tggaagggct aattcactcc  7620
caacgaagac aagatatcct tgatctgtgg atctaccaca caaggcta cttccctgat  7680
tggcagaact acacaccagg gccagggatc agatatccac tgacctttgg atggtgctac  7740
aagctagtac cagttgagca agagaaggta gaagaagcca atgaaggaga gaacacccgc  7800
ttgttacacc ctgtgagcct gcatgggatg gatgacccgg agagagaagt attagagtgg  7860
aggtttgaca gccgcctagc atttcatcac atggcccgag agctgcatcc ggactgtact  7920
gggtctctct ggttagacca gatctgagcc tgggagctct ctggctaact agggaaccca  7980
ctgcttaagc ctcaataaag cttgccttga gtgcttcaag tagtgtgtgc ccgtctgttg  8040
tgtgactctg gtaactagag atccctcaga cccttttagt cagtgtggaa aatctctagc  8100
```

```
agcatgtgag caaaaggcca gcaaaaggcc aggaaccgta aaaaggccgc gttgctggcg  8160
ttttctccata ggctccgccc ccctgacgag catcacaaaa atcgacgctc aagtcagagg  8220
tggcgaaacc cgacaggact ataaagatac caggcgtttc ccctggaag ctccctcgtg   8280
cgctctcctg ttccgaccct gccgcttacc ggatacctgt ccgcctttct cccttcggga  8340
agcgtggcgc tttctcatag ctcacgctgt aggtatctca gttcggtgta ggtcgttcgc  8400
tccaagctgg gctgtgtgca cgaaccccc gttcagcccg accgctgcgc cttatccggt   8460
aactatcgtc ttgagtccaa cccggtaaga cacgacttat cgccactggc agcagccact  8520
ggtaacagga ttagcagagc gaggtatgta ggcggtgcta cagagttctt gaagtggtgg  8580
cctaactacg gctacactag aagaacagta tttggtatct gcgctctgct gaagccagtt  8640
accttcggaa aaagagttgg tagctcttga tccggcaaac aaaccaccgc tggtagcggt  8700
ggtttttttg tttgcaagca gcagattacg cgcagaaaaa aaggatctca agaagatcct  8760
ttgatctttt ctacggggtc tgacgctcag tggaacgaaa actcacgtta agggatttg  8820
gtcatgagat tatcaaaaag gatcttcacc tagatccttt taaattaaaa atgaagtcag  8880
aaatcaatct aaagtatata tgagtaaact tggtctgaca gttaccaatg cttaatcagt  8940
gaggcaccta tctcagcgat ctgtctattt cgttcatcca tagttgcctg actccccgtc  9000
gtgtagataa ctacgatacg ggagggctta ccatctggcc ccagtgctgc aatgataccg  9060
cgagaccccac gctcaccggc tccagattta tcagcaataa accagccagc cggaagggcc  9120
gagcgcagaa gtggtcctgc aacttatcc gcctccatcc agtctattaa ttgttgccgg  9180
gaagctagag taagtagttc gccagttaat agtttgcgca acgttgttgc cattgctaca  9240
ggcatcgtgg tgtcacgctc gtcgtttggt atggcttcat tcagctccgg ttcccaacga  9300
tcaaggcgag ttacatgatc cccatgttg tgcaaaaaag cggttagctc cttcggtcct  9360
ccgatcgttg tcagaagtaa gttggccgca gtgttatgc tcatggttat ggcagcactg  9420
cataattctc ttactgtcat gccatccgta agatgctttt ctgtgactgg tgagtactca  9480
accaagtcat tctgagaata gtgtatgcgg cgaccgagtt gctcttgccc ggcgtcaata  9540
cgggataata ccgcgccaca tagcagaact ttaaaagtgc tcatcattgg aaaacgttct  9600
tcggggcgaa aactctcaag gatcttaccg ctgttgagat ccagttcgat gtaacccact  9660
cgtgcaccca actgatcttc agcatctttt actttcacca gcgtttctgg gtgagcaaaa  9720
acaggaaggc aaaatgccgc aaaaaaggga ataaggcga cacggaaatg ttgaatactc   9780
atactcttcc ttttcaata ttattgaagc atttatcagg gttattgtct catgagcgga   9840
tacatatttg aatgtattta gaaaataaa caaatagggg ttccgcgcac atttccccga  9900
aaagtgccac ctgac                                                    9915

SEQ ID NO: 53           moltype = AA   length = 11
FEATURE                 Location/Qualifiers
source                  1..11
                        mol_type = protein
                        organism = synthetic construct
SEQUENCE: 53
SPKKKRKVEA S                                                         11

SEQ ID NO: 54           moltype = AA   length = 11
FEATURE                 Location/Qualifiers
source                  1..11
                        mol_type = protein
                        organism = synthetic construct
SEQUENCE: 54
GPKKKRKVAA A                                                         11

SEQ ID NO: 55           moltype = AA   length = 7
FEATURE                 Location/Qualifiers
source                  1..7
                        mol_type = protein
                        organism = synthetic construct
SEQUENCE: 55
PKKKRKV                                                              7

SEQ ID NO: 56           moltype = AA   length = 16
FEATURE                 Location/Qualifiers
source                  1..16
                        mol_type = protein
                        organism = synthetic construct
SEQUENCE: 56
KRPAATKKAG QAKKKK                                                    16

SEQ ID NO: 57           moltype = AA   length = 9
FEATURE                 Location/Qualifiers
source                  1..9
                        mol_type = protein
                        organism = synthetic construct
SEQUENCE: 57
PAAKRVKLD                                                            9

SEQ ID NO: 58           moltype = AA   length = 11
FEATURE                 Location/Qualifiers
source                  1..11
                        mol_type = protein
                        organism = synthetic construct
SEQUENCE: 58
RQRRNELKRS P                                                         11
```

```
SEQ ID NO: 59          moltype = AA   length = 38
FEATURE                Location/Qualifiers
source                 1..38
                       mol_type = protein
                       organism = synthetic construct
SEQUENCE: 59
NQSSNFGPMK GGNFGGRSSG PYGGGGQYFA KPRNQGGY                              38

SEQ ID NO: 60          moltype = AA   length = 42
FEATURE                Location/Qualifiers
source                 1..42
                       mol_type = protein
                       organism = synthetic construct
SEQUENCE: 60
RMRIZFKNKG KDTAELRRRR VEVSVELRKA KKDEQILKRR NV                         42

SEQ ID NO: 61          moltype = AA   length = 8
FEATURE                Location/Qualifiers
source                 1..8
                       mol_type = protein
                       organism = synthetic construct
SEQUENCE: 61
VSRKRPRP                                                                8

SEQ ID NO: 62          moltype = AA   length = 8
FEATURE                Location/Qualifiers
source                 1..8
                       mol_type = protein
                       organism = synthetic construct
SEQUENCE: 62
PPKKARED                                                                8

SEQ ID NO: 63          moltype = AA   length = 8
FEATURE                Location/Qualifiers
source                 1..8
                       mol_type = protein
                       organism = synthetic construct
SEQUENCE: 63
POPKKKPL                                                                8

SEQ ID NO: 64          moltype = AA   length = 12
FEATURE                Location/Qualifiers
source                 1..12
                       mol_type = protein
                       organism = synthetic construct
SEQUENCE: 64
SALIKKKKKM AP                                                          12

SEQ ID NO: 65          moltype = AA   length = 5
FEATURE                Location/Qualifiers
source                 1..5
                       mol_type = protein
                       organism = synthetic construct
SEQUENCE: 65
DRLRR                                                                   5

SEQ ID NO: 66          moltype = AA   length = 7
FEATURE                Location/Qualifiers
source                 1..7
                       mol_type = protein
                       organism = synthetic construct
SEQUENCE: 66
PKQKKRK                                                                 7

SEQ ID NO: 67          moltype = AA   length = 10
FEATURE                Location/Qualifiers
source                 1..10
                       mol_type = protein
                       organism = synthetic construct
SEQUENCE: 67
RKLKKKIKKL                                                             10

SEQ ID NO: 68          moltype = AA   length = 10
FEATURE                Location/Qualifiers
source                 1..10
                       mol_type = protein
                       organism = synthetic construct
SEQUENCE: 68
```

```
REKKKFLKRR                                                            10

SEQ ID NO: 69          moltype = AA  length = 20
FEATURE                Location/Qualifiers
source                 1..20
                       mol_type = protein
                       organism = synthetic construct
SEQUENCE: 69
KRKGDEVDGV DEVAKKKSKK                                                 20

SEQ ID NO: 70          moltype = AA  length = 17
FEATURE                Location/Qualifiers
source                 1..17
                       mol_type = protein
                       organism = synthetic construct
SEQUENCE: 70
RKCLQAGMNL EARKTKK                                                    17

SEQ ID NO: 71          moltype = AA  length = 9
FEATURE                Location/Qualifiers
source                 1..9
                       mol_type = protein
                       organism = synthetic construct
SEQUENCE: 71
PAAKKKKLD                                                              9

SEQ ID NO: 72          moltype = DNA  length = 6802
FEATURE                Location/Qualifiers
source                 1..6802
                       mol_type = other DNA
                       organism = synthetic construct
SEQUENCE: 72
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggcctcta gactcgaggc gttgacattg attattgact agttattaat    180
agtaatcaat tacggggtca ttagttcata gcccatatat ggagttccgc gttacataac    240
ttacggtaaa tggcccgcct ggctgaccgc ccaacgaccc cgcccattg acgtcaataa     300
tgacgtatgt tcccatagta acgccaatag ggactttcca ttgacgtcaa tgggtggagt    360
atttacggta aactgcccac ttggcagtac atcaagtgta tcatatgcca agtacgcccc    420
ctattgacgt caatgacggt aaatggcccg cctggcatta tgcccagtac atgaccttat    480
gggactttcc tacttggcag tacatctacg tattagtcat cgctattacc atggtgatgc    540
ggttttggca gtacatcaat gggcgtggat agcggtttga ctcacgggga tttccaagtc    600
tccaccccat tgacgtcaat gggagtttgt tttggcacca aaatcaacgg gactttccaa    660
aatgtcgtaa caactccgcc ccattgacgc aaatgggcgg taggcgtgta cggtgggagg    720
tctatataag cagagctctc tggctaacta ccggtgccac catgccggca gctaagaaaa    780
agaaactgga tggcagcgtc gacatgagca aggacaagaa aaccaaggcc aagagaatgg    840
gcgtgaaggc cctgctggcc cacggcgagg acaagtgcac atgaccacc ttcggcaagg    900
gcaacagaag caagatcgag ttcaccgagg ctaccacgca cagagccctg agacacccca    960
agcacttcgg catcagaggc ttcgaggtga agaatcga cgagaacgtg gacctgtgcg     1020
gcgacctgga ggagggcaag accatcgagg ccctgctggt gaaccccagc gagaaggtgg    1080
gcgaggacta cctgaagctg aagggcacc tggagagaga attcttcggc agagagttcc    1140
cccacgacaa catcagaatc cagctgatct acaacatcct ggacatctac aagatcctga    1200
gcatgaacgt ggccgacatc ctgtacgccc tgggcaacat gcaggacacc gagctggaca    1260
tcgacatgtt cggccagagc ctgaacaacg gacaacct gaaggagtgc ctgaagaaga    1320
tgaggcccta catgggctac ttcggcgcca tcttcaagat cagccccgag ggcgagaaca    1380
tcgccgacag agagcacaac aagaaggtgc tgaagatcag cagcgtgctg agaaacgcca    1440
ccgcccacga caagcaggac gagtacccct ggttcaagag cagcgacatc tacgagcaa    1500
agatcttcaa ggccgacatg tggaagatca tcaaggacca gtacagagag aagatcaaga    1560
aggtgaacaa ggacttcctg agcaagaacg ccgtgaacat ggccatcctg ttcgacctgc    1620
tgaacgccag agacgtggag cagaagaagc agatcaccga cgagttctac agagattcca    1680
tcagaaagga cggcaagaac ctgggcatga acctggtgaa gatcagagac atcatcatcg    1740
acagatacgc cagcggcctg agagacaaga gcacgaccc cacagacag aagatcaacg    1800
tgatcgccga cttcctgatc ttcagagccc tgagccagaa ccgggcatc atcgacaaga    1860
ccgtgagcag cctgagactg accaaggacg aggaggacaa cgacgtg taccagaaga    1920
ccgccgagct ggtgtgggc atggtgagca ctgcctgac cccctacttc aacgacccca    1980
agaacaagta catcctgaag tacaaggacg ccaagacccc cggcgacttc gaggactgga    2040
tcaccagcaa gatcagcgag gacgacgcg agcccttcgt gaaggtgctg agcttcctgt    2100
gcaacttcct ggagggcaag gagatcaacg agctgctgac cgcctacatc cacaagtcg    2160
agtgcatcca ggacttcctg aacgtgatca cgcagcctggg cgagaacgtg cagttccagc    2220
ccagattcgc cctgttcaac aacgccagct cgcccagaa cgtggccgtg cagctgagaa    2280
tcctggccag catcggcaag atgaagccc acctgaccga ggccaagagg ccctgtaca    2340
aggccgccat cagaatgctg tgcccccg agaagtggga agtacacc agcgacgagt    2400
ggctggagaa gaacatgctg ctgaacgcg gacagaaa gaacgacaag aagaagagc    2460
aggtgaaccc cttcagaaac ttcatcgcg gcaactgt cagagagcga agattcatgt    2520
acctggtgag atacagcaag cccaaggcg tgagagcct catgcagaac agaagcatcg    2580
tgaactacgt gctgcacaga ctgccagcg gcaggtgca cagatacgcc agcgtgttcc    2640
ccgagaactt cgccgacctg gagcaggaga tcgacttcct gaccaagaag ctgttcgagt    2700
tcagcttcga ggagctgctg cacgagaagg acgtgatcct gaacaacagc agaagccaca    2760
agcccagcct ggagatcgag agactgaagg ccatcaccg cctgtacctg agcgtggcct    2820
```

```
acatcgccat caagaacatc gtgaaggcca acgccagata ctacatcgcc ttcgccgtgt    2880
tcgagagaga caaggagctg gtgaaggcca aggacgccag aatccagacc aagatccccg    2940
agacagactt ccccgactac ttctgcctga cccagtacta cctggacaga gacgaggaga    3000
agaagttccc cggcgacccc agagacaagg aggccttctt cgagcacctg agaaagacca    3060
agagacactt cagcaagcag tggagagagt ggctgaacga gaagatcgcc gacgccaaga    3120
gcagccaggc caccggcctg ctgctgagag aggccagaaa cgacgtggag cacctgaacg    3180
tgctgagagc catccccgac tacatccagg acttcagaca cggcgagaag ggcgagacag    3240
ccatgaacag ctacttcgag ctgtaccact acctgatgca gagactgatg ctgaagaaca    3300
ccgagctgga cctgagccac tggagcggct ggatcatgaa aagcggcaga cccgacagag    3360
acttgatcca gatcgccttc gtgagcctgc cctacaacct gcccagatac agaaacctga    3420
ccaaggagca ccacttcgac gacaccgtgc tgcagaagat cagagagaag gagagcctgg    3480
acacaggcgg cggccccggc ggcggcgccg ccgccggcag cggcagccct aagaaaaaac    3540
gaaaagttgg cagcggaagc aaaaggccgg cggccacgaa aaaggccggc caggcaaaaa    3600
agaaaaagct cgagtaccca tacgatgttc cagattacgc tgagaattcc aattatgttt    3660
tctgacttct ggctaataaa ggaaatttat tttcattgca atagtgtgtt ggaattttt    3720
gtgtctctca ggtaccgagg gcctattcc catgattcct tcatatttgc atatacgata     3780
caaggctgtt agagagataa ttggaattaa tttgactgta aacacaaaga tattagtaca    3840
aaatacgtga cgtagaaagt aataattct tgggtagttt gcagttttaa aattatgttt     3900
taaaatggac tatcatatgc ttaccgtaac ttgaaagtat ttcgatttct ggctttata     3960
tatcttgtgg aaaggacgaa acaccggaag ataactctac aaacctgtag ggttctgaga    4020
ctgggtgcag cctgggacca cttggcatgg tttttgcgg ccgcaggaac ccctagtgat     4080
ggagttggcc actccctctc tgcgcgctcg ctcgctcaaa gggccgggc gaccaaaggt     4140
cgcccgacgc ccgggctttg cccggcggc ctcagtgagc gagcgagcgc gcagctgcct     4200
gcaggggcgc ctgatgcggt attttctcct tacgcatctg tgcggtattt cacaccgcat    4260
acgtcaaagc aaccatagta cgcgcccgt agcggcgcat taagcgcggc gggtgtggtg     4320
gttacgcgca gcgtgaccgc tacacttgcc agcgccttag cgcccgctcc tttcgctttc    4380
ttcccttcct ttctcgccac gttcgccggc ttttcccgtc aagctctaaa tcggggctc     4440
cctttagggt tccgattag tgctttacgg cacctcgacc ccaaaaaact tgatttgggt    4500
gatggttcac gtagtgggcc atcgccctga tagacggttt ttcgcccttt gacgttggag    4560
tccacgttct ttaatagtgg actcttgttc caaactggaa caacactcaa ctctatctcg    4620
ggctattctt ttgatttata agggattttg ccgatttcgg tctattggtt aaaaaatgag    4680
ctgatttaac aaaaatttaa cgcgaatttt aacaaaatat taacgtttac aattttatgg    4740
tgcactctca gtacaatctg ctctgatgcc gcatagttaa gccagccccg acacccgcca    4800
acacccgctg acgcgccctg acgggcttgt ctgctcccgg catccgctta cagacaagct    4860
gtgaccgtct ccgggagctg catgtgtcag aggttttcac cgtcatcacc gaaacgcgcg    4920
agacgaaagg gcctcgtgat acgcctattt ttataggtta atgtcatgat aataatggtt    4980
tcttagacgt caggtggcac ttttcgggga atgtgcgcg gaacccctat tgtttatt      5040
ttctaaatac attcaaatat gtatccgctc atgagacaat aaccctgata aatgcttcaa    5100
taatattgaa aaaggaagag tatgagtatt caacatttcc gtgtcgccct tattccttt     5160
tttgcggcat tttgccttcc tgtttttgct cacccagaaa cgctggtgaa agtaaaagat    5220
gctgaagatc agttgggtgc acgagtgggt tacatcgaac tggatctcaa cagcggtaag    5280
atccttgaga gttttcgccc cgaagaacgt tttccaatga tgagcacttt taaagttctg    5340
ctatgtggcg cggtattatc ccgtattgac gccgggcaag agcaactcgg tcgccgcata    5400
cactattctc agaatgactt ggttgagtac tcaccagtca cagaaaagca tcttacggat    5460
ggcatgacag taagagaatt atgcagtgct gccataacca tgagtgataa cactgcggcc    5520
aacttacttc tgacaacgat cggaggaccg aaggagctaa ccgcttttt gcacaacatg    5580
ggggatcatg taactcgcct tgatcgttgg aaccggagct gaatgaagc cataccaaac    5640
gacgagcgtg acaccacgat gcctgtagca atggcaacaa cgttgcgcaa actattaact    5700
ggcgaactac ttactctagc ttcccggcaa caattaatag actggatgga gcggataaa    5760
gttgcaggac cacttctgcg ctcggccctt ccggctggct ggtttattgc tgataaatct    5820
ggagccggtg agcgtggaag ccgcggtatc attgcagcac tggggccaga tggtaagccc    5880
tcccgtatcg tagttatcta cacgacgggg agtcaggcaa ctatggatga acgaaataga    5940
cagatcgctg agataggtgc ctcactgatt aagcattggt aactgtcaga ccaagtttac    6000
tcatatatac tttagattga ttttaaaactt catttttaat ttaaaggat ctaggtgaag    6060
atccttttg ataatctcat gaccaaaatc ccttaacgtg agttttcgtt ccactgagcg    6120
tcagaccccg tagaaaagat caaaggatct tcttgagatc cttttttct gcgcgtaatc     6180
tgctgcttgc aaacaaaaaa accaccgcta ccagcggtgg tttgtttgcc ggatcaagag    6240
ctaccaactc tttttccgaa ggtaactggc ttcagcagag cgcagatacc aaatactgtt    6300
cttctagtgt agccgtagtt aggccaccac ttcaagaact ctgtagcacc gcctacatac    6360
ctcgctctgc taatcctgtt accagtggct gctgccagtg gcgataagtc gtgtcttacc    6420
gggttggact caagacgata gttaccggat aaggcgcagc ggtcgggctg aacggggggt    6480
tcgtgcacac agcccagctt ggagcgaacg acctacaccg aactgagata cctacagcgt    6540
gagctatgag aaagcgccac gcttcccgaa gggagaaagg cggacaggta tccggtaagc    6600
ggcagggtcg gaacaggaga gcgcacgagg gagcttccag ggggaaacgc ctggtatctt    6660
tatagtcctg tcgggtttcg ccacctctga cttgagcgtc gatttttgtg atgctcgtca    6720
ggggggcgga gcctatggaa aaacgccagc aacgcggcct ttttacggtt cctggccttt    6780
tgctggcctt ttgctcacat gt                                            6802

SEQ ID NO: 73        moltype = DNA   length = 29
FEATURE              Location/Qualifiers
source               1..29
                     mol_type = other DNA
                     organism = synthetic construct
SEQUENCE: 73
tgggtgcagc ctgggaccac ttggcatgg                                       29

SEQ ID NO: 74        moltype = DNA   length = 18
FEATURE              Location/Qualifiers
source               1..18
```

```
                        mol_type = other DNA
                        organism = synthetic construct
SEQUENCE: 74
agaaacgcca ccgcccac                                                    18

SEQ ID NO: 75           moltype = DNA   length = 18
FEATURE                 Location/Qualifiers
source                  1..18
                        mol_type = other DNA
                        organism = synthetic construct
SEQUENCE: 75
gcaaacgcca ccgccgcc                                                    18

SEQ ID NO: 76           moltype = DNA   length = 18
FEATURE                 Location/Qualifiers
source                  1..18
                        mol_type = other DNA
                        organism = synthetic construct
SEQUENCE: 76
agaaagacca agagacac                                                    18

SEQ ID NO: 77           moltype = DNA   length = 18
FEATURE                 Location/Qualifiers
source                  1..18
                        mol_type = other DNA
                        organism = synthetic construct
SEQUENCE: 77
gcaaagacca agagagcc                                                    18

SEQ ID NO: 78           moltype = DNA   length = 18
FEATURE                 Location/Qualifiers
source                  1..18
                        mol_type = other DNA
                        organism = synthetic construct
SEQUENCE: 78
agaaacgacg tggagcac                                                    18

SEQ ID NO: 79           moltype = DNA   length = 18
FEATURE                 Location/Qualifiers
source                  1..18
                        mol_type = other DNA
                        organism = synthetic construct
SEQUENCE: 79
gcaaacgacg tggaggcc                                                    18

SEQ ID NO: 80           moltype = DNA   length = 36
FEATURE                 Location/Qualifiers
source                  1..36
                        mol_type = other DNA
                        organism = synthetic construct
SEQUENCE: 80
ccgcacagtc cctacaggtt tgtagagtca tcttcc                                36

SEQ ID NO: 81           moltype = DNA   length = 36
FEATURE                 Location/Qualifiers
source                  1..36
                        mol_type = other DNA
                        organism = synthetic construct
SEQUENCE: 81
ggaagatgac tctacaaacc tgtagggact gtgcgg                                36

SEQ ID NO: 82           moltype = DNA   length = 36
FEATURE                 Location/Qualifiers
source                  1..36
                        mol_type = other DNA
                        organism = synthetic construct
SEQUENCE: 82
ggtgtacagg gtgcctggat ttgacagggt tacagc                                36

SEQ ID NO: 83           moltype = DNA   length = 36
FEATURE                 Location/Qualifiers
source                  1..36
                        mol_type = other DNA
                        organism = synthetic construct
SEQUENCE: 83
gctgtaaccc tgtcaaatcc aggcaccctg tacacc                                36

SEQ ID NO: 84           moltype = DNA   length = 36
FEATURE                 Location/Qualifiers
```

```
                   source               1..36
                                        mol_type = other DNA
                                        organism = synthetic construct
SEQUENCE: 84
ggtgtacagg gtgcctagat ttgacagggt tacagc                                   36

SEQ ID NO: 85          moltype = DNA   length = 36
FEATURE                Location/Qualifiers
source                 1..36
                                        mol_type = other DNA
                                        organism = synthetic construct
SEQUENCE: 85
gctgtaaccc tgtcaaatct aggcaccctg tacacc                                   36

SEQ ID NO: 86          moltype = DNA   length = 34
FEATURE                Location/Qualifiers
source                 1..34
                                        mol_type = other DNA
                                        organism = synthetic construct
SEQUENCE: 86
ggaagaactc tacaaacctg tagggttctg agac                                     34

SEQ ID NO: 87          moltype = DNA   length = 36
FEATURE                Location/Qualifiers
source                 1..36
                                        mol_type = other DNA
                                        organism = synthetic construct
SEQUENCE: 87
ggaagataac tctacaaacc tgtagagttc tgagac                                   36

SEQ ID NO: 88          moltype = DNA   length = 20
FEATURE                Location/Qualifiers
source                 1..20
                                        mol_type = other DNA
                                        organism = synthetic construct
SEQUENCE: 88
acctccacca tgccaagtgg                                                     20

SEQ ID NO: 89          moltype = DNA   length = 20
FEATURE                Location/Qualifiers
source                 1..20
                                        mol_type = other DNA
                                        organism = synthetic construct
SEQUENCE: 89
cagggtctcg attggatggc                                                     20

SEQ ID NO: 90          moltype = DNA   length = 30
FEATURE                Location/Qualifiers
source                 1..30
                                        mol_type = other DNA
                                        organism = synthetic construct
SEQUENCE: 90
tgccgttctt ctgcttgtcg gccatgatat                                          30

SEQ ID NO: 91          moltype = DNA   length = 7023
FEATURE                Location/Qualifiers
source                 1..7023
                                        mol_type = other DNA
                                        organism = synthetic construct
SEQUENCE: 91
cctgcaggca gctgcgcgct cgctcgctca ctgaggccgc ccgggcgtcg ggcgaccttt           60
ggtcgcccgg cctcagtgag cgagcgagcg cgcagagagg gagtggccaa ctccatcact          120
aggggttcct gcggcctcta gactcgaggc gttgacattg attattgact agttattaat          180
agtaatcaat tacggggtca ttagttcata gcccatatat ggagttccgc gttacataac          240
ttacggtaaa tggcccgcct ggctgaccgc ccaacgaccc ccgcccattg acgtcaataa          300
tgacgtatgt tcccatagta acgccaatag ggactttcca ttgacgtcaa tgggtggagt          360
atttacggta aactgcccac ttggcagtac atcaagtgta tcatatgcca agtacgcccc         420
ctattgacgt caatgacggt aaatggcccg cctggcatta tgcccagtac atgaccttat         480
gggactttcc tacttggcag tacatctacg tattagtcat cgctattacc atggtgatgc         540
ggttttggca gtacatcaat gggcgtggat agcggtttga ctcacgggga tttccaagtc         600
tccaccccat tgacgtcaat gggagtttgt tttggcacca aaatcaacgg gactttccaa         660
aatgtcgtaa caactccgcc ccattgacgc aaatgggcgg taggcgtgta cggtgggagg         720
tctatataag cagagctctc tggctaacta ccggtgccac catgccggca gctaagaaaa         780
agaaactgga tggcagcgtc gacatcgaga gaaaaaatc ctttgctaag ggcatgggcg         840
ttaagagcac tctggtgtca ggctctaaag tgtacatgaa gcacattgcc gagggctctg         900
atgctcgcct ggaaaaaatt gtggaaggag actcaatcag atccgtgaac gaggggaggg         960
ccttcagcgc cgagatggcc gacaagaatg ccggatataa gattgaaaac gctaagttca        1020
gccatcccaa gggatacgcc gtggtcgcca acaatcctct gtacactgga cctgtgcagc        1080
aggacatgtt aggtctgaag gagactctgg agaagaggta cttcggcgag tccgcagatg        1140
```

```
gcaacgacaa catttgcatt caggtgatcc ataacatcct ggacattgag aagatcctgg    1200
ccgagtatat caccaacgca gcctacgctg tgaataatat atctggtctg gataaggata    1260
tcattgggtt cgggaaattt tctaccgtgt acacctacga tgagtttaaa gaccccgagc    1320
accacagagc cgccttcaac aacaacgaca agctgatcaa tgccattaag gcacagtacg    1380
atgagttcga caattttctg gacaaccccc ggctgggcta cttcggccag gcttttttt    1440
ctaaggaagg ccgcaattac atcatcaact acggcaacga gtgctatgac attctggccc    1500
ttctgagcgg cctgaggcat tgggtggtgc ataacaacga gaggaatcc cgcatctcaa     1560
gaacatggct gtacaatctc gacaaaaacc tggacaatga gtacatttcc actctgaact    1620
atctgtacga caggatcacg aatgagctga ccaattcctt ttccaagaat agcgccgcca    1680
atgtgaacta catcgccgaa accctgggga tcaatcccgc cgagttcgcc gagcagtatt    1740
ttcgattcag catcatgaaa gagcagaaaa atctgggctt taatatcacc aaactgagag    1800
aagtgatgct ggacaggaag gatatgtctg agatcaggaa gaaccacaag gtgttcgaca    1860
gtatcagaac caaggtgtat acaatgatgg atttcgtgat ctataggtac tacattgagg    1920
aggacgccaa ggtggccgcc gccaacaaat ccctgcagaa tcccgagaag teectgtctg    1980
agaaggatat cttcgtcatc aacctgaggg gcagcttcaa tgatgaccag aaggacgctc    2040
tttactacga cgaagccaac cggatctggc ggaagctgga aaacatcatg cacaacatca    2100
aggagttccg cgggaacaaa acgggagt acaagaaaaa agacgctccc agactgccca     2160
gaatcctgcc tgcaggcagg gatgtgagcg cattctccaa gctgatgtac gccctgacaa    2220
tgttcctgga tggcaaggaa atcaacgacc tgctgaccac tctgatcaac aagtttgata    2280
acattcagag cttctctgaaa gtgatgcccc tgatcggagt gaatgcaaaa ttcgtcgaag    2340
aatacgcttt cttcaaggat tctgctaaaa tcgccgacga gctgaggctg attaagtcct    2400
ttgcaaggat ggggagcca atcgccgacg ccagaagagc catgtatatt gatgctatca    2460
gaatcctggg caccaatctg tcctatacg aactgaaggc cctggctgac acattttctc     2520
tggatgagaa tggtaacaag ctgaagaagg ggaagcacgg catgcgaaac tttattatta    2580
acaatgttat ctctaataag aggttccatt atctgattcg ctacggcgac cccgcccatt    2640
tgcacgagat cgccaagaat gaagccgtgg tgaagttcgt cctgggacgg atcgccgaca    2700
tccagaaaaa gcagggccag aatggcaaaa accagatcga cagatattat gagacttgca    2760
tcggcaagga taagggtaaa agtgtctccg agaaagtgga tgccctgact aagatcatta    2820
cggggatgaa ttacgaccag tttgacaaaa agaggagcgt gatcgaggac accggcagag    2880
agaatgccga gcgggagaag tttaagaaga tcatcagcct gtatctgacc gtgatttacc    2940
atatcctgaa gaatatcgtg aatatcaatg ccagatacgt gatcggcttc cactgcgtgg    3000
aaagagacgc ccagctctac aaagagaaag gctacgacat caatctgaag aagctggagg    3060
aaaagggctt tagcagcgtg acaaaactgt gtgcaggaat cgacgagact gcccctgaca    3120
agaggaagga cgtggagaaa gagatggccg aacgcgccaa ggagtctatc gactccctgg    3180
agtccgccaa ccccaagctg tacgccaact acatcaagta tagcgacgag aagaaggcag    3240
aagagttcac ccggcagatc aatagagaga aggccaaaac cgcactgaat gcctatctga    3300
ggaatacaaa gtgaacgtg attattagag aagatctgct gaggattgac aataagacct    3360
gtaccctatt caggaacaag gccgtgcatc tggaggtggc caggtacgtg catgcctata    3420
ttaatgatat agctgaagtc aactcctatt tccagctgta tcattcatc atgcagcgta    3480
ttattatgaa cgaaagatat gaaaagagct ccggcaaagt gtctgagtac ttcgatgccg    3540
tgaacgacga aaaaagtac aatgatcgcc tgctgaagct gctgtgtgtg cccttcgggt    3600
actgtatccc cagatttaag aatctgtcca ttgaagccct gttcgataga aacgaagccg    3660
ccaaattcga caaggataag aagaaggtga gcggcaatag tacaggcggc ggcccgggca    3720
gcggcgccgc cgccggcagc ggcagcccta agaaaaaaacg aaaagttggc agcggaagca    3780
aaaggccggc ggccacgaaa aaggccggcc aggcaaaaaa gaaaaagctc gagtacccat    3840
acgatgttcc agattacgct tgagaattcc ccttgagcat ctgacttctg gctaataaag    3900
gaaatttatt ttcattgcaa tagtgtgttg gaatttttg tgtctctcag gtaccgaggg    3960
cctatttccc atgattcctt catatttgca tatacgatac aaggctgtta gagagataat    4020
tggaattaat ttgactgtaa acacaaagat attagtacaa aatacgtgac gtagaaagta    4080
ataatttctt gggtagttg cagttttaaa attatgtttt aaaatggact atcatatgct    4140
taccgtaact tgaaagtatt tcgatttctt ggctttatat atcttgtgga aaggacgaaa    4200
caccgcaagt aaaccctac caactggtcg gggtttgaaa cgtggttgga gaactggatg    4260
tagatgggct gttttttgcg gccgcaggaa ccctagtga tggagttggc cactccctct    4320
ctgcgcgctc gctcgctcac tgaggccggg cgaccaaagg tcgcccgacg cccgggcttt    4380
gcccggcgg cctcagtgag cgagcgagcg cgcagctgcc tgcagggggg cctgatgcgg    4440
tattttctcc ttacgcatct gtgcggtatt tcacaccgca tacgtcaaag caaccatagt    4500
acgcgccctg tagcggcgca ttaagcgcgg cgggtgtggt ggttacgcgc agcgtgaccg    4560
ctacacttgc cagcgcctta gcgcccgctc ctttcgcttt cttcccttcc tttctcgcca    4620
cgttccgccg ctttccccgt caagctctaa atcgggggct ccctttaggg ttccgattta    4680
gtgctttacg gcacctcgac cccaaaaaac ttgatttggg tgatggttca cgtagtgggc    4740
catcgccctg atagacggtt tttcgccctt tgacgttgga gtccacgttc tttaatagtg    4800
gactcttgtt ccaaactgga acaacactca actctatctc gggctattct tttgatttat    4860
aagggatttt gccgatttcg gtctattggt taaaaaatga gctgatttaa caaaaattta    4920
acgcgaattt taacaaaata ttaacgttta caatttatg gtgcactctc agtacaatct    4980
gctctgatgc cgcatagtta agccagcccc gacacccgcc aacacccgct gacgcgccct    5040
gacgggcttg tctgctcccg gcatccgctt acagacaagc tgtgaccgtc tccgggagct    5100
gcatgtgtca gaggttttca ccgtcatcac cgaaacgcgc gagacgaaag gcctcgtga    5160
tacgcctatt tttataggtt aatgtcatga taataatggt ttcttagacg tcaggtggca    5220
cttttcgggg aaatgtgcgc ggaaccccta tttgtttatt tttctaaata cattcaaata    5280
tgtatccgct catgagacaa taaccctgat aaatgcttca ataatattga aaaaggaaga    5340
gtatgagtat tcaacatttc cgtgtcgccc ttattccctt ttttgcggca ttttgccttc    5400
ctgttttgc tcacccagaa acgctggtga agtaaaaga tgctgaagat cagttgggtg    5460
cacgagtggg ttacatcgaa ctggatctca acagcggtaa gatccttgag agttttcgcc    5520
ccgaagaacg ttttccaatg atgagcactt taaagttctg ctatgtggcg cggtattat    5580
cccgtattga cgccgggcaa gagcaactcg gtcgccgcat acactattct cagaatgact    5640
tggttgagta ctcaccagtc acagaaaagc atcttacgga tggcatgaca gtaagagaat    5700
tatgcagtgc tgccataacc atgagtgata acactgcggc caacttactt ctgacaacga    5760
tcggaggacc gaaggagcta accgcttttt tgcacaacat ggggggatcat gtaactcgcc    5820
ttgatcgttg ggaaccggag ctgaatgaag ccataccaaa cgacgagcgt gacaccacga    5880
```

```
tgcctgtagc aatggcaaca acgttgcgca aactattaac tggcgaacta cttactctag 5940
cttcccggca acaattaata gactggatgg aggcggataa agttgcagga ccacttctgc 6000
gctcggccct tccggctggc tggtttattg ctgataaatc tggagccggt gagcgtggaa 6060
gccgcggtat cattgcagca ctggggccag atggtaagcc ctcccgtatc gtagttatct 6120
acacgacggg gagtcaggca actatggatg aacgaaatag acagatcgct gagataggtg 6180
cctcactgat taagcattgg taactgtcag accaagttta ctcatatata ctttagattg 6240
atttaaaact tcatttttaa tttaaaagga tctaggtgaa gatccttttt gataatctca 6300
tgaccaaaat cccttaacgt gagttttcgt tccactgagc gtcagacccc gtagaaaaga 6360
tcaaaggatc ttcttgagat cctttttttc tgcgcgtaat ctgctgcttg caaacaaaaa 6420
aaccaccgct accagcggtg gtttgtttgc cggatcaaga gctaccaact cttttttccga 6480
aggtaactgg cttcagcaga gcgcagatac caaatactgt tcttctagtg tagccgtagt 6540
taggccacca cttcaagaac tctgtagcac cgcctacata cctcgctctg ctaatcctgt 6600
taccagtggc tgctgccagt ggcgataagt cgtgtcttac cgggttggac tcaagacgat 6660
agttaccgga taaggcgcag cggtcgggct gaacggggg ttcgtgcaca cagcccagct 6720
tggagcgaac gacctacacc gaactgagat acctacagcg tgagctatga aaagcgcca 6780
cgcttcccga agggagaaag gcggacaggt atccggtaag cggcagggtc ggaacaggag 6840
agcgcacgag ggagcttcca gggggaaacg cctggtatct ttatagtcct gtcgggtttc 6900
gccacctctg acttgagcgt cgatttttgt gatgctcgtc aggggggcgg agcctatgga 6960
aaaacgccag caacgcggcc tttttacggt tcctggcctt ttgctggcct tttgctcaca 7020
tgt                                                                  7023

SEQ ID NO: 92      moltype = DNA    length = 7394
FEATURE            Location/Qualifiers
source             1..7394
                   mol_type = other DNA
                   organism = synthetic construct
SEQUENCE: 92
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgaggc gttgacattg attattgact agttattaat 180
agtaatcaat tacggggtca ttagttcata gcccatatat ggagttccgc gttacataac 240
ttacggtaaa tggcccgcct ggctgaccgc ccaacgaccc ccgcccattg acgtcaataa 300
tgacgtatgt tcccatagta acgccaatag ggactttcca ttgacgtcaa tgggtggagt 360
atttacggta aactgcccac ttggcagtac atcaagtgta tcatatgcca agtacgcccc 420
ctattgacgt caatgacggt aaatggcccg cctggcatta tgcccagtac atgaccttat 480
gggactttcc tacttggcag tacatctacg tattagtcat cgctattacc atggtgatgc 540
ggttttggca gtacatcaat gggcgtggat agcggtttga ctcacgggga tttccaagtc 600
tccaccccat tgacgtcaat gggagtttgt tttggcacca aaatcaacgg gactttccaa 660
aatgtcgtaa caactccgcc ccattgacgc aaatgggcgg taggcgtgta cggtgggagg 720
tctatataag cagagctctc tggctaacta ccggtgccac catgccggca gctaagaaaa 780
agaaactgga tggcagcgtc gacatgaaca tccccgctct ggtggaaaac cagaagaagt 840
actttggcac ctacagcgtg atggccatgc tgaacgctca ccgtgctg gaccacatcc 900
agaaggtggc cgatattgag ggcgagcaga acagaaacaa cgagaatctg tggtttcaat 960
ccgtgatgag ccacctgtac aacgccaaga acggctacga caagcagccc gagaaaacca 1020
tgttcatcat cgagcggctg cagagctact tcccattcct gaagatcatg gccgagaacc 1080
agagagagta cagcaacggc aagtacaagc agaaccgcgt ggaagtgaac agcaacgaca 1140
tcttcgaggt gctgaagcgc gccttcggcg tgctgaagat gtacagggac ctgaccaacc 1200
actacaagac ctacgaggaa aagctgaacg acggctgcga gttcctgacc agcacagagc 1260
aacctctgag cggcatgatc aacaactact acacagtggc cctgcggaac atgaacgaga 1320
gatacgcta aagacagag gacctggcct tcatccagga caagcggttc aagttcgtga 1380
aggacgtca cggcaagaaa agtcccaag tgaataccgg attcttcctg agcctgcaga 1440
actacaacgg cgacacacag aagaagctgc acctgagcgg agtgggaatc gccctgctga 1500
tctgcctgtt cctggacaag cagtacatca acatctttct gagcaggctg cccatcttct 1560
ccagctacaa tgcccagagc gaggaacggc ggatcatcat cagatcctc ggcatcaaca 1620
gcatcaagct gcccaaggac cggatccaca gcgagaagtc caacaagagc gtggccatgg 1680
atatgctcaa cgaagtgaag cggtgccccg acgagctgtt cacaacactg tctgccgaga 1740
agcagtcccg gttcagaatc atcagcgacg accacaatga agtgctgatg aagcggagca 1800
gcgacagatt cgtgcctctg ctgctgcagt atatcgatta cggcaagctg ttcgaccaca 1860
tcaggttcca cgtgaacatg ggcaagctga gatacctgct gaaggccgac aagacctgca 1920
tcgacggcca gaccagagtc agagtgatcg agcagccct gaacggcttc ggcagactgg 1980
aagaggccga gacaatgcgg aagcaagaga cggcaccttc ggcaacagc ggcatccgga 2040
tcagagactt cgaaacatg aagcgggacg acgccaatcc tgccaactat ccctacatcg 2100
tggcaccta cacacactac atcctggaaa acaacaaggt cgagatgttt atcaacgaca 2160
aagaggacag cgccccactg ctgccgtga tcagggata tagatacgtg gtcaagacaa 2220
tccccagctg ccggatgagc acctggaaa ttcagccat ggccttccac atgtttctgt 2280
tcggcagcaa gaaaaccgag aagctgatcg tggacgtgca caaccggtac aagagactgt 2340
tccaggccat gcagaaagaa gaagtgaccg ccgagaatat cgccagcttc ggaatcgccg 2400
agagcgacct gcctcagaag atcctggatc tgatcagcgg caatgccaca ggcaaggatg 2460
tggcgcctt catcagactg accgtggacg acatgtggcg cgacaccgag cggagaatca 2520
agagattcaa ggacgaccgg aagtccattc tggacgccga caacaagatg ggaaagagag 2580
gcttcaagca gatctccaca ggcaagctgg ccgacttcct ggcaaggac atcgtgctgt 2640
tcagcccca cgtgaacgat ggcgagaaca gatcaccgg cctgaactac cggatcatgc 2700
agagcgccat tgccgtgtac gatagcggcg acgattacga ggcaagcag cagttcaagc 2760
tgtattcga gaaggcccgg ctgatcgata aggggcacaac agagcctcat ccatttctga 2820
acaaggtgtt cgcccgcagc atccccgcca atgccgtcga gttctacgag cgctacctcg 2880
tcgagcggaa gttctacctg accggcctgt ccaacgagat caagaaaggc aacagagtgg 2940
atgtgccctt catccggcgg gaccagaaca gtggaaaac accgccatg aagaccctgg 3000
gcagaatcta cagcgaggat ctgccgtgg aactgccag acagatgttc gacaatgaga 3060
tcaagtccca cctgaagtcc ctgccacaga tggaagcat cgacttcaac aatgccaacg 3120
```

```
tgacctatct gatcgccgag tacatgaaga gagtgctgga cgacgacttc cagaccttct 3180
accagtggaa ccgcaactac cggtacatgg acatgcttaa gggcgagtac gacagaaagg 3240
gctccctgca gcactgcttc accagcgtgg aagagagaga aggcctctgg aaagagcggg 3300
cctccagaac agagcggtac agaaagcagg ccagcaacaa gatccgcagc aaccggcaga 3360
tgagaacgc cagcagcgaa gagatcgaga caatcctgga taagcgcttc agcaacagcc 3420
ggaacgagta ccagaaaagc gagaaagtga tccggcgcta cagagtgcag gatgccctgc 3480
tgtttctgct ggccaaaaag accctgaccg aactggccga tttcgacggc gagaggttca 3540
aactgaaaga aatcatgccc gacgccgaga agggaatcct gagcgagatc atgcccatga 3600
gcttcacctt cgagaaaggc ggcaagaagt acaccatcac cagcgaggc atgaagctga 3660
agaactacgg cgacttcttt gtgctggcta gcgacaagag gatcggcaac ctgctggaac 3720
tcgtgggcag cgacatcgtg tccaaagagg atatcatgga agagttcaac aaatacgacc 3780
agtgcaggcc cgagatcagc tccatcgtgt tcaacctgga aaagtgggcc ttcgacacat 3840
accccgagct gtctgccaga gtggaccggg aagagaaggt ggacttcaag agcatcctga 3900
aaatcctgct gaacaacaag aacatcaaca aagacgagc cgacatcctg cggaagatcc 3960
ggaacgcctt cgatcacaac aattaccccg acaaaggcgc ggtggaaatc aaggccctgc 4020
ctgagatcgc catgagcatc aagaaggcct tggggagta cgccatcatg aagacaggcg 4080
gcggcccccgg cggcggcgcc gccgccggca gcggcagccc taagaaaaaa cgaaaagttg 4140
gcagcggaag caaaaggccg gcggccacga aaaaggccgg ccaggcaaaa aagaaaaagc 4200
tcgagtaccc atacgatgtt ccagattacg cttgagaatt cccccttgagc atctgacttc 4260
tggctaataa aggaaattta ttttcattgc aatagtgtgt tggaattttt tgtgtctctc 4320
aggtaccgag ggcctatttc ccatgattcc ttcatatttg catatacgat acaaggctgt 4380
tagagagata attggaatta atttgactgt aaacacaaga atattagtac aaaatacgtg 4440
acgtagaaag taataatttc ttgggtagtt tgcagtttta aaattatgtt ttaaaatgga 4500
ctatcatatg cttaccgtaa cttgaaagta tttcgatttc ttggctttat atatcttgtg 4560
gaaaggacga aacaccgtgg ttggagaact ggatgtagat gggctggttg tggaaggtcc 4620
agttttgagg ggctattaca acttttttgg ggccgcagga acccctagtg atggagttgg 4680
ccactcccc tctgcgcgct cgctcgctca ctgaggccgg gcgaccaaag gtcgcccgac 4740
gcccgggctt tgcccgggcg gcctcagtga gcgagcgagc gcgcagctgc ctgcagggc 4800
gcctgatgcg gtattttctc cttacgcatc tgtgcggtat ttcacaccgc atacgtcaaa 4860
gcaaccatag tacgcgccct gtagcgcgc attaagcgcg gcgggtgtgg tggttacgcg 4920
cagcgtgacc gctacacttg ccagcgcctt agcgcccgct cctttcgctt tcttccctttc 4980
ctttctcgcc acgttcgccg gctttccccg tcaagctcta aatcggggc tccctttagg 5040
gttccgattt agtgctttac ggcacctcga ccccaaaaaa cttgatttgg gtgatggttc 5100
acgtagtggg ccatcgccct gatagacggt ttttcgccct ttgacgttgg agtccacgtt 5160
ctttaatagt ggactcttgt tccaaactgg aacaacactc aactctatct cgggctattc 5220
ttttgattta aagggatttt tgccgatttc ggtctattgg ttaaaaaatg agctgattta 5280
acaaaaattt aacgcgaatt ttaacaaaat attaacgttt acaattttat ggtgcactct 5340
cagtacaatc tgctctgatg ccgcatagtt aagccagccc cgacacccgc caacacccgc 5400
tgacgcgccc tgacgggctt gtctgctccc ggcatccgct tacagacaag ctgtgaccgt 5460
ctccgggagc tgcatgtgtc agaggttttc accgtcatca ccgaaacgcg cgagacgaaa 5520
gggcctcgtg atacgcctat ttttataggt taatgtcatg ataataatgg tttcttagac 5580
gtcaggtggc acttttcggg gaaatgtgcg cggaacccct atttgtttat ttttctaaat 5640
acattcaaat atgtatccgc tcatgagaca ataaccctga taaatgcttc aataatattg 5700
aaaaaggaag agtatgagta ttcaacattt ccgtgtcgcc cttattccct tttttgcggc 5760
attttgcctt cctgttttt ctcacccaga aacgctggtg aaagtaaaag atgctgaaga 5820
tcagttgggt gcacgagtgg gttacatcga actggatctc aacagcggta agatccttga 5880
gagttttcgc cccgaagaac gttttccaat gatgagcact tttaaagttc tgctatgtgg 5940
cgcggtatta tcccgtattg acgccgggca agagcaactc ggtcgccgca tacactattc 6000
tcagaatgac ttggttgagt actcaccagt cacagaaaag catcttacgg atggcatgac 6060
agtaagagaa ttatgcagtg ctgccataac catgagtgat aacactgcgg ccaacttact 6120
tctgacaacg atcggaggac cgaaggagct aaccgctttt ttgcacaaca tgggggatca 6180
tgtaactcgc cttgatcgtt gggaaccgga gctgaatgaa gccataccaa acgacgagc 6240
tgacaccacg atgcctgtag caatggcaac aacgttgcgc aaactattaa ctggcgaact 6300
acttactcta gcttcccggc aacaattaat agactggatg gaggcggata agttgcagg 6360
accacttctg cgctcggccc ttccggctgg ctggtttatt gctgataaat ctggagccgg 6420
tgagcgtgga agccgcggta tcattgcagc actggggcca gatggtaagc cctcccgtat 6480
cgtagttatc tacacgacgg ggagtcaggc aactatggat gaacgaaata gacagatcgc 6540
tgagataggt gcctcactga ttaagcattg gtaactgtca gaccaagttt actcatatat 6600
actttagatt gatttaaaac ttcattttta atttaaaagg atctaggtga agatcctttt 6660
tgataatctc atgaccaaaa tcccttaacg tgagttttcg ttccactgag cgtcagaccc 6720
cgtagaaaag atcaaaggat cttcttgaga tcctttttt ctgcgcgtaa tctgctgctt 6780
gcaaacaaaa aaaccaccgc taccagcggt ggtttgtttg ccggatcaag agctaccaac 6840
tcttttccg aaggtaactg gcttcagcag agcgcagata ccaaatactg ttcttctagt 6900
gtagccgtag ttaggccacc acttcaagaa ctctgtagca ccgcctacat acctcgctct 6960
gctaatcctg ttaccagtgg ctgctgccag tggcgataag tcgtgtctta ccgggttgga 7020
ctcaagacga tagttaccgg ataaggcgca gcggtcgggc tgaacggggg gttcgtgcac 7080
acagcccagc ttggagcgaa cgacctacac cgaactgaga tacctacagc gtgagctatg 7140
agaaagcgcc acgcttcccg aagggagaaa ggcggacagg tatccggtaa gcggcagggt 7200
cggaacagga gagcgcacga gggagcttcc agggggaaac gcctggtatc tttatagtcc 7260
tgtcgggttt cgccacctct gacttgagcg tcgattttg tgatgctcgt caggggggcg 7320
gagcctatgg aaaaacgcca gcaacgcggc cttttacgg ttcctggcct tttgctggcc 7380
ttttgctcac atgt                                                   7394

SEQ ID NO: 93       moltype = DNA   length = 6447
FEATURE             Location/Qualifiers
source              1..6447
                    mol_type = other DNA
                    organism = synthetic construct
SEQUENCE: 93
```

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccgcca gctaagaaaa   780
agaaactgga tggcagcgtc gacgcccagg tgtccaaaca gaccagcaag aaaagggaac   840
tgagcatcga tgagtaccag ggtgctagaa agtggtgctt cacaatcgcc tttaacaaag   900
ctctggtcaa tagggataaa aacgatggcc tcttcgtgga gtccctgctg agacacgaga   960
agtacagcaa acacgactgg tacgacgagg ataccagagc cctgatcaag tgctccactc  1020
aggccgccaa tgcaaaggcc gaggtctcga gaaattattt cagccactac cggcactccc  1080
ccgggtgtct gaccttcact gcagaggatg agcttaggac aattatggag cgcgcctacg  1140
agagggccat ttttgagtgt cggcgaagag aaactgaggt gatcatcgag tttccatctc  1200
tgtttgaagg ggaccgcatc acaaccgccg gagtggtatt ttttgtgagt ttcttcgtgg  1260
aacggagagt gctggaccgg ctgtacgaggg cagttagtgg cctgaagaag acgagggggc  1320
agtacaagct gacaaggaaa gctctgagca tgtactgtct gaaagattcc agatttacaa  1380
aggcatggga taagagagtg ctcctctttc gcgatatcct ggcccagctg ggcagaatcc  1440
cagctgaggc ttacgagtac taccacgcg aacagggcga caaaagagg gccaacgaca  1500
atgagggcac caaccccaaa aggcacaagg ataagtttat tgagtttgca ctgcactacc  1560
tggaggccca gcactctgag atctgctttg gcagaaggca catcgtgaga gaggaagctg  1620
gcgccggcga tgagcacaag aagcacagaa ccaaagggaa ggtggtggtg gacttctcca  1680
agaaggatga ggatcagtct tactacatca gtaagaacaa cgtgattgtg aggatcgata  1740
agaatgccgg ccctcgctcc taccgcatgg ggctcaatga actgaagtac ctggtcctgc  1800
tctctctgca ggggaagggc gatgacgcta tcgccaagct gtataggtat cggcagcatg  1860
tggagaacat tctggacgtg gtgaaggtga ctgataaaga taaccacgtg ttcctgccaa  1920
ggtttgtgct cgaacagcac ggaatcggcc ggaaggcctt caagcagaga attgacgggc  1980
gcgtgaaaca tgtgcgcggg gtgtgggaaa agaagaaggc cgccacaaac gagatgacgc  2040
tgcacgagaa ggcccgcgac atcctccagt acgtgaatga gaattgcact cgcagcttca  2100
atcctggcga gtataacagg ctgctggtgt gcctggtggg taaagactgt gagaacttcc  2160
aggccggcct gaagcggctt cagctggctg agagaattga cggccgggtg tattctatct  2220
tcgcccagac ttctaccatc aatgaaatgc caaggtggt gtgtgaccag atcctcaatc  2280
ggctgtctcg aattgggat cagaagctgt acgactatgt gggcctgggc aagaaagatg  2340
agatcgacta taaacagaaa gtggcttggt tcaaagagca catcagtatc agacgcggct  2400
ttctgaggaa gaaattctgg tacgactcta aaaaggcctt cgctaagctg gtggaggagc  2460
acctggaatc cggaggcgga cagcgggatg tggggctgga taagaaatac taccacatcg  2520
atgccatcgg gagattcgag ggcgccaatc ctgtctgta cgaaaccctg gccagggaca  2580
ggctgtgcct gatgatggcc cagtactttc tgggctccac tcgcaaagag ctgggaaaca  2640
aaattgtgtg gagcaacgac tccatagagc tgccggtgga gggatctgtc gggaatgaaa  2700
aatcgatcgt gttctctgtg agcgattatg aaaactgta cgtcctggac gatgccagt  2760
ttctgggtag aatctgtgag tattttatgc cacatgaaaga cgaagatc agataccaca  2820
ccgtgtatga aaaggggttc agagcctaca cgacctgca gaaaaaatgc gtggaggccg  2880
tgctggcatt cgaagagaag gtggtgaagg ccaagaaaat gtctgagaaa gagggagccc  2940
actacatcga ctttcgcgag atcctggccc agaccatgtg caaggaagct gaaagacag  3000
ccgtcaataa ggtgagagg gccttctttc accacacct caattcgtg atcgacaatt  3060
ttggcctgtt cagcgatgtg atgaaaaaat acgcatcga gaaggagtgg aagtttccag  3120
tgaaaacagg cggcggcccc ggcggcgcg ccgccgccgg cagcggcagc cctaagaaaa  3180
aacgaaaagt tggcagcgga agcaaaaggc cggcggccac gaaaagggcc ggccaggcaa  3240
aaaagaaaaa gctcgagtac ccatacgatg ttccagatta cgcttgagaa ttcccccttga  3300
gcatctgact tctggctaat aaaggaaatt tattttcatt gcaatagtgt gttggaattt  3360
tttgtgtctc tcaggtaccg agggcctatt tcccatgatt ccttcatatt tgcatatacg  3420
atacaaggct gttagagaga taattggaat taatttgact gtaaacacaa agatattagt  3480
acaaatacg tgacgtagaa agtaataatt tcttgggtag tttgcagttt taaaattatg  3540
ttttaaaatg gactatcata tgcttaccgt aacttgaaag tatttcgatt tcttggcttt  3600
atatatcttg tggaaaggac gaaacaccgg tggttgaga actggatgta gatgggctgg  3660
ctggagcagc cccgatttg tggggtgatt acagcttttt tgcggccgca ggaacccta  3720
gtgatggagt tggccactcc ctctctgcgc gctcgctcgc tcactgaggc cgggcgacca  3780
aaggtcgccc gacgcccggg ctttgcccgg gcggcctcag tgagcgagcg agcgcgcag  3840
tgcctgcagg ggcgcctgat gcggtatttt ctccttacgc atctgtgcgg tatttcacac  3900
cgcatacgtc aaagcaacca tagtacgcgc cctgtagcgg cgcattaagc gcggcgggtg  3960
tggtggttac gcgcagcgtg accgctacac ttgccagcgc cttagcgccc gctcctttcg  4020
ctttcttccc ttcctttctc gccacgttcg ccggctttcc ccgtcaagct ctaaatcggg  4080
ggctcccttt agggttccga tttagtgctt tacggcacct cgaccccaaa aaacttgatt  4140
tgggtgatgg ttcacgtagt gggccatcgc cctgatagac ggtttttcgc cctttgacgt  4200
tggagtccac gttctttaat agtggactct tgttccaaac tggaacaaca ctcaactcta  4260
tctcgggcta ttcttttgat ttataaggga ttttgccgat ttcggtctat tggttaaaaa  4320
atgagctgat ttaacaaaaa tttaacgcga attttaacaa aatattaacg tttacaattt  4380
tatggtgcac tctcagtaca atctgctctg atgccgcata gttaagccag ttacgtacc  4440
cgccaacacc cgctgacgcg ccctgacggg cttgtctgct cccggcatcc gcttacagac  4500
aagctgtgac cgtctccggg agctgcatgt gtcagaggtt ttcaccgtca tcaccgaaac  4560
gcgcgagacg aaagggcctc gtgatacgcc tatttttata ggttaatgtc atgataataa  4620
tggtttctta gacgtcaggt ggcacttttc ggggaaatgt gcgcggaacc cctatttgtt  4680
tattttcta aatacattca aatatgtatc cgctcatgag acaataaccc tgataaatgc  4740
```

```
ttcaataata ttgaaaaagg aagagtatga gtattcaaca tttccgtgtc gcccttattc  4800
cctttttttgc ggcattttgc cttcctgttt ttgctcaccc agaaacgctg gtgaaagtaa  4860
aagatgctga agatcagttg ggtgcacgag tgggttacat cgaactggat ctcaacagcg  4920
gtaagatcct tgagagtttt cgccccgaag aacgttttcc aatgatgagc acttttaaag  4980
ttctgctatg tggcgcggta ttatcccgta ttgacgccgg gcaagagcaa ctcggtcgcg  5040
gcatacacta ttctcagaat gacttggttg agtactcacc agtcacagaa aagcatctta  5100
cggatggcat gacagtaaga gaattatgca gtgctgccat aaccatgagt gataacactg  5160
cggccaactt acttctgaca acgatcggag gaccgaagga gctaaccgct ttttttgcaca  5220
acatggggga tcatgtaact cgccttgatc gttgggaacc ggagctgaat gaagccatac  5280
caaacgacga gcgtgacacc acgatgcctg tagcaatggc aacaacgttg cgcaaactat  5340
taactggcga actacttact ctagcttccc ggcaacaatt aatagactgg atggaggcgg  5400
ataaagttgc aggaccactt ctgcgctcgg cccttccggc tggctggttt attgctgata  5460
aatctggagc cggtgagcgt ggaagccgcg gtatcattgc agcactgggg ccagatggta  5520
agccctcccg tatcgtagtt atctacacga cggggagtca ggcaactatg gatgaacgaa  5580
atagacagat cgctgagata ggtgcctcac tgattaagca ttggtaactg tcagaccaag  5640
tttactcata tatactttag attgatttaa aacttcattt ttaatttaaa aggatctagg  5700
tgaagatcct tttttgataat ctcatgacca aaatccctta acgtgagttt tcgttccact  5760
gagcgtcaga ccccgtagaa aagatcaaag gatcttcttg agatcctttt tttctgcgcg  5820
taatctgctg cttgcaaaca aaaaaaccac cgctaccagc ggtggtttgt ttgccggatc  5880
aagagctacc aactcttttt ccgaaggtaa ctggcttcag cagagcgcag ataccaaata  5940
ctgttcttct agtgtagccg tagttaggcc accacttcaa gaactctgta gcaccgccta  6000
catacctcgc tctgctaatc ctgttaccag tggctgctgc cagtggcgat aagtcgtgtc  6060
ttaccgggtt ggactcaaga cgatagttac cggataaggc gcagcggtcg ggctgaacgg  6120
ggggttcgtg cacacagccc agcttggagc gaacgaccta caccgaactg agatacctac  6180
agcgtgagct atgagaaagc gccacgcttc ccgaagggag aaaggcggac aggtatccgg  6240
taagcggcag ggtcggaaca ggagagcgca cgagggagct tccagggggga aacgcctggt  6300
atctttatag tcctgtcggg tttcgccacc tctgacttga gcgtcgattt ttgtgatgct  6360
cgtcaggggg gcggagccta tggaaaaacg ccagcaacgc ggcctttttta cggttcctgg  6420
ccttttgctg gccttttgct cacatgt                                       6447

SEQ ID NO: 94           moltype = DNA  length = 6492
FEATURE                 Location/Qualifiers
source                  1..6492
                        mol_type = other DNA
                        organism = synthetic construct
SEQUENCE: 94
cctgcaggca gctgcgcgct cgctcgctca ctgaggccgc ccgggcgtcg ggcgaccttt    60
ggtcgcccgg cctcagtgag cgagcgagcg cgcagagagg gagttggcca actccatcact  120
aggggttcct gcggcctcta gactcgaggc gttgacattg attattgact agttattaat  180
agtaatcaat tacggggtca ttagttcata gcccatatat ggagttccgc gttacataac  240
ttacggtaaa tggcccgcct ggctgaccgc ccaacgaccc ccgcccattg acgtcaataa  300
tgacgtatgt tcccatagta acgccaatag ggactttcca ttgacgtcaa tgggtggagt  360
atttacggta aactgcccac ttggcagtac atcaagtgta tcatatgcca agtacgcccc  420
ctattgacgt caatgacggt aaatggcccg cctggcatta tgcccagtac atgaccttat  480
gggactttcc tacttggcag tacatctacg tattagtcat cgctattacc atggtgatgc  540
ggttttggca gtacatcaat gggcgtggat agcggtttga ctcacgggga tttccaagtc  600
tccaccccat tgacgtcaat gggagttttgt tttggcacca aaatcaacgg gactttccaa  660
aatgtcgtaa caactccgcc ccattgacgc aaatgggcgg taggcgtgta cggtgggagg  720
tctatataag cagagctctc tggctaacta ccggtgccac catgccggca gctaagaaaa  780
agaaactgga tggcagcgtc gacaatggca tcgagctcaa aaaggaggaa gccgcatttt  840
atttcaacca ggcagaactc aatctgaagg ctattgaagga taatatcttc gacaaggaga  900
gaagaaagac cctgctgaat aaccctcaga ttctggccaa gatggaaaat tttatttta   960
actttagaga cgtgaccaag aacgccaagg gcgaaatcga ctgcctgctc ctgaagctgc  1020
gggagctgag aaatttctac tcacattatg tgcacaaaag gatgtgagg gaactgagca  1080
aggggagaa gccaattctg gagaagtatt atcagttttgc catcgagtct actggctctg  1140
agaacgtgaa actggagatc attgaaacg acgcctggct ggcagacgcc ggggtgctgt  1200
ttttttctgtg catcttcctg aaaaagtccc aggcgaacaa gttgatcagc ggcatctctg  1260
gtttttaagag aaacgacgat accggccaac ctcgcagaaa cctgttcact tatttcagca  1320
tcagggaggg gtacaaagtg gtgccagaga tgcagaaaca cttcctgctg ttctccctga  1380
tgaatcacct gagcaaccag gacgattaca ttgagaaggc ccaccagtca tacgatatcg  1440
gcgagggcct gttctttcat cgcatcgcca gtaccttcct gaacatcagc ggaatcctga  1500
ggaatatgaa gttttacacc atcagagcaa acggctggtt ggagcagaga ggcgagctga  1560
agagagagaa ggatattttc gcctgggagg agccattca gggcaactcc tacttcgaga  1620
tcaatgggca caaggagtg attggcgagg acgagtctgga agagctctgc tatgccttcc  1680
tgatcggcaa tcaggacgcc aacaaggtgg agggcaggat tacacagttt ctggagaagt  1740
tcagaaacgc caatagcgtg cagcaggtga aggacgatga gatgctgaaa cccgaatact  1800
tccccgccaa ttacttcgca gagagcgggg tgggacggat caaggatcga gtgctgaata  1860
ggctgaacaa ggctatcaag tccaacaagg ccaaaaaagg ggagattatc gcctatgaca  1920
agatgaggga ggtgatggcc ttcatcaaca actcactgcc tgtggacgag aagctgaagc  1980
ccaaagatta caaggtat ctgggcatgg tccggttctg ggacagggag aaagataata  2040
tcaagaggga gtttgagact aaggagtgga gcaagtatct gcccctccaac ttctggaccg  2100
ccaagaacct ggagcgcgtg tatggcctgg cacgcgagaa aaacgccgaa ctgttcaata  2160
agctgaaagc cgatgtggag aagatggacg agcgggagct ggagagtac cagaagatca  2220
atgatgcaaa ggacctgcc aatttgagac ggctcgcctc cgactttgga gtgaagtgga  2280
aggagaaaga ctgggatgaa tacagcggac agatcaagaa gcagattaca gactcccaga  2340
aactgactat catgaaacag aggatcaccg ctggcctgaa aaaaaacac ggaatcgaga  2400
atctgaatct ggaggatcacc atcgacatta acaaatcccg gaaggcgtg ctgaacgaga  2460
ttgccatccc ccgggggttc gtgaagaggc acatcctggg ttggcaggag agcgagaaag  2520
tgagcaagaa gattagggag gctgaatgtg aaattctgct gtccaaggag tacgaggagc  2580
```

```
tgagcaaaca gttttccag tctaaagact acgacaagat gaccaggata aacggactgt    2640
acgagaagaa caagctgatc gccctgatgg ccgtgtacct catggggcag ctgagaatcc    2700
tgttcaaaga gcacactaag ctggacgaca tcaccaagac taccgtggac ttcaagatca    2760
gtgataaggt caccgtgaaa atccccttca gcaattaccc tagcctggtg tacacaatgt    2820
cctccaaata cgtggacaat atcggaact acggattctc caacaaggat aaggataagc    2880
ccattctggg caaaatcgat gtgatcgaaa aacagagaat ggagttcatc aaggaagtgc    2940
tggggtttga gaagtatctt ttcgacgaca agattatcga taaaagtaag ttcgcagaca    3000
ccgccactca catctctttt gccgagatcg tggaggagct ggtggagaag ggctgggaca    3060
aggaccgcct gactaagctc aaagacgcta gaaacaaagc cctgcacggc gagatcctga    3120
cgggcaccag ctttgacgaa accaagtctc tgatcaatga gttgaagaag acaggcggcg    3180
gccccggcgg cggcgccgcc gccggcagcg gcagccctaa gaaaaaacga aaagttggca    3240
gcggaagcaa aaggccggcg gccacgaaaa aggccggcca ggcaaaaaag aaaaagctcg    3300
agtacccata cgatgttcca gattacgctt gagaattccc cttgagcatc tgacttctgg    3360
ctaataaagg aaatttattt tcattgcaat agtgtgttgg aatttttgt gtctctcagg    3420
taccgagggc ctatttccca tgattccttc atatttgcat atacgataca aggctgttag    3480
agagataatt ggaattaatt tgactgtaaa cacaaagata ttagtacaaa atacgtgacg    3540
tagaaagtaa taatttcttg ggtagtttgc agttttaaaa ttatgtttta aaatggacta    3600
tcatatgctt accgtaactt gaaagtattt cgatttcttg gctttatata tcttgtggaa    3660
aggacgaaac accggtggtt ggagaactgg atgtagatgg gctggctgtg atagacctcg    3720
atttgtgggg tagtaacagc tttttgcgg ccgcaggaac ccctagtgat ggagttggcc    3780
actccctctc tgcgcgctcg ctcgctcact gaggccgggc gaccaaaggt cgcccgacgc    3840
ccgggctttg cccgggcggc ctcagtgagc gagcgagcgc gcagctgcct gcaggggcgc    3900
ctgatgcggt attttctcct tacgcatctg tgcggtattt cacaccgcat acgtcaaagc    3960
aaccatagta cgcgccctgt agcggcgcat taagcgcggc gggtgtggtg gttacgcgca    4020
gcgtgaccgc tacacttgcc agcgccttag cgcccgctcc tttcgctttc ttcccttcct    4080
ttctcgccac gttcgccggc tttccccgtc aagctctaaa tcggggggct ccctttaggg    4140
tccgatttag tgctttacgg cacctcgacc ccaaaaaact tgatttgggt gatggttcac    4200
gtagtgggcc atcgccctga tagacggttt ttcgcccttt gacgttggag tccacgttct    4260
ttaatagtgg actcttgttc caaactggaa caacactcaa ctctatctcg gctattctt    4320
ttgatttata agggattttg ccgatttcgg tctattggtt aaaaaatgag ctgatttaac    4380
aaaaatttaa cgcgaatttt aacaaaatat taacgtttac aattttatgg tgcactctca    4440
gtacaatctg ctctgatgcc gcatagttaa gccagccccg acaccccgcca cacccgctg    4500
acgcgccctg acgggcttgt ctgctcccgg catccgctta cagacaagct gtgaccgtct    4560
ccgggagctg catgtgtcag aggttttcac cgtcatcacc gaaacgcgcg agacgaaagg    4620
gcctcgtgat acgcctattt ttataggtta atgtcatgat aataatggtt tcttagacgt    4680
caggtggcac ttttcgggga aatgtgcgcg gaaccctat tgtttatttt ttctaaatac    4740
attcaaatat gtatccgctc atgagacaat aaccctgata aatgcttcaa taatattgaa    4800
aaaggaagag tatgagtatt caacatttcc gtgtcgccct tattcccttt tttgcggcat    4860
tttgccttcc tgtttttgct cacccagaaa cgctggtgaa agtaaaagat gctgaagatc    4920
agttgggtgc acgagtgggt tacatcgaac tggatctcaa cagcggtaag atccttgaga    4980
gttttcgccc cgaagaacgt tttccaatga tgagcacttt taaagttctg ctatgtggcg    5040
cggtattatc ccgtattgac gccgggcaag agcaactcgg tcgccgcata cactattctc    5100
agaatgactt ggttgagtac tcaccagtca cagaaaagca tcttacggat ggcatgacag    5160
taagagaatt atgcagtgct gccataacca tgagtgataa cactgcgcc aacttacttc    5220
tgacaacgat cggaggaccg aaggagctaa ccgcttttt gcacaacatg gggatcatg    5280
taactcgcct tgatcgttgg gaaccggagc tgaatgaagc cataccaaac gacgagcgtg    5340
acaccacgat gcctgtagca atggcaacaa cgttgcgcaa actattaact ggcgaactac    5400
ttactctagc ttcccggcaa caattaatag actggatgga ggcggataaa gttgcaggac    5460
cacttctgcg ctcggccctt ccggctggct ggtttattgc tgataaatct ggagccggtg    5520
agcgtggaag ccgcggtatc attgcagcac tggggccaga tggtaagccc tcccgtatcg    5580
tagttatcta cacgacgggg agtcaggcaa ctatggatga acgaaataga cagatcgctg    5640
agataggtgc ctcactgatt aagcattggt aactgtcaga ccaagtttac tcatatatac    5700
tttagattga tttaaaactt catttttaat ttaaaaggat ctaggtgaag atcctttttg    5760
ataatctcat gaccaaaatc ccttaacgtg agttttcgtt ccactgagcg tcagacccg    5820
tagaaaagat caaaggatct cttgagatc ctttttttct gcgcgtaatc tgctgcttgc    5880
aaacaaaaaa accaccgcta ccagcggtgg tttgtttgcc ggatcaagag ctaccaactc    5940
tttttccgaa ggtaactggc ttcagcagag cgcagatacc aaatactgtt cttctagtgt    6000
agccgtagtt aggccaccac ttcaagaact ctgtagcacc gcctacatac ctcgctctgc    6060
taatcctgtt accagtggct gctgccagtg gcgataagtc gtgtcttacc gggttggact    6120
caagacgata gttaccggat aaggcgcagc ggtcgggctg aacggggggt tcgtgcacac    6180
agcccagctt ggagcgaacg acctacaccg aactgagata cctacagcgt gagctatgag    6240
aaagcgccac gcttcccgaa gggagaaagg cggacaggta tccggtaagc ggcagggtcg    6300
gaacaggaga gcgcacgagg gagcttccag ggggaaacgc ctggtatctt tatagtcctg    6360
tcgggtttcg ccacctctga cttgagcgtc gatttttgtg atgctcgtca ggggggcgga    6420
gcctatggaa aaacgccagc aacgcggcct ttttacggtt cctggccttt tgctggcctt    6480
ttgctcacat gt                                                        6492

SEQ ID NO: 95         moltype = DNA  length = 70
FEATURE               Location/Qualifiers
source                1..70
                      mol_type = other DNA
                      organism = synthetic construct
SEQUENCE: 95
tgccgttctt ctgcttgtcg gccatgatat agacgttgtg gctgttgtag ttgtactcca    60
gcttgtgccc                                                            70

SEQ ID NO: 96         moltype = DNA  length = 6793
FEATURE               Location/Qualifiers
source                1..6793
```

```
                mol_type = other DNA
                organism = synthetic construct
SEQUENCE: 96
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgagca aggacaagaa aaccaaggcc aagagaatgg   840
gcgtgaaggc cctgctggcc cacggcgagg acaagctgac catgaccacc ttcggcaagg   900
gcaacagaag caagatcgag ttcaccgagg gctaccacgg cagagccctg agacacccca   960
agcacttcgg catcagaggc ttcgaggtga agaatcgacg agaacgtg gacctgtgcg  1020
gcgacctgga ggagggcaag accatcgagg ccctgctggt gaaccccagc gagaaggtgg  1080
gcgaggacta cctgaagctg aagggcaccc tggagaagaa attcttcggc agagagttcc  1140
cccacgacaa catcagaatc cagctgatct acaacatcct ggacatctac aagatcctga  1200
gcatgaacgt ggccgacatc ctgtacgccc tggcaacat gcaggacacc gagctggaca  1260
tcgacatgtt cggccagagc ctgaacaacg aggacaacct gaaggagtgc ctgaagagaa  1320
tgaggcccta catgggctac ttcggcgaca tcttcaagat cagccccaag ggcgagaaca  1380
tcgccgacag agagcacaac aagaaggtgc tgagatgcat cagcgtgctg gcaaacgcca  1440
ccgccgccga caagcaggac gagtacccct ggttcaagag cagcgacatc tacgagacaa  1500
agatcttcaa ggccgacatg tggaagatca tcaaggacca gtacagagag aagatcaaga  1560
aggtgaacaa ggacttcctg agcaagaacg ccgtgaacat ggccatcctg ttcgacctgc  1620
tgaacgccaa agacgtggag cagaagaagc agatcaccga cgagttctac agattccacc  1680
tcagaaagga cggcaagaac ctgggcatga acctggtgaa gatcagagag atcatcatcg  1740
acagatacgc cagcggcctg agagacaaga gcacgaccc ccacagacag aagatcaacg  1800
tgatcgccga cttcctgatc ttcagagccc tgagccagaa cacgggcatc atcgacaaga  1860
ccgtgagcga cctgagactg accaaggacg aggaggaaga ggactgccgtg taccagaacg  1920
ccgccgagct ggtgtgggc atggtgagca actgcctgac ccctacttc aacgacccca  1980
agaacaagta catcctgaag tacaaggacg ccaagacccc cggcgacttc gaggactgga  2040
tcaccagcaa gatcagcgag gacgacgcg agcccttcgt gaaggtgctg agcttcctgt  2100
gcaacttcct ggagggcaag gagatcaacg agctgctgac cctcctacatc cacaagttcg  2160
agtgcatcca ggacttcctg aacgtgatca gcagcctggg cgagaacatc cagttccagc  2220
ccagattcgc cctgttcaac aacgccagct cgcccagaa cgtggccgtg cagctgagaa  2280
tcctggccaa catcggcaag atgaagcccg acctgaccga ggccaagagg cccctgtaca  2340
aggcccat cagaatgctg tgcccccccg agaagtggca agatacgcc agcgacgagt  2400
ggctggagaa gaacatgctg ctgaacagcg aggacagaaa gaacgacaag aagaagaagc  2460
aggtgaaccc cttcagaaac ttcatcgccg gcaacgtgat cgagcagaga gattcatgt  2520
acctggtgag atacagcaag cccaaggccg tgagagccat catgcagaac agaagcatcg  2580
tgaactacgt gctgcacaga ctgcccagcg agcaggtgca agatacgcc agcgtgttcc  2640
ccgagaactt cgccgacctg agcaggagaa tcgacttcct gaccaagaag ctgttcgagt  2700
tcagcttcga ggagctgctg cacgagaagg acgtgatcct gaacaacagc agaagccaca  2760
agcccagcct ggagatcgag agactgaagg ccatcaccgg cctgtacctg agcgtggcct  2820
acatcgccat caaggacatc gtgaaggcca acgccagata ctacatcgcc ttcgccgtgt  2880
tcgagagaga caaggagctg gtgaaggcca aggacgccag aatccagacc aagatccccc  2940
agacagactt ccccgactac ttctgcctga cccagtacta cctggacaga acgaggaga  3000
agaagttccc cggcgacccc agagacaagg aggccttctt cgagcacctg caaagacca  3060
agagacctt cagcaagcag tggagagagt ggctgaacga gaagatcgcc gacgccaaga  3120
gcagccaggc caccgccctg ctgctgagag aggccgcaaa cgacgtggag gccctgaacg  3180
tgctgagagc catccccgac tacatccagg acttcagaca cggcgagaag ggcgagacag  3240
ccatgaacag ctacttcgag ctgtaccact acctgatgca gagactgatg ctgaagaaca  3300
ccgagctgga cctgagcac tggagcgct ggatcatgaa agcggcaga cccgacagag  3360
acttgatcca gatcgccttc gtgagcctgg cctacaacct gcccagatac agaaacctga  3420
ccaaggagca ccacttcgac gacaccgtgc tgcagaagat cagagagaag gagagcctgg  3480
acacaggcgg cggccccggc ggcggcgccg ccgccgggcag cggcagccct aagaaaaaac  3540
gaaaagttgg cagcggaagc aaaaggccgg cggccacgga aaaggccggc caggcaaaaa  3600
agaaaaagct cgagtaccca tacgatgttc cagattacgc ttgagaattc cccttgagca  3660
tctgacttct ggctaataaa ggaaatttat tttcattgca atagtgtgtt ggaattttt  3720
gtgtctctca ggtaccgagg cctatttcc catgattcct tcatattgc atatacgata  3780
caaggctgtt agagagataa ttggaattaa tttgactgta aacacaaaga tattagtaca  3840
aaatacgtga cgtagaaagt aataattct tgggtagttt gcagttttaa aattatgttt  3900
taaaatggac tatcatatgc ttaccgtaac ttgaaagtat tcgatttct tggctttata  3960
tatcttgtgg aaaggacgaa acaccggaag ataactctac aaacctgtag ggttctgaga  4020
cggagaccac ggcaggtctc attttttgcg gccgcaggaa cccctagtga tggagttggc  4080
cactccctct ctgcgcgctc gctcgctcac tgaggccggg cgaccaaagg tcgcccgacg  4140
cccgggctt gccggcgg cctcagtgag cgagcgagcg cgcagctgcc tgcagggcg  4200
cctgatgcgg tattttctcc ttacgcatct gtgcggtatt tcacaccgca tacgtcaaag  4260
caaccatagt acgcgccctg tagcggcgca ttaagcgcgg cgggtgtggt ggttacgcgc  4320
agcgtgaccg ctacacttgc cagcgcctta gcgcccgctc ctttcgcttt cttccctctcc  4380
tttctcgcca cgttcgccgg ctttccccgt caagctctaa atcgggggct ccctttaggg  4440
ttccgattta gtgctttacg gcacctcgac cccaaaaaac ttgatttggg tgatggttca  4500
cgtagtgggc catcgccctg atagacggtt tttcgccctt tgacgttgga gtccacgttc  4560
```

```
tttaatagtg gactcttgtt ccaaactgga acaacactca actctatctc gggctattct 4620
tttgatttat aagggatttt gccgatttcg gtctattggt taaaaaatga gctgatttaa 4680
caaaaattta acgcgaattt taacaaaata ttaacgttta caattttatg gtgcactctc 4740
agtacaatct gctctgatgc cgcatagtta agccagcccc gacacccgcc aacacccgct 4800
gacgcgccct gacgggcttg tctgctcccg gcatccgctt acagacaagc tgtgaccgtc 4860
tccgggagct gcatgtgtca gaggttttca ccgtcatcac cgaaacgcgc gagacgaaag 4920
ggcctcgtga tacgcctatt tttataggtt aatgtcatga taataatggt ttcttagacg 4980
tcaggtggca cttttcgggg aaatgtgcgc ggaacccta tttgtttatt tttctaaata 5040
cattcaaata tgtatccgct catgagacaa taaccctgat aaatgcttca ataataattga 5100
aaaaggaaga gtatgagtat tcaacatttc cgtgtcgccc ttattcccctt ttttgcggca 5160
ttttgccttc ctgtttttgc tcacccagaa acgctggtga agtaaaaga tgctgaagat 5220
cagttgggtg cacgagtggg ttacatcgaa ctggatctca acagcggtaa gatccttgag 5280
agttttcgcc ccgaagaacg ttttccaatg atgagcactt ttaaagttct gctatgtggc 5340
gcggtattat cccgtattga cgccgggcaa gagcaactcg gtcgccgcat acactattct 5400
cagaatgact tggttgagta ctcaccagtc acagaaaagc atcttacgga tggcatgaca 5460
gtaagagaat tatgcagtgc tgccataacc atgagtgata acactgcggc caacttactt 5520
ctgacaacga tcggaggacc gaaggagcta accgcttttt tgcacaacat gggggatcat 5580
gtaactcgcc ttgatcgttg ggaaccggag ctgaatgaag ccataccaaa cgacgagcgt 5640
gacaccacga tgcctgtagc aatggcaaca acgttgcgca aactattaac tggcgaacta 5700
cttactctag cttcccggca acaattaata gactggatgg aggcggataa agttgcagga 5760
ccacttctgc gctcggccct tccggctggc tggtttattg ctgataaatc tggagccggt 5820
gagcgtggaa gccgcggtat cattgcagca ctggggccag atggtaagcc ctcccgtatc 5880
gtagttatct acacgacggg gagtcaggca actatgatg aacgaaatag acagatcgct 5940
gagataggtg cctcactgat taagcattgg taactgtcag accaagttta ctcatatata 6000
ctttagattg atttaaaact tcattttaa tttaaaagga tctaggtgaa gatcctttt 6060
gataatctca tgaccaaaat cccttaacgt gagttttcgt tccactgagc gtcagacccc 6120
gtagaaaaga tcaaaggatc ttcttgagat cctttttttc tgcgcgtaat ctgctgcttg 6180
caaacaaaaa aaccaccgct accagcggtg gtttgtttgc cggatcaaga gctaccaact 6240
ctttttccga aggtaactgg cttcagcaga gcgcagatac caaatactgt tcttctagtg 6300
tagccgtagt taggccacca cttcaagaac tctgtagcac cgcctacata cctcgctctg 6360
ctaatcctgt taccagtggc tgctgccagt ggcgataagt cgtgtcttac cgggttggac 6420
tcaagacgat agttaccgga taaggcgcag cggtcgggct gaacggggggg ttcgtgcaca 6480
cagcccagct tggagcgaac gacctacacc gaactgagat acctacagcg tgagctatga 6540
gaaagcgcca cgcttcccga agggagaaag gcggacaggt atccggtaag cggcagggtc 6600
ggaacaggag agcgcacgag ggagcttcca gggggaaacg cctggtatct ttatagtcct 6660
gtcgggtttc gccacctctg acttgagcgt cgatttttgt gatgctcgtc agggggggcgg 6720
agcctatgga aaaacgccag caacgcggcc ttttacggt tcctggcctt ttgctggcct 6780
tttgctcaca tgt                                                 6793

SEQ ID NO: 97        moltype = DNA   length = 7830
FEATURE              Location/Qualifiers
source               1..7830
                     mol_type = other DNA
                     organism = synthetic construct
SEQUENCE: 97
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgaggc gttgacattg attattgact agttattaat 180
agtaatcaat tacggggtca ttagttcata gcccatatat ggagttccgc gttacataac 240
ttacggtaaa tggcccgcct ggctgaccgc ccaacgaccc ccgcccattg acgtcaataa 300
tgacgtatgt tcccatagta acgccaatag ggactttcca ttgacgtcaa tgggtggagt 360
atttacggta aactgcccac ttggcagtac atcaagtgta tcatatgcca agtacgcccc 420
ctattgacgt caatgacggt aaatggcccg cctggcatta tgcccagtac atgaccttat 480
gggactttcc tacttggcag tacatctacg tattagtcat cgctattacc atggtgatgc 540
ggttttggca gtacatcaat gggcgtggat agcggtttga ctcacgggga tttccaagtc 600
tccaccccat tgacgtcaat gggagtttgt tttggcacca aaatcaacgg gactttccaa 660
aatgtcgtaa caactccgcc ccattgacgc aaatgggcgg taggcgtgta cggtgggagg 720
tctatataag cagagctctc tggctaacta ccggtgccac catgagcaag gacaagaaaa 780
ccaaggccaa ggaatgggc gtgaaggcc tgctggccaa cggcgaggac aagctgacca 840
tgaccacctt cggcaagggc aacagcagat cgacgagt caccgagggc taccacgga 900
gagccctgga cacccaag cacttcgca tcagaggctt cgaggtgaga gaatcgacg 960
agaacgtgga cctgtgcggc gacctggagg agggcaagac catcgaggcc ctgctggtga 1020
accccagcga agggtgggc gaggactacc tgaagctgaa gggcacctg gagaagagat 1080
tcttcggcag agagttcccc acgacaaca tcagaatcca gctgatctac aacatcctgg 1140
acatctacaa gatcctggc atgaactgg ccgacatcct gtacgccctg ggcaacatgc 1200
aggacaccga gctggacatc gacatgttcg ccagagcct gaacaacgag gacaacctga 1260
aggagtgcct gaagagaatg agccctaca tgggctactt cggcgacatc ttcaagatca 1320
gccccaaggg cgagaacatc gccgacagag agcacaacaa gaaggtgctg agatgcatca 1380
gcgtgctggc aaacgccacc gccgcgaca acagaggga ccccctgtc ttcaagagca 1440
gcgacatcta cgagacaaag atcttcaagg ccgacatgtg aagatcatc aaggaccagt 1500
acagagagaa gatcaagaag gtgaacaagg acttctgag caagaaccgc gtgaacatgg 1560
ccatcctgtt cgacctgctg aacgccagag acgtggagca aagaagcag atcaccgacg 1620
agttctcag attcaccatc agaaaggacg gcaagaacct gggcatgaac ctggtgaaga 1680
tcagaagat catcatcgac agatacgcca gcgcctgga agcaagaag cacgacccca 1740
acagacagaa gatcaacgtg atcgccgact tcctgatctt cagaccctg agccagaacc 1800
agggcatcat cgacaagacc gtgagcgcc tgagactgac caagacgag gaggaagg 1860
accacgtgta ccgaaacgcc gccgagctgg tgtgggcat ggtgagcaac tgcctgaccc 1920
cctacttcaa cgaccccaag aacaagtaca tcctgaagta caggacgcc aagaccccg 1980
gcgacttcga ggactggatc accagcaaga tcagcgagga cgacggcgag cccttcgtga 2040
```

```
aggtgctgag cttcctgtgc aacttcctgg agggcaagga gatcaacgag ctgctgaccg  2100
cctacatcca caagttcgag tgcatccagg acttcctgaa cgtgatcagc agcctgggcg  2160
agaacgtgca gttccagccc agattcgccc tgttcaacaa cgccagcttc gcccagaacg  2220
tggccgtgca gctgagaatc ctggccagca tcggcaagat gaagcccgac ctgaccgagg  2280
ccaagaggcc cctgtacaag gccgccatca gaatgctgtg ccccccgag aagtgggaga  2340
agtacaccag cgacgagtgg ctggagaaga acatgctgct gaacagcgag gacagaaaga  2400
acgacaagaa gaagaagcag gtgaacccct tcagaaactt catcgccggc aacgtgatcg  2460
agagcagaag attcatgtac ctggtgagat acagcaagcc caaggccgtg agagccatca  2520
tgcagaacag aagcatcgtg aactacgtgc tgcacagact gcccagcgag caggtgcaca  2580
gatacgccag cgtgttcccc gagaacttcg ccgacctgga gcaggagatc gacttcctga  2640
ccaagaagct gttcgagttc agcttcgagg agctgctgca cgagaaggac gtgatcctga  2700
acaacagcag aagccacaag cccagcctgg agatcgagag actgaaggcc atcaccggcc  2760
tgtacctgag cgtggcctac atcgccatca gaaacatcgt gaaggccaac gccagatact  2820
acatcgcctt cgccgtgttc gagagagaca aggagctggt gaaggccaag gacgccagaa  2880
tccagaccaa gatccccgag acagacttcc ccgactactt ctgcctgacc cagtactacc  2940
tggacagaga cgaggagaag aagttccccg gcgaccccag agacaaggag gccttcttcg  3000
agcacctggc aaagaccaag agagcctca gcaagcagtg gagagagtgg ctgaacgaga  3060
agatccgcga cgccaagagc agccaggcca ccggcctgct gctgagagag gccgcaaacg  3120
acgtggaggc cctgaacgtg ctgagagcca tccccgacta catccaggac ttcagacacg  3180
gcgagaaggg cgagacagcc atgaacagct acttcgagct gtaccactac ctgatgcaga  3240
gactgatgct gaagaacacc gagctggacc tgagccactg gagcggctgg atcatgagaa  3300
gcggcagacc cgacagagac ttgatccaga tcgccttcgt gagcctggcc tacaacctgc  3360
ccagatacag aaacctgacc aaggagcacc acttcgacga caccgtgctg cagaagatca  3420
gagagaagga gagcctggac ctgcctccac ttgaaagact gacactggga tcccagctgc  3480
atttaccgca ggttttagct gacgctgtct cacgcctggt cctgggtaag tttggtgacc  3540
tgaccgacaa cttctcctcc cctcacgctc gcagaaaagt gctggctgga gtcgtcatga  3600
caacaggcac agatgttaaa gatgccaagg tgataagtga ttctacagga ggcaaatgta  3660
ttaatggtga atacatgagt gatcgtggcc ttgcattaaa tgactgccat gcagaaataa  3720
tatctcggag atccttgctc agatttcttt atacacaact tgagctttac ttaaataaca  3780
aagatgatca aaaaagatcc atctttcaga aatcagagcg aggggggttt aggctgaagg  3840
agaatgtcca gtttcatctg tacatcagca cctctccctg tggagatgcc agaatcttct  3900
caccacatga gccaatcctg gaagaaccag cagatagaca cccaaatcgt aaagcaagag  3960
gacagctacg gaccaaaata gagtctggtc aggggacgat tccagtgcgc tccaatgcga  4020
gcatccaaac gtgggacggg gtgctgcaag gggagcggct gctcaccatg tcctgcagtg  4080
acaagattgc acgctggaac gtggtggca tccagggatc actgctcagc atttcgtgg  4140
agcccattta cttctcgagc atcatcctgg gcagccttta ccacggggac caccttttcca  4200
gggccatgta ccagcggatc tccaacatag aggacctgcc acctctctac accctcaaca  4260
agcctttgct cagtggcatc agcaatgcag aagcacggca gccagggaag gcccccaact  4320
tcagtgatca ctggacggta ggcgactccg ctattaggt catcaacgcc acgactgggga  4380
aggatgagct gggccgcgcg tcccgcctgt gtaagcacgc gttgtactgt cgctggatgc  4440
gtgtgcacgg caaggttccc tcccacttac tacgctccaa gattaccaag cccaacgtgt  4500
accatgagtc caagctggcg gcaaaggagt accaggccgc caaggcgcgt ctgttcacag  4560
ccttcatcaa ggcggggcg ggggcctggg tggagaagcc caccagttcat gaccagttcg  4620
cactcacgta agaattcccc ttgagcatct gacttctggc taataaagga aatttatttt  4680
cattgcaata gtgtgttgga attttttgtg tctctcaggt accgagggcc tatttcccat  4740
gattccttca tatttgcata tacgatacaa ggctgttaga gagataattg gaattaattt  4800
gactgtaaac acaaagatat tagtacaaaa tacgtgacgt agaaagtaat aatttcttgg  4860
gtagtttgca gttttaaaat tatgttttaa aatggactac catatgctta ccgtaacttg  4920
aaagtatttc gatttcttgg ctttatatat cttgtggaaa ggacgaaaca ccggaagata  4980
actctacaaa cctgtagggt tctgagactg ccgttcttct gcttgtcggc catgatatag  5040
acgttgtgac tgttgtagtt gtactccagc ttgtgccatt ttttgcggcc gcaggaaccc  5100
ctagtgatgg agttgccac tccctctctg cgcgctcgct cgctcactga ggccgggcga  5160
ccaaaggtcg cccgacgccc gggctttgcc cggcgcct cagtgagcga gcgagcgcgc  5220
agctgcctgc aggggcgcct gatgcggtat tttctcctta cgcatctgtg cggtatttca  5280
caccgcatac gtcaaagcaa ccatagtacg cgccctgtag cggcgcatta agcgcggcgg  5340
gtgtggtggt tacgcgcagc gtgaccgcta cacttgccag cgccttagcg cccgctcctt  5400
tcgctttctt cccttccttt ctcgccacgt tcgccggctt tccccgtcaa gctctaaatc  5460
gggggctccc tttagggttc cgatttagtg ctttacggca cctcgacccc aaaaaacttg  5520
atttgggtga tggttcacgt agtgggccat cgccctgata gacggttttt cgccctttga  5580
cgttggagtc cacgttcttt aatagtggac tcttgttcca aactggaaca acactcaact  5640
ctatctcggg ctattctttt gatttataag ggatttgcc gatttcggtc tattggttaa  5700
aaaatgagct gatttaacaa aaatttaacg cgaattttaa caaaatatta cgtttacaa  5760
ttttatggtg cactctcagt acaatctgct ctgatgccgc atagttaagc cagccccgac  5820
acccgccaac acccgctgac gcgccctgac gggcttgtct gctcccggca tccgcttaca  5880
gacaagctgt gaccgtctcc gggagctgca tgtgtcagag gttttcaccg tcatcaccga  5940
aacgcgcgag acgaaagggc ctcgtgatac gcctattttt ataggttaat gtcatgataa  6000
taatggtttc ttagacgtca ggtggcactt ttcggggaaa tgtgcgcgga acccctattt  6060
gtttattttt ctaaatacat tcaaatatgt atccgctcat gagacaataa ccctgataaa  6120
tgcttcaata atattgaaaa aggaagagta tgagtattca acatttccgt gtcgccctta  6180
ttcccttttt tgcggcattt tgccttcctg tttttgctca cccagaaacg ctggtgaaag  6240
taaaagatgc tgaagatcag ttgggtgcac gagtgggtta tcatcaactg gatctcaaca  6300
gcggtaagat ccttgagagt tttcgccccg aagaacgttt tccaatgatg agcacttta  6360
aagttctgct atgtggcgcg gtattatccc gtattgacgc cgggcaagag caactcggtc  6420
gccgcataca ctattctcag aatgacttgg ttgagtactc accagtcaca gaaaagcatc  6480
ttacggatgg catgacagta agagaattat gcagtgctgc cataaccatg agtgataaca  6540
ctgcggccaa cttacttctg acaacgatcg gaggaccgaa ggagctaacc gcttttttgc  6600
acaacatggg ggatcatgta actcgccttg atcgttggga accggagctg aatgaagcca  6660
taccaaacga cgagcgtgac accacgatgc ctgtagcaat ggcaacaacg ttgcgcaaac  6720
tattaactgg cgaactactt actctagctt cccggcaaca attaatagac tggatggagg  6780
```

```
cggataaagt tgcaggacca cttctgcgct cggcccttcc ggctggctgg tttattgctg      6840
ataaatctgg agccggtgag cgtggaagcc gcggtatcat tgcagcactg gggccagatg      6900
gtaagccctc ccgtatcgta gttatctaca cgacggggag tcaggcaact atggatgaac      6960
gaaatagaca gatcgctgag ataggtgcct cactgattaa gcattggtaa ctgtcagacc      7020
aagtttactc atatatactt tagattgatt taaaactttt ttttaattt aaaaggatct      7080
aggtgaagat ccttttgat aatctcatga ccaaaatccc ttaacgtgag ttttcgttcc      7140
actgagcgtc agacccgta gaaaagatca aaggatcttc ttgagatcct ttttttctgc      7200
gcgtaatctg ctgcttgcaa acaaaaaaac caccgctacc agcggtggtt tgtttgccgg      7260
atcaagagct accaactctt tttccgaagg taactggctt cagcagagcg cagataccaa      7320
atactgttct tctagtgtag ccgtagttag gccaccactt caagaactct gtagcaccgc      7380
ctacatacct cgctctgcta atcctgttac cagtggctgc tgccagtggc gataagtcgt      7440
gtcttaccgg gttggactca agacgatagt taccggataa ggcgcagcgg tcgggctgaa      7500
cggggggttc gtgcacacag cccagcttgg agcgaacgac ctacaccgaa ctgagatacc      7560
tacagcgtga gctatgagaa agcgccacgc ttcccgaaga gagaaaggcg gacaggtatc      7620
cggtaagcgg cagggtcgga acaggagagc gcacgaggga gcttccaggg ggaaacgcct      7680
ggtatcttta tagtcctgtc gggtttcgcc acctctgact tgagcgtcga ttttttgtgat      7740
gctcgtcagg gggcggagc ctatggaaaa acgccagcaa cgcggccttt ttacggttcc      7800
tggccttttg ctggccttt gctcacatgt                                      7830

SEQ ID NO: 98           moltype = DNA  length = 7892
FEATURE                 Location/Qualifiers
source                  1..7892
                        mol_type = other DNA
                        organism = synthetic construct
SEQUENCE: 98
cctgcaggca gctgcgcgct cgctcgctca ctgaggccgc ccgggcgtcg ggcgaccttt        60
ggtcgcccgg cctcagtgag cgagcgagcg cgcagagagg gagtggccaa ctccatcact       120
aggggttcct gcggcctcta gactcgaggc gttgacattg attattgact agttattaat       180
agtaatcaat tacggggtca ttagttcata gcccatatat ggagttccgc gttacataac       240
ttacggtaaa tggcccgcct ggctgaccgc ccaacgaccc cgcccattg acgtcaataa       300
tgacgtatgt tcccatagta acgccaatag ggactttcca ttgacgtcaa tgggtggagt       360
atttacggta aactgcccac ttggcagtac atcaagtgta tcatatgcca agtacgcccc       420
ctattgacgt caatgacggt aaatggcccg cctggcatta tgcccagtac atgacctta       480
gggactttcc tacttggcag tacatctacg tattagtcat cgctattacc atggtgatgc       540
ggttttggca gtacatcaat gggcgtggat agcggtttga ctcacgggga tttccaagtc       600
tccaccccat tgacgtcaat gggagtttgt tttggcacca aaatcaacgg gactttccaa       660
aatgtcgtaa caactccgcc ccattgacgc aaatgggcgg taggcgtgta cggtgggagg       720
tctatataag cagagctctc tggctaacta ccggtgccac catgagcaag gacaagaaaa       780
ccaaggccaa gaaatgggc gtgaaggcc tgctgaccca cggcagaga agctgaccaa        840
tgaccacctt cggcaagggc aacagaagca gatcgagtt caccgagggc taccacggca       900
gagccctgga gacacccaag cacttcggca tcagaggctt cgaggtgaga agaatcgacg       960
agaacgtgga cctgtgcggc gacctggagg agggcaagac catcgaggcc ctgctggtga      1020
accccagcga gaaggtgggc gaggactacc tgaagctgaa cggcacctg gagaagagat      1080
tcttcggcag agagttcccc cacgacaaca tcagaatcca gctgatctac aacatcctgg      1140
acatctacaa gatcctgggc atgaacgtgg ccgacatcct gtacgccctg ggcaacatgc      1200
aggacaccga gctggacatc gacatgttcg gccagagcct gaacaacgag gacaacctga      1260
aggagtgcct gaagagaatg aggccctaca tgggctactt cggcgacctc ttcaagatca      1320
gccccaaggg cgagaacatc gccgacagag agcacaacaa gaaggtgctg agatgcatca      1380
gcgtgctggc aaacgccacc gccgccgaca gcaggacga gtaccctggc ttcaagagca      1440
gcgacatcta cgagacaaag atcttcaagg ccgacatgtg gaagatcatc aaggaccagt      1500
acagagacaa gatcaagaag gtgaacaagg acttcctgga caaggaacgc gtgaacatga      1560
ccatcctgtt cgacctgctg aacgccagag acgtggagca gaagaagcag atcaccgacg      1620
agttctacag attcaccatc agaaaggacg caagaacct gggcatgaac ctggtgaaga      1680
tcagagagat catcatcgac agatacgcca gcggcctgag agacaagaag cacgaccccc      1740
acagcagaa gatcaacgtg atcgccgact tcctgatctt cagagcccctg agccagaacc      1800
agggcatcat cgacaagacc gtgagcagcc tgagactgaa caaggacgag gaggagaagg      1860
accacgtgta ccagaacgcc gccgagctgg tgtgggcat ggtgagcaac tgcctgaccc      1920
cctacttcca cgaccccaag aacaagtaca tcctgaagta caggacgcc aagacccccg      1980
gcgacttcga ggactggatc accagcaaga tcagcgagga cgccgcgag cccttcgtga      2040
aggtgctgag cttcctgtgc aacttcctgg agggcaagga gatcaacgag ctgctgaccg      2100
cctacatcca caagttcgag tgcatccagg acttcctgaa cgtgatcagc agcctgggcg      2160
agaacgtgca gttccagccc agattcgccc tgttcaacaa cgccagcttc gcccagaacc      2220
tggccgtgca gctgagaatc ctggccagca tcggcaagat gaagcccgac ctgaccgagg      2280
ccaagaggcc cctgtacaag gccgccatca gaatcgcctg ccccccgag aagtggggaa      2340
agtacaccag cgacgagtgg ctgagaagaa catgctgctg aacagcgag gacagaagaa      2400
acgcaagaa gaagaagcag gtgaacccct tcagaaactt catcgccggc aacgtgatcg      2460
agagcagaag attcatgtac ctggtgagat acagcaagcc caaggccgtg agagccatca      2520
tgcagaacag aagcatcgtg aactacgtgc tgcacagact gccccagcgc caggtgcaca      2580
gatccccag cgtgttcccc gagaacttcg ccgacctgga gcaggatc gacttcctga      2640
ccaagaagct gttcgagttc agcttcgagg agctgctgca cgagaaggac gtgatcctga      2700
acaacagcag aagccacaag cccagcctgg agatcgagag actgaaggcc atcaccggcc      2760
tgtacctgag cgtggcctac atcgccatca gaacatcgt gaaggccaac gccagatact      2820
acatcgcctt cgccgtgttc gagagagaca aggagctggt gaaggccaag gacgccgaaa      2880
tccagacca gatcccgag acagacttcc ccgactactt cgtgcctgac cagtactacc      2940
tggacagaga cgaggagaag aagttccccg cgaccccga agacaaggag gccttcttcg      3000
agcacctggc aaagaccaag agagcttca gcaagcagtg gagagagtgg ctgaacgaga      3060
agatccgcca cgccaagagc agccaggcca ccggcctgct gctgagagag ccgcaaacg      3120
acgtggaggc cctgaacgtg ctgagagcca tccccgacta catccaggac ttcagacacg      3180
gcgagaaggg cgagacagcc atgaacagct acttcgagct gtaccactac ctgatgcaga      3240
```

```
gactgatgct gaagaacacc gagctggacc tgagccactg gagcggctgg atcatgagaa   3300
gcggcagacc cgacagagac ttgatccaga tcgccttcgt gagcctggcc tacaacctgc   3360
ccagatacag aaacctgacc aaggagcacc acttcgacga caccgtgctg cagaagatca   3420
gagagaagga gagcctggac ggatcccttc aactgcctcc acttgaaaga ctgacactgg   3480
gatcccagct gcatttaccg caggttttag ctgacgctgt ctcacgcctg gtcctgggta   3540
agtttggtga cctgaccgac aacttctcct cccctcacgc tcgcagaaaa gtgctggctg   3600
gagtcgtcat gacaacaggc acagatgtta aagatgccaa ggtgataagt gtttctacag   3660
gaggcaaatg tattaatggt gaatacatga gtgatcgtgg ccttgcatta aatgactgcc   3720
atgcagaaat aatatctcgg agatccttgc tcagatttct ttatacacaa cttgagcttt   3780
acttaaataa caaagatgat caaaaaagat ccatctttca gaaatcagag cgagggggt   3840
ttaggctgaa ggagaatgtc cagtttcatc tgtacatcag cacctctccc tgtgtgagatg   3900
ccagaatctt ctcaccacat gagccaatcc tggaagaacc agcagataga cacccaaatc   3960
gtaaagcaag aggacagcta cggaccaaaa tagagtctgg tcaggggacg attccagtgc   4020
gctccaatgc gagcatccaa acgtgggacg gggtgctgca aggggagcgg ctgctcacca   4080
tgtcctgcag tgacaagatt gcacgctgga acgtggtggg catccaggga tcactgctca   4140
gcattttcgt ggagcccatt tacttctcga gcatcatcct gggcagcctt taccacgggg   4200
accacctttc cagggccatg taccagcgga tctccaacat agaggacctg ccacctctct   4260
acaccctcaa caagcctttg ctcagtgtgca tcagcaatgc agaagcacgg cagccaggga   4320
aggcccccaa cttcagtgtc aactggacgg taggcgactc cgctattgag gtcatcaacg   4380
ccacgactgg gaaggatgag ctgggccgcg cgtcccgcct gtgtaagcac gcgttgtact   4440
gtcgctggat gcgtgtgcac ggcaaggttc cctcccactt actacgctcc aagattacca   4500
agcccaacgt gtaccatgga tccaagctgg cggcaaagga gtaccaggcc gccaaggcgc   4560
gtctgttcac agccttcatc aaggcggggc tgggggcctg ggtggagaag cccaccgagc   4620
aggaccagtt ctcactcacg taagcggccg ctcgagtcta gagggcccgt ttaaacccgc   4680
tgatcagcct cgagaattcc ccttgagcat ctgacttctg gctaataaag gaaatttatt   4740
ttcattgcaa tagtgtgttg gaatttttg tgtctctcga gtaccgaggg cctatttccc   4800
atgattcctt catatttgca tatacgatac aaggctgtta gagagataat tggaattaat   4860
ttgactgtaa acacaaagat attagtacaa aatacgtgac gtagaaagta ataatttctt   4920
gggtagtttg cagttttaaa attatgtttt aaaatggact atcatatgct taccgtaact   4980
tgaaagtatt tcgatttctt ggctttatat atcttgtgga aaggacgaaa caccggaaga   5040
taactctaca aacctgtagg gttctgagac tgccgttctt ctgcttgtcg gccatgatat   5100
agacgttgtg gctgttgtag ttgtactcca gcttgtgccc tttttgcgg ccgcaggaac   5160
ccctagtgat ggagttggcc actccctctc tgcgcgctcg ctcgctcact gaggccgggc   5220
gaccaaaggt cgcccgacgc ccgggctttg ccgggcggc ctcagtgagc gagcgagcgc   5280
gcagctgcct gcaggggcgc ctgatgcggt attttctcct tacgcatctg tgcggtattt   5340
cacaccgcat acgtcaaagc aaccatagta cgcgccctgt agcggcgcat taagcgcggc   5400
gggtgtggtg gttacgcgca gcgtgaccgc tacacttgcc agcgccttag cgcccgctcc   5460
tttcgctttc ttcccttcct ttctcgccac gttcgccggc tttccccgtc aagctctaaa   5520
tcggggggctc cctttagggt tccgatttag tgctttacgg cacctcgacc ccaaaaaact   5580
tgatttgggt gatggttcac gtagtgggcc atcgccctga tagacggttt ttcgcccttt   5640
gacgttggag tccacgttct ttaatagtgg actcttgttc caaactggaa caacactcaa   5700
ctctatctcg ggctattctt ttgatttata agggattttg ccgatttcgg tctattggtt   5760
aaaaaatgag ctgatttaac aaaaaatttaa cgcgaatttt aacaaaatat taacgtttac   5820
aattttatgg tgcactctca gtacaatctg ctctgatgcc gcatagttaa gccagccccg   5880
acacccgcca cacccgctg acgcgccctg acgggcttgt ctgctcccgg catccgctta   5940
cagacaagct gtgaccgtct ccgggagctg catgtgtcag aggttttcac cgtcatcacc   6000
gaaacgcgcg agacgaaagg gcctcgtgat acgcctattt ttataggtta atgtcatgat   6060
aataatggtt tcttagacgt caggtggcac ttttcgggga aatgtgcgcg gaacccctat   6120
ttgtttattt ttctaaatac attcaaatat gtatccgctc atgagacaat aaccctgata   6180
aatgcttcaa taatattgaa aaaggaagag tatgagtatt caacatttcc gtgtcgccct   6240
tattccctt ttttgcggcat tttgccttcc tgtttttgct cacccagaaa cgctggtgaa   6300
agtaaaagat gctgaagatc agttgggtgc acgagtgggt tacatcgaac tggatctcaa   6360
cagcggtaag atccttgaga gttttcgccc cgaagaacgt tttccaatga tgagcacttt   6420
taaagttctg ctatgtggcg cggtattatc ccgtattgac gccgggcaag agcaactcgg   6480
tcgccgcata cactattctc agaatgactt ggttgagtac tcaccagtca cagaaaagca   6540
tcttacggat ggcatgacag taagagaatt atgcagtgct gccataacca tgagtgataa   6600
cactgcggcc aacttacttc tgacaacgat cggaggaccg aaggagctaa ccgcttttt   6660
gcacaacatg ggggatcatg taactcgcct tgatcgttgg gaaccggagc tgaatgaagc   6720
cataccaaac gacgagcgtg acaccacgat gcctgtagca atggcaacaa cgttgcgcaa   6780
actattaact ggcgaactac ttactctagc ttcccggcaa caattaatag actgatgga   6840
ggcggataaa gttgcaggac cacttctgcg ctcggccctt ccgctggct ggtttattgc   6900
tgataaatct ggagccggtg agcgtggaag ccgcggtatc attgcagcac tggggccaga   6960
tggtaagccc tcccgtatcg tagttatcta cacgacgggg agtcaggcaa ctatggatga   7020
acgaaataga cagatcgctg agataggtgc ctcactgatt aagcattgt aactgtcaga   7080
ccaagtttac tcatatatac tttagattga tttaaaactt catttttaat ttaaaaggat   7140
ctaggtgaag atcctttttg ataatctcat gaccaaaatc ccttaacgtg agttttcgtt   7200
ccactgagcg tcagaccccg tagaaaagat caaaggatct tcttgagatc cttttttct   7260
gcgcgtaatc tgctgcttgc aaacaaaaaa accaccgcta ccagcggtgg tttgtttgcc   7320
ggatcaagag ctaccaactc tttttccgaa ggtaactggc ttcagcagag cgcagatacc   7380
aaatactgtt cttctagtgt agccgtagtt aggccaccac ttcaagaact ctgtagcacc   7440
gcctacatac ctcgctctgc taatcctgtt accagtggct gctgccagtg gcgataagtc   7500
gtgtcttacc gggttggact caagacgata gttaccggat aaggcgcagc ggtcgggctg   7560
aacgggggt tcgtgcacac agcccagctt ggagcgaacg acctacaccg aactgagata   7620
cctacagcgt gagctatgag aaagcgccac gcttcccgaa gggagaaagg cggacaggta   7680
tccggtaagc ggcagggtcg gaacaggaga gcgcacgagg gagcttccag ggggaaacgc   7740
ctggtatctt tatagtcctg tcgggtttcg ccacctctga cttgagctc gattttttgtg   7800
atgctcgtca gggggggcgga gcctatgaa aaacgccagc aacgcggcct ttttacggtt   7860
cctggccttt tgctggcctt tgctcacat gt                                 7892
```

```
SEQ ID NO: 99              moltype = DNA   length = 7943
FEATURE                    Location/Qualifiers
source                     1..7943
                           mol_type = other DNA
                           organism = synthetic construct
SEQUENCE: 99
cctgcaggca gctgcgcgct cgctcgctca ctgaggccgc ccgggcgtcg ggcgacctt     60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgagcaag gacaagaaaa   780
ccaaggccaa gagaatgggc gtgaaggccc tgctggccca cggcgaggac aagctgacca   840
tgaccacctt cggcaagggc aacagaagca agatcgagtt caccgagggc taccacggca   900
gagccctgga gacaccaag cacttcggca tcagaggctt cgaggtgaga agaatcgacg   960
agaacgtgga cctgtgcggc gacctggagg agggcaagac catcgaggcc ctgctggtga  1020
accccagcga aaggtgggc gaggactacc tgaagctgaa gggccaccctg agaagagat   1080
tcttcggcag agagttcccc cacgacaaca tcagaatcca gctgatctac aacatcctgg  1140
acatctacaa gatcctgggc atgaacgtgg ccgacatcct gtacgccctg ggcaacatgc  1200
aggacaccga gctggacatc gacatgttcg gccagagcct gaacaacgag gacaacctga  1260
aggagtgcct gaagagaatg aggccctaca tgggctactt cggcgacatc ttcaagatca  1320
gccccaaggg cgagaacatc gccgacagag cacaacaa aaggtgctg agatgcatca   1380
gcgtgctggc aaacgccacc gccgccgaca agcaggacga gtaccctgg ttcaagagca  1440
gcgacatcta cgagacaaag atcttcaagg ccgacatgtg gaagatcatc aaggaccagt  1500
acagagagaa gatcaagaag gtgaacaagg acttcctgag caagaacgcc gtgaacatgg  1560
ccatcctgtt cgacctgctg aacgccagag acgtggagca agaagcag atcaccgacg   1620
agttctacag attcaccatc agaaaggacg gcaagaacat gggcatgaac ctggtgaaga  1680
tcagagagat catcatcgac agatacgcca gcggcctgag agacaagaag cacgaccccc  1740
acagacagaa gatcaacgtg atcgccgact tcctgatctt cagagccctg agccagaacc  1800
agggcatcat cgacaagacc gtgagcagcc tgagactgac caaggacgag gaggagaagg  1860
accacgtgta ccagaacgcc gccgagctgg tgtggggcat ggtgagcaac tgcctgaccc  1920
cctacttcaa cgaccccaag aacaagtaca cctgaagta caaggacgcc aagacccccg  1980
gcgacttcga ggactggatc accagcaaga tcagcgagga cgacggcgag ccttcgtga   2040
aggtgctgag cttcctgtgc aacttcctgg agggcaagga gatcaacgag ctgctcgaccg  2100
cctacatcca caagttcgag tgcatccagg acttcctgaa cgtgatcagc agcctgggcg  2160
agaacgtgca gttccagccc agattcgccc tgttcaacaa cgcagcttc gcccagaacg   2220
tggccgtgca gctgagaatc ctggccagca tcgcaagat aagcccgac ctgaccgagg   2280
ccaagagcc cctgtacaag gccgccatca gaatgctgtg ccccccgag aagtgggaga   2340
agtacacccag cgacgagtgg ctggagaaga acatgctgct gaacagcgag gacagaaaga   2400
acgacaagaa gaagaacgag gtgaacccct tcagaaactt catcgccggc aacgtgatcg  2460
agagcagaag attcatgtac ctggtgagat acagcaagcc caaggccgtg agagccatca  2520
tgcagaacag aagcatcgtg aactacgtgc tgcacagact gcccagcgag caggtgcaca  2580
gatacgccca cgtgttcccc gagaacttcg ccgacctgga gcaggagatc gacttcctga  2640
ccaagaagct gttcgagttc agcttcgagg agctgctgca cgagaaggac gtgatcctga  2700
acaacagcag aagccacaag cccagcctgg agatcgagag actgaaggcc atcaccggcc  2760
tgtacctgag cgtggcctac atcgccatca gaaacatcgt gaaggccaac gccagatact  2820
acatcgcctt cgccgtgttc gagagagaca aggagctggt gaaggccaag gacgccgaaa  2880
tccagaccaa gatccccgag acagacttcc ccgactactt ctgcctgacc cagtactacc  2940
tggacagaga cgaggagaag aagttccccg cgaccccag agacaaggag gccttcttcg   3000
agcacctggc aaagaccaag agagccttca gcaagcagtg gagagagtgg ctgaacgaga  3060
agatcgccga cgccaagagc agccaggcca ccggcctgct gctgagagag ccgcaaacg   3120
acgtggaggc cctgaacgtg ctgagagcca tccccgacta catccaggac ttcagacgag  3180
gcgagaaggg cgagacgcc atgaacagct acttcgagct gtaccactac ctgatgcaga   3240
gactgatgct gaagaacacc gagctggacc tgaccactg agcggctgg atcatgagaa   3300
gcggcagacc cgacagagac ttgatccaga tcgccttcgt gagcctggcc tacaacctgc  3360
ccagatacag aaacctgacc aaggagcacc acttcgacga caccgtgctg cagaagatca  3420
gagagaagga gagcctggac gccgaggccg ccgcaagga ggcgccgcc aaggaggccg   3480
ccgccaaggc cggatccctt caactgcctc cacttgaaag actgacactg ggatcccagc  3540
tgcatttacc gcaggtttta gctgacgctg tctcacgcct ggtcctgggt aagtttggtg  3600
acctgaccga caacttctcc tcccctcacg ctcgcagaaa agtgctggct ggagtcgtca  3660
tgcaacagg cacagatgtt aaagatgcca aggtgataag tgtttctaca ggaggcaaat  3720
gtattaatgg tgaatacatg agtgatcgtg gccttgcatt aaatgactgc catgcagaaa  3780
taatatctcg gagatccttg ctcagatttc tttatacaca acttgagctt tacttaaata  3840
acaaagatga tcaaaaaga tccatctttc agaaatcaga gcgaggggg tttaggctga   3900
aggagaatgt ccagtttcat ctgtacatca gcacctctcc ctgtggagat gccagaatct  3960
tctcaccaca tgagccaatc ctggaagaac cagcagatag acacccaaat cgtaaagcaa  4020
gaggacagct acggaccaaa atagagtctg gtcaggtc cgctccaatg   4080
cgagcatcca aacgtgggac ggggtgctgc aaggggagcg gctgctcacc atgtcctgca  4140
gtgacaagat tgcacgctgg aacgtggtgg gcatccaggg atcactgctc agcattttcg  4200
tggagcccat ttacttctcg agcatcatcc tgggcagcct ttaccacggg gaccaccttt  4260
ccagggccat gtaccagcgg atctccaaca tagaggcct gccacctctc tacaccctca   4320
acaagccttt gctcagtggc atcagcaatg cagaagcacg gcagccaggg aaggcccca   4380
```

```
acttcagtgt caactggacg gtaggcgact ccgctattga ggtcatcaac gccacgactg   4440
ggaaggatga gctgggccgc gcgtcccgcc tgtgtaagca cgccgttgtac tgtcgctgga   4500
tgcgtgtgca cggcaaggtt ccctcccact tactacgctc caagattacc aagcccaacg   4560
tgtaccatga gtccaagctg gcggcaaagg agtaccaggc cgccaaggcg cgtctgttca   4620
cagccttcat caaggcgggg ctggggggcct gggtggaaga gcccaccgag caggaccagt   4680
tctcactcac gtaagcggcc gctcgagtct agagggcccg tttaaacccg ctgatcagcc   4740
tcgagaattc cccttgagca tctgacttct ggctaataaa ggaaatttat tttcattgca   4800
atagtgtgtt ggaatttttt gtgtctctca ggtaccgagg gcctattcc catgattcct    4860
tcatatttgc atatacgata caaggctgtt agagagataa ttggaattaa tttgactgta   4920
aacacaaaga tattagtaca aaatacgtga cgtagaaagt aataatttct tgggtagttt   4980
gcagttttaa aattatgttt taaaatggac tatcatatgc ttaccgtaac ttgaaagtat   5040
ttcgattttct tggctttata tatcttgtgg aaaggacgaa acaccggaag ataactctac   5100
aaacctgtag ggttctgaga ctgccgttct tctgcttgtc ggccatgata tagacgttgt   5160
ggctggttgta gttgtactcc agcttgtgcc cttttttgcg gccgcaggaa ccctagtga   5220
tggagttggc cactccctct ctgcgcgctc gctcgctcac tgaggccggg cgaccaaagg   5280
tcgcccgacg cccgggcttt gcccgggcgg cctcagtgag cgagcgagcg cgcagctgcc   5340
tgcagggggcg cctgatgcgg tattttctcc ttacgcatct gtgcggtatt tcacaccgca   5400
tacgtcaaag caaccatagt taagcgccctg tagcggcgca ttaagcgcgg cgggtgtggt   5460
ggttacgcgc agcgtgaccg ctacacttgc cagcgcctta gcgcccgctc ctttcgcttt   5520
cttcccttcc tttctcgcca cgttcgccgg ctttccccgt caagctctaa atcggggggct   5580
cccctttaggg ttccgattta gtgctttacg gcacctcgac cccaaaaaac ttgatttggg   5640
tgatggttca cgtagtgggc catcgccctg atagacggtt tttcgccctt tgacgttgga   5700
gtccacgttc tttaatagtg gactcttgtt ccaaactgga acaacactca actctatctc   5760
gggctattct tttgatttat aagggatttt gccgatttcg gtctattggt taaaaaatga   5820
gctgatttaa caaaaattta acgcgaattt taacaaaata ttaacgttta caattttatg   5880
gtgcactctc agtacaatct gctctgatgc cgcatagtta agccagcccc gacacccgcc   5940
aacacccgct gacgcgccct gacgggcttg tctgctcccg gcatccgctt acagacaagc   6000
tgtgaccgtc tccgggagct gcatgtgtca gaggttttca ccgtcatcac cgaaacgcgc   6060
gagacgaaag ggcctcgtga tacgcctatt tttataggtt aatgtcatga taataatggt   6120
ttcttagacg tcaggtggca cttttcgggg aaatgtgcgc ggaaccccta tttgtttatt   6180
tttctaaata cattcaaata tgtatccgct catgagacaa taaccctgat aaatgcttca   6240
ataattga aaaaggaaga gtatgagtat tcaacatttc cgtgtcgccc ttattccctt    6300
ttttgcggca ttttgccttc ctgttttttgc tcacccagaa acgctggtga agtaaaaga    6360
tgctgaagat cagttgggtg cacgagtggg ttacatcgaa ctggatctca acagcggtaa   6420
gatccttgag agttttcgcc ccgaagaacg ttttccaatg atgagcactt ttaaagttct   6480
gctatgtggc gcggtattat cccgtattga cgccgggcaa gagcaactcg gtcgccgcat   6540
acactattct cagaatgact tggttgagta ctcaccagtc acagaaaagc atcttacgga   6600
tggcatgaca gtaagagaat tatgcagtgc tgccataacc atgagtgata acactgcggc   6660
caacttacttt ctgacaacga tcggaggacc gaaggagctca accgcttttt tgcacaacat   6720
gggggatcat gtaactcgcc ttgatcgttg gaaccggag ctgaatgaag ccataccaaa    6780
cgacgagcgt gacaccacga tgcctgtagc aatggcaaca acgttgcgca aactattaac   6840
tggcgaacta cttactctag cttcccgcca caattaata gactggatgg aggcggataa   6900
agttgcagga ccacttctgc gctcggccct tccggctggc tggtttattg ctgataaatc   6960
tggagccggt gagcgtggaa gccgcggtat cattgcagca ctggggccag atggtaagcc   7020
ctcccgtatc gtagttatct acacgacggg gagtcaggca actatggatg aacgaaatag   7080
acagatcgct gagataggtg cctcactgat taagcattgg taactgtcag accaagttta   7140
ctcatatata ctttagattg atttaaaact tcattttaa ttaaaaagga tctaggtgaa   7200
gatcctttt gataatctca tgaccaaaat cccttaacgt gagttttcgt tccactgagc   7260
gtcagacccc gtagaaaaga tcaaaggatc ttcttgagat cctttttttc tgcgcgtaat   7320
ctgctgcttg caaacaaaaa aaccaccgct accagcggtg gtttgtttgc cggatcaaga   7380
gctaccaact ctttttccga aggtaactgg cttcagcaga gcgcagatac caaatactgt   7440
tcttctagtg tagccgtagt taggccacca cttcaagaac tctgtagcac cgcctacata   7500
cctcgctctg ctaatcctgt taccagtggc tgctgccagt ggcgataagt cgtgtcttac   7560
cgggttggac tcaagacgat agttaccgga taaggcgcag cggtcgggct gaacgggggg   7620
ttcgtgcaca cagcccagct tggagcgaac gacctacacc gaactgagat acctacagcg   7680
tgagctatga gaaagcgcca cgcttcccga agggagaaag gcggacaggt atccggtaag   7740
cggcagggtc ggaacaggag agcgcacgag ggagcttcca gggggaaacg cctggtatct   7800
ttatagtcct gtcgggtttc gccacctctg acttgagcgt cgatttttgt gatgctcgtc   7860
aggggggggcg agcctatgga aaaacgccag caacgcggcc ttttacggt tcctggcctt   7920
ttgctggcct tttgctcaca tgt                                          7943

SEQ ID NO: 100           moltype = DNA   length = 7937
FEATURE                  Location/Qualifiers
source                   1..7937
                         mol_type = other DNA
                         organism = synthetic construct
SEQUENCE: 100
cctgcaggca gctgcgcgct cgctcgctca ctgaggccgc ccgggcgtcg gcgacctttt    60
ggtcgcccgg cctcagtgag cgagcgagcg cgcagagagg gagtgcgcaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
```

```
tctatataag cagagctctc tggctaacta ccggtgccac catgagcaag gacaagaaaa    780
ccaaggccaa gagaatgggc gtgaaggccc tgctggccca cggcgaggac aagctgacca    840
tgaccacctt cggcaagggc aacagaagca agatcgagtt caccgagggc taccacggca    900
gagccctgga gacacccaag cacttcggca tcagaggctt cgaggtgaga agaatcgacg    960
agaacgtgga cctgtgcggc gacctggagg agggcaagac catcgaggcc ctgctggtga   1020
accccagcga gaaggtgggc gaggactacc tgaagctgaa gggcaccctg gagaagagat   1080
tcttcggcag agagttcccc cacgacaaca tcagaatcca gctgatctac aacatcctgg   1140
acatctacaa gatcctgggc atgaacgtgg ccgacatcct gtacgccctg ggcaacatgc   1200
aggacaccga gctggacatc gacatgttcg gccagagcct gaacaacgag gacaacctga   1260
aggagtgcct gaagagaatg aggccctaca tgggctactt cggcgacatc ttcaagatca   1320
gccccaaggg cgagaacatc gccgacagag agcacaacaa gaaggtgctg agatgcatca   1380
gcgtgctggc aaacgccacc gccgccgaca gcaggacgag gtaccctggt tcaagagca   1440
gcgacatcta cgagacaaag atcttcaagg ccgacatgtg gaagatcatc aaggaccagt   1500
acagagagaa gatcaagaag gtgaacaagg acttcctgga caagaacgcc gtgaactgg   1560
ccatcctgtt cgacctgctg aacgccagag acgtggagca gaagaagcag atcaccgacg   1620
agttctacag attcaccatc agaaggacg gcaagaacct gggcatgaac ctggtgaaga   1680
tcagagagat catcatcgac agatacgcca gcggcctgag agacaagaag cacgaccccc   1740
acagacagaa gatcaacgtg atcgccgact tcctgatctt cagagccctg agccagaacc   1800
agggcatcat cgacaagacc gtgagcagcc tgaactgcaa caaggacgag gaggagaagg   1860
accacgtgta ccagaacgcc gccgagctgg tgtggcat ggtgagcaac tgcctgaccc   1920
cctacttcaa cgaccccaag aacaagtaca tcctgaagta caaggacgcc aagaccccg   1980
gcgacttcga ggactggatc acacagaaga tcagcgaggc agcggccgag cccttcgtga   2040
aggtgctgag cttcctgtgc aacttcctgg agggcaagga gatcaacgag ctgctgaccg   2100
cctacatcca caagttcgag tgcatccagg acttcctgaa cgtgatcagc agcctgggcg   2160
agaacgtgca gttccagccc agattcgccc tgttcaacaa cgccagcttc gcccagaacg   2220
tggccgtgca gctgagaatc ctggccagca tcggcaagat gaagcccgac gtgaccgacg   2280
ccaagaggcc cctgtacaag gccgccatca gaatgctgtg cccccccgag aagtgggaga   2340
agtacaccag cgacgagtgg ctggagaaga acatgctgct gaacagcgag gacagaaaga   2400
acgacaagaa gaagaagcag gtgaaccct tcagaaactt catcgccggc aacgtgatcg   2460
agagcaagaa gattcatgtac ctggtgagat acagcaagcc caaggccgtg agagccatca   2520
tgcagaacag aagcatcgtg aactacgtgc tgcacagact gcccagcgac caggtgcaca   2580
gatacgccag cgtgttcccc gagaacttcg ccgacctgga gcaggagatc gacttcctga   2640
ccaagaagct gttcgagttc agcttcgagg agctgctgca cgagaaggac gtgatcctga   2700
acaacagcag aagccacaag cccagcctgg agatcgagag actgaaggcc atcaccgacg   2760
tgtacctgag cgtggcctac atcgccatca agaacatcgt gaaggccaac gccagatact   2820
acatcgcctt cgccgtgttc gagagagaca aggagctggt gaaggccaag gacgccagaa   2880
tccagaccaa gatccccgag acagacttcc ccgactactt ctgcctgacc cagtactacc   2940
tggacagaga cgaggagaag aagttccccg cgaccccag agacaaggag gccttcttcg   3000
agcacctggc aaagaccaag agagccttca gcaagcagtg gcaaggatgg ctgaacgaga   3060
agatcgccga cgccaagagc agccaggcca ccggcctgct gctgagagag gccgcaaacg   3120
acgtggaggc cctgaacgtg ctgagagcca tccccgacta catccaggac ttcagacacg   3180
gcgagaaggg cgagacagcc atgaacagct acttcgagct gtaccactac ctgatgcaga   3240
gactgatgct gaagaacacc gagctggacc tgagccactg gaggctgg atcatgaaa   3300
gcggcagacc cgacagagac ttgatccaga tcgccttcgt gagcctggcc tacaacctgc   3360
ccagatacag aaacctgacc aaggagcacc acttcgacga caccgtgctg cagaagatca   3420
gagagaagga gagcctggac ggtggcgag gttctggtgg cggaggttct ggtggcggag   3480
gttctggatc ccttcaactg cctccacttg aaagactgac actgggatcc cagctgcatt   3540
taccgcaggt tttagctgac gctgtctcac gcctggtcct gggtaagttt ggtgacctga   3600
ccgacaactt ctcctcccct cacgctcgca gaaaagtgct ggctggagtc gtcatgacaa   3660
caggcacaga tgttaaagat gccaaggtga taagtgtttc tacaggaggc aaatgtatta   3720
atggtgaata catgagtgat cgtggccttg cattaaatga ctgccatgca gaaataatat   3780
ctcggagatc cttgctcaga tttcttata cacaacttga gctttactta aataacaaag   3840
atgatcaaaa aagatccatc tttcagaaat cagagcgagg ggggtttagg ctgaaggaga   3900
atgtccagtt tcatctgtac atcagcacct ctccctgtgg agatgccaga atcttctcac   3960
cacatgagcc aatcctggaa gaaccagcag atagacaccc aaatcgtaaa gcaagaggac   4020
agctacggac caaaatagag tctggtcagg gacgattcc agtgcgctcc aatgcgagca   4080
tccaaacgtg gacgggggtg ctgcaagggg agcggctgct caccatgtcc tgcagtgaca   4140
agattgcacg ctggaacgtg gtgggcatcc agggatcact gctcagcatt ttcgtggagc   4200
ccatttactt ctcgagcatc atcctgggca gccttttacca cggggaccac cttttccaggg   4260
ccatgtacca gcggatctcc aacatagagg acctgccacc tctctacacc ctcaacaagc   4320
ctttgctcag tggcatcagc aatgcagaag cacggcagcc agggaaggcc cccaacttca   4380
gtgtcaactg gacggtaggc gactccgcta ttgaggtcat caacgccacg actgggaagg   4440
atgagctggg ccgcgcgtcc cgcctgtgta agcacgcgt gtactgtcgc tggatgcgtg   4500
tgcacggcaa ggttccctcc cacttactac gctccaagat taccaagccc aacgtgcact   4560
atgagtccaa gctggcggca aaggagtacc aggccgccaa ggcgcgtctg ttcacagcct   4620
tcatcaaggc ggggctgggg cctgggtgg agaagcccac cgagcaggac cagttctcac   4680
tcacgtaagc ggccgctcga gtctagaggg cccgtttaaa cccgctgatc agcctcgaga   4740
attcccttg agcatctgac ttctggctaa taaaggaaat ttattttcat tgcaatagtg   4800
tgttggaatt ttttgtgtct ctcaggtacc gagggcctaa ttcccatgat tccttcatat   4860
ttgcatatac gatacaaggc tgttagagag ataattggaa ttaatttgac tgtaaacaca   4920
aagatattag tacaaaatac gtgacgtaga aagtaataat ttcttgggta gtttgcagtt   4980
ttaaaattat gttttaaaat ggactatcat atgcttaccg taacttgaaa gtatttcgat   5040
ttcttggctt tatatatcc gtggaaagga cgaaacaccg aagataact ctacaaacct   5100
gtagggttct gagactgccg ttcttctgct tgtcggcaat gatatagcg ttgtggctgt   5160
tgtagttgta ctccagcttg tgccttttt tgcggccgac ggaaccccta gtgatgagt   5220
tggcactcc ctctctgcgc gctcgctcgc tcactgaggc cgggcgacca aagtcgccc   5280
gacgcccggg ctttgcccgg gcggcctcag tgagcgagcg agcgcgcagc tgcctgcagg   5340
ggcgcctgat gcggtatttt ctccttacgc atctgtgcgg tatttcacac cgcatacgtc   5400
aaagcaacca tagtacgcgc cctgtagcgg cgcattaagc gcggcgggtg tggtggttac   5460
```

```
gcgcagcgtg accgctacac ttgccagcgc cttagcgccc gctcctttcg ctttcttccc   5520
ttcctttctc gccacgttcg ccggctttcc ccgtcaagct ctaaatcggg ggctcccttt   5580
agggttccga tttagtgctt tacggcacct cgaccccaaa aaacttgatt tgggtgatgg   5640
ttcacgtagt gggccatcgc cctgatagac ggttttcgc cctttgacgt tggagtccac    5700
gttctttaat agtggactct tgttccaaac tggaacaaca ctcaactcta tctcgggcta   5760
ttcttttgat ttataaggga ttttgccgat ttcggtctat tggttaaaaa atgagctgat   5820
ttaacaaaaa tttaacgcga attttaacaa aatattaacg tttacaattt tatggtgcac   5880
tctcagtaca atctgctctg atgccgcata gttaagccag ccccgacacc cgccaacacc   5940
cgctgacgcg ccctgacggg cttgtctgct cccggcatcc gcttacagac aagctgtgac   6000
cgtctccggg agctgcatgt gtcagaggtt ttcaccgtca tcaccgaaac gcgcgagacg   6060
aaagggcctc gtgatacgcc tatttttata ggttaatgtc atgataataa tggtttctta   6120
gacgtcaggt ggcactttc ggggaaatgt gcgcggaacc cctatttgtt tattttcta    6180
aatacattca aatatgtatc cgctcatgag acaataaccc tgataaatgc ttcaataata   6240
ttgaaaaagg aagagtatga gtattcaaca tttccgtgtc gcccttattc ccttttttgc   6300
ggcatttgc cttcctgttt ttgctcaccc agaaacgctg gtgaaagtaa aagatgctga   6360
agatcagttg ggtgcacgag tgggttacat cgaactggat ctcaacagcg gtaagatcct   6420
tgagagtttt cgccccgaag aacgttttcc aatgatgagc acttttaaag ttctgctatg   6480
tggcgcggta ttatcccgta ttgacgccgg gcaagagcaa ctcggtcgcc gcatacacta   6540
ttctcagaat gacttggttg agtactcacc agtcacagaa aagcatctta cggatgcat    6600
gacagtaaga gaattatgca gtgctgccat aaccatgagt gataacactg cggccaactt   6660
acttctgaca acgatcggag gaccgaagga gctaaccgct tttttgcaca catgggggga   6720
tcatgtaact cgccttgatc gttgggaacc ggagctgaat gaagccatac caaacgacga   6780
gcgtgacacc acgatgcctg tagcaatggc aacaacgttg cgcaaactat taactggcga   6840
actacttact ctagcttccc ggcaacaatt aatagactgg atggaggcgg ataaagttgc   6900
aggaccactt ctgcgctcgg cccttccggc tggctggttt attgctgata aatctggagc   6960
cggtgagcgt ggaagccgcg gtatcattgc agcactgggg ccagatggta agccctcccg   7020
tatcgtagtt atctcacgga cggggagtca ggcaactatg gatgaacgaa atagacagat   7080
cgctgagata ggtgcctcac tgattaagca ttggtaactg tcagaccaag tttactcata   7140
tatactttag attgatttaa aacttcattt ttaatttaaa aggatctagg tgaagatcct   7200
ttttgataat ctcatgacca aaatccctta acgtgagttt tcgttccact gagcgtcaga   7260
ccccgtagaa aagatcaaag gatcttcttg agatcctttt tttctgcgcg taatctgctg   7320
cttgcaaaca aaaaaccac cgctaccagc ggtggtttgt ttgccggatc aagagctacc   7380
aactcttttt ccgaaggtaa ctggcttcag cagagcgcag ataccaaata ctgttcttct   7440
agtgtagccg tagttaggcc accacttcaa gaactctgta gcaccgccta catacctcgc   7500
tctgctaatc ctgttaccag tggctgctgc cagtggcgat aagtcgtgtc ttaccgggtt   7560
ggactcaaga cgatagttac cggataaggc gcagcggtcg ggctgaacgg ggggttcgtg   7620
cacacagccc agcttggagc gaacgaccta caccgaactg atacctac agcgtgagct     7680
atgagaaagc gccacgcttc ccgaagggag aaaggcggac aggtatccgg taagcggcag   7740
ggtcggaaca ggagagcgca cagggagct tccagggga aacgcctggt atctttatag    7800
tcctgtcggg tttcgccacc tctgacttga gcgtcgattt ttgtgatgct cgtcaggggg   7860
gcggagccta tggaaaaacg ccagcaacgc ggccttttta cggttcctgg ccttttgctg   7920
gccttttgct cacatgt                                                  7937
```

SEQ ID NO: 101           moltype = DNA   length = 4828
FEATURE                  Location/Qualifiers
source                   1..4828
                         mol_type = other DNA
                         organism = synthetic construct
SEQUENCE: 101

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcatt   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa    300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catggtgagc aagggcgagg   780
agctgttcac cggggtggtg cccatcctgg tcgagctgga cggcgacgta aacggccaca   840
agttcagcgt gtccggcgag ggcgagggcg atgccaccta cggcaagctg accctgaagt   900
tcatctgcac caccggcaag ctgcccgtgc cctggcccac cctcgtgacc accctgacct   960
acggcgtgca gtgcttcagc cgctaccccg accacatgaa gcagcacgac ttcttcaagt   1020
ccgccatgcc cgaaggctac gtccaggagc gcaccatctt cttcaaggac gacggcaact   1080
acaagacccg cgccgaggtg aagttcgagg gcgacaccct ggtgaaccgc atcgagctga   1140
agggcatcga cttcaaggag gacggcaaca tcctggggca caagctggag tacaactaca   1200
acagccacaa cgtctatatc atggccgaca agcagaagaa cggcatcaag gtgaacttca   1260
agatccgcca caacatcgag gacggcagcg tgcagctcgc cgaccactac cagcagaaca   1320
cccccatcgg cgacggcccc gtgctgctgc ccgacaacca ctacctgagc acccagtccg   1380
ccctgagcaa agaccccaac gagaagcgcg atcacatggt cctgctggag ttcgtgaccg   1440
ccgccgggat cactctcggc atggacgagc tgtacaagta aagcggccgc gactctagag   1500
ctcgctgatc agcctcgact gtgccttcta gttgccagcc atctgttgtt tgcccctccc   1560
ccgtgccttc cttgaccctg gaaggtgcca ctcccactgt cctttcctaa taaaatgagg   1620
aaattgcatc gcattgtctg agtaggtgtc attctattct ggggggtggg gtggggcagg   1680
acagcaaggg gaggattgg gaagagaata gcaggcatgc tggggaggta ccagggcct    1740
atttcccatg attccttcat atttgcatat acgatacaag gctgttagag agataattgg   1800
```

```
aattaatttg actgtaaaca caaagatatt agtacaaaat acgtgacgta gaaagtaata 1860
atttcttggg tagtttgcag ttttaaaatt atgttttaaa atggactatc atatgcttac 1920
cgtaacttga aagtatttcg atttcttggc tttatatatc ttgtggaaag gacgaaacac 1980
cggagaccac ggcaggtctc agttttagta ctctggaaac agaatctact aaaacaaggc 2040
aaaatgccgt gtttatctcg tcaacttgtt ggcgagattt ttgccgccgc aggaaccct 2100
agtgatggag ttggccactc cctctctgcg cgctcgctcg ctcactgagg ccgggcgacc 2160
aaaggtcgcc cgacgcccgg gctttgcccg ggcggcctca gtgagcgagc gagcgcgcag 2220
ctgcctgcag gggcgcctga tgcggtattt tctccttacg catctgtgcg gtatttcaca 2280
ccgcatacgt caaagcaacc atagtacgcg ccctgtagcg cgcattaag cgcggcgggt 2340
gtggtggtta cgcgcagcgt gaccgctaca cttgccagcg ccctagcgcc cgctcctttc 2400
gctttcttcc cttcctttct cgccacgttc gccggctttc cccgtcaagc tctaaatcgg 2460
gggctccctt tagggttccg atttagtgct ttacggcacc tcgacccaa aaacttgat 2520
ttgggtgatg gttcacgtag tgggccatcg ccctgataga cggttttcg cccttgacg 2580
ttggagtcca cgttctttaa tagtggactc ttgttccaaa ctggaacaac actcaaccct 2640
atctcgggct attcttttga tttataaggg attttgccga tttcggccta ttggttaaaa 2700
aatgagctga tttaacaaaa atttaacgcg aattttaaca aaatattaac gtttacaatt 2760
ttatggtgca ctctcagtac aatctgctct gatgccgcat agttaagcca gccccgacac 2820
ccgccaacac ccgctgacgc gccctgacgg gcttgtctgc tcccggcatc cgcttacaga 2880
caagctgtga ccgtctccgg gagctgcatg tgtcagaggt tttcaccgtc atcaccgaaa 2940
cgcgcgagac gaaagggcct cgtgatacgc ctatttttat aggttaatgt catgataata 3000
atggtttctt agacgtcagg tggcacttt cggggaaatg tgcgcggaac ccctatttgt 3060
ttatttttct aaatacattc aaatatgtat ccgctcatga gacaataacc ctgataaatg 3120
cttcaataat attgaaaaag gaagagtatg agtattcaac atttccgtgt cgcccttatt 3180
cccttttttg cggcatttg ccttcctgtt tttgctcacc cagaaacgct ggtgaaagta 3240
aaagatgctg aagatcagtt gggtgcacga gtgggttaca tcgaactgga tctcaacagc 3300
ggtaagatcc ttgagagttt tcgccccgaa gaacgttttc caatgatgag cacttttaaa 3360
gttctgctat gtggcgcggt attatcccgt attgacgccg ggcaagagca actcggtcgc 3420
cgcatacact attctcagaa tgacttggtt gagtactcac cagtcacaga aaagcatctt 3480
acggatggca tgacagtaag agaattatgc agtgctgcca taaccatgag tgataacact 3540
gcggccaact tacttctgac aacgatcgga ggaccgaagg agctaaccgc tttttttgcac 3600
aacatggggg atcatgtaac tcgccttgat cgttgggaac cggagctgaa tgaagccata 3660
ccaaacgacg agcgtgacac cacgatgcct gtagcaatgg caacaacgtt gcgcaaacta 3720
ttaactggcg aactacttac tctagcttcc cggcaacaat taatagactg gatggaggcg 3780
gataaagttg caggaccact tctgcgctcg gcccttccgg ctggctggtt tattgctgat 3840
aaatctggag ccggtgagcg tggaagccgc ggtatcattg cagcactggg gccagatggt 3900
aagccctccc gtatcgtagt tatctcacacg acggggagtc aggcaactat ggatgaacga 3960
aatagacaga tcgctgagat aggtgcctca ctgattaagc attggtaact gtcagaccaa 4020
gtttactcat atatacttta gattgattta aaacttcatt tttaatttaa aaggatctag 4080
gtgaagatcc tttttgataa tctcatgacc aaaatccctt aacgtgagtt ttcgttccac 4140
tgagcgtcag accccgtaga aaagatcaaa ggatcttctt gagatccttt ttttctgcgc 4200
gtaatctgct gcttgcaaac aaaaaaacca ccgctaccag cggtggtttg tttgccggat 4260
caagagctac caactctttt tccgaaggta actggcttca gcagagcgca gataccaaat 4320
actgtccttc tagtgtagcc gtagttaggc caccacttca agaactctgt agcaccgcct 4380
acatacctcg ctctgctaat cctgttacca gtggctgctg ccagtggcga taagtcgtgt 4440
cttaccgggt tggactcaag acgatagtta ccggataagg cgcagcggtc gggctgaacg 4500
gggggttcgt gcacacagcc cagcttggag cgaacgacct acaccgaact gagatacta 4560
cagcgtgagc tatgagaaag cgccacgctt cccgaaggga gaaaggcgga caggtatccg 4620
gtaagcggca gggtcggaac aggagagcgc acgagggagc ttccaggggg aaacgcctgg 4680
tatctttata gtcctgtcgg gtttcgccac ctctgacttg agcgtcgatt tttgtgatgc 4740
tcgtcagggg gcggagcct atggaaaaac gccagcaacg cggccttttt acggttcctg 4800
gccttttgct ggccttttgc tcacatgt                                      4828
```

SEQ ID NO: 102        moltype = DNA  length = 7141
FEATURE               Location/Qualifiers
source                1..7141
                       mol_type = other DNA
                       organism = synthetic construct
SEQUENCE: 102

```
ttggggttgc gccttttcca aggcagccct gggtttgcgc agggacgcgg ctgctctggg 60
cgtggttccg ggaaacgcag cggcgccgac cctgggtctc gcacattctt cacgtccgtt 120
cgcagcgtca cccggatctt cgccgctacc cttgtgggcc cccggcgac gcttcctgct 180
ccgcccctaa gtcgggaagg ttccttgcgg ttcgcggcgt gccggacgtg acaaacggaa 240
gccgcacgtc tcactagtac cctcgcagac ggacagcgcc agggagcaat ggcagcgcgc 300
cgaccgcgat gggcgtgtgc caatagcggc tgctcagcag gcgagcagcgc 360
cgggaagggg cggtgcggga ggcggggtgt ggggcggtag tgtgggccct gttcctgccc 420
gcgcggtgtt ccgcattctg caagcctccg gagcgcacgt cggcagtcgg ctccctcgtt 480
gaccgaatca ccgacctctc tccccagggg gatccaccgg agcttaccat gaccgagtac 540
aagcccacgg tgcgcctcgc caccgccgac gacgtcccca gggccgtacg caccctcgcc 600
gccgcgttcg ccgactaccc cgccacgcgc cacaccgtcg atccggaccg ccacatcgag 660
cgggtcaccg agctgcaaga actcttcctc acgcgcgtcg ggctcgacat cggcaaggtg 720
tgggtcgcgg acgacggcgc cgccgtggcg gtctggacca cgccggagag cgtcgaagcg 780
ggggcggtgt cgccgagat cggccgcgc atggccagt gagcggttc ccggctggcc 840
gcgcagcaac agatggaagg cctcctggcg ccgcaccggc caaggagcc cgcgtggttc 900
ctggccacgg tcggcgtctc gcccgaccac cagggcaagg gtctgggcag cgccgtcgtg 960
ctccccggag tggaggcggc cgagcgcgcc gggtgcccgg cttcctgga gacttccgcg 1020
ccccgcaacc tccccttcta cgagcggctc ggcttcaccg tcaccgccga cgtcgaggtg 1080
cccgaaggac cgcgcacctg gtgcatgacc cgcaagcccg tgcctgacg cccgccccac 1140
gacccgcagc gcccgaccga aaggagcgca cgaccccatg catcggtacc tttaagacca 1200
atgacttaca aggcagctgt agatcttagc cacttttaa aagaaagggg gggactggaa 1260
```

```
gggctaattc actcccaacg aagacaagat ctgcttttg cttgtactgg gtctctctgg   1320
ttagaccaga tctgagcctg ggagctctct ggctaactag ggaacccact gcttaagcct   1380
caataaagct tgccttgagt gcttcaagta gtgtgtgccc gtctgttgtg tgactctggt   1440
aactagagat ccctcagacc cttttagtca gtgtggaaaa tctctagcag tagtagttca   1500
tgtcatctta ttattcagta tttataactt gcaaagaaat gaatatcaga gagtgagagg   1560
aacttgttta ttgcagctta taatggttac aaataaagca atagcatcac aaatttcaca   1620
aataaagcat ttttttcact gcattctagt tgtggtttgt ccaaactcat caatgtatct   1680
tatcatgtct ggctctagct atcccgcccc taactccgcc catcccgccc ctaactccgc   1740
ccagttccgc ccattctccg ccccatggct gactaatttt ttttatttat gcagaggccg   1800
aggccgcctc ggcctctgag ctattccaga agtagtgagg aggctttttt ggaggcctag   1860
ggacgtaccc aattcgccct atagtgagtc gtattacgcg cgctcactgg ccgtcgtttt   1920
acaacgtcgt gactgggaaa accctggcgt tacccaactt aatcgccttg cagcacatcc   1980
ccctttcgcc agctggcgta atagcgaaga ggcccgcacc gatcgccctt cccaacagtt   2040
gcgcagcctg aatggcgaat gggacgcgcc ctgtagcggc gcattaagcg cggcgggtgt   2100
ggtggttacg cgcagcgtga ccgctacact tgccagcgcc ctagcgcccg ctcctttcgc   2160
tttcttccct tcctttctcg ccacgttcgc cggctttccc cgtcaagctc taaatcgggg   2220
gctcccttta gggttccgat ttagtgcttt acggcaccct gaccccaaaa aacttgatta   2280
gggtgatggt tcacgtagtg gccatcgcc ctgatagacg gtttttcgcc ctttgacgtt   2340
ggagtccacg ttctttaata gtggactctt gttccaaact ggaacaacac tcaaccctat   2400
ctcggtctat tcttttgatt tataagggat tttgccgatt tcggcctatt ggttaaaaaa   2460
tgagctgatt taacaaaaat ttaacgcgaa ttttaacaaa atattaacgc ttacaattta   2520
ggtggcactt ttcggggaaa tgtgcgcgga acccctattt gtttatttt ctaaatacat   2580
tcaaatatgt atccgctcat gagacaataa ccctgataaa tgcttcaata atattgaaaa   2640
aggaagagta tgagtattca acatttccgt gtcgccctta ttcccttttt tgcggcattt   2700
tgccttcctg ttttgctca cccagaaacg ctggtgaaag taaaagatgc tgaagatcag   2760
ttgggtgcac gagtgggtta catcgaactg gatctcaaca gcggtaagat ccttgagagt   2820
tttcgccccg aagaacgttt tccaatgatg agcactttta aagttctgct atgtggcgcg   2880
gtattatccc gtattgacgc cgggcaagag caactcggtc gccgcataca ctattctcag   2940
aatgacttgg ttgagtactc accagtcaca gaaaagcatc ttacgatgg catgacagta   3000
agagaattat gcagtgctgc cataaccatg agtgataaa ctgcggccaa cttacttctg   3060
acaacgatcg gaggaccgaa ggagctaacc gcttttttgc acaacatggg ggatcatgta   3120
actgccttg atcgttggga accggagctg aatgaagcca taccaaacga cgagcgtgac   3180
accacgatgc ctgtagcaat ggcaacaacg ttgcgcaaac tattaactgg cgaactactt   3240
actctagctt cccggcaaca attaatagac tggatggagg cggataaagt tgcaggacca   3300
cttctgcgct cggcccttcc ggctggctgg tttattgctg ataaatctgg agccggtgag   3360
cgtgggtctc gcggtatcat tgcagcactg gggccagatg gtaagccctc ccgtatcgta   3420
gttatctaca cgacggggag tcaggcaact atggatgaac gaaatagaca gatcgctgag   3480
ataggtgcct cactgattaa gcattggtaa ctgtcagacc aagtttactc atatatactt   3540
tagattgatt taaaacttca ttttaattt aaaaggatct aggtgaagat ccttttttgat   3600
aatctcatga ccaaaatccc ttaacgtgag ttttcgttcc actgagcgtc agacccccgta   3660
gaaaagatca aaggatcttc ttgagatcct ttttttctgc gcgtaatctg ctgcttgcaa   3720
acaaaaaaac caccgctacc agcggtggtt tgtttgccgg atcaagagct accaactctt   3780
tttccgaagg taactggctt cagcagagcg cagataccaa atactgttct tctagtgtag   3840
ccgtagttag gccaccactt caagaactct gtagcaccgc ctacatacct cgctctgcta   3900
atcctgttac cagtggctgc tgccagtggc gataagtcgt gtcttaccgg gttggactca   3960
agacgatagt taccggataa ggcgcagcgg tcgggctgaa cggggggttc gtgcacacag   4020
cccagcttgg agcgaacgac ctacaccgaa ctgagatacc tacagcgtga gctatgagaa   4080
agcgccacgc ttcccgaagg gagaaaggcg gacaggtatc cggtaagcgg cagggtcgga   4140
acaggagagc gcacgaggga gcttccaggg gaaacgcct ggtatcttta tagtcctgtc   4200
gggtttcgcc acctctgact tgagcgtcga ttttgtgat gctcgtcagg gggcggagc   4260
ctatgaaaa acgccagcaa cgcggccttt ttacggttcc tggccttttg ctggccttt   4320
gctcacatgt tctttcctgc gttatcccct gattctgtgg ataaccgtat taccgccttt   4380
gagtgagctg ataccgctcg ccgcagccga acgaccgagc gcagcgagtc agtgagcgag   4440
gaagcggaag agcgcccaat acgcaaaccg cctctccccg cgcgttggcc gattcattaa   4500
tgcagctgca acgacaggtt tcccgactgg aaagcgggca gtgagcgcaa cgcaattaat   4560
gtgagttagc tcactcatta ggcaccccag gctttacact ttatgcttcc ggctcgtatg   4620
ttgtgtggaa ttgtgagcgg ataacaattt cacacaggaa acagctatga ccatgattac   4680
gccaagcgcg caattaaccc tcactaaagg gaacaaaagc tggagctgca agcttaatgt   4740
agtcttatgc aatactcttg tagtcttgca acatggtaac gatgagttag caacatgcct   4800
tacaaggaga gaaaagcac cgtgcatgcc gattggtgga gtaaggtgg tacgatcgtg   4860
ccttattagg aaggcaacag acgggtctga catggattgg acgaaccact gaattgccgc   4920
attgcagaga tattgtattt aagtgcctag ctcgatacat aaacgggtct ctctggttag   4980
accagatctg agcctgggag ctctctggct aactaggaa cccactgctt aagcctcaat   5040
aaagcttgcc ttgagtgctt caagtagtgt gtgcccgtct gttgtgtgac tctggtaact   5100
agagatccct cagacccttt tagtcagtgt ggaaaatctc tagcagtggc gcccgaacag   5160
ggacttgaaa gcgaaaggga accagagga gctctctcga cgcaggactc ggcttgctga   5220
agcgcgcacg gcaagaggcg aggggcggcg actggtgagt acgccaaaaa ttttgactag   5280
cggaggctag aaggagagag atgggtgcga gagcgtcagt attaagcggg ggagaattag   5340
atcgcgatgg gaaaaaattc ggttaaggcc aggggggaaag aaaaaatata aattaaaaca   5400
tatagtatgg gcaagcaggg agctagaacg attcgcagtt aatcctggcc tgttagaaac   5460
atcagaaggc tgtagacaaa tactgggaca gctacaacca tcccttcaga caggatcaga   5520
agaacttaga tcattatata atacagtagc aaccctctat tgtgtgcatc aaaggataga   5580
gataaaagac accaaggaag ctttagacaa gatagaggaa gagcaaaaca aaagtaagac   5640
caccgcacag caagcggccg ctgatcttca gacctggagg aggagatatg agggacaatt   5700
ggagaagtga attatataaa tataaagtag taaaaattga accattagga gtagcaccca   5760
ccaaggcaaa gagaagagtg gtgcagagag aaaaaagagc agtgggaata ggagctttgt   5820
tccttgggtt cttgggagca gcaggaagca ctatgggcgc agcgtcaatg acgctgacgg   5880
tacaggccaa acaattattg tctggtatag tgcagcagca gaacaatttg ctgagggcta   5940
ttgaggcgca acagcatctg ttgcaactca cagtctgggg catcaagcag ctccaggcaa   6000
```

```
gaatcctggc tgtggaaaga tacctaaagg atcaacagct cctggggatt tggggttgct 6060
ctggaaaact catttgcacc actgctgtgc cttggaatgc tagttggagt aataaatctc 6120
tggaacagat ttggaatcac acgacctgga tggagtggga cagagaaatt aacaattaca 6180
caagcttaat acactcctta attgaagaat cgcaaaacca gcaagaaaag aatgaacaag 6240
aattattgga attagataaa tgggcaagtt tgttggaatg gtttaacata acaaattggc 6300
tgtggtatat aaaattattc ataatgatag taggaggctt ggtaggttta agaatagttc 6360
ttgctgtact ttcatagtg aatagagtta ggcaggata ttcaccatta tcgtttcaga 6420
cccacctccc aaccccgagg ggacccgaca ggcccgaagg aatagaagaa gaaggtggag 6480
agagagacag agacagatcc attcgattag tgaacggatc tcgacggtat cgatcacgag 6540
actagcctcg agcggccgcc cccttcaccg agggcctatt tcccatgatt ccttcatatt 6600
tgcatatacg atacaaggct gttagagaga taattggaat taatttgact gtaaacacaa 6660
agatattagt acaaaatacg tgacgtagaa agtaataatt tcttgggtag tttgcagttt 6720
taaaattatg ttttaaaatg gactatcata tgcttaccgt aacttgaaag tatttcgatt 6780
tcttgctttt atatatcttg tggaaaggac gaaacacctg ccgttcttct gcttgtcggc 6840
catgatatag acgttgtggc tgttgtagtt gtactccagc ttgtgcccgt tgtgaaggt 6900
ccagttttga ggggctatta caactttttt gaattctcga cctcgagaca aatggcagta 6960
ttcatccaca atttaaaag aaaagggggg attgggggt acagtgcagg ggaaagaata 7020
gtagacataa tagcaacaga catacaaact aaagaattac aaaaacaaat tacaaaaatt 7080
caaaattttc gggtttatta cagggacagc agagatccac tttggccgcg gctcgagggg 7140
g                                                                7141

SEQ ID NO: 103        moltype = DNA  length = 16
FEATURE               Location/Qualifiers
source                1..16
                      mol_type = other DNA
                      organism = synthetic construct
SEQUENCE: 103
agggcgagga gctgtt                                                 16

SEQ ID NO: 104        moltype = DNA  length = 19
FEATURE               Location/Qualifiers
source                1..19
                      mol_type = other DNA
                      organism = synthetic construct
SEQUENCE: 104
gtacagctcg tccatgccg                                              19

SEQ ID NO: 105        moltype = DNA  length = 33
FEATURE               Location/Qualifiers
source                1..33
                      mol_type = other DNA
                      organism = synthetic construct
SEQUENCE: 105
aaccaaggcc aaggcaatgg gcgtgaaggc cct                              33

SEQ ID NO: 106        moltype = DNA  length = 33
FEATURE               Location/Qualifiers
source                1..33
                      mol_type = other DNA
                      organism = synthetic construct
SEQUENCE: 106
attgccttgg ccttggtttt cttgtccttg ctc                              33

SEQ ID NO: 107        moltype = DNA  length = 33
FEATURE               Location/Qualifiers
source                1..33
                      mol_type = other DNA
                      organism = synthetic construct
SEQUENCE: 107
cgccagaagc aagatcgagt tcaccgaggg cta                              33

SEQ ID NO: 108        moltype = DNA  length = 35
FEATURE               Location/Qualifiers
source                1..35
                      mol_type = other DNA
                      organism = synthetic construct
SEQUENCE: 108
tcgatcttgc ttctggcgcc cttgccgaag gtggt                            35

SEQ ID NO: 109        moltype = DNA  length = 33
FEATURE               Location/Qualifiers
source                1..33
                      mol_type = other DNA
                      organism = synthetic construct
SEQUENCE: 109
caacgcaagc aagatcgagt tcaccgaggg cta                              33

SEQ ID NO: 110        moltype = DNA  length = 33
FEATURE               Location/Qualifiers
```

```
source                  1..33
                        mol_type = other DNA
                        organism = synthetic construct
SEQUENCE: 110
tcgatcttgc ttgcgttgcc cttgccgaag gtg                              33

SEQ ID NO: 111          moltype = DNA   length = 33
FEATURE                 Location/Qualifiers
source                  1..33
                        mol_type = other DNA
                        organism = synthetic construct
SEQUENCE: 111
taccacggcg cagccctgga gacacccaag cac                              33

SEQ ID NO: 112          moltype = DNA   length = 33
FEATURE                 Location/Qualifiers
source                  1..33
                        mol_type = other DNA
                        organism = synthetic construct
SEQUENCE: 112
cagggctgcg ccgtggtagc cctcggtgaa ctc                              33

SEQ ID NO: 113          moltype = DNA   length = 40
FEATURE                 Location/Qualifiers
source                  1..40
                        mol_type = other DNA
                        organism = synthetic construct
SEQUENCE: 113
aagcacttcg gcatcgcagg cttcgaggtg agaagaatcg                       40

SEQ ID NO: 114          moltype = DNA   length = 33
FEATURE                 Location/Qualifiers
source                  1..33
                        mol_type = other DNA
                        organism = synthetic construct
SEQUENCE: 114
tgcgatgccg aagtgcttgg gtgtctccag ggc                              33

SEQ ID NO: 115          moltype = DNA   length = 34
FEATURE                 Location/Qualifiers
source                  1..34
                        mol_type = other DNA
                        organism = synthetic construct
SEQUENCE: 115
ttcgaggtga gcagaatcga cgagaacgtg gacc                             34

SEQ ID NO: 116          moltype = DNA   length = 33
FEATURE                 Location/Qualifiers
source                  1..33
                        mol_type = other DNA
                        organism = synthetic construct
SEQUENCE: 116
gattctgctc acctcgaagc ctctgatgcc gaa                              33

SEQ ID NO: 117          moltype = DNA   length = 33
FEATURE                 Location/Qualifiers
source                  1..33
                        mol_type = other DNA
                        organism = synthetic construct
SEQUENCE: 117
aggtgagaag caatcgacga gaacgtggac ctg                              33

SEQ ID NO: 118          moltype = DNA   length = 33
FEATURE                 Location/Qualifiers
source                  1..33
                        mol_type = other DNA
                        organism = synthetic construct
SEQUENCE: 118
gtcgattgct tctcacctcg aagcctctga tgc                              33

SEQ ID NO: 119          moltype = DNA   length = 33
FEATURE                 Location/Qualifiers
source                  1..33
                        mol_type = other DNA
                        organism = synthetic construct
SEQUENCE: 119
aagaatcgac gaggccgtgg acctgtgcgg cga                              33

SEQ ID NO: 120          moltype = DNA   length = 33
```

```
FEATURE              Location/Qualifiers
source               1..33
                     mol_type = other DNA
                     organism = synthetic construct
SEQUENCE: 120
acggcctcgt cgattcttct cacctcgaag cct                                33

SEQ ID NO: 121       moltype = DNA   length = 33
FEATURE              Location/Qualifiers
source               1..33
                     mol_type = other DNA
                     organism = synthetic construct
SEQUENCE: 121
tggtggcccc cagcgagaag gtgggcgagg act                                33

SEQ ID NO: 122       moltype = DNA   length = 33
FEATURE              Location/Qualifiers
source               1..33
                     mol_type = other DNA
                     organism = synthetic construct
SEQUENCE: 122
tctcgctggg ggccaccagc agggcctcga tgg                                33

SEQ ID NO: 123       moltype = DNA   length = 34
FEATURE              Location/Qualifiers
source               1..34
                     mol_type = other DNA
                     organism = synthetic construct
SEQUENCE: 123
aagaacgccg tggccatggc catcctgttc gacc                               34

SEQ ID NO: 124       moltype = DNA   length = 33
FEATURE              Location/Qualifiers
source               1..33
                     mol_type = other DNA
                     organism = synthetic construct
SEQUENCE: 124
catggccacg gcgttcttgc tcaggaagtc ctt                                33

SEQ ID NO: 125       moltype = DNA   length = 34
FEATURE              Location/Qualifiers
source               1..34
                     mol_type = other DNA
                     organism = synthetic construct
SEQUENCE: 125
tgttcgacct gctggccgcc agagacgtgg agca                               34

SEQ ID NO: 126       moltype = DNA   length = 33
FEATURE              Location/Qualifiers
source               1..33
                     mol_type = other DNA
                     organism = synthetic construct
SEQUENCE: 126
cggccagcag gtcgaacagg atggccatgt tca                                33

SEQ ID NO: 127       moltype = DNA   length = 33
FEATURE              Location/Qualifiers
source               1..33
                     mol_type = other DNA
                     organism = synthetic construct
SEQUENCE: 127
cgcagacgtg gagcagaaga agcagatcac cga                                33

SEQ ID NO: 128       moltype = DNA   length = 36
FEATURE              Location/Qualifiers
source               1..36
                     mol_type = other DNA
                     organism = synthetic construct
SEQUENCE: 128
ttctgctcca cgtctgcggc gttcagcagg tcgaac                             36

SEQ ID NO: 129       moltype = DNA   length = 33
FEATURE              Location/Qualifiers
source               1..33
                     mol_type = other DNA
                     organism = synthetic construct
SEQUENCE: 129
gagttctacg cattcaccat cagaaaggac ggc                                33
```

```
SEQ ID NO: 130              moltype = DNA  length = 33
FEATURE                     Location/Qualifiers
source                      1..33
                            mol_type = other DNA
                            organism = synthetic construct
SEQUENCE: 130
ggtgaatgcg tagaactcgt cggtgatctg ctt                                33

SEQ ID NO: 131              moltype = DNA  length = 33
FEATURE                     Location/Qualifiers
source                      1..33
                            mol_type = other DNA
                            organism = synthetic construct
SEQUENCE: 131
ttcaccatcg caaaggacgg caagaacctg ggc                                33

SEQ ID NO: 132              moltype = DNA  length = 34
FEATURE                     Location/Qualifiers
source                      1..34
                            mol_type = other DNA
                            organism = synthetic construct
SEQUENCE: 132
gtcctttgcg atggtgaatc tgtagaactc gtcg                               34

SEQ ID NO: 133              moltype = DNA  length = 33
FEATURE                     Location/Qualifiers
source                      1..33
                            mol_type = other DNA
                            organism = synthetic construct
SEQUENCE: 133
caaggccctg ggcatgaacc tggtgaagat cag                                33

SEQ ID NO: 134              moltype = DNA  length = 34
FEATURE                     Location/Qualifiers
source                      1..34
                            mol_type = other DNA
                            organism = synthetic construct
SEQUENCE: 134
ttcatgccca gggccttgcc gtcctttctg atgg                               34

SEQ ID NO: 135              moltype = DNA  length = 33
FEATURE                     Location/Qualifiers
source                      1..33
                            mol_type = other DNA
                            organism = synthetic construct
SEQUENCE: 135
catggccctg gtgaagatca gagagatcat cat                                33

SEQ ID NO: 136              moltype = DNA  length = 33
FEATURE                     Location/Qualifiers
source                      1..33
                            mol_type = other DNA
                            organism = synthetic construct
SEQUENCE: 136
atcttcacca gggccatgcc caggttcttg ccg                                33

SEQ ID NO: 137              moltype = DNA  length = 35
FEATURE                     Location/Qualifiers
source                      1..35
                            mol_type = other DNA
                            organism = synthetic construct
SEQUENCE: 137
gtgaagatcg cagagatcat catcgacaga tacgc                              35

SEQ ID NO: 138              moltype = DNA  length = 33
FEATURE                     Location/Qualifiers
source                      1..33
                            mol_type = other DNA
                            organism = synthetic construct
SEQUENCE: 138
gatctctgcg atcttcacca ggttcatgcc cag                                33

SEQ ID NO: 139              moltype = DNA  length = 33
FEATURE                     Location/Qualifiers
source                      1..33
                            mol_type = other DNA
                            organism = synthetic construct
SEQUENCE: 139
tcatcatcga cgcatacgcc agcggcctga gag                                33
```

```
SEQ ID NO: 140           moltype = DNA  length = 33
FEATURE                  Location/Qualifiers
source                   1..33
                         mol_type = other DNA
                         organism = synthetic construct
SEQUENCE: 140
cgtatgcgtc gatgatgatc tctctgatct tca                                      33

SEQ ID NO: 141           moltype = DNA  length = 33
FEATURE                  Location/Qualifiers
source                   1..33
                         mol_type = other DNA
                         organism = synthetic construct
SEQUENCE: 141
cctggcagac aagaagcacg accccacag aca                                       33

SEQ ID NO: 142           moltype = DNA  length = 33
FEATURE                  Location/Qualifiers
source                   1..33
                         mol_type = other DNA
                         organism = synthetic construct
SEQUENCE: 142
tgcttcttgt ctgccaggcc gctggcgtat ctg                                      33

SEQ ID NO: 143           moltype = DNA  length = 33
FEATURE                  Location/Qualifiers
source                   1..33
                         mol_type = other DNA
                         organism = synthetic construct
SEQUENCE: 143
ccacgcacag aagatcaacg tgatcgccga ctt                                      33

SEQ ID NO: 144           moltype = DNA  length = 33
FEATURE                  Location/Qualifiers
source                   1..33
                         mol_type = other DNA
                         organism = synthetic construct
SEQUENCE: 144
ttgatcttct gtgcgtgggg gtcgtgcttc ttg                                      33

SEQ ID NO: 145           moltype = DNA  length = 33
FEATURE                  Location/Qualifiers
source                   1..33
                         mol_type = other DNA
                         organism = synthetic construct
SEQUENCE: 145
acagaagatc gccgtgatcg ccgacttcct gat                                      33

SEQ ID NO: 146           moltype = DNA  length = 33
FEATURE                  Location/Qualifiers
source                   1..33
                         mol_type = other DNA
                         organism = synthetic construct
SEQUENCE: 146
atcacggcga tcttctgtct gtgggggtcg tgc                                      33

SEQ ID NO: 147           moltype = DNA  length = 36
FEATURE                  Location/Qualifiers
source                   1..36
                         mol_type = other DNA
                         organism = synthetic construct
SEQUENCE: 147
acttcctgat cttcgcagcc ctgagccaga accagg                                   36

SEQ ID NO: 148           moltype = DNA  length = 32
FEATURE                  Location/Qualifiers
source                   1..32
                         mol_type = other DNA
                         organism = synthetic construct
SEQUENCE: 148
ctgcgaagat caggaagtcg gcgatcacgt tg                                       32

SEQ ID NO: 149           moltype = DNA  length = 33
FEATURE                  Location/Qualifiers
source                   1..33
                         mol_type = other DNA
                         organism = synthetic construct
SEQUENCE: 149
```

```
ccaggcccag ggcatcatcg acaagaccgt gag                                33

SEQ ID NO: 151          moltype = DNA   length = 34
FEATURE                 Location/Qualifiers
source                  1..34
                        mol_type = other DNA
                        organism = synthetic construct
SEQUENCE: 150
atgatgccct gggcctggct cagggctctg aaga                               34

SEQ ID NO: 151          moltype = DNA   length = 33
FEATURE                 Location/Qualifiers
source                  1..33
                        mol_type = other DNA
                        organism = synthetic construct
SEQUENCE: 151
cagcctggca ctgaccaagg acgaggagga gaa                                33

SEQ ID NO: 152          moltype = DNA   length = 33
FEATURE                 Location/Qualifiers
source                  1..33
                        mol_type = other DNA
                        organism = synthetic construct
SEQUENCE: 152
ttggtcagtg ccaggctgct cacggtcttg tcg                                33

SEQ ID NO: 153          moltype = DNA   length = 34
FEATURE                 Location/Qualifiers
source                  1..34
                        mol_type = other DNA
                        organism = synthetic construct
SEQUENCE: 153
accacgtgta ccaggccgcc gccgagctgg tgtg                               34

SEQ ID NO: 154          moltype = DNA   length = 33
FEATURE                 Location/Qualifiers
source                  1..33
                        mol_type = other DNA
                        organism = synthetic construct
SEQUENCE: 154
cggcctggta cacgtggtcc ttctcctcct cgt                                33

SEQ ID NO: 155          moltype = DNA   length = 33
FEATURE                 Location/Qualifiers
source                  1..33
                        mol_type = other DNA
                        organism = synthetic construct
SEQUENCE: 155
tggtgagcgc ctgcctgacc ccctacttca acg                                33

SEQ ID NO: 156          moltype = DNA   length = 33
FEATURE                 Location/Qualifiers
source                  1..33
                        mol_type = other DNA
                        organism = synthetic construct
SEQUENCE: 156
tcaggcaggc gctcaccatg ccccacacca gct                                33

SEQ ID NO: 157          moltype = DNA   length = 33
FEATURE                 Location/Qualifiers
source                  1..33
                        mol_type = other DNA
                        organism = synthetic construct
SEQUENCE: 157
ctacttcgcc gaccccaaga acaagtacat cct                                33

SEQ ID NO: 158          moltype = DNA   length = 33
FEATURE                 Location/Qualifiers
source                  1..33
                        mol_type = other DNA
                        organism = synthetic construct
SEQUENCE: 158
ttggggtcgg cgaagtaggg ggtcaggcag ttg                                33

SEQ ID NO: 159          moltype = DNA   length = 33
FEATURE                 Location/Qualifiers
source                  1..33
                        mol_type = other DNA
                        organism = synthetic construct
```

```
SEQUENCE: 159
caaggccaag tacatcctga agtacaagga cgc                                33

SEQ ID NO: 160         moltype = DNA   length = 35
FEATURE                Location/Qualifiers
source                 1..35
                       mol_type = other DNA
                       organism = synthetic construct
SEQUENCE: 160
aggatgtact tggccttggg gtcgttgaag taggg                              35

SEQ ID NO: 161         moltype = DNA   length = 6798
FEATURE                Location/Qualifiers
source                 1..6798
                       mol_type = other DNA
                       organism = synthetic construct
SEQUENCE: 161
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccacccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccaa catgccggcg gctaagaaaa   780
agaaactgga tggcagcgtc gacatgagca aggacaagaa aaccaaggcc aagagaatgt   840
gcgtgaaggc cctgctggcc cacggcgagg acaagctgac catgaccacc ttcggcaagg   900
gcaacagaag caagatcgag ttcaccgagg ctaccacgg cagagccctg agacacccaa   960 
agcacttcgg catcagaggc ttcgaggtga aagaatcgca cgaacgtg gacctgtgcg    1020
gcgacctgga ggagggcaag accatcgagg ccctgctggt gaaccccagc gagaaggtgg   1080
gcgaggacta cctgaagctg aagggcaccc tggagaagag attcttcggc agagagttcc   1140
cccacgacaa catcagaatc cagctgatct acaacatcct ggacatctac aagatcctgg   1200
gcatgaacgt ggccgacatc ctgtacgccc tgggcaacat gcaggacacc gagctggaca   1260
tcgacatgtt cggccagagc ctgaacaacg aggacaacct ggaggagtgc ctgaagaaa   1320
tgaggcccta catgggctac ttcgcgaca tcttcaagat cagccccaag ggcgagaaca   1380
tcgccgacag agagcacaac aagaaggtgc tgagatgcat cagcgtgctg agaaacgcca   1440
ccgcccacga caagcaggac gagtacccct ggttcaagag cagcgacatc tacgagacaa   1500
agatcttcaa ggccgacatg tggaagatca tcaaggacca gtacagagag aagatcaaga   1560
aggtgaacaa ggacttcctg agcaagaacg ccgtgaacat ggccatcctg ttcgacctgc   1620
tgaacgccag agacgtggag cagaagaagc agatcaccga cgattctac agattcacca   1680
tcagaaagga cggcaagaac ctgggcatga acctggtgaa gatcagagag atcatcatcg   1740
acagatacgc cagcggcctg agagacaaga agcacgacaa ccacagacaa aagatcaacg   1800
tgatcgccga cttcctgatc ttcagagccc tgaccagaa ccagggcatc atcgacaaga   1860
ccgtgagcag cctgagactg accaaggacg aggaggagaa ggaccacgtg taccagaacg   1920
ccgccgagct ggtgtggggc atggtgagca actgcctgac ccctacttc aacgacccca   1980
agaacaagta catcctgaag tacaaagacg ccaagacccc cggacttcg gaggactgga   2040
tcaccagcaa gatcagcgag gacgacgcg agcccttcgt gaaggtgctg agcttcctgt   2100
gcaacttcct ggagggcaag gagatcaacg agctgctgac cgcctacatc acaagttcg   2160
agtgcatcca ggacttcctg aacgtgatca gcagcctggg cgagaacgtg cagttccagc   2220
ccagattcgc cctgttcaac aacgccagct tcgcccacaa cgtgccgtg cagctgagaa   2280
tcctggccag catcggcaag atgaagccc acctgaccga ggccaagag ccctgtaca   2340
aggccgccat cagaatgctg tgccccccg agaagtggga agtacacc agcgacgagt   2400
ggctggagaa gaacatgctg ctgaacgcg aggacagaaa gaacgacaag aagaagaagc   2460
aggtgaaccc cttcagaaac ttcatcgccg gcaacgtgat cgagagcaga agattcatgt   2520
acctggtgag atacagcaag cccaaggccg tgagagccat catgcagaan agaagcatcg   2580
tgaactacgt gctgcacaga ctgcccagcg agcaggtgca cagatacgcc agcgtgttcc   2640
ccgagaactt cgccgacctg gagcaggaga tcgacttcct gaccaagaag ctgttcgagt   2700
tcagcttcga ggagctgctg cacgagaagg acgtgatcct gaacaacagc agaagccaca   2760
agcccagcct ggagatcgag agactgaagg ccatcaccgg cctgtacctg agcgtggcct   2820
acatcgccat caagaacatc gtgaaggcca acgccagata ctacatcgcc ttcgccgtgt   2880
tcgagagaga caaggagctg gtgaaggcca aggacgccag aatccagacc aagatccccg   2940
agacagactt ccccgactac ttctgcctga cccagtacta cctggacaga gacgaggaga   3000
agaagttcc ccggcgaccc agagacaagg aggccttctt cgaccacctg agaaagacca   3060
agagacactt cagcaagcag tggagagagt ggctgaactg gaagatcgc agccaaga    3120
gcagccaggc caccggcctg ctgctgagag aggccagaaa cgacgtggag cacctgaacg   3180
tgctgagagc catccccgac tacatccagg acttcagaca cggcgagaag ggcgagcag   3240
ccatgaacag ctacctcgag ctgtaccact acctgatgca gagactgatg ctgaagaaca   3300
ccgagctgga cctgagccac tggagcggct ggatcatgag aagcggcaga cccgacgag   3360
acttgatcca gatccccttc gtgagcctgg cctacaacct ggagaaactga   3420
ccaaggagca ccacttcgac gacaccgtgc tgcagaagat cagagagaag gagagcctgg   3480
acacaggcgg cggccccggc ggcggcgccg ccgccggcag cggcagccct aagaaaaaac   3540
gaaaagttgg cagcggaagc aaaagcgg cggccacga aaaggccggc caggcaaaaa   3600
agaaaaagct cgagtaccca tacgatgttc cagattacgc ttgagaattc cccttgcag   3660
tctgacttct ggctaataaa ggaaatttat tttcattgca atagtgtgtt ggaatttttt   3720
```

```
gtgtctctca ggtaccgagg gcctatttcc catgattcct tcatatttgc atatacgata  3780
caaggctgtt agagagataa ttggaattaa tttgactgta aacacaaaga tattagtaca  3840
aaatacgtga cgtagaaagt aataatttct tgggtagttt gcagttttaa aattatgttt  3900
taaaatggac tatcatatgc ttaccgtaac ttgaaagtat ttcgatttct tggctttata  3960
tatcttgtgg aaaggacgaa acaccggaag ataactctac aaacctgtag ggttctgaga  4020
cataacattt ccgaagacga caagattttt ttgcggccgc aggaacccct agtgatggag  4080
ttggccactc cctctctgcg cgctcgctcg ctcactgagg ccgggcgacc aaaggtcgcc  4140
cgacgcccgg gctttgcccg gcggcctca gtgagcgagc gagcgcgcag ctgcctgcag  4200
gggcgcctga tgcggtattt tctccttacg catctgtgcg gtatttcaca ccgcatacgt  4260
caaagcaacc atagtacgcg ccctgtagcg gcgcattaag cgcggcgggt gtggtggtta  4320
cgcgcagcgt gaccgctaca cttgccagcg ccttagcgcc cgctcctttc gctttcttcc  4380
cttcctttct cgccacgttc gccggctttc ccgtcaagc tctaaatcgg gggctccctt  4440
tagggttccg atttagtgct ttacggcacc tcgaccccaa aaaacttgat tgggtgatg  4500
gttcacgtag tgggccatcg ccctgataga cggtttttcg ccctttgacg ttggagtcca  4560
cgttctttaa tagtggactc ttgttccaaa ctggaacaac actcaactct atctcgggct  4620
attctttga tttataaggg attttgccga tttcggtcta ttggttaaaa aatgagctga  4680
tttaacaaaa atttaacgcg aattttaaca aaatattaac gtttacaatt ttatggtgca  4740
ctctcagtac aatctgctct gatgccgcat agttaagcca gccccgacac ccgccaacac  4800
ccgctgacgc gccctgacgg gcttgtctgc tcccggcatc cgcttacaga caagctgtga  4860
ccgtctccgg gagctgcatg tgtcagaggt tttcaccgtc atcaccgaaa cgcgcgagac  4920
gaaagggcct cgtgatacgc ctatttttat aggttaatgt catgataata atggtttctt  4980
agacgtcagg tggcacttt cggggaaatg tgcgcggaac ccctatttgt ttatttttct  5040
aaatacattc aaatatgtat ccgctcatga gacaataacc ctgataaatg cttcaataat  5100
attgaaaaag gaagagtatg agtattcaac atttccgtgt cgcccttatt cccttttttg  5160
cggcattttg ccttcctgtt tttgctcacc cagaaacgct ggtgaaagta aaagatgctg  5220
aagatcagtt gggtgcacga gtgggttaca tcgaactgga tctcaacagc ggtaagatcc  5280
ttgagagttt tcgccccgaa gaacgttttc caatgatgag cacttttaaa gttctgctat  5340
gtggcgcggt attatcccgt attgacgccg ggcaagagca actcggtcgc cgcatacact  5400
attctcagaa tgacttggtt gagtactcac cagtcacaga aaagcatctt acggatggca  5460
tgacagtaag agaattatgc agtgctgcca taaccatgag tgataacact gcggccaact  5520
tacttctgac aacgatcgga ggaccgaagg agctaaccgc ttttttgcac aacatggggg  5580
atcatgtaac tcgccttgat cgttgggaac cggagctgaa tgaagccata ccaaacgacg  5640
agcgtgacac cacgatgcct gtagcaatgg caacaacgtt gcgcaaacta ttaactggcg  5700
aactacttac tctagcttcc cggcaacaat taatagactg gatggaggcg gataaagttg  5760
caggaccact tctgcgctcg gcccttccgg ctggctggtt tattgctgat aaatctggag  5820
ccggtgagcg tggaagccgc ggtatcattg cagcactggg gccagatggt aagccctccc  5880
gtatcgtagt tatctacacg acgggagtc aggcaactat ggatgaacga atagacaga  5940
tcgctgagat aggtgcctca ctgattaagc attggtaact gtcagaccaa gtttactcat  6000
atatacttta gattgattta aaacttcatt tttaatttaa aaggatctag gtgaagatcc  6060
tttttgataa tctcatgacc aaaatccctt aacgtgagtt ttcgttccac tgagcgtcag  6120
accccgtaga aagatcaaa ggatcttctt gagatccttt tttctgcgc gtaatctgct  6180
gcttgcaaac aaaaaaacca ccgctaccag cggtggtttg tttgccggat caagagctac  6240
caactctttt tccgaaggta actggcttca gcagagcgca gataccaaat actgttcttc  6300
tagtgtagcc gtagttaggc caccacttca agaactctgt agcaccgcct acatacctcg  6360
ctctgctaat cctgttacca gtggctgctg ccagtggcga taagtcgtgt cttaccgggt  6420
tggactcaag acgatagtta ccggataagg cgcagcggtc gggctgaacg ggggttcgt  6480
gcacacagcc cagcttggag cgaacgacct acaccgaact gagataccta cagcgtgagc  6540
tatgagaaag cgccacgctt cccgaaggga gaaaggcgga caggtatccg gtaagcggca  6600
gggtcggaac aggagagcgc acgagggagc ttccaggggg aaacgcctgg tatctttata  6660
gtcctgtcgg gtttcgccac ctctgacttg agcgtcgatt tttgtgatgc tcgtcagggg  6720
ggcggagcct atgaaaaac gccagcaacg cggccttttt acgttcctg gccttttgct  6780
ggccttttgc tcacatgt                                                6798

SEQ ID NO: 162       moltype = DNA   length = 25
FEATURE              Location/Qualifiers
source               1..25
                     mol_type = other DNA
                     organism = synthetic construct
SEQUENCE: 162
ataacatttc cgaagacgac aagat                                         25

SEQ ID NO: 163       moltype = DNA   length = 31
FEATURE              Location/Qualifiers
source               1..31
                     mol_type = other DNA
                     organism = synthetic construct
SEQUENCE: 163
taccacggcg cagccctgga gacacccaag c                                  31

SEQ ID NO: 164       moltype = DNA   length = 32
FEATURE              Location/Qualifiers
source               1..32
                     mol_type = other DNA
                     organism = synthetic construct
SEQUENCE: 164
ggtgaatgcg tagaactcgt cggtgatctg ct                                 32

SEQ ID NO: 165       moltype = DNA   length = 33
FEATURE              Location/Qualifiers
```

```
source                  1..33
                        mol_type = other DNA
                        organism = synthetic construct
SEQUENCE: 165
gagttctacg cattcaccat cagaaaggac ggc                               33

SEQ ID NO: 166          moltype = DNA   length = 27
FEATURE                 Location/Qualifiers
source                  1..27
                        mol_type = other DNA
                        organism = synthetic construct
SEQUENCE: 166
cagggctgcg ccgtggtagc cctcggt                                      27

SEQ ID NO: 167          moltype = DNA   length = 31
FEATURE                 Location/Qualifiers
source                  1..31
                        mol_type = other DNA
                        organism = synthetic construct
SEQUENCE: 167
taccacggcg cagccctgga gacacccaag c                                 31

SEQ ID NO: 168          moltype = DNA   length = 33
FEATURE                 Location/Qualifiers
source                  1..33
                        mol_type = other DNA
                        organism = synthetic construct
SEQUENCE: 168
cgtatgcgtc gatgatgatc tctctgatct tca                               33

SEQ ID NO: 169          moltype = DNA   length = 31
FEATURE                 Location/Qualifiers
source                  1..31
                        mol_type = other DNA
                        organism = synthetic construct
SEQUENCE: 169
tcatcatcga cgcatacgcc agcggcctga g                                 31

SEQ ID NO: 170          moltype = DNA   length = 27
FEATURE                 Location/Qualifiers
source                  1..27
                        mol_type = other DNA
                        organism = synthetic construct
SEQUENCE: 170
cagggctgcg ccgtggtagc cctcggt                                      27

SEQ ID NO: 171          moltype = DNA   length = 33
FEATURE                 Location/Qualifiers
source                  1..33
                        mol_type = other DNA
                        organism = synthetic construct
SEQUENCE: 171
gagttctacg cattcaccat cagaaaggac ggc                               33

SEQ ID NO: 172          moltype = DNA   length = 33
FEATURE                 Location/Qualifiers
source                  1..33
                        mol_type = other DNA
                        organism = synthetic construct
SEQUENCE: 172
cgtatgcgtc gatgatgatc tctctgatct tca                               33

SEQ ID NO: 173          moltype = DNA   length = 31
FEATURE                 Location/Qualifiers
source                  1..31
                        mol_type = other DNA
                        organism = synthetic construct
SEQUENCE: 173
tcatcatcga cgcatacgcc agcggcctga g                                 31

SEQ ID NO: 174          moltype = DNA   length = 32
FEATURE                 Location/Qualifiers
source                  1..32
                        mol_type = other DNA
                        organism = synthetic construct
SEQUENCE: 174
ggtgaatgcg tagaactcgt cggtgatctg ct                                32

SEQ ID NO: 175          moltype = DNA   length = 31
```

```
FEATURE                 Location/Qualifiers
source                  1..31
                        mol_type = other DNA
                        organism = synthetic construct
SEQUENCE: 175
taccacggcg cagccctgga gacacccaag c                              31

SEQ ID NO: 176          moltype = DNA   length = 32
FEATURE                 Location/Qualifiers
source                  1..32
                        mol_type = other DNA
                        organism = synthetic construct
SEQUENCE: 176
ggtgaatgcg tagaactcgt cggtgatctg ct                             32

SEQ ID NO: 177          moltype = DNA   length = 33
FEATURE                 Location/Qualifiers
source                  1..33
                        mol_type = other DNA
                        organism = synthetic construct
SEQUENCE: 177
gagttctacg cattccacat cagaaaggac ggc                            33

SEQ ID NO: 178          moltype = DNA   length = 33
FEATURE                 Location/Qualifiers
source                  1..33
                        mol_type = other DNA
                        organism = synthetic construct
SEQUENCE: 178
cgtatgcgtc gatgatgatc tctctgatct tca                            33

SEQ ID NO: 179          moltype = DNA   length = 31
FEATURE                 Location/Qualifiers
source                  1..31
                        mol_type = other DNA
                        organism = synthetic construct
SEQUENCE: 179
tcatcatcga cgcatacgcc agcggcctga g                              31

SEQ ID NO: 180          moltype = DNA   length = 27
FEATURE                 Location/Qualifiers
source                  1..27
                        mol_type = other DNA
                        organism = synthetic construct
SEQUENCE: 180
cagggctgcg ccgtggtagc cctcggt                                   27

SEQ ID NO: 181          moltype = DNA   length = 33
FEATURE                 Location/Qualifiers
source                  1..33
                        mol_type = other DNA
                        organism = synthetic construct
SEQUENCE: 181
aagaatcgac gaggccgtgg acctgtgcgg cga                            33

SEQ ID NO: 182          moltype = DNA   length = 31
FEATURE                 Location/Qualifiers
source                  1..31
                        mol_type = other DNA
                        organism = synthetic construct
SEQUENCE: 182
gatctctgcg atcttcacca ggttcatgcc c                              31

SEQ ID NO: 183          moltype = DNA   length = 35
FEATURE                 Location/Qualifiers
source                  1..35
                        mol_type = other DNA
                        organism = synthetic construct
SEQUENCE: 183
gtgaagatcg cagagatcat catcgacaga tacgc                          35

SEQ ID NO: 184          moltype = DNA   length = 27
FEATURE                 Location/Qualifiers
source                  1..27
                        mol_type = other DNA
                        organism = synthetic construct
SEQUENCE: 184
acggcctcgt cgattcttct cacctcg                                   27
```

```
SEQ ID NO: 185          moltype = DNA   length = 33
FEATURE                 Location/Qualifiers
source                  1..33
                        mol_type = other DNA
                        organism = synthetic construct
SEQUENCE: 185
aagaatcgac gaggccgtgg acctgtgcgg cga                                   33

SEQ ID NO: 186          moltype = DNA   length = 35
FEATURE                 Location/Qualifiers
source                  1..35
                        mol_type = other DNA
                        organism = synthetic construct
SEQUENCE: 186
aggatgtact tggccttggg gtcgttgaag taggg                                 35

SEQ ID NO: 187          moltype = DNA   length = 32
FEATURE                 Location/Qualifiers
source                  1..32
                        mol_type = other DNA
                        organism = synthetic construct
SEQUENCE: 187
caaggccaag tacatcctga agtacaagga cg                                    32

SEQ ID NO: 188          moltype = DNA   length = 27
FEATURE                 Location/Qualifiers
source                  1..27
                        mol_type = other DNA
                        organism = synthetic construct
SEQUENCE: 188
acggcctcgt cgattcttct cacctcg                                          27

SEQ ID NO: 189          moltype = DNA   length = 33
FEATURE                 Location/Qualifiers
source                  1..33
                        mol_type = other DNA
                        organism = synthetic construct
SEQUENCE: 189
aagaatcgac gaggccgtgg acctgtgcgg cga                                   33

SEQ ID NO: 190          moltype = DNA   length = 31
FEATURE                 Location/Qualifiers
source                  1..31
                        mol_type = other DNA
                        organism = synthetic construct
SEQUENCE: 190
tctcgctggg ggccaccagc agggcctcga t                                     31

SEQ ID NO: 191          moltype = DNA   length = 25
FEATURE                 Location/Qualifiers
source                  1..25
                        mol_type = other DNA
                        organism = synthetic construct
SEQUENCE: 191
tggtggcccc cagcgagaag gtggg                                            25

SEQ ID NO: 192          moltype = DNA   length = 27
FEATURE                 Location/Qualifiers
source                  1..27
                        mol_type = other DNA
                        organism = synthetic construct
SEQUENCE: 192
acggcctcgt cgattcttct cacctcg                                          27

SEQ ID NO: 193          moltype = DNA   length = 34
FEATURE                 Location/Qualifiers
source                  1..34
                        mol_type = other DNA
                        organism = synthetic construct
SEQUENCE: 193
aagaacgccg tggccatggc catcctgttc gacc                                  34

SEQ ID NO: 194          moltype = DNA   length = 31
FEATURE                 Location/Qualifiers
source                  1..31
                        mol_type = other DNA
                        organism = synthetic construct
SEQUENCE: 194
gatctctgcg atcttcacca ggttcatgcc c                                     31
```

```
SEQ ID NO: 195          moltype = DNA  length = 35
FEATURE                 Location/Qualifiers
source                  1..35
                        mol_type = other DNA
                        organism = synthetic construct
SEQUENCE: 195
gtgaagatcg cagagatcat catcgacaga tacgc                                35

SEQ ID NO: 196          moltype = DNA  length = 25
FEATURE                 Location/Qualifiers
source                  1..25
                        mol_type = other DNA
                        organism = synthetic construct
SEQUENCE: 196
catggccacg gcgttcttgc tcagg                                           25

SEQ ID NO: 197          moltype = DNA  length = 34
FEATURE                 Location/Qualifiers
source                  1..34
                        mol_type = other DNA
                        organism = synthetic construct
SEQUENCE: 197
aagaacgccg tggccatggc catcctgttc gacc                                 34

SEQ ID NO: 198          moltype = DNA  length = 35
FEATURE                 Location/Qualifiers
source                  1..35
                        mol_type = other DNA
                        organism = synthetic construct
SEQUENCE: 198
aggatgtact tggccttggg gtcgttgaag taggg                                35

SEQ ID NO: 199          moltype = DNA  length = 32
FEATURE                 Location/Qualifiers
source                  1..32
                        mol_type = other DNA
                        organism = synthetic construct
SEQUENCE: 199
caaggccaag tacatcctga agtacaagga cg                                   32

SEQ ID NO: 200          moltype = DNA  length = 25
FEATURE                 Location/Qualifiers
source                  1..25
                        mol_type = other DNA
                        organism = synthetic construct
SEQUENCE: 200
catggccacg gcgttcttgc tcagg                                           25

SEQ ID NO: 201          moltype = DNA  length = 25
FEATURE                 Location/Qualifiers
source                  1..25
                        mol_type = other DNA
                        organism = synthetic construct
SEQUENCE: 201
tggtggcccc cagcgagaag gtggg                                           25

SEQ ID NO: 202          moltype = DNA  length = 25
FEATURE                 Location/Qualifiers
source                  1..25
                        mol_type = other DNA
                        organism = synthetic construct
SEQUENCE: 202
catggccacg gcgttcttgc tcagg                                           25

SEQ ID NO: 203          moltype = DNA  length = 34
FEATURE                 Location/Qualifiers
source                  1..34
                        mol_type = other DNA
                        organism = synthetic construct
SEQUENCE: 203
aagaacgccg tggccatggc catcctgttc gacc                                 34

SEQ ID NO: 204          moltype = DNA  length = 31
FEATURE                 Location/Qualifiers
source                  1..31
                        mol_type = other DNA
                        organism = synthetic construct
SEQUENCE: 204
```
tctcgctggg ggccaccagc agggcctcga t                                        31

SEQ ID NO: 205         moltype = DNA  length = 33
FEATURE                Location/Qualifiers
source                 1..33
                       mol_type = other DNA
                       organism = synthetic construct
SEQUENCE: 205
aagaatcgac gaggccgtgg acctgtgcgg cga                                      33

SEQ ID NO: 206         moltype = DNA  length = 25
FEATURE                Location/Qualifiers
source                 1..25
                       mol_type = other DNA
                       organism = synthetic construct
SEQUENCE: 206
catggccacg gcgttcttgc tcagg                                               25

SEQ ID NO: 207         moltype = DNA  length = 34
FEATURE                Location/Qualifiers
source                 1..34
                       mol_type = other DNA
                       organism = synthetic construct
SEQUENCE: 207
aagaacgccg tggccatggc catcctgttc gacc                                     34

SEQ ID NO: 208         moltype = DNA  length = 31
FEATURE                Location/Qualifiers
source                 1..31
                       mol_type = other DNA
                       organism = synthetic construct
SEQUENCE: 208
gatctctgcg atcttcacca ggttcatgcc c                                        31

SEQ ID NO: 209         moltype = DNA  length = 35
FEATURE                Location/Qualifiers
source                 1..35
                       mol_type = other DNA
                       organism = synthetic construct
SEQUENCE: 209
gtgaagatcg cagagatcat catcgacaga tacgc                                    35

SEQ ID NO: 210         moltype = DNA  length = 27
FEATURE                Location/Qualifiers
source                 1..27
                       mol_type = other DNA
                       organism = synthetic construct
SEQUENCE: 210
acggcctcgt cgattcttct cacctcg                                             27

SEQ ID NO: 211         moltype = DNA  length = 33
FEATURE                Location/Qualifiers
source                 1..33
                       mol_type = other DNA
                       organism = synthetic construct
SEQUENCE: 211
aagaatcgac gaggccgtgg acctgtgcgg cga                                      33

SEQ ID NO: 212         moltype = DNA  length = 31
FEATURE                Location/Qualifiers
source                 1..31
                       mol_type = other DNA
                       organism = synthetic construct
SEQUENCE: 212
tctcgctggg ggccaccagc agggcctcga t                                        31

SEQ ID NO: 213         moltype = DNA  length = 25
FEATURE                Location/Qualifiers
source                 1..25
                       mol_type = other DNA
                       organism = synthetic construct
SEQUENCE: 213
tggtggcccc cagcgagaag gtggg                                               25

SEQ ID NO: 214         moltype = DNA  length = 25
FEATURE                Location/Qualifiers
source                 1..25
                       mol_type = other DNA
                       organism = synthetic construct

```
SEQUENCE: 214
catggccacg gcgttcttgc tcagg                                              25

SEQ ID NO: 215          moltype = DNA   length = 34
FEATURE                 Location/Qualifiers
source                  1..34
                        mol_type = other DNA
                        organism = synthetic construct
SEQUENCE: 215
aagaacgccg tggccatggc catcctgttc gacc                                    34

SEQ ID NO: 216          moltype = DNA   length = 27
FEATURE                 Location/Qualifiers
source                  1..27
                        mol_type = other DNA
                        organism = synthetic construct
SEQUENCE: 216
acggcctcgt cgattcttct cacctcg                                            27

SEQ ID NO: 217          moltype = DNA   length = 32
FEATURE                 Location/Qualifiers
source                  1..32
                        mol_type = other DNA
                        organism = synthetic construct
SEQUENCE: 217
acaagaaatc caaggccaag agaatgggcg tg                                      32

SEQ ID NO: 218          moltype = DNA   length = 32
FEATURE                 Location/Qualifiers
source                  1..32
                        mol_type = other DNA
                        organism = synthetic construct
SEQUENCE: 218
ggccttggat ttcttgtcct tgctcatgtc ga                                      32

SEQ ID NO: 219          moltype = DNA   length = 34
FEATURE                 Location/Qualifiers
source                  1..34
                        mol_type = other DNA
                        organism = synthetic construct
SEQUENCE: 219
agaatgggcg tgaagtccct gctggccac ggcg                                     34

SEQ ID NO: 220          moltype = DNA   length = 32
FEATURE                 Location/Qualifiers
source                  1..32
                        mol_type = other DNA
                        organism = synthetic construct
SEQUENCE: 220
gacttcacgc ccattctctt ggccttggtt tt                                      32

SEQ ID NO: 221          moltype = DNA   length = 32
FEATURE                 Location/Qualifiers
source                  1..32
                        mol_type = other DNA
                        organism = synthetic construct
SEQUENCE: 221
cttcctggaa aagaacgccg tgaacatggc ca                                      32

SEQ ID NO: 222          moltype = DNA   length = 34
FEATURE                 Location/Qualifiers
source                  1..34
                        mol_type = other DNA
                        organism = synthetic construct
SEQUENCE: 222
cgttcttttc caggaagtcc ttgttcacct tctt                                    34

SEQ ID NO: 223          moltype = DNA   length = 33
FEATURE                 Location/Qualifiers
source                  1..33
                        mol_type = other DNA
                        organism = synthetic construct
SEQUENCE: 223
gcaagaacaa ggtgaacatg gccatcctgt tcg                                     33

SEQ ID NO: 224          moltype = DNA   length = 33
FEATURE                 Location/Qualifiers
source                  1..33
                        mol_type = other DNA
```

|  |  |  |
|---|---|---|
| | organism = synthetic construct | |
| SEQUENCE: 224 | | |
| gttcaccttg ttcttgctca ggaagtcctt gtt | | 33 |
| | | |
| SEQ ID NO: 225 | moltype = DNA  length = 32 | |
| FEATURE | Location/Qualifiers | |
| source | 1..32 | |
| | mol_type = other DNA | |
| | organism = synthetic construct | |
| SEQUENCE: 225 | | |
| gtgaacatag ccatcctgtt cgacctgctg aa | | 32 |
| | | |
| SEQ ID NO: 226 | moltype = DNA  length = 32 | |
| FEATURE | Location/Qualifiers | |
| source | 1..32 | |
| | mol_type = other DNA | |
| | organism = synthetic construct | |
| SEQUENCE: 226 | | |
| aggatggcta tgttcacggc gttcttgctc ag | | 32 |
| | | |
| SEQ ID NO: 227 | moltype = DNA  length = 37 | |
| FEATURE | Location/Qualifiers | |
| source | 1..37 | |
| | mol_type = other DNA | |
| | organism = synthetic construct | |
| SEQUENCE: 227 | | |
| tgttcgacct gctgaaggcc agagacgtgg agcagaa | | 37 |
| | | |
| SEQ ID NO: 228 | moltype = DNA  length = 32 | |
| FEATURE | Location/Qualifiers | |
| source | 1..32 | |
| | mol_type = other DNA | |
| | organism = synthetic construct | |
| SEQUENCE: 228 | | |
| cttcagcagg tcgaacagga tggccatgtt ca | | 32 |
| | | |
| SEQ ID NO: 229 | moltype = DNA  length = 35 | |
| FEATURE | Location/Qualifiers | |
| source | 1..35 | |
| | mol_type = other DNA | |
| | organism = synthetic construct | |
| SEQUENCE: 229 | | |
| cgacgagtac tacagattca ccatcagaaa ggacg | | 35 |
| | | |
| SEQ ID NO: 230 | moltype = DNA  length = 32 | |
| FEATURE | Location/Qualifiers | |
| source | 1..32 | |
| | mol_type = other DNA | |
| | organism = synthetic construct | |
| SEQUENCE: 230 | | |
| atctgtagta ctcgtcggtg atctgcttct tc | | 32 |
| | | |
| SEQ ID NO: 231 | moltype = DNA  length = 37 | |
| FEATURE | Location/Qualifiers | |
| source | 1..37 | |
| | mol_type = other DNA | |
| | organism = synthetic construct | |
| SEQUENCE: 231 | | |
| aacctgggct tcaacctggt gaagatcaga gagatca | | 37 |
| | | |
| SEQ ID NO: 232 | moltype = DNA  length = 32 | |
| FEATURE | Location/Qualifiers | |
| source | 1..32 | |
| | mol_type = other DNA | |
| | organism = synthetic construct | |
| SEQUENCE: 232 | | |
| aggttgaagc ccaggttctt gccgtccttt ct | | 32 |
| | | |
| SEQ ID NO: 233 | moltype = DNA  length = 32 | |
| FEATURE | Location/Qualifiers | |
| source | 1..32 | |
| | mol_type = other DNA | |
| | organism = synthetic construct | |
| SEQUENCE: 233 | | |
| catgagcctg gtgaagatca gagagatcat ca | | 32 |
| | | |
| SEQ ID NO: 234 | moltype = DNA  length = 32 | |
| FEATURE | Location/Qualifiers | |
| source | 1..32 | |

```
                        mol_type = other DNA
                        organism = synthetic construct
SEQUENCE: 234
tcttcaccag gctcatgccc aggttcttgc cg                                       32

SEQ ID NO: 235          moltype = DNA   length = 37
FEATURE                 Location/Qualifiers
source                  1..37
                        mol_type = other DNA
                        organism = synthetic construct
SEQUENCE: 235
gcatgaacat cgtgaagatc agagagatca tcatcga                                  37

SEQ ID NO: 236          moltype = DNA   length = 32
FEATURE                 Location/Qualifiers
source                  1..32
                        mol_type = other DNA
                        organism = synthetic construct
SEQUENCE: 236
cttcacgatg ttcatgccca ggttcttgcc gt                                       32

SEQ ID NO: 237          moltype = DNA   length = 40
FEATURE                 Location/Qualifiers
source                  1..40
                        mol_type = other DNA
                        organism = synthetic construct
SEQUENCE: 237
ggcatgaacc tgaagaagat cagagagatc atcatcgaca                               40

SEQ ID NO: 238          moltype = DNA   length = 33
FEATURE                 Location/Qualifiers
source                  1..33
                        mol_type = other DNA
                        organism = synthetic construct
SEQUENCE: 238
cttcttcagg ttcatgccca ggttcttgcc gtc                                      33

SEQ ID NO: 239          moltype = DNA   length = 32
FEATURE                 Location/Qualifiers
source                  1..32
                        mol_type = other DNA
                        organism = synthetic construct
SEQUENCE: 239
gagatcatga tcgacagata cgccagcggc ct                                       32

SEQ ID NO: 240          moltype = DNA   length = 34
FEATURE                 Location/Qualifiers
source                  1..34
                        mol_type = other DNA
                        organism = synthetic construct
SEQUENCE: 240
ctgtcgatca tgatctctct gatcttcacc aggt                                     34

SEQ ID NO: 241          moltype = DNA   length = 32
FEATURE                 Location/Qualifiers
source                  1..32
                        mol_type = other DNA
                        organism = synthetic construct
SEQUENCE: 241
atcatcgaga gatacgccag cggcctgaga ga                                       32

SEQ ID NO: 242          moltype = DNA   length = 34
FEATURE                 Location/Qualifiers
source                  1..34
                        mol_type = other DNA
                        organism = synthetic construct
SEQUENCE: 242
gcgtatctct cgatgatgat ctctctgatc ttca                                     34

SEQ ID NO: 243          moltype = DNA   length = 32
FEATURE                 Location/Qualifiers
source                  1..32
                        mol_type = other DNA
                        organism = synthetic construct
SEQUENCE: 243
acaagaagta cgaccccac agacagaaga tc                                        32

SEQ ID NO: 244          moltype = DNA   length = 32
FEATURE                 Location/Qualifiers
```

```
source                  1..32
                        mol_type = other DNA
                        organism = synthetic construct
SEQUENCE: 244
ggggtcgtac ttcttgtctc tcaggccgct gg                              32

SEQ ID NO: 245          moltype = DNA   length = 36
FEATURE                 Location/Qualifiers
source                  1..36
                        mol_type = other DNA
                        organism = synthetic construct
SEQUENCE: 245
aagaagcacg actcccacag acagaagatc aacgtg                          36

SEQ ID NO: 246          moltype = DNA   length = 32
FEATURE                 Location/Qualifiers
source                  1..32
                        mol_type = other DNA
                        organism = synthetic construct
SEQUENCE: 246
tgggagtcgt gcttcttgtc tctcaggccg ct                              32

SEQ ID NO: 247          moltype = DNA   length = 33
FEATURE                 Location/Qualifiers
source                  1..33
                        mol_type = other DNA
                        organism = synthetic construct
SEQUENCE: 247
ccgtcagaca gaagatcaac gtgatcgccg act                             33

SEQ ID NO: 248          moltype = DNA   length = 37
FEATURE                 Location/Qualifiers
source                  1..37
                        mol_type = other DNA
                        organism = synthetic construct
SEQUENCE: 248
tgatcttctg tctgacgggg tcgtgcttct tgtctct                         37

SEQ ID NO: 249          moltype = DNA   length = 32
FEATURE                 Location/Qualifiers
source                  1..32
                        mol_type = other DNA
                        organism = synthetic construct
SEQUENCE: 249
gaagatctac gtgatcgccg acttcctgat ct                              32

SEQ ID NO: 250          moltype = DNA   length = 32
FEATURE                 Location/Qualifiers
source                  1..32
                        mol_type = other DNA
                        organism = synthetic construct
SEQUENCE: 250
cgatcacgta gatcttctgt ctgtgggggt cg                              32

SEQ ID NO: 251          moltype = DNA   length = 32
FEATURE                 Location/Qualifiers
source                  1..32
                        mol_type = other DNA
                        organism = synthetic construct
SEQUENCE: 251
caggaccagg gcatcatcga caagaccgtg ag                              32

SEQ ID NO: 252          moltype = DNA   length = 34
FEATURE                 Location/Qualifiers
source                  1..34
                        mol_type = other DNA
                        organism = synthetic construct
SEQUENCE: 252
atgatgccct ggtcctggct cagggctctg aaga                            34

SEQ ID NO: 253          moltype = DNA   length = 34
FEATURE                 Location/Qualifiers
source                  1..34
                        mol_type = other DNA
                        organism = synthetic construct
SEQUENCE: 253
tcatcgacaa gctcgtgagc agcctgagac tgac                            34

SEQ ID NO: 254          moltype = DNA   length = 33
```

```
FEATURE              Location/Qualifiers
source               1..33
                     mol_type = other DNA
                     organism = synthetic construct
SEQUENCE: 254
tcacgagctt gtcgatgatg ccctggttct ggc                                    33

SEQ ID NO: 255       moltype = DNA   length = 32
FEATURE              Location/Qualifiers
source               1..32
                     mol_type = other DNA
                     organism = synthetic construct
SEQUENCE: 255
tgagactgtc caaggacgag gaggagaagg ac                                     32

SEQ ID NO: 256       moltype = DNA   length = 32
FEATURE              Location/Qualifiers
source               1..32
                     mol_type = other DNA
                     organism = synthetic construct
SEQUENCE: 256
gtccttggac agtctcaggc tgctcacggt ct                                     32

SEQ ID NO: 257       moltype = DNA   length = 37
FEATURE              Location/Qualifiers
source               1..37
                     mol_type = other DNA
                     organism = synthetic construct
SEQUENCE: 257
aaggacgagg aggacaagga ccacgtgtac cagaacg                                37

SEQ ID NO: 258       moltype = DNA   length = 32
FEATURE              Location/Qualifiers
source               1..32
                     mol_type = other DNA
                     organism = synthetic construct
SEQUENCE: 258
ttgtcctcct cgtccttggt cagtctcagg ct                                     32

SEQ ID NO: 259       moltype = DNA   length = 35
FEATURE              Location/Qualifiers
source               1..35
                     mol_type = other DNA
                     organism = synthetic construct
SEQUENCE: 259
acgtgtacca gaacgaggcc gagctggtgt ggggc                                  35

SEQ ID NO: 260       moltype = DNA   length = 33
FEATURE              Location/Qualifiers
source               1..33
                     mol_type = other DNA
                     organism = synthetic construct
SEQUENCE: 260
cctcgttctg gtacacgtgg tccttctcct cct                                    33

SEQ ID NO: 261       moltype = DNA   length = 32
FEATURE              Location/Qualifiers
source               1..32
                     mol_type = other DNA
                     organism = synthetic construct
SEQUENCE: 261
aaggtgagca actgcctgac ccctacttc aa                                      32

SEQ ID NO: 262       moltype = DNA   length = 34
FEATURE              Location/Qualifiers
source               1..34
                     mol_type = other DNA
                     organism = synthetic construct
SEQUENCE: 262
aggcagttgc tcaccttgcc ccacaccagc tcgg                                   34

SEQ ID NO: 263       moltype = DNA   length = 32
FEATURE              Location/Qualifiers
source               1..32
                     mol_type = other DNA
                     organism = synthetic construct
SEQUENCE: 263
atggtgagga actgcctgac ccctacttc aa                                      32
```

```
SEQ ID NO: 264          moltype = DNA  length = 32
FEATURE                 Location/Qualifiers
source                  1..32
                        mol_type = other DNA
                        organism = synthetic construct
SEQUENCE: 264
aggcagttcc tcaccatgcc ccacaccagc tc                                   32

SEQ ID NO: 265          moltype = DNA  length = 33
FEATURE                 Location/Qualifiers
source                  1..33
                        mol_type = other DNA
                        organism = synthetic construct
SEQUENCE: 265
caagaacggg tacatcctga agtacaagga cgc                                  33

SEQ ID NO: 266          moltype = DNA  length = 34
FEATURE                 Location/Qualifiers
source                  1..34
                        mol_type = other DNA
                        organism = synthetic construct
SEQUENCE: 266
aggatgtacc cgttcttggg gtcgttgaag tagg                                 34

SEQ ID NO: 267          moltype = DNA  length = 32
FEATURE                 Location/Qualifiers
source                  1..32
                        mol_type = other DNA
                        organism = synthetic construct
SEQUENCE: 267
agaacaagga catcctgaag tacaaggacg cc                                   32

SEQ ID NO: 268          moltype = DNA  length = 32
FEATURE                 Location/Qualifiers
source                  1..32
                        mol_type = other DNA
                        organism = synthetic construct
SEQUENCE: 268
caggatgtcc ttgttcttgg ggtcgttgaa gt                                   32

SEQ ID NO: 269          moltype = DNA  length = 33
FEATURE                 Location/Qualifiers
source                  1..33
                        mol_type = other DNA
                        organism = synthetic construct
SEQUENCE: 269
agtacaagct cgccaagacc cccggcgact tcg                                  33

SEQ ID NO: 270          moltype = DNA  length = 38
FEATURE                 Location/Qualifiers
source                  1..38
                        mol_type = other DNA
                        organism = synthetic construct
SEQUENCE: 270
tcttggcgag cttgtacttc aggatgtact tgttcttg                             38

SEQ ID NO: 271          moltype = DNA  length = 32
FEATURE                 Location/Qualifiers
source                  1..32
                        mol_type = other DNA
                        organism = synthetic construct
SEQUENCE: 271
ttcgaggagt ggatcaccag caagatcagc ga                                   32

SEQ ID NO: 272          moltype = DNA  length = 32
FEATURE                 Location/Qualifiers
source                  1..32
                        mol_type = other DNA
                        organism = synthetic construct
SEQUENCE: 272
gtgatccact cctcgaagtc gccggggtc tt                                    32

SEQ ID NO: 273          moltype = DNA  length = 33
FEATURE                 Location/Qualifiers
source                  1..33
                        mol_type = other DNA
                        organism = synthetic construct
SEQUENCE: 273
caagatcaag gaggacgacg gcgagccctt cgt                                  33
```

```
SEQ ID NO: 274          moltype = DNA  length = 33
FEATURE                 Location/Qualifiers
source                  1..33
                        mol_type = other DNA
                        organism = synthetic construct
SEQUENCE: 274
tcgtcctcct tgatcttgct ggtgatccag tcc                                   33

SEQ ID NO: 275          moltype = DNA  length = 19
FEATURE                 Location/Qualifiers
source                  1..19
                        mol_type = other DNA
                        organism = synthetic construct
SEQUENCE: 275
ccagggacca tgttttgcc                                                   19

SEQ ID NO: 276          moltype = DNA  length = 21
FEATURE                 Location/Qualifiers
source                  1..21
                        mol_type = other DNA
                        organism = synthetic construct
SEQUENCE: 276
cgaagacgac aagatggaca a                                                21

SEQ ID NO: 277          moltype = DNA  length = 36
FEATURE                 Location/Qualifiers
source                  1..36
                        mol_type = other DNA
                        organism = synthetic construct
variation               26
                        note = n is a or g
SEQUENCE: 277
ggaagatnac tctacaaacc tgtagngnnn nnnnnn                                36

SEQ ID NO: 278          moltype = DNA  length = 36
FEATURE                 Location/Qualifiers
source                  1..36
                        mol_type = other DNA
                        organism = synthetic construct
variation               8
                        note = n is a or g
variation               26
                        note = n is a or g
variation               28
                        note = n is a or t
variation               29
                        note = n is c or t
variation               30
                        note = n is c or t
variation               31
                        note = n is g or t
variation               32
                        note = n is g or t
variation               33
                        note = n is a or g
variation               34
                        note = n is c or g
variation               35
                        note = n is a or g
variation               36
                        note = n is c or g
SEQUENCE: 278
ggaagatnac tctacaaacc tgtagngnnn nnnnnn                                36

SEQ ID NO: 279          moltype = AA  length = 17
FEATURE                 Location/Qualifiers
source                  1..17
                        mol_type = protein
                        organism = synthetic construct
SEQUENCE: 279
AEAAAKEAAA KEAAAKA                                                     17

SEQ ID NO: 280          moltype = AA  length = 15
FEATURE                 Location/Qualifiers
source                  1..15
                        mol_type = protein
                        organism = synthetic construct
SEQUENCE: 280
```

```
GGGGSGGGGS GGGGS                                                             15

SEQ ID NO: 281         moltype = DNA  length = 36
FEATURE                Location/Qualifiers
source                 1..36
                       mol_type = other DNA
                       organism = synthetic construct
SEQUENCE: 281
ggaagataac tctacaaacc tgtagggttc tgagac                                      36

SEQ ID NO: 282         moltype = RNA  length = 36
FEATURE                Location/Qualifiers
source                 1..36
                       mol_type = other RNA
                       organism = synthetic construct
SEQUENCE: 282
ggaagataac tctacaaacc tgtagagttc tgagac                                      36

SEQ ID NO: 283         moltype = AA   length = 25
FEATURE                Location/Qualifiers
source                 1..25
                       mol_type = protein
                       organism = synthetic construct
SEQUENCE: 283
LGHKLEYNYN SHNVYIMADK QKNGI                                                  25

SEQ ID NO: 284         moltype = DNA  length = 73
FEATURE                Location/Qualifiers
source                 1..73
                       mol_type = other DNA
                       organism = synthetic construct
SEQUENCE: 284
tggggcacaa gctggagtac aactacaaca gccacaacgt ctatatcatg gccgacaagc            60
agaagaacgg cat                                                               73
```

CRISPR-CAS13 SYSTEM AND USE THEREOF

CROSS-REFERENCE TO RELATED APPLICATIONS

This application is a continuation application of PCT/CN2023/115093, filed on Aug. 25, 2023, which claims priorities from Chinese patent application CN2022110353428, filed on Aug. 26, 2022 and Chinese patent application CN2023104578804, filed on Apr. 24, 2023, the entire contents of which are hereby incorporated by reference.

REFERENCE TO SEQUENCE LISTING

The instant application contains a Sequence Listing as an XML file entitled "P24410729US_CA_SEQ.xml" created on Jul. 31, 2024 and having a size of 447,376 bytes.

TECHNICAL FIELD

The present disclosure relates to the field of CRISPR gene editing, particularly relates to a CRISPR-Cas13 system and use thereof.

BACKGROUND

CRISPR-Cas13 is an RNA targeting and editing system based on the bacterial immune system that protects bacteria from viruses. The CRISPR-Cas13 system is similar to the CRISPR-Cas9 system, but unlike Cas9 proteins which target DNA, Cas13 proteins target RNA.

CRISPR-Cas13 belongs to Type VI CRISPR-Cas13 system, which contains a single effector protein, Cas13. Currently, CRISPR-Cas13 can be divided into multiple subtypes (e.g., Cas13a, Cas13b, Cas13c, and Cas13d) according to phylogeny. However, a need remains for a novel Cas13 system that has compact size (e.g., suitable for AAV delivery), high editing efficiency in mammalian cells (e.g., RNA targeting/cleavage activity), and/or low cytotoxicity (e.g., cellular dormancy and apoptosis caused by collateral RNA degradation).

SUMMARY

One aspect of the disclosure provided herein relates to a Cas13 protein, wherein the amino acid sequence of the Cas 13 protein has at least 90% sequence identity compared to SEQ ID NO: 1.

In some embodiments, the Cas13 protein forms a CRISPR complex with a guide polynucleotide comprising a direct repeat sequence linked to a guide sequence that is engineered to hybridize with a target RNA.

In some embodiments, the Cas13 protein can form a CRISPR complex with a guide polynucleotide, and the CRISPR complex can sequence-specifically bind to the target RNA.

In some embodiments, the Cas13 protein can form a CRISPR complex with a guide polynucleotide comprising a direct repeat sequence linked to a guide sequence that is engineered to guide the sequence-specific binding of the CRISPR complex to the target RNA.

In some embodiments, the amino acid sequence of the Cas13 protein has at least 95% sequence identity compared to SEQ ID NO: 1. In some embodiments, the amino acid sequence of the Cas13 protein has at least 96% sequence identity compared to SEQ ID NO: 1. In some embodiments, the amino acid sequence of the Cas13 protein has at least 97% sequence identity compared to SEQ ID NO: 1. In some embodiments, the amino acid sequence of the Cas13 protein has at least 98% sequence identity compared to SEQ ID NO: 1. In some embodiments, the amino acid sequence of the Cas13 protein has at least 99% sequence identity compared to SEQ ID NO: 1. In some embodiments, the amino acid sequence of the Cas13 protein has at least 99.5% sequence identity compared to SEQ ID NO: 1. In some embodiments, the amino acid sequence of the Cas13 protein is as shown in SEQ ID NO: 1.

The Cas13 protein (i.e. C13-2 protein) with the sequence of SEQ ID NO: 1 in the present disclosure was identified based on bioinformatics analysis of prokaryotic genomes and metagenomes in the CNGB database (China National Gene Bank) and, followed by subsequent activity validation. In some embodiments, the Cas13 protein in the present disclosure derives from the species comprising a genome having an average nucleotide identity (ANI) of ≥95% with the genome of No. CNA0009596 in the CNGB database.

Average nucleotide identity (ANI) is an indicator that evaluates the similarity of all orthologous protein coding genes between two genomes at the nucleic acid level. For bacteria/archaea, the threshold ANI=95% is generally used as the basis for determining whether they are the same species (Richter M, Rosselló-Móra R. Shifting the genetic gold standard for the prokaryotic species definition. Proc Natl Acad Sci USA. 2009 Nov. 10; 106 (45): 19126-31). Therefore, the present disclosure is defined based on the above threshold, and the species with an ANI value ≥95% of the reference genome are considered the same species, wherein the Cas13 protein has homology and similar function with the protein claimed by the present disclosure, which belongs to the scope of the present disclosure. ANI analysis tools include programs such as FastANI, JSpecies, etc.

In some embodiments, compared to SEQ ID NO: 1, the amino acid sequence of the Cas13 protein comprises one, two, three, four, five, six, seven or more mutations, such as a single amino acid insertion, a single amino acid deletion, a single amino acid substitution, or a combination thereof.

In some embodiments, the Cas13 protein comprises one or more mutations in the catalytic domain and has reduced RNA cleavage activity.

In some embodiments, the Cas13 protein comprises one mutation in the catalytic domain and has reduced RNA cleavage activity. In some embodiments, the Cas13 protein comprises one or more mutations in one or both HEPN domains and substantially lacks RNA cleavage activity. In some embodiments, the Cas13 protein comprises one mutation in any one of both HEPN domain and substantially lacks RNA cleavage activity.

The expression "substantially lack RNA cleavage activity" refers to the retention of ≤50%, ≤40%, ≤30%, ≤20%, ≤10%, ≤5%, or ≤1% of RNA cleavage activity compared to the wild-type Cas13 protein, or the absence of detectable RNA cleavage activity.

In some embodiments, the RxxxxH motif of the Cas13 protein (x represents any amino acid, RxxxxH can also be referred to as Rx4H or R4xH) comprises one or more mutations and substantially lacks RNA cleavage activity.

In some embodiments, the Cas13 protein comprises a mutation at the position corresponding to the RxxxxH motifs at positions 210-215, 750-755, and/or 785-790 of the reference protein as shown in SEQ ID NO: 1.

In some embodiments, the Cas13 protein comprises a mutation at the position corresponding to the RxxxxH motif at positions 210-215 of the reference protein as shown in SEQ ID NO: 1. In some embodiments, the Cas13 protein comprises a mutation at the position corresponding to the RxxxxH motif at positions 750-755 of the reference protein as shown in SEQ ID NO: 1. In some embodiments, the Cas13 protein comprises a mutation at the position corresponding to the RxxxxH motif at positions 785-790 of the reference protein as shown in SEQ ID NO: 1.

In some embodiments, the Cas13 protein comprises a mutation at the position corresponding to the RxxxxH motifs at positions 210-215 and 750-755 of the reference protein as shown in SEQ ID NO: 1.

In some embodiments, the Cas13 protein comprises a mutation at the position corresponding to the RxxxxH motifs at positions 210-215 and 785-790 of the reference protein as shown in SEQ ID NO: 1.

In some embodiments, the Cas13 protein comprises a mutation at the position corresponding to the RxxxxH motifs at positions 750-755 and 785-790 of the reference protein as shown in SEQ ID NO: 1.

In some embodiments, the Cas13 protein comprises a mutation at the position corresponding to the RxxxxH motifs at positions 210-215, 750-755 and 785-790 of the reference protein as shown in SEQ ID NO: 1.

In some embodiments, the RxxxxH motif is mutated to AxxxxxH, RxxxxA, or AxxxxxA. In some embodiments, the RxxxxH motif is mutated to AxxxxxH. In some embodiments, the RxxxxH motif is mutated to RxxxxA. In some embodiments, the RxxxxH motif is mutated to AxxxxxA.

In some embodiments, the Cas13 protein comprises 1, 2, 3, 4, 5, or 6 mutations at the position corresponding to the amino acid residues R210, H215, R750, H755, R785, and/or H790 of the reference protein as shown in SEQ ID NO: 1. In some embodiments, the amino acid residues of the Cas13 protein are mutated to A (alanine) at the position corresponding to the amino acid residues R210, H215, R750, H755, R785, and/or H790 of the reference protein as shown in SEQ ID NO: 1.

In some embodiments, the amino acid sequence of the Cas13 protein comprises a mutation at the position corresponding to the amino acid residues R210 and H215 of the reference protein as shown in SEQ ID NO: 1. In some embodiments, the amino acid sequence of the Cas13 protein comprises a mutation at the position corresponding to the amino acid residues R750 and H755 of the reference protein as shown in SEQ ID NO: 1. In some embodiments, the amino acid sequence of the Cas13 protein comprises a mutation at the position corresponding to the amino acid residues R785 and H790 of the reference protein as shown in SEQ ID NO: 1.

In some embodiments, the amino acid sequence of the Cas13 protein comprises a mutation at the position corresponding to the amino acid residues R210, H215, R750 and H755 of the reference protein as shown in SEQ ID NO: 1.

In some embodiments, the Cas13 protein comprises a mutation at the position corresponding to the amino acid residues R750, H755, R785 and H790 of the reference protein as shown in SEQ ID NO: 1.

In some embodiments, the Cas13 protein comprises a mutation at the position corresponding to the amino acid residues R210, H215, R785 and H790 of the reference protein as shown in SEQ ID NO: 1.

In some embodiments, the Cas13 protein comprises a mutation at the position corresponding to the amino acid residues R210, H215, R750, H755, R785 and H790 of the reference protein as shown in SEQ ID NO: 1.

In some embodiments, the position corresponding to the amino acid residues R210, R750, or R785 is mutated to A. In some embodiments, the position corresponding to the amino acid residues H215, H755, or H790 is mutated to A. In some embodiments, the position corresponding to the amino acid residues R210, H215, R750, H755, R785, and H790 are all mutated to A.

In some embodiments, the Cas13 protein is obtained by introducing a mutation in the RxxxxH motifs at positions 210-215, 750-755, and/or 785-790 of the sequence as shown in SEQ ID NO: 1.

In some embodiments, the Cas13 protein is obtained by introducing 1, 2, 3, 4, 5, or 6 mutations at positions R210, H215, R750, H755, R785, and/or H790 of the sequence as shown in SEQ ID NO: 1. In some embodiments, the Cas13 protein is obtained by mutating the amino acid residues to A (alanine) at positions R210, H215, R750, H755, R785, and/or H790 of the sequence as shown in SEQ ID NO: 1.

In some embodiments, the Cas13 protein is obtained by mutating the amino acid residues to A at positions R210, H215, R785, and H790 of the sequence as shown in SEQ ID NO: 1. In some embodiments, the Cas13 protein is obtained by mutating the amino acid residues to A at positions R210, H215, R750, and H755 of the sequence as shown in SEQ ID NO: 1. In some embodiments, the Cas13 protein is obtained by mutating the amino acid residues to A at positions R750, H755, R785, and H790 of the sequence as shown in SEQ ID NO: 1. In some embodiments, the Cas13 protein is obtained by mutating the amino acid residues to A at positions R210, H215, R750, H755, R785, and H790 of the sequence as shown in SEQ ID NO: 1.

In some embodiments, the Cas13 protein comprises at least one mutation at the position corresponding to the amino acid residue at positions 40-91, 146-153, 158-176, 182-209, 216-253, 271-287, 341-353, 379-424, 456-477, 521-557, 575-588, 609-625, 700-721, 724-783, 796-815, 828-852 or 880-893 of the reference protein as shown in SEQ ID NO: 1.

In some embodiments, compared with the reference protein as shown in SEQ ID NO: 1, the Cas13 protein comprises any one or more mutations at the position corresponding to the following amino acid residues of the reference protein as shown in SEQ ID NO: 1: R11, N34, R35, R47, R58, R63, R64, N68, N87, N265, N274, R276, R290, R294, N299, N303, R308, R314, R320, R328, N332, R341, N346, R358, N372, N383, N390, N394, R47+R290, R47+R314, R290+R314, R47+R290+R314, R308+N68, N394+N68, N87+N68, R308+N265, N394+N265, N87+N265, R308+N68+N265, N87+N68+N265, T7, A16, S260, A263, M266, N274, F288, M302, N303, L304, V305, I311, D313, H324, P326, H327, N332, N346, T353, T360, E365, A373, M380, S382, K395, Y396, D402, D411, S418.

In some embodiments, compared with the reference protein as shown in SEQ ID NO: 1, the Cas13 protein comprises any one or more mutations at the position corresponding to the following amino acid residues of the reference protein as shown in SEQ ID NO: 1: R11, N34, R35, R47, R58, R63, R64, N68, N87, N265, N274, R276, R290, R294, N299, N303, R308, R314.

In some embodiments, compared with the reference protein as shown in SEQ ID NO: 1, the Cas13 protein comprises any one or more mutations at the positions corresponding to the following amino acid residues of the reference protein as shown in SEQ ID NO: 1: R47+R290, R47+R314, R290+R314, R47+R290+R314, N394+N265, N87+N265, A263, M266, N274, F288, V305, I311, D313, H324, T360, E365, A373, M380, D402, D411, S418.

In some embodiments, the Cas13 protein comprises a mutation at the position corresponding to amino acid residue R11 of the reference protein as shown in SEQ ID NO: 1.

In some embodiments, the Cas13 protein comprises a mutation at the position corresponding to amino acid residue N34 of the reference protein as shown in SEQ ID NO: 1.

In some embodiments, the Cas13 protein comprises a mutation at the position corresponding to amino acid residue R35 of the reference protein as shown in SEQ ID NO: 1.

In some embodiments, the Cas13 protein comprises a mutation at the position corresponding to amino acid residue R47 of the reference protein as shown in SEQ ID NO: 1.

In some embodiments, the Cas13 protein comprises a mutation at the position corresponding to amino acid residue R58 of the reference protein as shown in SEQ ID NO: 1.

In some embodiments, the Cas13 protein comprises a mutation at the position corresponding to amino acid residue R63 of the reference protein as shown in SEQ ID NO: 1.

In some embodiments, the Cas13 protein comprises a mutation at the position corresponding to amino acid residue R64 of the reference protein as shown in SEQ ID NO: 1.

In some embodiments, the Cas13 protein comprises a mutation at the position corresponding to amino acid residue N68 of the reference protein as shown in SEQ ID NO: 1.

In some embodiments, the Cas13 protein comprises a mutation at the position corresponding to amino acid residue N87 of the reference protein as shown in SEQ ID NO: 1.

In some embodiments, the Cas13 protein comprises a mutation at the position corresponding to amino acid residue N265 of the reference protein as shown in SEQ ID NO: 1.

In some embodiments, the Cas13 protein comprises a mutation at the position corresponding to amino acid residue N274 of the reference protein as shown in SEQ ID NO: 1.

In some embodiments, the Cas13 protein comprises a mutation at the position corresponding to amino acid residue R276 of the reference protein as shown in SEQ ID NO: 1.

In some embodiments, the Cas13 protein comprises a mutation at the position corresponding to amino acid residue R290 of the reference protein as shown in SEQ ID NO: 1.

In some embodiments, the Cas13 protein comprises a mutation at the position corresponding to amino acid residue R294 of the reference protein as shown in SEQ ID NO: 1.

In some embodiments, the Cas13 protein comprises a mutation at the position corresponding to amino acid residue N299 of the reference protein as shown in SEQ ID NO: 1.

In some embodiments, the Cas13 protein comprises a mutation at the position corresponding to amino acid residue N303 of the reference protein as shown in SEQ ID NO: 1.

In some embodiments, the Cas13 protein comprises a mutation at the position corresponding to amino acid residue R308 of the reference protein as shown in SEQ ID NO: 1.

In some embodiments, the Cas13 protein comprises a mutation at the position corresponding to amino acid residue R314 of the reference protein as shown in SEQ ID NO: 1.

In some embodiments, the Cas13 protein comprises a mutation at the position corresponding to amino acid residue R320 of the reference protein as shown in SEQ ID NO: 1.

In some embodiments, the Cas13 protein comprises a mutation at the position corresponding to amino acid residue R328 of the reference protein as shown in SEQ ID NO: 1.

In some embodiments, the Cas13 protein comprises a mutation at the position corresponding to amino acid residue N332 of the reference protein as shown in SEQ ID NO: 1.

In some embodiments, the Cas13 protein comprises a mutation at the position corresponding to amino acid residue R341 of the reference protein as shown in SEQ ID NO: 1.

In some embodiments, the Cas13 protein comprises a mutation at the position corresponding to amino acid residue N346 of the reference protein as shown in SEQ ID NO: 1.

In some embodiments, the Cas13 protein comprises a mutation at the position corresponding to amino acid residue R358 of the reference protein as shown in SEQ ID NO: 1.

In some embodiments, the Cas13 protein comprises a mutation at the position corresponding to amino acid residue N372 of the reference protein as shown in SEQ ID NO: 1.

In some embodiments, the Cas13 protein comprises a mutation at the position corresponding to amino acid residue N383 of the reference protein as shown in SEQ ID NO: 1.

In some embodiments, the Cas13 protein comprises a mutation at the position corresponding to amino acid residue N390 of the reference protein as shown in SEQ ID NO: 1.

In some embodiments, the Cas13 protein comprises a mutation at the position corresponding to amino acid residue N394 of the reference protein as shown in SEQ ID NO: 1.

In some embodiments, the Cas13 protein comprises mutations at positions corresponding to amino acid residues R47 and R290 of the reference protein as shown in SEQ ID NO: 1.

In some embodiments, the Cas13 protein comprises mutations at positions corresponding to amino acid residues R47 and R314 of the reference protein as shown in SEQ ID NO: 1.

In some embodiments, the Cas13 protein comprises mutations at positions corresponding to amino acid residues R290 and R314 of the reference protein as shown in SEQ ID NO: 1.

In some embodiments, the Cas13 protein comprises mutations at positions corresponding to amino acid residues R47, R290 and R314 of the reference protein as shown in SEQ ID NO: 1.

In some embodiments, the Cas13 protein comprises mutations at positions corresponding to amino acid residues R308 and N68 of the reference protein as shown in SEQ ID NO: 1.

In some embodiments, the Cas13 protein comprises mutations at positions corresponding to amino acid residues N394 and N68 of the reference protein as shown in SEQ ID NO: 1.

In some embodiments, the Cas13 protein comprises mutations at positions corresponding to amino acid residues N87 and N68 of the reference protein as shown in SEQ ID NO: 1.

In some embodiments, the Cas13 protein comprises mutations at positions corresponding to amino acid residues R308 and N265 of the reference protein as shown in SEQ ID NO: 1.

In some embodiments, the Cas13 protein comprises mutations at positions corresponding to amino acid residues N394 and N265 of the reference protein as shown in SEQ ID NO: 1.

In some embodiments, the Cas13 protein comprises mutations at positions corresponding to amino acid residues N87 and N265 of the reference protein as shown in SEQ ID NO: 1.

In some embodiments, the Cas13 protein comprises mutations at positions corresponding to amino acid residues R308, N68 and N265 of the reference protein as shown in SEQ ID NO: 1.

In some embodiments, the Cas13 protein comprises mutations at positions corresponding to amino acid residues N87, N68 and N265 of the reference protein as shown in SEQ ID NO: 1.

In some embodiments, the Cas13 protein comprises a mutation at the position corresponding to amino acid residue T7 of the reference protein as shown in SEQ ID NO: 1.

In some embodiments, the Cas13 protein comprises a mutation at the position corresponding to amino acid residue A16 of the reference protein as shown in SEQ ID NO: 1.

In some embodiments, the Cas13 protein comprises a mutation at the position corresponding to amino acid residue S260 of the reference protein as shown in SEQ ID NO: 1.

In some embodiments, the Cas13 protein comprises a mutation at the position corresponding to amino acid residue A263 of the reference protein as shown in SEQ ID NO: 1.

In some embodiments, the Cas13 protein comprises a mutation at the position corresponding to amino acid residue M266 of the reference protein as shown in SEQ ID NO: 1.

In some embodiments, the Cas13 protein comprises a mutation at the position corresponding to amino acid residue N274 of the reference protein as shown in SEQ ID NO: 1.

In some embodiments, the Cas13 protein comprises a mutation at the position corresponding to amino acid residue F288 of the reference protein as shown in SEQ ID NO: 1.

In some embodiments, the Cas13 protein comprises a mutation at the position corresponding to amino acid residue M302 of the reference protein as shown in SEQ ID NO: 1.

In some embodiments, the Cas13 protein comprises a mutation at the position corresponding to amino acid residue N303 of the reference protein as shown in SEQ ID NO: 1.

In some embodiments, the Cas13 protein comprises a mutation at the position corresponding to amino acid residue L304 of the reference protein as shown in SEQ ID NO: 1.

In some embodiments, the Cas13 protein comprises a mutation at the position corresponding to amino acid residue V305 of the reference protein as shown in SEQ ID NO: 1.

In some embodiments, the Cas13 protein comprises a mutation at the position corresponding to amino acid residue I311 of the reference protein as shown in SEQ ID NO: 1.

In some embodiments, the Cas13 protein comprises a mutation at the position corresponding to amino acid residue D313 of the reference protein as shown in SEQ ID NO: 1.

In some embodiments, the Cas13 protein comprises a mutation at the position corresponding to amino acid residue H324 of the reference protein as shown in SEQ ID NO: 1.

In some embodiments, the Cas13 protein comprises a mutation at the position corresponding to amino acid residue P326 of the reference protein as shown in SEQ ID NO: 1.

In some embodiments, the Cas13 protein comprises a mutation at the position corresponding to amino acid residue H327 of the reference protein as shown in SEQ ID NO: 1.

In some embodiments, the Cas13 protein comprises a mutation at the position corresponding to amino acid residue N332 of the reference protein as shown in SEQ ID NO: 1.

In some embodiments, the Cas13 protein comprises a mutation at the position corresponding to amino acid residue N346 of the reference protein as shown in SEQ ID NO: 1.

In some embodiments, the Cas13 protein comprises a mutation at the position corresponding to amino acid residue T353 of the reference protein as shown in SEQ ID NO: 1.

In some embodiments, the Cas13 protein comprises a mutation at the position corresponding to amino acid residue T360 of the reference protein as shown in SEQ ID NO: 1.

In some embodiments, the Cas13 protein comprises a mutation at the position corresponding to amino acid residue E365 of the reference protein as shown in SEQ ID NO: 1.

In some embodiments, the Cas13 protein comprises a mutation at the position corresponding to amino acid residue A373 of the reference protein as shown in SEQ ID NO: 1.

In some embodiments, the Cas13 protein comprises a mutation at the position corresponding to amino acid residue M380 of the reference protein as shown in SEQ ID NO: 1.

In some embodiments, the Cas13 protein comprises a mutation at the position corresponding to amino acid residue S382 of the reference protein as shown in SEQ ID NO: 1.

In some embodiments, the Cas13 protein comprises a mutation at the position corresponding to amino acid residue K395 of the reference protein as shown in SEQ ID NO: 1.

In some embodiments, the Cas13 protein comprises a mutation at the position corresponding to amino acid residue Y396 of the reference protein as shown in SEQ ID NO: 1.

In some embodiments, the Cas13 protein comprises a mutation at the position corresponding to amino acid residue D402 of the reference protein as shown in SEQ ID NO: 1.

In some embodiments, the Cas13 protein comprises a mutation at the position corresponding to amino acid residue D411 of the reference protein as shown in SEQ ID NO: 1.

In some embodiments, the Cas13 protein comprises a mutation at the position corresponding to amino acid residue S418 of the reference protein as shown in SEQ ID NO: 1.

In some embodiments, compared with the reference protein as shown in SEQ ID NO: 1, the Cas13 protein has the mutation to the same amino acid residue at the position corresponding to the mutation site in Table 24 or in Table 29 of the reference protein as shown in SEQ ID NO: 1.

In some embodiments, compared with the reference protein as shown in SEQ ID NO: 1, the Cas13 protein comprises the same mutations at the position corresponding to the mutation site in Table 24 or in Table 29 of the reference protein as shown in SEQ ID NO: 1.

In some embodiments, the Cas13 protein is obtained by introducing any one or more mutations at the following positions of the sequence as shown in SEQ ID NO: 1: R11, N34, R35, R47, R58, R63, R64, N68, N87, N265, N274, R276, R290, R294, N299, N303, R308, R314, R320, R328, N332, R341, N346, R358, N372, N383, N390, N394, R47+R290, R47+R314, R290+R314, R47+R290+R314, R308+N68, N394+N68, N87+N68, R308+N265, N394+N265, N87+N265, R308+N68+N265, N87+N68+N265, T7, A16, S260, A263, M266, N274, F288, M302, N303, L304, V305, I311, D313, H324, P326, H327, N332, N346, T353, T360, E365, A373, M380, S382, K395, Y396, D402, D411 and S418.

In some embodiments, the Cas13 protein is obtained by introducing any one or more mutations at the following positions of the sequence as shown in SEQ ID NO: 1: N34, R64, N68, N265, R276, R294, N299, R314, R47+R290, R47+R314, R290+R314, R47+R290+R314, N394+N265, N87+N265, A263, M266, N274, F288, V305, I311, D313, H324, T360, E365, A373, M380, D402 and D411.

In some embodiments, the Cas13 protein is obtained by introducing any one or more mutations in Table 24 or in Table 29 to the sequence as shown in SEQ ID NO: 1.

In some embodiments, the Cas13 protein is obtained by sequence deletion at the position corresponding to the amino acid residue at the position of 91-120, 141-180, 211-240, 331-360, 351-400, 431-460, 461-500, 511-550, 611-640, 631-660, 661-690, 691-760, 821-860, or 861-890 of the reference protein as shown in SEQ ID NO: 1.

In some embodiments, the Cas13 protein comprises the deletion of one or more amino acids at the position corresponding to the amino acid residue at the position of 348-350, 521-556, or 883-893 of the reference protein as shown in SEQ ID NO: 1.

In some embodiments, ≤300, ≤200, ≤150, ≤100, ≤90, ≤80, ≤70, ≤60, ≤50, ≤40, ≤30, ≤20, or ≤10 amino acid residues are deleted in the sequence deletion.

In some embodiments, the Cas13 protein is obtained by sequence deletion at the position of 91-120, 141-180, 211-240, 331-360, 351-400, 431-460, 461-500, 511-550, 611-640, 631-660, 661-690, 691-760, 821-860, or 861-890 of the sequence as shown in SEQ ID NO: 1.

The sequence deletion is a deletion of one or more amino acid residues.

Another aspect of the disclosure provided herein relates to a fusion protein.

In some embodiments of this disclosure, the fusion protein comprises the Cas13 protein described herein or a functional fragment thereof, and any one or more of the following fused to the Cas13 protein or the functional fragment thereof: a cytosine deaminase domain, an adenosine deaminase domain, a translational activation domain, a translational repression domain, an RNA methylation domain, an RNA demethylation domain, a nuclease domain, a splicing factor domain, a reporter domain, an affinity domain, a subcellular localization signal, a reporter tag, and an affinity tag.

In some embodiments of this disclosure, the fusion protein comprises the Cas13 protein described herein or a functional fragment thereof, and any one or more of the following fused to the Cas13 protein or the functional fragment thereof: a cytosine deaminase domain, an adenosine deaminase domain, a translational activation domain, a translational repression domain, an RNA methylation domain, an RNA demethylation domain, a nuclease domain, a splicing factor domain, a subcellular localization signal, a reporter tag, and an affinity tag.

In some embodiments of this disclosure, the fusion protein comprises the Cas13 protein described herein or the functional fragment thereof fused to a homologous or heterologous protein domain and/or a peptide tag. In some embodiments, the fusion does not alter the original function of the Cas13 protein or the functional fragments thereof.

The expression "do not alter the original function of the Cas13 protein or the functional fragments thereof" means that the fused protein still has the ability to recognize, bind and/or cleave a target RNA when used in combination with a gRNA. The ability of the fused protein to recognize, bind or cleave the target RNA when used in combination with the gRNA may be increased or decreased compared to the ability of the Cas13 protein to recognize, bind or cleave the target RNA when used in combination with the gRNA. As long as the fused protein can effectively recognize, bind or cleave the target RNA when used in combination with the gRNA, it belongs to the situation of "do not alter the original function of the Cas13 protein".

In some embodiments, the fusion protein comprises the Cas13 protein described herein fused to a homologous or heterologous protein domain and/or a peptide tag. In some embodiments, the fusion protein comprises the functional fragment of the Cas13 protein described herein fused to a homologous or heterologous protein domain and/or a peptide tag. For example, in some embodiments, the functional fragment is a fragment obtained from the Cas13 protein by deleting a partial sequence of the nuclease domain. In some embodiments, the functional fragment is a fragment obtained from the Cas13 protein by deleting the sequences corresponding to HEPN-1_I, HEPN-1_II, HEPN-2, NTD, Helical-1, and/or Helical-2 of C13-2. In some embodiments, the functional fragment is a fragment obtained from the Cas13 protein by deleting the sequences corresponding to HEPN-1_I, HEPN-1_II, and/or HEPN-2 of C13-2. In some embodiments, the functional fragment is a fragment obtained from the Cas13 protein by deleting the sequence corresponding to HEPN-1_I of C13-2. In some embodiments, the functional fragment is a fragment obtained from the Cas13 protein by deleting the sequence corresponding to HEPN-1_II of C13-2. In some embodiments, the functional fragment is a fragment obtained from the Cas13 protein by deleting the sequence corresponding to HEPN-2 of C13-2. In some embodiments, the functional fragment is a fragment obtained from the Cas13 protein by deleting the sequences corresponding to NTD and HEPN-1_I of C13-2.

In some embodiments, the Cas13 protein or the functional fragment thereof is fused to any one or more selected from the following: a cytosine deaminase domain, an adenosine deaminase domain, a translational activation domain, a translational repression domain, an RNA methylation domain, an RNA demethylation domain, a nuclease domain, a splicing factor domain, a reporter domain, an affinity domain, a subcellular localization signal, a reporter tag, and an affinity tag.

In some embodiments, the Cas13 protein or the functional fragment thereof is fused to a subcellular localization signal. In some embodiments, the subcellular localization signal is optionally selected from a nuclear localization signal (NLS), a nuclear export signal (NES), a chloroplast localization signal, or a mitochondrial localization signal.

In some embodiments, the Cas13 protein or the functional fragment thereof is fused to any one or more selected from the following: a cytosine deaminase domain, an adenosine deaminase domain, a translational activation domain, a translational repression domain, an RNA methylation domain, an RNA demethylation domain, a nuclease domain, a splicing factor domain, a reporter domain, an affinity domain, a subcellular localization signal, a reporter tag, and an affinity tag.

In some embodiments, the Cas13 protein or the functional fragment thereof is fused to a subcellular localization signal. In some embodiments, the subcellular localization signal is optionally selected from a nuclear localization signal (NLS), a nuclear export signal (NES), a chloroplast localization signal, or a mitochondrial localization signal.

In some embodiments, the Cas13 protein or the functional fragment thereof is fused to a homologous or heterologous nuclear localization signal (NLS). In some embodiments, the Cas13 protein or the functional fragment thereof is fused to a homologous or heterologous nuclear export signal (NES).

In some embodiments, the Cas13 protein or the functional fragment thereof is covalently linked to a protein domain and/or a peptide tag. In some embodiments, the Cas13 protein or the functional fragment is covalently linked to a protein domain and/or a peptide tag directly. In some embodiments, the Cas13 protein or the functional fragment thereof is covalently linked to a protein domain and/or a peptide tag by a linking sequence; furthermore, in some embodiments, the linking sequence is an amino acid sequence.

In some embodiments, the Cas13 protein or the functional fragment thereof of the fusion protein is linked to a homologous or heterologous protein domain and/or a polypeptide tag by a rigid linking peptide sequence. In some embodiments, the Cas13 protein portion of the fusion protein is linked to a homologous or heterologous protein domain and/or a polypeptide tag by a flexible linking peptide sequence. In some embodiments, the rigid linking peptide sequence is A(EAAAK)3A (SEQ ID NO: 279). In some embodiments, the flexible linking peptide sequence is (GGGGS)3 (SEQ ID NO: 280).

In some embodiments, the fusion protein can form a CRISPR complex with a guide polynucleotide, wherein the CRISPR complex can sequence-specifically bind to the target RNA. In some embodiments, the fusion protein comprises the Cas13 protein described herein fused to a homologous or heterologous protein domain and/or a peptide tag; wherein the fusion protein can form a CRISPR complex with a guide polynucleotide, and the CRISPR complex can sequence-specifically bind to the target RNA. In some embodiments, the fusion protein comprises the functional fragment of the Cas13 protein described herein fused to a homologous or heterologous protein domain and/or a peptide tag; wherein the fusion protein can form a CRISPR complex with a guide polynucleotide, and the CRISPR complex can sequence-specifically bind to the target RNA.

In some embodiments, the fusion protein can form a CRISPR complex with a guide polynucleotide comprising a direct repeat sequence linked to a guide sequence that is engineered to guide the sequence-specific binding of the CRISPR complex to the target RNA. In some embodiments, the fusion protein comprises the Cas13 protein described herein fused to a homologous or heterologous protein domain and/or a peptide tag; wherein the fusion protein can form a CRISPR complex with a guide polynucleotide comprising a direct repeat sequence linked to a guide sequence that is engineered to guide the sequence-specific binding of the CRISPR complex to the target RNA. In some embodiments, the fusion protein comprises a functional fragment of the Cas13 protein described herein fused to a homologous or heterologous protein domain and/or a peptide tag; wherein the fusion protein can form a CRISPR complex with a guide polynucleotide comprising a direct repeat sequence linked to a guide sequence that is engineered to guide the sequence-specific binding of the CRISPR complex to the target RNA.

In some embodiments, the fusion protein can form a CRISPR complex with a guide polynucleotide, and the CRISPR complex can sequence-specifically bind to and cleave the target RNA. In some embodiments, the fusion protein comprises the Cas13 protein described herein fused to a homologous or heterologous protein domain and/or a peptide tag; wherein the fusion protein can form a CRISPR complex with a guide polynucleotide, and the CRISPR complex can sequence-specifically bind to the target RNA. In some embodiments, the fusion protein comprises the functional fragment of the Cas13 protein described herein fused to a homologous or heterologous protein domain and/or a peptide tag; wherein the fusion protein can form a CRISPR complex with a guide polynucleotide, and the CRISPR complex can sequence-specifically bind to the target RNA.

In some embodiments, the structure of the fusion protein is NLS-Cas13 protein-SV40 NLS-nucleoplastin NLS.

Another aspect of the disclosure provided herein relates to a guide polynucleotide comprising (i) a direct repeat sequence having at least 50% sequence identity compared to any one of SEQ ID NO: 3 and SEQ ID NOs: 80-87, wherein the direct repeat sequence is linked to (ii) a homologous or heterologous guide sequence engineered to hybridize with a target RNA, wherein the guide polynucleotide can form a CRISPR complex with a Cas13 protein and guide the sequence-specific binding of the CRISPR complex to the target RNA.

In some embodiments, the Cas13 protein is Cas13a, Cas13b, Cas13c, or Cas13d. In some embodiments, the amino acid sequence of the Cas13 protein has at least 90%, at least 95%, at least 98%, or at least 99% sequence identity compared to SEQ ID NO: 1.

In some embodiments, the direct repeat sequence has at least 55%, at least 60%, at least 65%, at least 70%, at least 75%, at least 80%, at least 85%, at least 90%, at least 95%, or 100% sequence identity compared to any one of SEQ ID NO: 3 and SEQ ID NOs: 80-87. In some embodiments, the direct repeat sequence has at least 80% sequence identity compared to any one of SEQ ID NO: 3 and SEQ ID NOs: 80-87. In some embodiments, the direct repeat sequence has at least 85% sequence identity compared to any one of SEQ ID NO: 3 and SEQ ID NOs: 80-87. In some embodiments, the direct repeat sequence has at least 90% sequence identity compared to any one of SEQ ID NO: 3 and SEQ ID NOs: 80-87. In some embodiments, the direct repeat sequence has at least 95% sequence identity compared to any one of SEQ ID NO: 3 and SEQ ID NOs: 80-87. In some embodiments, the direct repeat sequence has 100% sequence identity compared to any one of SEQ ID NO: 3 and SEQ ID NOs: 80-87.

In some embodiments, the direct repeat sequence has at least 50%, at least 55%, at least 60%, at least 65%, at least 70%, at least 75%, at least 80%, at least 85%, at least 90%, at least 95%, or 100% sequence identity compared to any one of SEQ ID NOs: 3, 81, 82, 84, and 87.

In some embodiments, the direct repeat sequence has at least 70%, at least 75%, at least 80%, at least 85%, at least 90%, at least 95%, or 100% sequence identity compared to any one of SEQ ID NOs: 3 to 87.

In some embodiments, the 26th base of the direct repeat sequence corresponding to SEQ ID NO: 3 is A.

In some embodiments, the direct repeat sequence is GGAAGATN$_1$ACTCTACAAACCTGTAGN$_2$GN$_3$N$_4$N$_5$N$_6$N$_7$N$_8$N$_9$N$_{10}$N$_{11}$ (SEQ ID NO: 277); wherein N$_1$ and N$_3$-N$_{11}$ are optionally selected from A, C, G, T; and N$_2$ is optionally selected from A and G.

In some embodiments, the direct repeat sequence is GGAAGATN$_{12}$ACTCTACAAACCTGTAGN$_{13}$GN$_{14}$N$_{15}$N$_{16}$N$_{17}$N$_{18}$N$_{19}$N$_{20}$N$_{21}$N$_{22}$ (SEQ ID NO: 278); wherein N$_{12}$, N$_{13}$, N$_{19}$ and N$_{21}$ are optionally selected from A and G, N$_{14}$ is optionally selected from A and T, N$_{15}$ and N$_{16}$ are optionally selected from C and T, N$_{17}$ and N$_{18}$ are optionally selected from G and T, and N$_{20}$ and N$_{22}$ are optionally selected from C and G.

In some embodiments, the guide sequence is positioned at the 3' end of the direct repeat sequence. In some embodiments, the guide sequence is positioned at the 5' end of the direct repeat sequence.

In some embodiments, the guide sequence comprises 15-35 nucleotides. In some embodiments, the guide sequence hybridizes with the target RNA with no more than one nucleotide mismatch. In some embodiments, the direct repeat sequence comprises 25 to 40 nucleotides.

In some embodiments, the guide polynucleotide further comprises an aptamer sequence. In some embodiments, the aptamer sequence is inserted into a loop of the guide polynucleotide. In some embodiments, the aptamer sequence comprises an MS2 aptamer sequence, a PP7 aptamer sequence, or a Qβ aptamer sequence.

In some embodiments, the guide polynucleotide comprises a modified nucleotide. In some embodiments, the modified nucleotide comprises 2'-O-methyl, 2'-O-methyl-3'-phosphorothioate, or 2'-O-methyl-3'-thioPACE.

In some embodiments, the target RNA of the guide polynucleotide is located in the nucleus of a eukaryotic cell.

In some embodiments, the target RNA is optionally selected from TTR RNA, SOD1 RNA, PCSK9 RNA, VEGFA RNA, VEGFR1 RNA, PTBP1 RNA, AQp1 RNA, or ANGPTL3 RNA. Optionally, in some embodiments, the target RNA is selected from VEGFA RNA, PTBP1 RNA, AQp1 RNA, or ANGPTL3 RNA. Furthermore, the guide sequence is optionally selected from the sequences as shown in SEQ ID NO: 5, SEQ ID NO: 6, and SEQ ID NOs: 42-49 (used for targeting AQp1 RNA, PTBP1 RNA, and ANGPTL3 RNA, respectively). Preferably, the guide sequence is optionally selected from the sequences as shown in SEQ ID NO: 5, SEQ ID NO: 6, SEQ ID NO: 43, and SEQ ID NOs: 45-47.

In some embodiments, the Cas13 protein is Cas13a, Cas13b, Cas13c, or Cas13d. In some embodiments, the Cas13 protein is Cas13d. In some embodiments, the Cas13 protein has at least 90%, at least 95%, at least 98%, or at least 99% sequence identity compared to SEQ ID NO: 1.

Another aspect of the disclosure provided herein relates to a CRISPR-Cas13 system comprising: the Cas13 protein or the fusion protein described herein, or a nucleic acid encoding the Cas13 protein or the fusion protein, and a guide polynucleotide or a nucleic acid encoding the guide polynucleotide; wherein the guide polynucleotide comprises a direct repeat sequence linked to a guide sequence that is engineered to hybridize with the target RNA; and the guide polynucleotide can form a CRISPR complex with the Cas13 protein or the fusion protein and guide the sequence-specific binding of the CRISPR complex to the target RNA.

In some embodiments, the target RNA is optionally selected from TTR RNA, SOD1 RNA, PCSK9 RNA, VEGFA RNA, VEGFR1 RNA, PTBP1 RNA, AQp1 RNA, or ANGPTL3 RNA. Optionally, in some embodiments, the target RNA is optionally selected from VEGFA RNA, PTBP1 RNA, AQp1 RNA, or ANGPTL3 RNA. In some embodiments, the guide sequence is optionally selected from the sequences as shown in SEQ ID NO: 5, SEQ ID NO: 6, and SEQ ID NOs: 42-49 (used for targeting AQp1 RNA, PTBP1 RNA, and ANGPTL3 RNA, respectively). In some embodiments, the guide sequence is optionally selected from the sequences as shown in SEQ ID NO: 5, SEQ ID NO: 6, SEQ ID NO: 43, and SEQ ID NOs: 45-47.

In some embodiments, the direct repeat sequence has at least 70%, at least 75%, at least 80%, at least 85%, at least 90%, at least 95%, or 100% sequence identity compared to any one of SEQ ID NOs: 3, 81, 82, 84, and 87.

In some embodiments, the fusion protein comprises the Cas13 protein described herein or the functional fragment thereof fused to a homologous or heterologous protein domain and/or a peptide tag.

In some embodiments, the portion of the Cas13 protein or the functional fragment thereof of the fusion protein is fused to a homologous or heterologous nuclear localization signal (NLS). In some embodiments, the portion of the Cas13 protein or the functional fragment thereof of the fusion protein is fused to a homologous or heterologous nuclear export signal (NES).

In some embodiments, the Cas13 protein comprises a mutation in a catalytic domain and has reduced RNA cleavage activity. In some embodiments, the Cas13 protein comprises a mutation in one or both HEPN domains and substantially lacks RNA cleavage activity. In some embodiments, the "substantially lack RNA cleavage activity" refers to the retention of ≤50%, ≤40%, ≤30%, ≤20%, ≤10%, ≤5%, or ≤1% of RNA cleavage activity compared to wild-type Cas13 protein, or the absence of detectable RNA cleavage activity.

In some embodiments, the Cas13 protein or the functional fragments thereof of the fusion protein is covalently linked to a homologous or heterologous protein domain and/or a peptide tag directly. In some embodiments, the Cas13 protein part of the fusion protein is linked to a homologous or heterologous protein domain and/or a peptide tag by a peptide sequence.

In some embodiments, the protein domain comprises a cytosine deaminase domain, an adenosine deaminase domain, a translational activation domain, a translational repression domain, an RNA methylation domain, an RNA demethylation domain, a nuclease domain, or a splicing factor domain. In some embodiments, the Cas13 protein is covalently linked to an affinity tag or a reporter tag.

In some embodiments, the Cas13 protein has at least 95% sequence identity compared to SEQ ID NO: 1. In some embodiments, the Cas13 protein has at least 97% sequence identity compared to SEQ ID NO: 1. In some embodiments, the Cas13 protein has at least 98% sequence identity compared to SEQ ID NO: 1. In some embodiments, the Cas13 protein has at least 99% sequence identity compared to SEQ ID NO: 1. In some embodiments, the Cas13 protein has at least 99.5% sequence identity compared to SEQ ID NO: 1. In some embodiments, the Cas13 protein comprises the sequence as shown in SEQ ID NO: 1.

In some embodiments, the Cas13 protein derives from the species comprising a genome that has an average nucleotide identity (ANI) of ≥95% with the genome no. CNA0009596 in the CNGB database.

In some embodiments, the Cas13 protein does not exhibit a protospacer flanking sequence (PFS) requirement for RNA cleavage.

In some embodiments, the guide sequence is positioned at the 3' end of the direct repeat sequence. In some embodiments, the guide sequence is positioned at the 5' end of the direct repeat sequence.

In some embodiments, the guide sequence comprises 15-35 nucleotides. In some embodiments, the guide sequence hybridizes with the target RNA with no more than one nucleotide mismatch.

In some embodiments, the direct repeat sequence comprises 25 to 40 nucleotides.

In some embodiments, the direct repeat sequence has at least 80% sequence identity compared to any one of SEQ ID NO: 3 and SEQ ID NOs: 80-87. In some embodiments, the direct repeat sequence has at least 90% sequence identity compared to any one of SEQ ID NO: 3 and SEQ ID NOs: 80-87. In some embodiments, the direct repeat sequence has at least 95% sequence identity compared to any one of SEQ ID NO: 3 and SEQ ID NOs: 80-87. In some embodiments, the direct repeat sequence has 100% sequence identity compared to any one of SEQ ID NO: 3 and SEQ ID NOs: 80-87. In some embodiments, the direct repeat sequence is optionally selected from SEQ ID NO: 3 and SEQ ID NOs: 80-87.

In some embodiments, the guide polynucleotide further comprises an aptamer sequence. In some embodiments, the aptamer sequence is inserted into a loop of the guide polynucleotide. In some embodiments, the aptamer sequence comprises an MS2 aptamer sequence, a PP7 aptamer sequence, or a Qβ aptamer sequence.

In some embodiments, the CRISPR-Cas13 system comprises a fusion protein comprising an adaptor protein and a homologous or heterologous protein domain, or a nucleic acid encoding the fusion protein; wherein the adaptor protein is capable of binding to the aptamer sequence.

In some embodiments, the adaptor protein comprises MS2 phage coat protein, PP7 phage coat protein, or Qβ phage coat protein. In some embodiments, the protein domain comprises a cytosine deaminase domain, an adenosine deaminase domain, a translational activation domain, a translational repression domain, an RNA methylation domain, an RNA demethylation domain, a nuclease domain, a splicing factor domain, a reporter domain, an affinity domain, a reporter tag and an affinity tag.

In some embodiments, the guide polynucleotide comprises a modified nucleotide. In some embodiments, the modified nucleotide comprises 2'-O-methyl, 2'-O-methyl-3'-phosphorothioate, or 2'-O-methyl-3'-thioPACE.

In some embodiments, the Cas13 protein or fusion protein and the guide polynucleotide do not naturally occur together.

Another aspect of the disclosure provided herein relates to a CRISPR-Cas13 system, wherein the CRISPR-Cas13 system comprises any one of the Cas13 protein, the fusion protein thereof, or the nucleic acid encoding the same, and the guide polynucleotides, or the nucleic acid encoding the same described herein.

Another aspect of the disclosure provided herein relates to a vector system comprising the CRISPR-Cas13 system described herein, wherein the vector system comprises one or more vectors comprising a polynucleotide sequence encoding the Cas13 protein or the fusion protein described herein and a polynucleotide sequence encoding the guide polynucleotide.

Another aspect of the disclosure provided herein relates to an adeno-associated viral (AAV) vector comprising the CRISPR-Cas13 system described herein, wherein the AAV vector comprises a DNA sequence encoding the Cas13 protein or the fusion protein described herein and the guide polynucleotide.

Another aspect of the disclosure provided herein relates to a lipid nanoparticle comprising the CRISPR-Cas13 system described herein, wherein the lipid nanoparticle comprises the guide polynucleotide described herein and an mRNA encoding the Cas13 protein or the fusion protein described herein.

Another aspect of the disclosure provided herein relates to a lentiviral vector comprising the CRISPR-Cas13 system described herein, wherein the lentiviral vector comprises the guide polynucleotide described herein and an mRNA encoding the Cas13 protein or the fusion protein described herein. In some embodiments, the lentiviral vector is pseudotyped with a homologous or heterologous envelope protein such as VSV-G. In some embodiments, the mRNA encoding the Cas13 protein or fusion protein is linked to an aptamer sequence.

Another aspect of the disclosure provided herein relates to a ribonucleoprotein complex comprising the CRISPR-Cas13 system described herein, wherein the ribonucleoprotein complex is formed by the guide polynucleotide described herein and the Cas13 protein or the fusion protein described herein.

Another aspect of the disclosure provided herein relates to a viral-like particle comprising the CRISPR-Cas13 system described herein, wherein the viral-like particle comprises a ribonucleoprotein complex formed by the guide polynucleotide described herein and the Cas13 protein or the fusion protein described herein. In some embodiments, the Cas13 protein or the fusion protein is fused to a gag protein.

Another aspect of the disclosure provided herein relates to a eukaryotic cell comprising the CRISPR-Cas13 system described herein. In some embodiments, the eukaryotic cell is a mammalian cell. In some embodiments, the eukaryotic cell is a human cell.

Another aspect of the disclosure provided herein relates to a pharmaceutical composition comprising the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein.

Another aspect of the disclosure provided herein relates to a pharmaceutical composition comprising the CRISPR-Cas13 system described herein.

Another aspect of the disclosure relates to an in vitro composition comprising the CRISPR-Cas13 system described herein, and a labeled detector RNA that is not hybridizable with or targeted by the guide polynucleotide.

Another aspect of the disclosure provided herein relates to an isolated nucleic acid encoding the Cas13 protein or the fusion protein described herein.

Another aspect of the disclosure provided herein relates to an isolated nucleic acid encoding the guide polynucleotide described herein.

Another aspect of the disclosure provided herein relates to a CRISPR-Cas13 system comprising any one of the Cas13 protein or the nucleic acids encoding the same, and the guide polynucleotides or the nucleic acid encoding the same described herein.

Another aspect of the disclosure provided herein relates to a use of the CRISPR-Cas13 system described herein in the detection of a target RNA in a nucleic acid sample suspected of comprising the target RNA or in the preparation of a reagent for detecting a target RNA in a nucleic acid sample suspected of comprising the target RNA.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in any one of the following or in the preparation of a reagent for achieving any one of the following schemes:
cleaving one or more target RNA molecules or nicking one or more target RNA molecules; activating or upregulating one or more target RNA molecules; activating or inhibiting translation of one or more target RNA molecules; inactivating one or more target RNA molecules; visualizing, labeling or detecting one or more target RNA molecules; binding one or more target RNA molecules; transporting one or more target RNA molecules; and masking one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in the cleavage of one or more target RNA molecules or in the preparation of a reagent for cleaving one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in binding one or more target RNA molecules.

Another aspect of the disclosure provided herein relates to a use of the CRISPR-Cas13 system described herein in preparing a reagent for binding or cleaving one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in cleaving or editing a target RNA in a mammalian cell; wherein the editing is base editing.

Another aspect of the disclosure provided herein relates to a use of the CRISPR-Cas13 system described herein in preparing a reagent for cleaving or editing a target RNA in a mammalian cell; wherein the editing is a base editing.

Another aspect of the present disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in activating or upregulating one or more target RNA molecules or in preparing a reagent for activating or upregulating one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in inhibiting the translation of one or more target RNA molecules or in preparing a reagent for inhibiting the translation of one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in inactivating one or more target RNA molecules or in preparing a reagent for inactivating one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in visualizing, labeling or detecting one or more target RNA molecules or in preparing a reagent for visualizing, labeling or detecting one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in transporting one or more target RNA molecules or in preparing a reagent for transporting one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in masking one or more target RNA molecules or in preparing a reagent for masking one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in the diagnosis, treatment, or prevention of a disease or disorder associated with the target RNA.

Another aspect of the disclosure provided herein relates to a use of the CRISPR-Cas13 system described herein in the diagnosis, treatment, or prevention of a disease or disorder associated with the target RNA.

Another aspect of the disclosure provided herein relates to a method for diagnosing, treating, or preventing a disease or disorder associated with the target RNA, wherein the method is to administer the Cas13 protein described herein, the fusion protein described herein, the guide polynucleotide described herein, the CRISPR-Cas13 system described herein, or the isolated nucleic acid described herein to a sample of a subject in need thereof, or to a subject in need thereof.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in the manufacture of a medicament for the diagnosis, treatment, or prevention of a disease or disorder associated with the target RNA.

Another aspect of the disclosure provided herein relates to a use of the CRISPR-Cas13 system described herein in the manufacture of a medicament for the diagnosis, treatment, or prevention of a disease or disorder associated with the target RNA.

Based on common knowledge in the field, the above preferred conditions can be combined arbitrarily to obtain the preferred examples of the present disclosure.

The reagents and raw materials used in the present disclosure are commercially available.

DETAILED DESCRIPTION

Figure 1:
FIG. 1 shows the CRISPR locus of a CRISPR-Cas13 system, including a CRISPR array and coding sequences for C13-2 protein.

The present disclosure is further illustrated by the following embodiments, but does not thereby limit the present disclosure within the scope of these embodiments. Experimental methods for which specific conditions are not indicated in the following embodiments shall be selected in accordance with conventional methods and conditions, or in accordance with product instructions.

As used herein, the term "sequence identity" (identity or percent identity) is used to refer to the matching situation of sequences between two polypeptides or between two nucleic acids.

When a position in two sequences being compared is occupied by the same base or amino acid monomer subunit (e.g., a position in each of two DNA molecules is occupied by adenine, or a position in each of two polypeptides is occupied by lysine), then the molecules are identical at such position. The "percent identity" between two sequences is a function of the number of matched positions shared by the two sequences divided by the number of positions being compared×100%. For example, if there are 6 matches in 10 positions of two sequences, the two sequences have 60% sequence identity. Typically, the comparison is made when aligning two sequences to produce maximum sequence identity. Such a comparison can be made by using disclosed and commercially available alignment algorithms and programs, such as but not limited to Clustal Ω, MAFFT, Probcons, T-Coffee, Probalign, BLAST, which can be reasonably selected to use by a person skilled in the art. Those skilled in the art can determine suitable parameters for sequence alignment, such as any algorithms needed to achieve a superior alignment or optimal alignment for the full length of the compared sequences, and any algorithms needed to achieve a topical superior alignment or optimal alignment for the compared sequences.

As used herein, the term "guide polynucleotide" is used to refer to a molecule in the CRISPR-Cas system that forms a CRISPR complex with a Cas protein and guides the CRISPR complex to a target sequence. Typically, the guide polynucleotide comprises a scaffold sequence linked to the guide sequence, which can hybridize with the target sequence. The scaffold sequence usually comprises direct repeat sequences, and sometimes can also comprises a tracrRNA sequences. When the scaffold sequence does not comprise a tracrRNA sequence, the guide polynucleotide comprises both the guide sequence and the direct repeat sequence, in which case the guide polynucleotide can also be referred to as a crRNA.

CRISPR-Cas13 System

Class 2 CRISPR-Cas systems endow microbes with diverse mechanisms for adaptive immunity.

Provided herein is an analysis of prokaryotic genomes and metagenomes to identify a previously uncharacterized RNA-guided, RNA-targeting CRISPR-Cas13 systems comprising C13-2 (also referred to as CasRfg.4), which is classified as a Type VI system. Engineered CRISPR-Cas13 systems based on C13-2 have robust activity in human cells. As a compact single effector Cas13 enzyme, C13-2 can also be flexibly packaged into an AAV vector. The results herein present C13-2 as a programmable RNA-binding module for efficient targeting of cellular RNA, thereby providing a general platform for transcriptome engineering and therapeutic and diagnostic methods.

As described in Example 1, a CRISPR-Cas13 system comprising C13-2 was identified based on bioinformatic analysis of prokaryotic genomes and metagenomes in NCBI GenBank and CNGB database, followed by experimental validation of targeted RNA cleavage activity in human cells.

Figure 2:
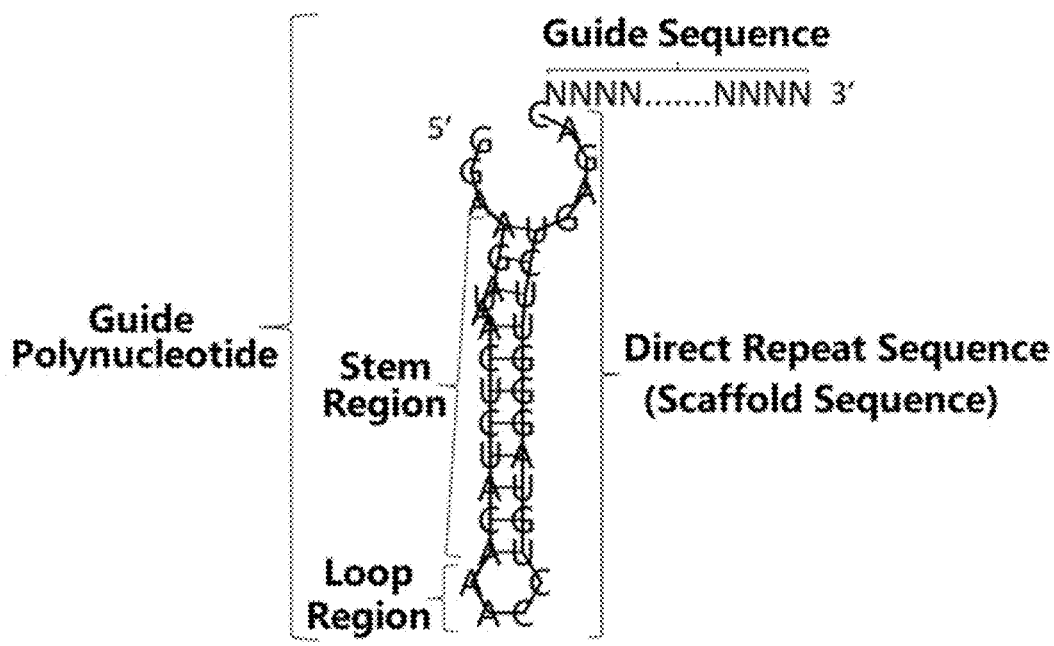
FIG. 2 shows the structure of the C13-2 guide polynucleotide, which consists of a direct repeat sequence and a guide sequence. In this figure the scaffold sequence is the same as the direct repeat sequence; the guide sequence consists of a variable number of various nucleotides, with N representing any nucleotide in the figure. The secondary structure of the direct repeat sequence (SEQ ID NO: 3) is predicted and obtained by RNAfold, which is shown in the figure. The stem-loop structure could be seen, and the stem region contains various complementary base pairs.
Figure 8:
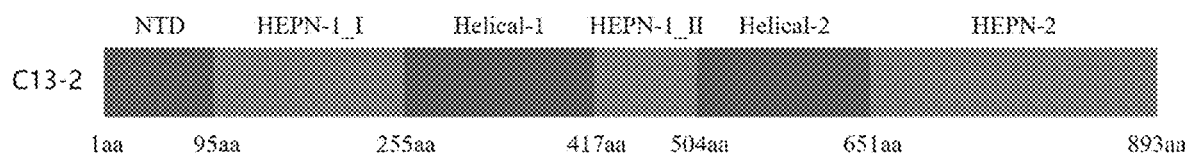
FIG. 8 shows in silico predicted C13-2 domain; in the figure, positions 1-95 are NTD domain, positions 96-255 are HEPN-1_I domain, positions 256-417 are Helical-1 domain, positions 418-504 are HEPN-1_II domain, positions 505-651 are Helical-2 domain, and positions 652-893 are HEPN-2 domain.

The CRISPR-Cas13 system comprising C13-2 is a Type-VI CRISPR-Cas system. FIG. 1 shows the CRISPR locus of the CRISPR-Cas13 system comprising C13-2. The protein sequence of the wild-type C13-2 is provided as SEQ ID NO: 1. The DNA coding sequence of the wild-type C13-2 is provided as SEQ ID NO: 9. FIG. 8 shows the in silico predicted structural domains of C13-2, which includes NTD, HEPN-1_I, HEPN-1_II, and HEPN-2, wherein NTD is the N terminus domain. The Helical-1 and Helical-2 domains are positioned between HEPN-1_I and HEPN-1_II, and between HEPN-1_II and HEPN-2, respectively. The direct repeat sequence of the C13-2 guide polynucleotide is provided as SEQ ID NO: 3. FIG. 2 shows the RNA secondary structure of the direct repeat sequence of the C13-2 guide polynucleotide as predicted by RNAfold. An engineered CRISPR-Cas13 system described herein can efficiently knockdown endogenous target RNAs in human cells, paving the way for RNA-targeting applications as part of a transcriptome engineering toolbox. In some embodiments, C13-2-mediated knockdown is capable of achieving higher efficiency and/or specificity relative to the knockdown mediated by CasRx, PspCas13b, Cas13X.1 and/or Cas13Y.1 across diverse endogenous transcripts.

Accordingly, one aspect of the disclosure provided herein relates to a CRISPR-Cas13 system, composition, or kit, comprising: a Cas13 protein or a fusion protein having at least 90% sequence identity compared to SEQ ID NO: 1, or a nucleic acid encoding the Cas13 protein, and a guide polynucleotide or a nucleic acid encoding the guide polynucleotide; wherein the guide polynucleotide comprises a direct repeat sequence linked to a guide sequence that is engineered to hybridize with the target RNA; and the guide polynucleotide is capable of forming a CRISPR complex with the Cas13 protein and guiding the sequence-specific binding of the CRISPR complex to the target RNA.

In some embodiments, the guide polynucleotide comprising a direct repeat sequence linked to a guide sequence that is engineered to hybridize with the target RNA; wherein the guide polynucleotide is capable of forming a CRISPR complex with the Cas13 protein and guiding the CRISPR complex to sequence-specifically bind to and cleave the target RNA.

In some embodiments, the polynucleotide sequence encoding the Cas13 protein or the fusion protein and/or the polynucleotide sequence encoding the guide polynucleotide is operably linked to a regulatory sequence. In some embodiments, the polynucleotide sequence encoding the Cas13 protein or the fusion protein is operably linked to a regulatory sequence. In some embodiments, the polynucleotide sequence encoding the guide polynucleotide is operably linked to a regulatory sequence. In some embodiments, the regulatory sequence of the polynucleotide sequence encoding the Cas13 protein or the fusion protein and the regulatory sequence of the polynucleotide sequence encoding the guide polynucleotide are the same or different.

In some embodiments, the Cas13 protein described herein comprises at least 90%, at least 91%, at least 92%, at least 93%, at least 94%, at least 95%, at least 96%, at least 97%, at least 98%, at least 99%, or at least 99.5% sequence identity compared to SEQ ID NO: 1. In some embodiments, the Cas13 protein described herein comprises at least 90%, at least 91%, at least 92%, at least 93%, at least 94%, at least 95%, at least 96%, at least 97%, at least 98%, or at least 99% sequence identity compared to the protein sequence encoded by SEQ ID NO: 9. When the CRISPR-Cas13 system comprises a fusion protein comprising the Cas13 protein, and a protein domain and/or a peptide tag, the percentage of sequence identity is calculated between the Cas13 portion of the fusion protein and the reference sequence.

In some embodiments, the Cas13 protein described herein derives from the species comprising a genome that has an average nucleotide identity (ANI) of ≥95% with the genome no. CNA0009596 in the CNGB database.

In some embodiments, the Cas13 protein described herein comprises one or more (e.g., 1 or 2) native HEPN domains, each comprising an RX4H amino acid motif (wherein X indicates any amino acid, and the subscript "4" represents four consecutive amino acids). In some embodiments, a first catalytic RX4H motif is located at amino acid positions 210-215 of SEQ ID NO: 1, and a second catalytic RX4H motif is located at amino acid positions 785-790 of SEQ ID NO: 1, and a third RX4H motif is located at amino acid positions 750-755 of SEQ ID NO: 1. In some embodiments, the Cas13 protein described herein comprises one or more mutated HEPN domains. In some embodiments, the mutated Cas13 protein can process its guide polynucleotide, but cannot cleave the target RNA.

In some embodiments, the Cas13 protein described herein does not exhibit a protospacer flanking sequence (PFS) requirement for RNA cleavage.

The CRISPR-Cas13 system described herein can be introduced into cells (or to a cell-free system) in multiple non-limiting ways: (i) as Cas13 mRNA and guide polynucleotide, (ii) as part of a single vector or plasmid, or divided into multiple vectors or plasmids, (iii) as a separate Cas13 protein and guide polynucleotide, or (iv) as an RNP complex of the Cas13 protein and guide polynucleotide.

In some embodiments, the CRISPR-Cas13 system, composition, or kit comprises a nucleic acid molecule encoding the Cas13 protein, wherein the coding sequence is codon optimized for expression in a eukaryotic cell. In some embodiments, the CRISPR-Cas13 system, composition, or kit comprises a nucleic acid molecule encoding the Cas13 protein, wherein the coding sequence is codon optimized for expression in a mammalian cell. In some embodiments, the CRISPR-Cas13 system, composition, or kit comprises a nucleic acid molecule encoding the Cas13 protein, wherein the coding sequence is codon optimized for expression in a human cell.

In some embodiments, the nucleic acid molecule encoding the Cas13 protein is a plasmid. In some embodiments, the nucleic acid molecule encoding the Cas13 protein is part of the genome of a viral vector, such as the DNA genome of an AAV vector flanked by ITRs. In some embodiments, the nucleic acid molecule encoding the Cas13 protein is an mRNA.

Guide Polynucleotide

In some embodiments, the guide polynucleotide of the CRISPR-Cas13 system is a guide RNA. In some embodiments, the guide polynucleotide is a chemically-modified guide polynucleotide. In some embodiments, the guide polynucleotide comprises at least one chemically-modified nucleotide. In some embodiments, the guide polynucleotide is a hybrid RNA-DNA guide. In some embodiments, the guide polynucleotide is a hybrid RNA-LNA (locked nucleic acid) guide.

In some embodiments, the guide polynucleotide comprises at least one guide sequence (also referred to as spacer sequence) linked to at least one direct repeat sequence (direct repeat, DR). In some embodiments, the guide sequence is positioned at the 3' end of the direct repeat sequence. In some embodiments, the guide sequence is positioned at the 5' end of the direct repeat sequence.

In some embodiments, the guide sequence comprises at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, or at least 30 nucleotides. In some embodiments, the guide sequence comprises no more than 60 nucleotides, no more than 55 nucleotides, no more than 50 nucleotides, no more than 45 nucleotides, no more than 40 nucleotides, no more than 35 nucleotides, or no more than 30 nucleotides. In some embodiments, the guide sequence comprises 15-20 nucleotides, 20-25 nucleotides, 25-30 nucleotides, 30-35 nucleotides, or 35-40 nucleotides.

In some embodiments, the guide sequence has sufficient complementarity with the target RNA sequence to hybridize with the target RNA and guide the sequence-specific binding of the CRISPR-Cas13 complex to the target RNA. In some embodiments, the guide sequence has 100% complementarity with the target RNA (or region of the RNA to be targeted), but the guide sequence can have less than 100% complementarity with the target RNA, such as at least 80%, at least 85%, at least 90%, at least 95%, at least 98%, or at least 99% complementarity with the target RNA.

In some embodiments, the guide sequence is engineered to hybridize with the target RNA with no more than two mismatches. In some embodiments, the guide sequence is engineered to hybridize with the target RNA with no more than one mismatch. In some embodiments, the guide sequence is engineered to hybridize with the target RNA with or without a mismatch.

In some embodiments, the direct repeat sequence comprises at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides, at least 31 nucleotides, at least 32 nucleotides, at least 33 nucleotides, at least 34 nucleotides, at least 35 nucleotides, or at least 36 nucleotides. In some embodiments, the direct repeat comprises no more than 60 nucleotides, no more than 55 nucleotides, no more than 50 nucleotides, no more than 45 nucleotides, no more than 40 nucleotides, or no more than 35 nucleotides. In some embodiments, the direct repeat sequence comprises 20-25 nucleotides, 25-30 nucleotides, 30-35 nucleotides, or 35-40 nucleotides.

In some embodiments, the direct repeat sequence is modified to substitute at least one complementary base pair in the stem region shown in FIG. 2 with a different complementary base pair. In some embodiments, the direct repeat sequence is modified to vary the number of complementary base pairs in the stem region shown in FIG. 2. In some embodiments, the direct repeat sequence is modified to vary the number of nucleotides in the loop region shown in FIG. 2 (e.g., 3, 4, or 5 nucleotides in the loop). In some embodiments, the direct repeat sequence is modified to vary the nucleotide sequence in the loop region. In some embodiments, an aptamer sequence is inserted within or appended to the end of the direct repeat sequence. In some embodiments, the direct repeat sequence comprises at least 60%, at least 70%, at least 80%, at least 85%, at least 90%, at least 91%, at least 92%, at least 93%, at least 94%, at least 95%, at least 96%, at least 97%, at least 98%, at least 99%, or at least 100% sequence identity compared to any one of SEQ ID NO: 3 and SEQ ID NOs: 80-87.

In some embodiments, the CRISPR-Cas13 system, composition, or kit comprises at least 2, at least 3, at least 4, at least 5, at least 10, or at least 20 different guide polynucleotides. In some embodiments, the guide polynucleotides target at least 2, at least 3, at least 4, at least 5, at least 10, or at least 20 different target RNA molecules, or target at least 2, at least 3, at least 4, at least 5, at least 10, or at least 20 different regions of one or more target RNA molecules.

In some embodiments, the guide polynucleotide includes a constant direct repeat sequence positioned upstream of a variable guide sequence. In some embodiments, a plurality of guide polynucleotides are part of an array (which can be part of a vector, such as a viral vector or plasmid). For example, a guide array including the sequence DR-spacer-DR-spacer-DR-spacer, may include three unique unprocessed guide polynucleotides (one for each DR-spacer sequence). Once introduced into a cell or cell-free system, the array is processed by the Cas13 protein into three individual mature guide polynucleotides. This allows for multiplexing, e.g. the delivery of multiple guide polynucleotides to a cell or system to target multiple target RNAs or multiple regions within a single target RNA.

The ability of a guide polynucleotide to guide sequence-specific binding of a CRISPR complex to a target RNA may be assessed by any suitable assay. For example, the components of a CRISPR system sufficient to form a CRISPR complex, including the guide polynucleotide to be tested, may be provided to a host cell having the corresponding target RNA molecule, such as by transfection with vectors encoding the components of a CRISPR complex, followed by an assessment of preferential cleavage within the target sequence. Similarly, cleavage of a target RNA sequence may be evaluated in a test tube by providing the target RNA, components of a CRISPR complex, including the guide polynucleotide to be tested and a control guide polynucleotide different from the test guide polynucleotide, and comparing the binding ability or rate of cleavage at the target RNA between the test and control guide polynucleotide.

Cas13 Mutants

In some embodiments, the Cas13 protein provided herein comprises one or more mutations, such as a single amino acid insertion, a single amino acid deletion, a single amino acid substitution, or combinations thereof, compared to wild-type C13-2 protein (SEQ ID NO: 1).

In some examples, the Cas13 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 amino acid changes (such as insertion, deletion or substitution), compared to wild-type C13-2 protein (SEQ ID NO: 1), but retains the ability to bind target RNA molecules complementary to the guide sequence of the guide polynucleotide, and/or retains the ability to process an guide array RNA transcripts into guide polynucleotide molecules. In some examples, the Cas13 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 amino acid changes (such as insertion, deletion or substitution), compared to wild-type C13-2 protein (SEQ ID NO: 1), but retains the ability to bind target RNA molecules complementary with the guide sequence of the guide polynucleotide.

In some examples, the Cas13 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes (such as insertion, deletion or substitution), compared to wild-type C13-2 protein (SEQ ID NO: 1), but retains the ability to bind target RNA molecules complementary with the guide sequence of the guide polynucleotide, and/or retains the ability to process a guide array RNA transcript into guide polynucleotide molecules.

In some embodiments, the Cas13 protein comprises one or more mutations in the catalytic domain and has reduced RNA cleavage activity. In some embodiments, the Cas13 protein comprises one mutation in the catalytic domain and has reduced RNA cleavage activity. In some embodiments, the Cas13 protein comprises one or more mutations in one or both HEPN domains and substantially lacks RNA cleavage activity. In some embodiments, the Cas13 protein comprises a mutation in one or both HEPN domains and substantially lacks RNA cleavage activity. In some embodiments, the "substantially lack RNA cleavage activity" refers to the retention of ≤50%, ≤40%, ≤30%, ≤20%, ≤10%, ≤5%, or ≤1% of RNA cleavage activity compared to wild-type Cas13 protein, or the absence of detectable RNA cleavage activity.

In some embodiments, the Cas13 protein comprises at least 90%, at least 91%, at least 92%, at least 93%, at least 94%, at least 95%, at least 96%, at least 97%, at least 98%, or at least 99% sequence identity compared to SEQ ID NO: 1. In some embodiments, the Cas13 protein comprises at least 90%, at least 91%, at least 92%, at least 93%, at least 94%, at least 95%, at least 96%, at least 97%, at least 98%, or at least 99% sequence identity compared to the protein sequence encoded by SEQ ID NO: 9. When the CRISPR-Cas13 system comprises a fusion protein of the Cas13 protein with a protein domain and/or a peptide tag, the percentage of sequence identity is calculated between the Cas13 portion of the fusion protein and the reference sequence.

In some embodiments, the Cas13 protein can form a CRISPR complex with a guide polynucleotide, and the CRISPR complex is capable of sequence-specifically binding to the target RNA.

In some embodiments, the Cas13 protein is capable of forming a CRISPR complex with a guide polynucleotide comprising a direct repeat sequence linked to a guide sequence that is engineered to guide the sequence-specific binding of the CRISPR complex to the target RNA.

One type of modification or mutation includes the substitution of amino acids for amino acid residues having a similar biochemical property, i.e., a conservative substitution (such as conservative substitutions of 1-4, 1-8, 1-10, or 1-20 amino acids). Typically, the conservative substitution has little to no impact on the activity of the resulting protein or peptide.

For example, a conservative substitution is an amino acid substitution in a Cas13 protein that does not substantially affect the binding of the Cas13 protein to a target RNA molecule complementary with the guide sequence of the gRNA molecule, and/or the processing of the guide array RNA transcript into gRNA molecules. An alanine scan can be used to identify which amino acid residues in a Cas13 protein, can tolerate an amino acid substitutions. In one example, when an alanine or other conservative amino acid is substituted for 1-4, 1-8, 1-10, or 1-20 native amino acids, the ability of a variant Cas13 protein to modify gene expression in a CRISPR-Cas system is altered by no more than 25%, e.g., no more than 20%, e.g., no more than 10%. Examples of amino acids that may be substituted and are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in maintaining the following effects: (a) the structure of the polypeptide backbone in the area of the substitution, e.g., as a helical or a sheet conformation; (b) the charge or hydrophobicity of the area interacting with the target site; or (c) the bulk of the side chain. The substitutions that in general are expected to produce the greatest changes in polypeptide function are: (a) a hydrophilic residue, e.g., serine or threonine, is substituted for (or by) a hydrophobic residue, e.g., leucine, isoleucine, phenylalanine, valine or alanine (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine.

In some embodiments, the Cas13 protein comprises one or more mutations at amino acid positions 40-91 of SEQ ID NO: 1 (i.e., the region from the 40th amino acid to the 91st amino acid in the sequence of SEQ ID NO: 1, including the 40th amino acid and the 91st amino acid). In some embodiments, the Cas13 protein comprises one or more mutations at amino acid positions 146-153 of SEQ ID NO: 1. In some embodiments, the Cas13 protein comprises one or more mutations at amino acid positions 158-176 of SEQ ID NO: 1. In some embodiments, the Cas13 protein comprises one or more mutations at amino acid positions 182-209 of SEQ ID NO: 1. In some embodiments, the Cas13 protein comprises one or more mutations at amino acid positions 216-253 of SEQ ID NO: 1. In some embodiments, the Cas13 protein comprises one or more mutations at amino acid positions 271-287 of SEQ ID NO: 1. In some embodiments, the Cas13 protein comprises one or more mutations at amino acid positions 341-353 of SEQ ID NO: 1. In some embodiments, the Cas13 protein comprises one or more mutations at amino acid positions 379-424 of SEQ ID NO: 1. In some embodiments, the Cas13 protein comprises one or more mutations at amino acid positions 456-477 of SEQ ID NO: 1. In some embodiments, the Cas13 protein comprises one or more mutations at amino acid positions 521-557 of SEQ ID NO: 1. In some embodiments, the Cas13 protein comprises one or more mutations at amino acid positions 575-588 of SEQ ID NO: 1. In some embodiments, the Cas13 protein comprises one or more mutations at amino acid positions 609-625 of SEQ ID NO: 1. In some embodiments, the Cas13 protein comprises one or more mutations at amino acid positions 700-721 of SEQ ID NO: 1. In some embodiments, the Cas13 protein comprises one or more mutations at amino acid positions 724-783 of SEQ ID NO: 1. In some embodiments, the Cas13 protein comprises one or more mutations at amino acid positions 796-815 of SEQ ID NO: 1. In some embodiments, the Cas13 protein comprises one or more mutations at amino acid positions 828-852 of SEQ ID NO: 1. In some embodiments, the Cas13 protein comprises one or more mutations at amino acid positions 880-893 of SEQ ID NO: 1.

In some embodiments, the Cas13 protein comprises deletion of one or more amino acids at amino acid positions 348-350 of SEQ ID NO: 1 (i.e., the 348th amino acid, the 349th amino acid, and the 350th amino acid in the sequence of SEQ ID NO: 1). In some embodiments, the Cas13 protein comprises deletion of one or more amino acids at amino acid positions 521-556 of SEQ ID NO: 1. In some embodiments, the Cas13 protein comprises deletion of one or more amino acids at amino acid positions 883-893 of SEQ ID NO: 1.

In some embodiments, the RxxxxH motif of the Cas13 protein (x represents any amino acid, RxxxxH can also be referred to as Rx4H or R4xH) comprises one or more mutations and substantially lacks RNA cleavage activity.

In some embodiments, the Cas13 protein comprises a mutation at the position corresponding to the RxxxxH motifs at positions 210-215, 750-755, and/or 785-790 of the reference protein as shown in SEQ ID NO: 1.

In some embodiments, the Cas13 protein comprises a mutation at the position corresponding to the RxxxxH motif at positions 210-215 of the reference protein as shown in SEQ ID NO: 1. In some embodiments, the Cas13 protein comprises a mutation at the position corresponding to the RxxxxH motif at positions 750-755 of the reference protein as shown in SEQ ID NO: 1. In some embodiments, the Cas13 protein comprises a mutation at the position corresponding to the RxxxxH motif at positions 785-790 of the reference protein as shown in SEQ ID NO: 1.

In some embodiments, the Cas13 protein comprises a mutation at the position corresponding to the RxxxxH motifs at positions 210-215 and 750-755 of the reference protein as shown in SEQ ID NO: 1.

In some embodiments, the Cas13 protein comprises a mutation at the position corresponding to the RxxxxH motifs at positions 210-215 and 785-790 of the reference protein as shown in SEQ ID NO: 1.

In some embodiments, the Cas13 protein comprises a mutation at the position corresponding to the RxxxxH motifs at positions 750-755 and 785-790 of the reference protein as shown in SEQ ID NO: 1.

In some embodiments, the Cas13 protein comprises a mutation at the position corresponding to the RxxxxH motifs at positions 210-215, 750-755 and 785-790 of the reference protein as shown in SEQ ID NO: 1.

In some embodiments, the RxxxxH motif is mutated to AxxxxxH, RxxxxA, or AxxxxxA. In some embodiments, the RxxxxH motif is mutated to AxxxxxH. In some embodiments, the RxxxxH motif is mutated to RxxxxA. In some embodiments, the RxxxxH motif is mutated to AxxxxxA.

In some embodiments, the Cas13 protein comprises 1, 2, 3, 4, 5, or 6 mutations at the position corresponding to the amino acid residues R210, H215, R750, H755, R785, and/or H790 of the reference protein as shown in SEQ ID NO: 1. In some embodiments, the amino acid residues of the Cas13 protein at the position corresponding to the amino acid residues R210, H215, R750, H755, R785, and/or H790 of the reference protein as shown in SEQ ID NO: 1 is mutated to A (alanine).

In some embodiments, the Cas13 protein comprises a mutation at the position corresponding to the amino acid residues R210 and H215 of the reference protein as shown in SEQ ID NO: 1. In some embodiments, the Cas13 protein comprises a mutation at the position corresponding to the amino acid residues R750 and H755 of the reference protein as shown in SEQ ID NO: 1. In some embodiments, the Cas13 protein comprises a mutation at the position corresponding to the amino acid residues R785 and H790 of the reference protein as shown in SEQ ID NO: 1.

In some embodiments, the Cas13 protein comprises a mutation at the position corresponding to the amino acid residues R210, H215, R750 and H755 of the reference protein as shown in SEQ ID NO: 1.

In some embodiments, the Cas13 protein comprises a mutation at the position corresponding to the amino acid residues R750, H755, R785 and H790 of the reference protein as shown in SEQ ID NO: 1.

In some embodiments, the Cas13 protein comprises a mutation at the position corresponding to the amino acid residues R210, H215, R785 and H790 of the reference protein as shown in SEQ ID NO: 1.

In some embodiments, the Cas13 protein comprises a mutation at the position corresponding to the amino acid residues R210, H215, R750, H755, R785 and H790 of the reference protein as shown in SEQ ID NO: 1.

In some embodiments, the position corresponding to the amino acid residue R210, R750, or R785 is mutated to A. In some embodiments, the position corresponding to the amino acid residue H215, H755, or H790 is mutated to A. In some embodiments, the positions corresponding to the amino acid residues R210, H215, R750, H755, R785, and H790 are all mutated to A.

In some embodiments, the Cas13 protein is obtained by introducing a mutation in the RxxxxH motifs at the position 210-215, 750-755, and/or 785-790 of the sequence as shown in SEQ ID NO: 1.

In some embodiments, the Cas13 protein is obtained by introducing 1, 2, 3, 4, 5, or 6 mutations at the position R210, H215, R750, H755, R785, and/or H790 of the sequence as shown in SEQ ID NO: 1. In some embodiments, the Cas13 protein is obtained by mutating the amino acid residues at the position R210, H215, R750, H755, R785, and/or H790 of the sequence as shown in SEQ ID NO: 1 to A (alanine).

In some embodiments, the Cas13 protein is obtained by mutating the amino acid residues at the position R210, H215, R785, and H790 of the sequence as shown in SEQ ID NO: 1 to A. In some embodiments, the Cas13 protein is obtained by mutating the amino acid residues at the position R210, H215, R750, and H755 of the sequence as shown in SEQ ID NO: 1 to A. In some embodiments, the Cas13 protein is obtained by mutating the amino acid residues at the position R750, H755, R785, and H790 of the sequence as shown in SEQ ID NO: 1 to A. In some embodiments, the Cas13 protein is obtained by mutating the amino acid residues at the position R210, H215, R750, H755, R785, and H790 of the sequence as shown in SEQ ID NO: 1 to A.

In some embodiments, the Cas13 protein comprises at least one mutation at the position corresponding to amino acid residue positions 40-91, 146-153, 158-176, 182-209, 216-253, 271-287, 341-353, 379-424, 456-477, 521-557, 575-588, 609-625, 700-721, 724-783, 796-815, 828-852 or 880-893 of the reference protein as shown in SEQ ID NO: 1. In some embodiments, the Cas13 protein comprises deletion of one or more amino acids at the position corresponding to amino acid residue positions 348-350, 521-556, or 883-893 of the reference protein as shown in SEQ ID NO: 1.

In some embodiments, compared with the reference protein as shown in SEQ ID NO: 1, the Cas13 protein comprises any one or more mutations at the position corresponding to the following amino acid residues of the reference protein as shown in SEQ ID NO: 1: R11, N34, R35, R47, R58, R63, R64, N68, N87, N265, N274, R276, R290, R294, N299, N303, R308, R314, R320, R328, N332, R341, N346, R358, N372, N383, N390 N394, R47+R290, R47+R314, R290+ R314, R47+R290+R314, R308+N68, N394+N68, N87+ N68, R308+N265, N394+N265, N87+N265, R308+N68+ N265, N87+N68+N265, T7, A16, S260, A263, M266, N274, F288, M302, N303, L304, V305, I311, D313, H324, P326, H327, N332, N346, T353, T360, E365, A373, M380, S382, K395, Y396, D402, D411, S418.

In some embodiments, compared with the reference protein as shown in SEQ ID NO: 1, the position of the Cas13 protein corresponding to the mutation sites in Table 24 of the reference protein as shown in SEQ ID NO: 1 is mutated to the same amino acid residue. In some embodiments, compared with the reference protein as shown in SEQ ID NO: 1, the Cas13 protein comprises the same mutation at the positions corresponding to the mutation sites in Table 24 of the reference protein as shown in SEQ ID NO: 1.

In some embodiments, the Cas13 protein is obtained by introducing any one or more mutations at the following positions of the sequence as shown in SEQ ID NO: 1: R11, N34, R35, R47, R58, R63, R64, N68, N87, N265, N274, R276, R290, R294, N299, N303, R308, R314, R320, R328, N332, R341, N346, R358, N372, N383, N390, N394, R47+ R290, R47+R314, R290+R314, R47+R290+R314, R308+ N68, N394+N68, N87+N68, R308+N265, N394+N265, N87+N265, R308+N68+N265, N87+N68+N265, T7, A16, S260, A263, M266, N274, F288, M302, N303, L304, V305, I311, D313, H324, P326, H327, N332, N346, T353, T360, E365, A373, M380, S382, K395, Y396, D402, D411, S418.

In some embodiments, the Cas13 protein is obtained by introducing any one or more mutations in Table 24 to the sequence as shown in SEQ ID NO: 1.

In some embodiments, the Cas13 protein is obtained by sequence deletion at the position corresponding to amino acid residue positions 91-120, 141-180, 211-240, 331-360, 351-400, 431-460, 461-500, 511-550, 611-640, 631-660, 661-690, 691-760, 821-860, or 861-890 of the reference protein as shown in SEQ ID NO: 1.

In some embodiments, ≤300, ≤200, ≤150, ≤100, ≤90, ≤80, ≤70, ≤60, ≤50, ≤40, ≤30, ≤20, or ≤10 amino acid residues are deleted in the sequence deletion.

In some embodiments, the Cas13 protein is obtained by sequence deletion at positions 91-120, 141-180, 211-240, 331-360, 351-400, 431-460, 461-500, 511-550, 611-640, 631-660, 661-690, 691-760, 821-860, or 861-890 of the sequence as shown in SEQ ID NO: 1.

Subcellular Localization Signal (or Referred to as Localization Signal)

In some embodiments, the Cas13 protein or the functional fragment thereof is fused to at least one homologous or heterologous subcellular localization signal. Exemplary subcellular localization signals include organelle localization signals, such as a nuclear localization signal (NLS), a nuclear export signal (NES) or a mitochondrial localization signal.

In some embodiments, the Cas13 protein or the functional fragment thereof is fused to at least one homologous or heterologous NLS. In some embodiments, the Cas13 protein or the functional fragment thereof is fused to at least two NLSs. In some embodiments, the Cas13 protein or the functional fragment thereof is fused to at least three NLSs. In some embodiments, the Cas13 protein or the functional fragment thereof is fused to at least one N-terminus NLS and at least one C-terminus NLS. In some embodiments, the Cas13 protein or the functional fragment thereof is fused to at least two C-terminus NLSs. In some embodiments, the Cas13 protein or the functional fragment thereof is fused to at least two N-terminus NLSs.

In some embodiments, the NLS is independently selected from SPKKKRKVEAS (SEQ ID NO: 53), GPKKKRK-VAAA (SEQ ID NO: 54), PKKKRKV (SEQ ID NO: 55), KRPAATKKAGQAKKKK (SEQ ID NO: 56), PAAKRVKLD (SEQ ID NO: 57), RQRRNELKRSP (SEQ ID NO: 58), NQSSNFGPMKGGNFG-GRSSGPYGGGGQYFAKPRNQGGY (SEQ ID NO: 59), RMRIZFKNKGKDTAELRRRRVEVSVELRKAKKD-EQILKRRNV (SEQ ID NO: 60), VSRKRPRP (SEQ ID NO: 61), PPKKARED (SEQ ID NO: 62), POPKKKPL (SEQ ID NO: 63), SALIKKKKKMAP (SEQ ID NO: 64), DRLRR (SEQ ID NO: 65), PKQKKRK (SEQ ID NO: 66), RKLKK-KIKKL (SEQ ID NO: 67), REKKKFLKRR (SEQ ID NO: 68), KRKGDEVDGVDEVAKKKSKK (SEQ ID NO: 69), or RKCLQAGMNLEARKTKK (SEQ ID NO: 70), and PAAKKKKLD (SEQ ID NO: 71).

In some embodiments, the Cas13 protein or the functional fragment thereof is fused to at least one homologous or heterologous NES. In some embodiments, the Cas13 protein or the functional fragment thereof is fused to at least two NESs. In some embodiments, the Cas13 protein or the functional fragment thereof is fused to at least three NESs. In some embodiments, the Cas13 protein or the functional fragment thereof is fused to at least one N-terminus NES and at least one C-terminus NES. In some embodiments, the Cas13 protein or the functional fragment thereof is fused to at least two C-terminus NESs. In some embodiments, the Cas13 protein or the functional fragment thereof is fused to at least two N-terminus NESs.

In some embodiments, the NES is independently selected from an adenovirus type 5 E1B NES, an HIV Rev NES, a MAPK NES, and a PTK2 NES.

In some embodiments, the Cas13 protein or the functional fragment thereof is fused to homologous or heterologous NLS and NES, wherein a cleavable linker is positioned between the NLS and the NES. In some embodiments, the NES facilitates the production of delivery particles (e.g., viral-like particles) comprising the Cas13 protein or the functional fragment thereof in a production cell line. In some embodiments, cleavage of the linker in a target cell may expose the NLS and facilitate nuclear localization of the Cas13 protein or the functional fragment thereof in the target cell.

Protein Domain and Polypeptide Tag

In some embodiments, the Cas13 protein or the functional fragment thereof is covalently linked or fused to a homologous or heterologous protein domain and/or a polypeptide tag. In some embodiments, the Cas13 protein or the functional fragment thereof is fused to a homologous or heterologous protein domain and/or a polypeptide tag.

In some embodiments, the protein domain and polypeptide tag are optionally selected from: a cytosine deaminase domain, an adenosine deaminase domain, a translational activation domain, a translational repression domain, an RNA methylation domain, an RNA demethylation domain, a ribonuclease domain, a splicing factor domain, a reporter domain, an affinity domain, a subcellular localization signal, a reporter tag, and an affinity tag.

In some embodiments, the protein domain comprises a cytosine deaminase domain, an adenosine deaminase domain, a translational activation domain, a translational repression domain, an RNA methylation domain, an RNA demethylation domain, a ribonuclease domain, a splicing factor domain, a reporter domain, and an affinity domain. In some embodiments, the polypeptide tag comprises a reporter tag and an affinity tag.

In some embodiments, the length of the amino acid sequence of the protein domain is ≥40 amino acids, ≥50 amino acids, ≥60 amino acids, ≥70 amino acids, ≥80 amino acids, ≥90 amino acids, ≥100 amino acids, ≥150 amino acids, ≥200 amino acids, ≥250 amino acids, ≥300 amino acids, ≥350 amino acids, or ≥400 amino acids.

Exemplary protein domains include those can cleave RNA (e.g., a PIN endonuclease domain, an NYN domain, an SMR domain from SOT1, or an RNase domain from Staphylococcal nuclease), those can affect RNA stability (e.g., tristetraprolin (TTP) or domains from UPF1, EXOSC5, and STAU1), those can edit a nucleotide or ribonucleotide (e.g., a cytidine deaminase, PPR protein, adenosine deaminase, ADAR family protein, or APOBEC family protein), those can activate translation (e.g., eIF4E and other translation initiation factors, a domain of the yeast poly(A)-binding protein or GLD2), those can inhibit translation (e.g., Pumilio or FBF PUF proteins, deadenylases, CAF1, Argonaute proteins), those can methylate RNA (e.g., domains from m6A methyltransferase factors such as METTL14, METTL3, or WTAP), those can demethylate RNA (e.g., human alkylation repair homolog 5), those can affect splicing (e.g., the RS-rich domain of SRSF1, the Gly-rich domain of hnRNP A1, the alanine-rich motif of RBM4, or the proline-rich motif of DAZAP1), those can enable affinity purification or immunoprecipitation, and those can enable proximity-based protein labeling and identification (e.g., a biotin ligase (such as BirA) or a peroxidase (such as APEX2) in order to biotinylate proteins that interact with the target RNA).

In some embodiments, the protein domain comprises an adenosine deaminase domain. In some embodiments, a Cas13 protein described herein with a mutated HEPN domain, a catalytically inactive Cas13 protein, or the functional fragment thereof is covalently linked or fused to an adenosine deaminase domain to guide A-to-I deaminase activity on RNA transcripts in mammalian cells. Adenosine deaminase domains engineered based on ADAR2 for targeting A-to-I RNA editing are described in Cox et al., Science 358(6366):1019-1027 (2017), which is incorporated herein by reference in its entirety. In other embodiments, the adenosine deaminase domain is covalently linked or fused to an adaptor protein which is capable of binding to an aptamer sequence inserted within or appended to the guide polynucleotide, thereby allowing the adenosine deaminase domain to be non-covalently linked to the Cas13 protein or the functional fragment thereof that is complexed with the guide polynucleotide.

In some embodiments, the protein domain comprises a cytosine deaminase domain. In some embodiments, a Cas13 protein described herein with a mutated HEPN domain, a catalytically inactive Cas13 protein, or the functional fragment thereof is covalently linked or fused to a cytosine deaminase domain to guide C-to-U deaminase activity on RNA transcripts in mammalian cells. Cytosine deaminase domains evolved from ADAR2 for targeting C-to-U RNA editing are described in Abudayyeh et al., Science 365 (6451):382-386 (2019), which is incorporated herein by reference in its entirety. In other embodiments, the cytosine deaminase domain is covalently linked or fused to an adaptor protein which is capable of binding to an aptamer sequence inserted within or appended to the guide polynucleotide, thereby allowing the cytosine deaminase domain to be non-covalently linked to the Cas13 protein or the functional fragment thereof that is complexed with the guide polynucleotide.

In some embodiments, the protein domain comprises a splicing factor domain. In some embodiments, a Cas13 protein described herein with a mutated HEPN domain, a catalytically inactive Cas13 protein, or the functional fragment thereof is covalently linked or fused to a splicing factor domain to guide alternative splicing of the target RNA in mammalian cells. Splicing factor domains for targeting selective splicing are described in Konermann et al., Cell 173(3):665-676 (2018), which is incorporated herein by reference in its entirety. Non-limiting examples of the splicing factor domain include RS-rich domain of SRSF1, Gly-rich domain of hnRNPA1, alanine-rich motif of RBM4, or proline-rich motif of DAZAP1. In other embodiments, the splicing factor domain is covalently linked or fused to an adaptor protein which is capable of binding to an aptamer sequence inserted within or appended to the guide polynucleotide, thereby allowing the splicing factor domain to be non-covalently linked to the Cas13 protein or the functional fragment thereof that is complexed with the guide polynucleotide.

In some embodiments, the protein domain comprises a translational activation domain. In some embodiments, a Cas13 protein described herein with a mutated HEPN domain, a catalytically inactive Cas13 protein, or the functional fragment thereof is covalently linked or fused to a translational activation domain for activating or increasing expression of the target RNA. Non-limiting examples of the translational activation domain include eIF4E and other translation initiation factors, a domain of the yeast poly(A)-binding protein or GLD2. In other embodiments, the translational activation domain is covalently linked or fused to an adaptor protein which is capable of binding to an aptamer sequence inserted within or appended to the guide polynucleotide, thereby allowing the translational activation domain to be non-covalently linked to the Cas13 protein or the functional fragment thereof that is complexed with the guide polynucleotide.

In some embodiments, the protein domain comprises a translational repression domain. In some embodiments, a Cas13 protein described herein with a mutated HEPN domain, a catalytically inactive Cas13 protein, or the functional fragment thereof is covalently linked or fused to a translational repression domain for repressing or decreasing expression of the target RNA. Non-limiting examples of the translational repression domain include Pumilio or FBF PUF proteins, deadenylases, CAF1, Argonaute proteins. In other embodiments, the translational repression domain is covalently linked or fused to an adaptor protein which is capable of binding to an aptamer sequence inserted within or appended to the guide polynucleotide, thereby allowing the translational repression domain to be non-covalently linked to the Cas13 protein or the functional fragment thereof that is complexed with the guide polynucleotide.

In some embodiments, the protein domain comprises an RNA methylation domain. In some embodiments, a Cas13 protein described herein with a mutated HEPN domain, a catalytically inactive Cas13 protein, or the functional fragment thereof is covalently linked or fused to a RNA methylation domain for methylation of the target RNA. Non-limiting examples of the RNA methylation domain include m6A domains such as METTL14, METTL3, or WTAP. In other embodiments, the RNA methylation domain is covalently linked or fused to an adaptor protein which is capable of binding to an aptamer sequence inserted within or appended to the guide polynucleotide, thereby allowing the RNA methylation domain to be non-covalently linked to the Cas13 protein or the functional fragment thereof that is complexed with the guide polynucleotide.

In some embodiments, the protein domain comprises an RNA demethylation domain. In some embodiments, a Cas13 protein described herein with a mutated HEPN domain, a catalytically inactive Cas13 protein, or the functional fragment thereof is covalently linked or fused to a RNA demethylation domain for demethylation of the target RNA. Non-limiting examples of the RNA methylation domain include human alkylation repair homolog 5 or ALKBH5. In other embodiments, the RNA demethylation domain is covalently linked or fused to an adaptor protein which is capable of binding to an aptamer sequence inserted within or appended to the guide polynucleotide, thereby allowing the RNA demethylation domain to be non-covalently linked to the Cas13 protein or the functional fragment thereof that is complexed with the guide polynucleotide.

In some embodiments, the protein domain comprises a ribonuclease domain. In some embodiments, a Cas13 protein described herein with a mutated HEPN domain, a catalytically inactive Cas13 protein, or the functional fragment thereof is covalently linked or fused to a ribonuclease domain for cleavage of the target RNA. Non-limiting examples of the ribonuclease domain include a PIN endonuclease domain, an NYN domain, an SMR domain from SOT1, or an RNase domain from Staphylococcal nuclease.

In some embodiments, the protein domain comprises an affinity domain or reporter domain. In some embodiments, a Cas13 protein or the functional fragment thereof described herein is covalently linked or fused to a reporter domain such as a fluorescent protein. Non-limiting examples of the reporter domain include GST, HRP, CAT, GFP, HcRed, DsRed, CFP, YFP, or BFP.

In some embodiments, a Cas13 protein described herein is covalently linked or fused to a polypeptide tag. In some embodiments, an example of the polypeptide tag is a small polypeptide sequence. In some embodiments, the length of the amino acid sequence of the polypeptide tag is ≤50 amino acids, ≤40 amino acids, ≤30 amino acids, ≤25 amino acids, ≤20 amino acids, ≤15 amino acids, ≤10 amino acids, or ≤5 amino acids. In some embodiments, a Cas13 protein described herein is covalently linked or fused to an affinity tag such as a purification tag. Non-limiting examples of the affinity tag include HA-tag, His-tag (such as 6-His), Myc-tag, E-tag, S-tag, calmodulin tag, FLAG-tag, GST-tag, MBP-tag, Halo tag, or biotin.

In some embodiments, the dead C13-2 mutant (R210A+H215A+R750A+H755A+R785A+H790A) is fused to a protein domain and/or a peptide tag.

In some embodiments, the Cas13 protein is fused to ADAR.

In some embodiments, the dead C13-2 mutant (R210A+H215A+R750A+H755A+R785A+H790A) is fused to a cytosine deaminase or an adenine deaminase.

In some embodiments, the dead C13-2 mutant (R210A+H215A+R750A+H755A+R785A+H790A) is covalently linked to a cytosine deaminase or an adenine deaminase directly, by rigid linker peptide sequence A(EAAAK)$_3$A, or by flexible linker peptide sequence (GGGGS)$_3$.

Aptamer Sequence

In some embodiments, the guide polynucleotide further comprises an aptamer sequence.

In some embodiments, the aptamer sequence is inserted into a loop of the guide polynucleotide.

In some embodiments, the aptamer sequence is inserted into the tetra loop of the guide polynucleotide. An example of tetra loop of the guide polynucleotide is shown in FIG. 2. In some embodiments, the aptamer sequence is appended to an end of the guide polynucleotide.

Insertion of an aptamer sequence into a guide polynucleotide of the CRISPR-Cas system is described in Konermann et al., Nature 517:583-588 (2015), which is incorporated herein by reference in its entirety. In some embodiments, the aptamer sequence includes an MS2 aptamer sequence, a PP7 aptamer sequence, or a Qβ aptamer sequence.

Adaptor Protein

In some embodiments, the CRISPR-Cas13 system further comprises a fusion protein comprising an adaptor protein and a homologous or heterologous protein domain and/or a polypeptide tag, or a nucleic acid encoding the fusion protein, wherein the adaptor protein is capable of binding to the aptamer sequence.

Fusion proteins of an adaptor protein and a protein domain are described in Konermann et al., Nature 517:583-588 (2015), which is incorporated herein by reference in its entirety. In some embodiments, the adaptor protein includes an MS2 phage coat protein (MCP), a PP7 phage coat protein (PCP), or a Qβ phage coat protein (QCP). In some embodiments, the protein domain comprises a cytosine deaminase domain, an adenosine deaminase domain, a translational activation domain, a translational repression domain, an RNA methylation domain, an RNA demethylation domain, a nuclease domain, a splicing factor domain, an affinity domain or a reporter domain.

Modified Guide Polynucleotide

In some embodiments, the guide polynucleotide comprises a modified nucleotide. In some embodiments, the modified nucleotide comprises 2'-O-methyl, 2'-O-methyl-3'phosphorothioate, or 2'-O-methyl-3'thioPACE. In some embodiments, the guide polynucleotide is a chemically-modified guide polynucleotide. Chemically-modified guide polynucleotide is described in Hendel et al., Nat. Biotechnol. 33(9):985-989 (2015), which is incorporated herein by reference in its entirety.

In some embodiments, the guide polynucleotide is a hybrid RNA-DNA guide, a hybrid RNA-LNA (locked nucleic acid) guide, a hybrid DNA-LNA guide, or a hybrid DNA-RNA-LNA guide. In some embodiments, the direct repeat sequence comprises one or more ribonucleotides substituted with corresponding deoxyribonucleotides. In some embodiments, the guide sequence comprises one or more ribonucleotides substituted with corresponding deoxyribonucleotides. Hybrid RNA-DNA guide polynucleotides are described in WO2016/123230, which is incorporated herein by reference in its entirety.

Vector System

Another aspect of the disclosure provided herein relates to a vector system comprising the CRISPR-Cas13 system described herein, wherein the vector system comprises one or more vectors comprising a polynucleotide sequence encoding the Cas13 protein and a polynucleotide sequence encoding the guide polynucleotide.

In some embodiments, the vector system comprises at least one plasmid or viral vector (e.g., retrovirus, lentivirus, adenovirus, adeno-associated virus, or herpes simplex virus). In some embodiments, the polynucleotide sequence encoding the Cas13 protein or fusion protein and the polynucleotide sequence encoding the guide polynucleotide are located on the same vector. In some embodiments, the polynucleotide sequence encoding the Cas13 protein or fusion protein and the polynucleotide sequence encoding the guide polynucleotide are located on a plurality of vectors.

In some embodiments, the polynucleotide sequence encoding the Cas13 protein or fusion protein and/or the polynucleotide sequence encoding the guide polynucleotide is operably linked to a regulatory sequence. In some embodiments, the polynucleotide sequence encoding the Cas13 protein or fusion protein is operably linked to a regulatory sequence. In some embodiments, the polynucleotide sequence encoding the guide polynucleotide is operably linked to a regulatory sequence. In some embodiments, the regulatory sequence of the polynucleotide sequence encoding a Cas13 protein or fusion protein and the regulatory sequence of the polynucleotide sequence encoding a guide polynucleotide are the same or different. In some embodiments, the regulatory sequence is optionally selected from promoters, enhancers, internal ribosomal entry sites (IRES), and other expression control elements (e.g., transcription termination signals, such as polyadenylation signals and poly-U sequences). In some embodiments, the regulatory sequence includes the regulatory sequence that enables the constitutive expression of the nucleotide sequence in many types of host cells, as well as the regulatory sequence that enables the expression of the nucleotide sequence only in certain host cells (e.g., tissue-specific regulatory sequence). A tissue-specific promoter can be directly expressed primarily in a desired tissue of interest, such as muscle, neuron, bone, skin, blood, specific organs (e.g., liver, pancreas), or particular cell types (e.g., lymphocytes). Regulatory elements can also direct expression in a temporal-dependent manner, such as in a cell-cycle dependent or developmental stage-dependent manner, which may or may not be tissue or cell-type specific. In some embodiments, the regulatory sequence is an enhancer element such as WPRE, a CMV enhancer, an R-U5' segment in LTR of HTLV-I, a SV40 enhancer, or an intron sequence between exons 2 and 3 of rabbit β-globin.

In some embodiments, the vector comprises a pol III promoter (e.g., U6 and H1 promoters), a pol II promoter (e.g., the retroviral Rous sarcoma virus (RSV) LTR promoter (optionally with the RSV enhancer), a cytomegalovirus (CMV) promoter (optionally with the CMV enhancer), a SV40 promoter, a dihydrofolate reductase promoter, a β-actin promoter, a phosphoglycerol kinase (PGK) promoter, or an EF1α promoter), or a pol III promoter and a pol II promoter.

In some embodiments, the promoter is a constitutive promoter that is continuously active and is not subject to regulation by external signals or molecules. Suitable constitutive promoters include, but are not limited to CMV, RSV, SV40, EF1α, CAG, and beta-actin. In some embodiments, the promoter is an inducible promoter that is regulated by an external signal or molecule (e.g., a transcription factor).

In some embodiments, the promoter is a tissue-specific promoter, which can be used to drive tissue-specific expression of the Cas13 protein or fusion protein. Suitable muscle specific promoters include, but are not limited to CK8, MHCK7, Myoglobin promoter (Mb), Desmin promoter, muscle creatine kinase promoter (MCK) and variants thereof, and SPc5-12 synthetic promoter. Suitable immune cell specific promoters include, but are not limited to, B29 promoter (B cells), CD14 promoter (monocytic cells), CD43 promoter (leukocytes and platelets), CD68 (macrophages), and SV40/CD43 promoter (leukocytes and platelets). Suitable blood cell specific promoters include, but are not limited to, CD43 promoter (leukocytes and platelets), CD45 promoter (hematopoietic cells), INF-β (hematopoietic cells), WASP promoter (hematopoietic cells), SV40/CD43 promoter (leukocytes and platelets), and SV40/CD45 promoter (hematopoietic cells). Suitable pancreatic specific promoters include, but are not limited to, Elastase-1 promoter. Suitable endothelial cell specific promoters include, but are not limited to, Flt-1 promoter and ICAM-2 promoter. Suitable neuronal tissue/cell specific promoters include, but are not limited to, GFAP promoter (astrocytes), SYN1 promoter (neurons), and NSE/RU5' (mature neurons). Suitable kidney specific promoters include, but are not limited to, NphsI promoter (podocytes). Suitable bone specific promoters include, but are not limited to, OG-2 promoter (osteoblasts, odontoblasts). Suitable lung specific promoters include, but are not limited to, SP-B prompter (lung). Suitable liver specific promoters include, but are not limited to, SV40/Alb promoter. Suitable heart specific promoters include, but are not limited to, α-MHC.

AAV Vector

Another aspect of the disclosure provided herein relates to an adeno-associated viral (AAV) vector comprising the CRISPR-Cas13 system described herein, wherein the AAV vector comprises a DNA encoding the Cas13 protein or the fusion protein and the guide polynucleotide.

Delivery of a CRISPR-Cas system by an AAV vector is described in Maeder et al., Nature Medicine 25:229-233 (2019), which is incorporated herein by reference in its entirety. In some embodiments, the AAV vector comprises an ssDNA genome comprising coding sequences for the Cas13 protein or the fusion protein and the guide polynucleotide flanked by ITRs.

In some embodiments, the CRISPR-Cas13 system described herein is packaged in an AAV vector, such as AAV1, AAV2, AAV3, AAV4, AAV5, AAV6, AAV7, AAV8, AAV9, and AAVrh74. In some embodiments, the CRISPR-Cas13 system described herein is packaged in an AAV vector comprising an engineered capsid having tissue-tropism, such as an engineered muscle-tropism capsid. Engineering of AAV capsids with tissue-tropism by directed evolution is described in Tabebordbar et al., Cell 184:4919-4938 (2021), which is incorporated herein by reference in its entirety.

Lipid Nanoparticle

Another aspect of the disclosure provided herein relates to a lipid nanoparticle (LNP) comprising the CRISPR-Cas13 system described herein, wherein the LNP comprises the guide polynucleotide described herein and an mRNA encoding the Cas13 protein or the fusion protein described herein.

LNP delivery of CRISPR-Cas systems is described in Gillmore et al., N. Engl. J. Med., 385:493-502 (2021), which is incorporated herein by reference in its entirety. In some embodiments, in addition to the RNA payload (Cas13 mRNA and guide polynucleotide), the LNP comprises four components: a cationic or ionizable lipid, cholesterol, a helper lipid, and a PEG-lipid. In some embodiments, the cationic or ionizable lipid comprises cKK-E12, C12-200, ALC-0315, DLin-MC3-DMA, DLin-KC2-DMA, FTT5, Moderna SM-102, and Intellia LP01. In some embodiments, the PEG-lipid comprises PEG-2000-C-DMG, PEG-2000-DMG, or ALC-0159. In some embodiments, the helper lipid comprises DSPC. Components of LNPs are described in Paunovska et al., Nature Reviews Genetics 23:265-280 (2022), which is incorporated herein by reference in its entirety.

Lentiviral Vector

Another aspect of the disclosure provided herein relates to a lentiviral vector comprising the CRISPR-Cas13 system described herein, wherein the lentiviral vector comprises the guide polynucleotide described herein and the mRNA encoding the Cas13 protein or the fusion protein described herein. In some embodiments, the lentiviral vector is pseudotyped with a homologous or heterologous envelope protein such as VSV-G. In some embodiments, the mRNA encoding the Cas13 protein or the fusion protein is linked to an aptamer sequence.

RNP Complex

Another aspect of the disclosure provided herein relates to a ribonucleoprotein complex comprising the CRISPR-Cas13 system described herein, wherein the ribonucleoprotein complex is formed by the guide polynucleotide and the Cas13 protein or the fusion protein described herein. In some embodiments, the ribonucleoprotein complex can be delivered to eukaryotic cells, mammalian cells, or human cells by microinjection or electroporation. In some embodiments, the ribonucleoprotein complex can be packaged in a viral-like particle and delivered to a mammalian or human subject in vivo.

Viral-Like Particle

Another aspect of the disclosure provided herein relates to a viral-like particle (VLP) comprising the CRISPR-Cas13 system described herein, wherein the viral-like particle comprises the guide polynucleotide and the Cas13 protein or the fusion protein described herein; or a ribonucleoprotein complex formed by the guide polynucleotide and the Cas13 protein or the fusion protein.

Engineered VLPs are described in Banskota et al., Cell 185(2):250-265 (2022), Mangeot et al., Nature Communications 10(1):1-15 (2019), Campbell, et al., Molecular Therapy 27:151-163 (2019), Campbell, et al., Molecular Therapy, 27 (2019): 151-163, and Mangeot et al., Molecular Therapy, 19(9):1656-1666 (2011), which are incorporated herein by reference in its entirety. In some embodiments, the engineered VLP is pseudotyped with a homologous or heterologous envelope protein such as VSV-G. In some embodiments, the Cas13 protein is fused to a gag protein (e.g., MLVgag) by a cleavable linker, wherein the cleavage of the linker in the target cell exposes a NLS positioned between the linker and the Cas13 protein. In some embodiments, the fusion protein comprises (e.g., from 5' to 3') a gag protein (e.g., MLVgag), one or more NESs, a cleavable linker, one or more NLSs, and a Cas13 protein, such as described in Banskota et al. Cell 185(2):250-265 (2022). In some embodiments, the Cas13 protein is fused to a first dimerizable domain that is capable of dimerization or heterodimerization with a second dimerizable domain fused to a membrane protein, wherein the presence of a ligand facilitates said dimerization and enriches the Cas13 protein or the fusion protein into the VLP, such as described in Campbell, et al., Molecular Therapy 27:151-163 (2019).

Cells

Another aspect of the disclosure provided herein relates to a cell comprising the CRISPR-Cas13 system described herein. The cell (e.g., which can be used to generate a cell-free system) can be eukaryotic or prokaryotic. Examples of such cells include, but are not limited to bacteria, archaea, plant, fungal, yeast, insect, and mammalian cells, such as *Lactobacillus, Lactococcus, Bacillus* (such as *B. subtilis*), *Escherichia* (such as *E. coli*), *Clostridium, Saccharomyces* or *Pichia* (such as *S. cerevisiae* or *P. pastoris*), *Kluyveromyces lactis, Salmonella typhimurium, Drosophila* cells, *C. elegans* cells, *Xenopus* cells, SF9 cells, C129 cells, 293 cells, *Neurospora*, and immortalized mammalian cell lines (e.g., *Hela* cells, myeloid cell lines, and lymphoid cell lines).

In some embodiments, the cell is a prokaryotic cell, such as a bacterial cell, such as *E. coli*. In some embodiments, the cell is a eukaryotic cell, such as a mammalian cell or a human cell. In some embodiments, the cell is a primary eukaryotic cell, a stem cell, a tumor/cancer cell, a circulating tumor cell (CTC), a blood cell (e.g., T cell, B cell, NK cell, Tregs, etc.), a hematopoietic stem cell, a specialized immune cell (e.g., tumor-infiltrating lymphocyte or tumor-suppressed lymphocytes), a stromal cell in the tumor microenvironment (e.g., cancer-associated fibroblasts, etc.). In some embodiments, the cell is a brain or neuronal cell of the central or peripheral nervous system (e.g., neurons, astrocytes, microglia cells, retinal ganglion cells, rod/cone cells, etc.).

Target RNA Molecule

The CRISPR-Cas13 system, composition, or kit described herein can be used to target one or more target RNA molecules, such as the target RNA molecules present in a biological sample, an environmental sample (e.g., soil, air or water sample), etc. In some embodiments, the target RNA is a coding RNA such as a pre-mRNA or a mature mRNA. In some embodiments, the target RNA is a nuclear RNA. In some embodiments, the target RNA is an RNA transcript located in the nucleus of a eukaryotic cell. In some embodiments, the target RNA is a non-coding RNA such as functional RNA, siRNA, microRNA, snRNA, snoRNA, piRNA, scaRNA, tRNA, rRNA, lncRNA, or lincRNA.

In some embodiments, in addition to targeting the target RNA molecule, the CRISPR-Cas13 system, composition, or kit described herein performs one or more of the following functions on the target RNA: cleaving one or more target RNA molecules or nicking one or more target RNA molecules, activating or upregulating one or more target RNA molecules, activating or inhibiting translation of one or more target RNA molecules, deactivating one or more target RNA molecules, visualizing, labeling, or detecting one or more target RNA molecules, binding one or more target RNA molecules, editing one or more target RNA molecules, transporting one or more target RNA molecules, and masking one or more target RNA molecules. In some examples, the CRISPR-Cas13 system, composition, or kit described herein modifies one or more target RNA molecules, the modifying one or more target RNA molecules including one or more of the following: an RNA base substitution, an RNA base deletion, an RNA base insertion, a break in the target RNA, an RNA methylation, and an RNA demethylation. In some embodiments, the CRISPR-Cas13 system, composition, or kit described herein can target one or more target RNA molecules. In some embodiments, the CRISPR-Cas13 system, composition, or kit described herein can bind one or more target RNA molecules. In some embodiments, the CRISPR-Cas13 system, composition, or kit described herein can cleave one or more target RNA molecules. In some embodiments, the CRISPR-Cas13 system, composition, or kit described herein can activate translation of one or more target RNA molecules. In some embodiments, the CRISPR-Cas13 system, composition, or kit described herein can inhibit translation of one or more target RNA molecules. In some embodiments, the CRISPR-Cas13 system, composition, or kit described herein can detect one or more target RNA molecules. In some embodiments, the CRISPR-Cas13 system, composition, or kit described herein can edit one or more target RNA molecules.

In some embodiments, the target RNA is AQp1 RNA. Knocking-down the level of AQp1 RNA using the CRISPR-Cas13 system described herein can reduce the production of aqueous humor and lowers intraocular pressure, which can be used for treatment of diseases such as glaucoma. In some embodiments, the target RNA is AQp1 RNA, and the guide sequence of the guide polynucleotide is SEQ ID NO: 5.

In some embodiments, the target RNA is PTBP1 RNA. Knocking-down the level of PTBP1 RNA using the CRISPR-Cas13 system described herein can facilitate the transdifferentiation of brain astrocytes into neurons, which can be used for treatment of diseases such as Parkinson's disease. In some embodiments, the target RNA is PTBP1 RNA, and the guide sequence of the guide polynucleotide is SEQ ID NO: 6.

In some embodiments, the target RNA is VEGFA RNA. Knocking-down the level of VEGFA RNA using the CRISPR-Cas13 system described herein can prevent choroidal neovascularization, which can be used for treatment of diseases such as age-related macular degeneration.

In some embodiments, the target RNA is ANGPTL3 RNA. Knocking-down the level of ANGPTL3 RNA using the CRISPR-Cas13 system described herein can lower blood lipids such as low-density lipoprotein cholesterol (LDL-C), which can be used for treatment of atherosclerotic cardiovascular diseases such as hyperlipidemia and familial hypercholesterolemia. In some embodiments, the target RNA is ANGPTL3 RNA, and the guide sequence of the guide polynucleotide is selected from any one or more of SEQ ID NOs: 42-49.

Therapeutic Applications

A further aspect of the disclosure provided herein relates to a pharmaceutical composition comprising the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particles described herein, or the eukaryotic cells described herein. The pharmaceutical composition can comprises, for example, an AAV vector encoding the Cas13 protein or the fusion protein and the guide polypeptide described herein. The pharmaceutical composition can comprises, for example, a lipid nanoparticle comprising the guide polypeptide described herein and an mRNA encoding the Cas13 protein or the fusion protein. The pharmaceutical composition can comprises, for example, a lentiviral vector comprising the guide polypeptide described herein and an mRNA encoding the Cas13 protein or the fusion protein. The pharmaceutical composition can comprises, for example, a viral-like particle comprising the guide polynucleotide described herein and the Cas13 protein or the fusion protein; or a ribonucleoprotein complex formed by the guide polynucleotide and the Cas13 protein or the fusion protein.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in cleaving and editing the target RNA in a mammalian cell.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in any one of the following: cleaving one or more target RNA molecules or nicking one or more target RNA molecules; activating or upregulating one or more target RNA molecules; activating or inhibiting translation of one or more target RNA molecules; inactivating one or more target RNA molecules; visualizing, labelling or detecting one or more target RNA molecules; binding one or more target RNA molecules; transporting one or more target RNA molecules; and masking one or more target RNA molecules.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in modifying one or more target RNA molecules in a mammalian cell, wherein the modifying one or more target RNA molecules comprises one or more of the following: an RNA base substitution, an RNA base deletion, an RNA base insertion, a break in the target RNA, an RNA methylation, and an RNA demethylation.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in diagnosing, treating, or preventing a disease or disorder associated with the target RNA. In some embodiments, the disease or disorder is Parkinson's disease. In some embodiments, the disease or disorder is Parkinson's disease, and the target RNA is PTBP1 RNA. In some embodiments, the disease or disorder is glaucoma. In some embodiments, the disease or disorder is glaucoma, and the target RNA is AQp1 RNA. In some embodiments, the disease or disorder is amyotrophic lateral sclerosis. In some embodiments, the disease or disorder is amyotrophic lateral sclerosis, and the target RNA is superoxide dismutase 1 (SOD1) RNA. In some embodiments, the disease or disorder is age-related macular degeneration, and the target RNA is VEGFA RNA. In some embodiments, the disease or disorder is age-related macular degeneration, and the target RNA is VEGFA RNA or VEGFR1 RNA. In some embodiments, the disease or disorder is increase of plasma LDL cholesterol level. In some embodiments, the disease or disorder is increase of plasma LDL cholesterol level, and the target RNA is PCSK9 RNA or ANGPTL3 RNA.

Another aspect of the disclosure provided herein relates to a use of the CRISPR-Cas13 system described herein, the Cas13 protein described herein, the fusion protein described herein, the guide polynucleotide described herein, the nucleic acid described herein, the vector system described herein, the lipid nanoparticle described herein, the lentiviral vector described herein, the ribonucleoprotein complex described herein, the viral-like particle described herein, or the eukaryotic cell described herein in the manufacture of a medicaments for diagnosing, treating, or preventing a disease or disorder associated with the target RNA. In some embodiments, the disease or disorder is Parkinson's disease. In some embodiments, the disease or disorder is glaucoma. In some embodiments, the disease or disorder is amyotrophic lateral sclerosis. In some embodiments, the disease or disorder is age-related macular degeneration. In some embodiments, the disease or disorder is increase of plasma LDL cholesterol level. In some embodiments, the disease or disorder is Parkinson's disease, and the target RNA is PTBP1 RNA. In some embodiments, the disease or disorder is glaucoma, and the target RNA is AQp1 RNA. In some embodiments, the disease or disorder is amyotrophic lateral sclerosis, and the target RNA is superoxide dismutase 1 (SOD1) RNA. In some embodiments, the disease or disorder is age-related macular degeneration, and the target RNA is VEGFA RNA or VEGFR1 RNA. In some embodiments, the disease or disorder is increase of plasma LDL cholesterol level, and the target RNA is PCSK9 RNA or ANGPTL3 RNA.

In some embodiments, the pharmaceutical composition is delivered to a human subject in vivo. The pharmaceutical composition can be delivered by any effective route. Exemplary routes of administration include, but are not limited to, intravenous infusion, intravenous injection, intraperitoneal injection, intramuscular injection, intratumoral injection, subcutaneous injection, intradermal injection, intraventricular injection, intravascular injection, intracerebellar injection, intraocular injection, subretinal injection, intravitreal injection, intracameral injection, intratympanic injection, intranasal administration, and inhalation.

In some embodiments, the method for targeting an RNA results in editing the sequence of a target RNA. For example, by using a Cas13 protein or fusion protein with a non-mutated HEPN domain, and a guide polynucleotide comprising a guide sequence specific for the target RNA, the target RNA can be cleaved or nicked at a precise location (nick, e.g. cleaving either single strand when the target RNA is present as a double-stranded nucleic acid molecule). In some examples, such a method is used to decrease expression of a target RNA, which will decrease translation of the corresponding protein. Such a method can be used in a cell where increased expression of an RNA is not desired. In one example, the RNA is associated with a disease such as cystic fibrosis, Huntington's disease, Tay-Sachs, Fragile X syndrome, Fragile X-associated tremor/ataxia syndrome, muscular dystrophy, myotonic dystrophy, spinal muscular atrophy, spinocerebellar ataxia, age-related macular degeneration, or familial ALS. In another example, the RNA is associated with cancer (e.g., lung cancer, breast cancer, colon cancer, liver cancer, pancreas cancer, prostate cancer, bone cancer, brain cancer, skin cancer (such as melanoma) or kidney cancer). Examples of target RNAs include, but are not limited to, those associated with cancer (e.g., PD-L1, BCR-ABL, Ras, Raf, p53, BRCA1, BRCA2, CXCR4, β-catenin, HER2, and CDK4). Editing such target RNAs can have therapeutic effects.

In some embodiments, the RNA is expressed in an immune cell. For example, the target RNA can encode for a protein leading to the repression of a desirable immune response (e.g., tumor infiltration). Knocking down of such an RNA could enable progression of such a desirable immune response (e.g., PD1, CTLA4, LAG3, TIM3). In another example, the target RNA encodes a protein resulting in the undesirable activation of an immune response, for example in the context of an autoimmune disease such as multiple sclerosis, Crohn's disease, lupus, or rheumatoid arthritis.

Diagnostic Applications

Another aspect of the disclosure provided herein relates to an in vitro composition comprising the CRISPR-Cas13 system described herein, and a labeled detector RNA that is not hybridizable with the guide polynucleotide described herein.

A further aspect of the disclosure provided herein relates to use of the CRISPR-Cas13 system described herein in the detection of a target RNA in a nucleic acid sample suspected of comprising the target RNA.

In some embodiments, the method for detecting RNA including a Cas13 protein or the fusion protein fused to a fluorescent protein or other detectable labels along with a guide polynucleotide comprising a guide sequence specific for the target RNA. Binding of a Cas13 protein or the fusion protein to the target RNA can be visualized by microscopy or other methods of imaging.

In another example, RNA aptamer sequences can be appended to or inserted within the guide polynucleotide, such as MS2, PP7, Qβ, and other aptamers. The introduction of proteins that specifically bind to these aptamers, e.g., the MS2 phage coat protein fused to a fluorescent protein or other detectable labels can be used to detect the target RNA, because the Cas13-guide-target RNA complex will be labeled by the aptamer interaction.

In some embodiments, the method for detecting a target RNA in a cell-free system results in a detectable label or enzyme activity. For example, by using a Cas13 protein, a guide polynucleotide comprising a guide sequence specific for the target RNA, and a detectable label, the target RNA will be recognized by Cas13. The binding of the target RNA by Cas13 triggers its RNase activity, which can lead to the cleavage of the target RNA as well as the detectable label.

In some embodiments, the detectable label is an RNA linked to a fluorescent probe and quencher. The intact detectable RNA links the fluorescent probe and quencher, suppresses fluorescence. Upon cleavage by Cas13 of the detectable RNA, the fluorescent probe is released from the quencher and displays fluorescent activity. Such a method can be used to determine if a target RNA is present in a lysed cell sample, lysed tissue sample, blood sample, saliva sample, environmental sample (e.g. a water, soil, or air sample), or other lysed cells or cell-free sample.

Such a method can also be used to detect a pathogen, such as a virus or bacteria, or to diagnose a disease state, e.g. a cancer.

In some embodiments, the detection of the target RNA aids in the diagnosis of a disease and/or pathological state, or the existence of a viral or bacterial infection. For example, Cas13 mediated detection of non-coding RNAs such as PCA3 can be used to diagnose prostate cancer if detected in the patient's urine. In another example, Cas13 mediated detection of the lncRNA-AA174084, which is a biomarker of gastric cancer, can be used to diagnose gastric cancer.

EXAMPLES

Example 1: Screening of C13-2 Protein

1. Annotation for CRISPR and Gene

The microbial genome from NCBI GenBank and CNGB (China National GenBank) databases was used to predict whole-genomic proteins by a software, followed with the prediction of CRISPR Array in genome by a software.

2. Preliminary Screening of Protein

Redundant proteins were removed by clustering, while filtering out proteins with amino acid sequence lengths less than 800 aa (amino acids) or greater than 1400 aa.

3. Acquisition of CRISPR-Associated Protein

The protein sequence within 10 kb upstream and downstream of the CRISPR Array were compared with the sequence of a known Cas13, and the proteins with an e-value greater than 1*e-5 were filtered out. Then, by comparing with the NR library of NCBI, and the patent library of EBI, and proteins with high similarity were filtered out. Candidate proteins were obtained via further selection. By experimental verification, C13-2 protein was finally obtained (SEQ ID NO: 1, 893 aa). C13-2 protein is also referred to as CasRfg.4 protein.

The source of genomic sequence of the C13-2 protein is shown in Table 1.

TABLE 1

The source of genomic sequence of the C13-2 protein

| Protein | Database | Genome No. | Position of corresponding coding sequence in the genome | Annotation on the source of species in the database |
|---|---|---|---|---|
| C13-2 | CNGB | CNA0009596 | F4453_scaffolds_778:1543:4224:+ | metagenome |

The DNA coding sequence of natural (wild-type) C13-2 protein is as shown in SEQ ID NO: 9.

The structure of gene locus of C13-2 proteins is as shown in FIG. 1, comprising CRISPR Array and C13-2 coding sequence.

The direct repeat (DR) sequence or scaffold sequence used in combination with C13-2 could be: 5'-GGAAGAUAACUCUACAAACCUGUAGG-GUUCUGAGAC-3' (SEQ ID NO: 3).

The RNA secondary structure of the said direct repeat sequence was predicted by RNAfold and presented in FIG. 2.

Example 2: Preparation, Isolation and Purification of C13-2 Proteins

I. Plasmid Construction 1. pET28a vector plasmid was taken, cleaved by double enzyme digestion via BamHI and XhoI, and subjected to agarose gel electrophoresis. A linearized vector was recovered by cutting the gel, a DNA fragment containing the coding sequence of a protein (which encodes the C13-2 protein and the nuclear localization sequence) was inserted into the cloning area of the vector pET28a by homologous recombination, and the vector was transformed into Stbl3 competent by a reaction solution, coated onto an LB plates containing kanamycin sulfate, and incubated overnight at 37° C., and clones were picked for sequencing and identification.

The constructed recombinant vector was named C13-2-pET28a (SEQ ID NO: 10). The recombinant vector was used for expressing a C13-2 recombinant protein (SEQ ID NO: 11). The architecture of the recombinant C13-2 protein was His tag-NLS-Cas13-SV40 NLS-nucleoplasmin NLS.

2. Positive clones with correct sequences were incubated overnight, subjected to plasmid extraction, then transformed into an expression strain RIPL-BL21 (DE3), coated onto an LB plates containing kanamycin sulfate, and incubated overnight at 37° C.

II. Protein Expression

1. Monoclones were picked and plated into 5 mL LB culture solution containing kanamycin sulfate, and incubated overnight at 37° C.

2. They were transferred into 500 mL of LB culture solution containing kanamycin sulfate at the volume ratio of 1:100, cultured at 220 rpm at 37° C. until the OD value was 0.6, added with IPTG to a final concentration of 0.2 mM, and induced at 16° C. for 24 h.

3. Collection of bacteria by centrifuging: the bacteria were rinsed with 15 mL PBS, then centrifuged for collection, added with a lysis buffer for ultrasonic crushing, and centrifuged at 10,000 g for 30 min to obtain a supernatant containing the recombinant protein, and the supernatant was filtered through a 0.45 μm filter membrane before purification on a column.

III. Protein Purification

Figure 3:
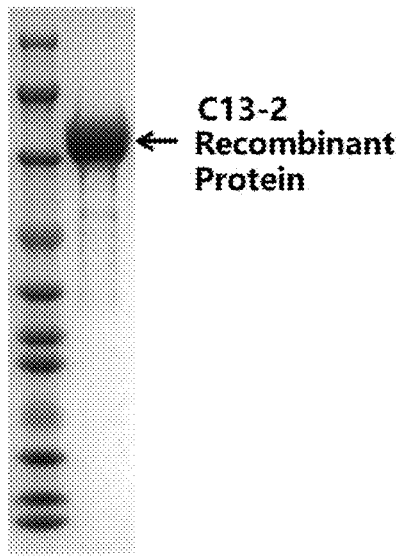
FIG. 3 shows expression and purification of recombinant C13-2 protein.

The purification was performed by MAC (Ni Sepharose 6 Fast Flow, CYTIVA®) and HITRAP HEPARIN HP (CYTIVA®). Upon SDS-PAGE electrophoresis, the purified C13-2 recombinant protein was shown in a band (see FIG. 3).

Example 3: Verification of Editing Efficacy on an Exogenous Gene

1. Synthesis of the Vector to be Verified and Control Vector Targeting EGFP The sequence for synthesis of expression vectors expressing foreign EGFP was as shown in SEQ ID NO: 13, and the structure of the plasmid was CMV-EGFP. The plasmid of the verified vector of C13-2 protein targeting EGFP was synthesized, with the full-length sequence as shown in SEQ ID NO: 14. The structure of the plasmid was CMV-C13-2-U6-gRNA.

EGFP was used as an exogenous reporter gene, and its nucleic acid sequence (720 bp) was as shown in SEQ ID NO: 12.

The guide sequence targeting EGFP was: ugccguucuucugc-uugucggccaugauau (SEQ ID NO:4).

2. Transfection of a 293T Cell with the Vector to be Verified

The plasmid expressing the exogenous EGFP was transfected into a 293T cell in a 24-well plate with the plasmid of the verified vector of C13-2 protein targeting EGFP at a ratio of 1:2 (166 ng:334 ng).

The transfection method was as follows:

1. The 293T cells were digested by trypsin (0.25% of Trypsin, EDTA, Thermo, 25200056), counted, and plated into a 24-well plates at 2×10$^5$ cells according to 500 μL per well.

2. For each transfected sample, the complex was prepared according to the following steps:
   a. Each well of the 24-well plate into which the cells were added, was added with 50 μL of serum-free Opti-MEM™ I (Thermo, 11058021) reduced serum medium for dilution of the aforementioned plasmid DNA (500 ng), and mixed gently.
   b. It was gently mixed with Lipofectamine™ 2000 (Thermo, 11668019) before use, and then 1 μL of the Lipofectamine™ 2000 was diluted in each well, i.e., in 50 μL of the Opti-MEM™ I medium. It was incubated at room temperature for 5 minutes. Note: it was continued to perform step c within 25 minutes.

c. After incubation for 5 minutes, the diluted DNA was combined with the diluted Lipofectamine™ 2000. They were gently mixed and incubated at room temperature for 20 minutes (the solution might be cloudy visually). Note: the complex was stabilized at room temperature for 6 hours. The complex was added into the 293T cells and mixed, and detected by a flow cytometer after 48 h.

3. Detection of the Down-Regulation Effect on EGFP Expression by Flow Cytometer

The description of cells and plasmids as used was as shown in Table 2 below:

TABLE 2

Grouping for Experiments

| Group for experiments | Notes |
|---|---|
| 293T | Cell vector control |
| EGFP | Transfected with expression vector of exogenous EGFP |
| C13-2 | Transfected with expression vector of EGFP and verified vector of C13-2 targeting EGFP |

At 48 h after transfection, the cells obtained were digested with trypsin (0.25% of Trypsin, EDTA, Thermo), and centrifuged at 300 g for 5 min, the supernatant was discarded, and the cells in each well were resuspended with 500 μL of PBS. The EGFP fluorescent expression was detected by a flow cytometer, wherein the cell debris were removed by FCS-A and SSC-A gating, and then detection was conducted by the flow cytometer and the data was collected.

The Mean-FITC-A results of the FITC channel were collected and recorded, and the down-regulation amplitude was calculated according to the following calculation formula:
wherein the GFP fluorescence of the EGFP group was a, and the GFP fluorescence of other groups was x. Down-regulation amplitude (%)=(a−x)÷a×100, wherein the blank control group did not participate in the comparison. The down-regulation amplitude results were as shown in Table 3, wherein the expression was down-regulated with 64.49% with C13-2 targeting EGFP.

TABLE 3

Results of GFP fluorescence as detected by a flow cytometer

| Group | Down-regulation amplitude of GFP fluorescence (%) |
|---|---|
| 293T | N/A |
| EGFP | 0.00 |
| C13-2 | 64.49 |

Example 4: Verification of Editing Efficacy on an Endogenous Gene

I. Construction of Vectors Targeting AQp1 and PTBP1

The plasmid for expression vector C13-2-BsaI was synthesized, wherein the sequence is as shown in SEQ ID NO: 15.

The target nucleic acid selected in the experiment were AQp1 (Aquaporin 1) and PTBP1 (Polypyrimidine Tract Binding Protein 1), wherein AQp1 was verified by using a 293T cell line with high expression of AQp1, and PTBP1 was verified by using a 293T cell line.

The method for constructing the 293T cell line with high expression of Aqp1 (293T-AQp1 cell): a vector Lv-AQp1-T2a-GFP with over-expression of the AQP1 gene and the EGFP gene (SEQ ID NO: 16) was constructed. AQp1 and EGFP were spaced apart by a 2A peptide. The Lv-AQp1-T2a-GFP plasmid was packaged into a lentivirus and transduced into 293T cells to form a cell line stably overexpressing AQp1 gene.

```
The guide sequence of an AQp1-targeting
gRNA was:
                               (SEQ ID NO: 5)
agggcagaaccgaugcugaugaagac.

The guide sequence of an PTBP1-targeting
gRNA was:
                               (SEQ ID NO: 6)
GUGGUUGGAGAACUGGAUGUAGAUGGGCUG.
```

A target site-targeted fragment was obtained by using a primer annealing manner, wherein the primers were as follows:

```
PTBP1-targeting:
Forward Primer:
                              (SEQ ID NO: 22)
5'-AGACGTGGTTGGAGAACTGGATGTAGATGGGCTG-3'

Reverse Primer:
                              (SEQ ID NO: 23)
5'-AAAACAGCCCATCTACATCCAGTTCTCCAACCAC-3'

AQp1-targeting:
Forward Primer:
                              (SEQ ID NO: 23)
5'-AGACagggcagaaccgatgctgatgaagac-3'

Reverse Primer:
                              (SEQ ID NO: 24)
5'-AAAAgtcttcatcagcateggttctgccct-3'
```

The primer annealing reaction system was as follows: it was incubated in a PCR instrument at 95° C. for 5 minutes, then immediately taken out and incubated on ice for 5 minutes, so that the primers were annealed to each other to form a double-stranded DNA with sticky ends.

| | |
|---|---|
| Oligo-F (10 μM) | 2 μL |
| Oligo-R (10 μM) | 2 μL |
| 10× endonuclease reaction buffer* | 2 μL |
| Deionized water | up to 20 μL |

After the synthesized Cas13-2-BsaI vector plasmid was digested with a Bsa I endonuclease, the annealed products and the backbones purified and recovered after the digestion were subjected to linkage with a T4 DNA ligase. After the transformation into *Escherichia coli*, the positive clones were selected and the plasmids were extracted. C13-2 vector (vector plasmids of C13-2 targeting AQp1 or PTBP1) was obtained for the following C13-2 experimental group.

The structure of C13-2 vector was CMV-C13-2U6-gRNA, and the vector could be used to express C13-2 protein and gRNA targeting Aqp1 or PTBP1.

The following control vectors were prepared by conventional methods:

CasRx-AQp1 plasmid, the positive control vector of CasRx targeting AQp1, with the sequence of which was as shown in SEQ ID NO: 17 and the structure of which was CMV-CasRx-U6-gRNA.

The plasmid comprises the sequence encoding CasRx (the amino acid sequence was as shown in SEQ ID NO: 2).

shRNA-AQp1 plasmid, the positive control vector of shRNA targeting AQp1, with the sequence of which was as shown in SEQ ID NO: 19, was used to express shRNA molecule. The sequence of the shRNA molecule was:

```
                                            (SEQ ID NO: 7)
CCACGACCCUCUUUGUCUUCACUCGAGUGAAGACAAAGAGGGUCGUGG.
``` shRNA-PTBP1 plasmid, the positive control vector of shRNA targeting PTBP1, with the sequence of which was as shown in SEQ ID NO: 20, was used to express shRNA molecule. The sequence of the shRNA molecule was:

```
                                            (SEQ ID NO: 8)
CAGCCCAUCUACAUCCAGUUCCUCGAGGAACUGGAUGUAGAUGGGCUG.
```

CasRx-blank plasmid, the blank control vector, could express CasRx and gRNA, where the gRNA did not targets AQp1 or PTBP1. The sequence of the plasmid was as shown in SEQ ID NO: 21, and the structure of the plasmid was CMV-CasRx-U6-gRNA.

II. Transfection of 293T Cells and 293T-AQp1 Cells with the Vector to be Verified 293T-AQp1 cells were transfected with the control plasmids or vector plasmids targeting AQp1 at 500 ng in a 24-well plate. 293T cells were transfected with the control plasmids or vector plasmids targeting PTBP1 at 500 ng in a 24-well plate.

The transfection method was as follows:

1. The cells were digested by trypsin (0.25% of Trypsin, EDTA, Thermo), counted, and plated into a 24-well plates at $2 \times 10^5$ cells according to 500 µL per well.

2. For each transfected sample, the complex was prepared according to the following steps:
   a. Each well of the 24-well plate into which the cells were added, was added with 50 µL of serum-free Opti-MEM™ I (Thermo, 25200056) reduced serum medium for dilution of the aforementioned plasmid DNA, and mixed gently.
   b. Lipofectamine™ 2000 (Thermo, 11668019) was gently mixed before use, and then 1.8 µL of Lipofectamine™ 2000 was diluted in each well, i.e., in 50 µL of the Opti-MEM™ I medium. It was incubated at room temperature for 5 minutes. Note: it was continued to perform step c within 25 minutes.
   c. After incubation for 5 minutes, the diluted DNA was combined with the diluted Lipofectamine™ 2000. They were gently mixed and incubated at room temperature for 20 minutes (the solution might be cloudy visually). Note: the complex was stabilized at room temperature for 6 hours.

The complex was added into the cells and mixed.

III. Detection of the RNA of the Target Gene by qPCR

At 48 h after transfection, the cells were subjected to RNA extraction with a SteadyPure Universal RNA Extraction Kit AG21017 kit, and the RNA concentration was detected with an ultramicro spectrophotometer. The RNA product was reverse transcribed by using an Evo M-MLV Mix Kit with gDNA Clean for qPCR reverse transcription kit, and the reverse transcribed product was detected by using a SYBR® Green Premix Pro Taq HS qPCR Kit.

Primers used in the qPCR were as follows:

```
Detection of PTBP1:
Forward Primer:
                                           (SEQ ID NO: 26)
5'-ATTGTCCCAGATATAGCCGTTG-3'

Reverse Primer:
                                           (SEQ ID NO: 27)
5'-GCTGTCATTTCCGTTTGCTG-3'

Detection of AQp1:
Forward Primer:
                                           (SEQ ID NO: 28)
5'-gctcttctggagggcagtgg-3'

Reverse Primer:
                                           (SEQ ID NO: 29)
5'-cagtgtgacagccgggttgag-3'

Detection of internal reference GAPDH:
Forward primer:
                                           (SEQ ID NO: 30)
5'-CCATGGGGAAGGTGAAGGTC-3'

Reverse primer:
                                           (SEQ ID NO: 31)
5'-GAAGGGGTCATTGATGGCAAC-3'
```

A reaction system was configured according to the instructions of the SYBR® Green Premix Pro Taq HS qPCR Kit, and detected by using a QuantStudio™ 5 Real-Time PCR System.

In this experiment, the target RNA was calculated by using a relative quantitative method, namely a $2^{-\Delta\Delta Ct}$ method.

The calculation method was as follows:

$$\Delta Ct = Ct(AQp1) - Ct(GAPDH) \text{ or } Ct(PTBP1) - Ct(GAPDH)$$

$$\Delta\Delta Ct = \Delta Ct(\text{a sample to be verified, such as C13-2}) - \Delta Ct(\text{CasRx-blank or C13-2-BsaI})$$

$$2^{-\Delta\Delta Ct} = 2^{\wedge}(-\Delta\Delta Ct).$$

Figure 4:
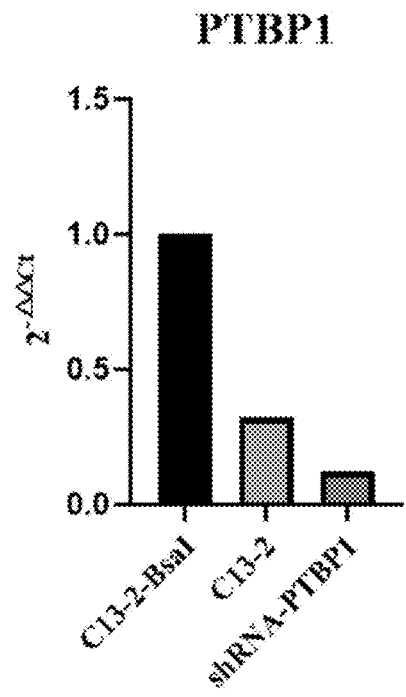
FIG. 4 shows high activity of C13-2 in downregulating PTBP1 (Polypyrimidine Tract Binding Protein 1) RNA in 293T cells.
Figure 5:
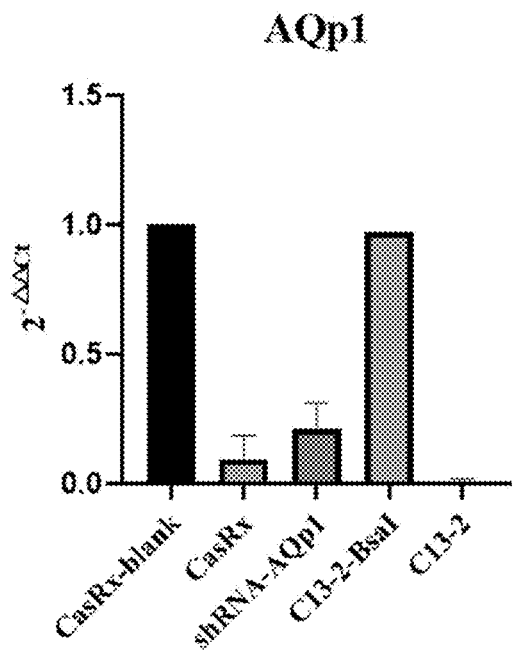
FIG. 5 shows higher activity of C13-2 compared to CasRx and shRNA in downregulating AQp1 (Aquaporin 1) RNA in 293T cells.

The amount of RNA of AQp1 and PTBP1 were calculated according to the aforementioned calculation method. For verification experiment targeting PTBP1, the results were as shown in Table 4 and FIG. 4. For verification targeting AQp1, the experiments were conducted in triplicate as independent biological experiments (the transfection operation was conducted in 293T cells of the same batch), and the average results of the triplicate were obtained, the results of which were as shown in Table 5 and FIG. 5.

TABLE 4

| The knockdown test results of PTBP1 RNA | |
|---|---|
| Groups for experiments | PTBP1 RNA level |
| C13-2-BsaI | 1.00 |
| C13-2 | 0.32 |
| shRNA-PTBP1 | 0.12 |

TABLE 5

Knockdown test results of AQp1 RNA

| Group for experiments | AQp1 RNA level | | | |
|---|---|---|---|---|
| | Experiment 1 | Experiment 2 | Experiment 3 | Average |
| CasRx-blank | 1.00 | 1.00 | 1.00 | 1.00 |
| CasRx | 0.04 | 0.04 | 0.20 | 0.09 |
| shRNA-AQp1 | 0.10 | 0.23 | 0.30 | 0.21 |
| C13-2-BsaI | — | 0.97 | — | 0.97 |
| C13-2 | 0.02 | 0.00 | 0.00 | 0.01 |

Note:
"—" represents for no detection.
C13-2-BsaI and CasRx-blank were control groups without targeting AQp1 or PTBP1.

The experimental results demonstrated that in combination with the gRNA of the present example, C13-2 showed obvious editing efficiency, wherein the editing activity targeting PTBP1 was high while the editing activity targeting AQp1 was higher than CasRx.

Example 5: Editing Efficiency Comparison with Disclosed Cas13 Proteins

I. Construction of an Editing Vector Targeting Endogenous Gene PTBP1

U.S. Pat. No. 10,476,825B2 discloses the Cas13 protein from BMZ-11B_GL0037771, and the Cas13 protein was named as C13-113 (the amino acid sequence of said protein was as shown in SEQ ID NO: 32 herein) in the present example. The direct repeat sequence used in this example corresponding to C13-113 was as shown in SEQ ID NO: 33.

Cas protein MBR0191107.1 was disclosed in GenBank, named as C13-114 (the amino acid sequence of this protein was as shown in SEQ ID NO: 34 herein). The direct repeat sequence used in this example corresponding to C13-114 was as shown in SEQ ID NO: 35.

The expression vectors C13-113-BsaI (SEQ ID NO: 36) and C13-114-BsaI (SEQ ID NO: 37) for C13-113 and C13-114 were synthesized by a reagent company.

According to the method described in Example 4, the fragments targeting the target sites were obtained by primer annealing means, wherein the primers used were as follows:
PTBP1-Targeting

```
C13-113:
Forward Primer:
                             (SEQ ID NO: 38)
5'-CAACGTGGTTGGAGAACTGGATGTAGATGGGCTG-3'

Reverse Primer:
                             (SEQ ID NO: 23)
5'-AAAACAGCCCATCTACATCCAGTTCTCCAACCAC-3'

C13-114:
Forward Primer:
                             (SEQ ID NO: 39)
5'-atctGTGGTTGGAGAACTGGATGTAGATGGGCTG-3'

Reverse Primer:
                             (SEQ ID NO: 23)
5'-AAAACAGCCCATCTACATCCAGTTCTCCAACCAC-3'
```

According to the method described in Example 4, the synthesized plasmids C13-113-BsaI and C13-114-BsaI were digested with a Bsa I endonuclease, and linked to the annealed products with a T4 DNA ligase. After the transformation into *Escherichia coli*, the positive clones were selected and the plasmids were extracted. The 293T cells (293T cells from different batches used in Example 4) were subject to detection at 72 h after transfection. The blank control group was transfected with C13-2-BsaI in Example 4, respectively.

At 72 h after transfection, the cells were subject to RNA extraction, reverse transcription and qPCR (with the same primers used in Example 4) according to the method described in Example 4.

A reaction system was configured according to the instructions of the SYBR® Green Premix Pro Taq HS qPCR Kit, and detected by using a QuantStudio™ 5 Real-Time PCR System.

The amount of PTBP1 RNA was calculated by using a $2^{-\Delta\Delta Ct}$ method.

The calculation method was as follows:

$$\Delta Ct = Ct(PTBP1) - Ct(GAPDH)$$

$$\Delta\Delta Ct = \Delta Ct(\text{a sample to be verified}) - \Delta Ct(\text{C13-2-BsaI})$$

$$2^{-\Delta\Delta Ct} = 2\char`\^(-\Delta\Delta Ct).$$

Figure 6:
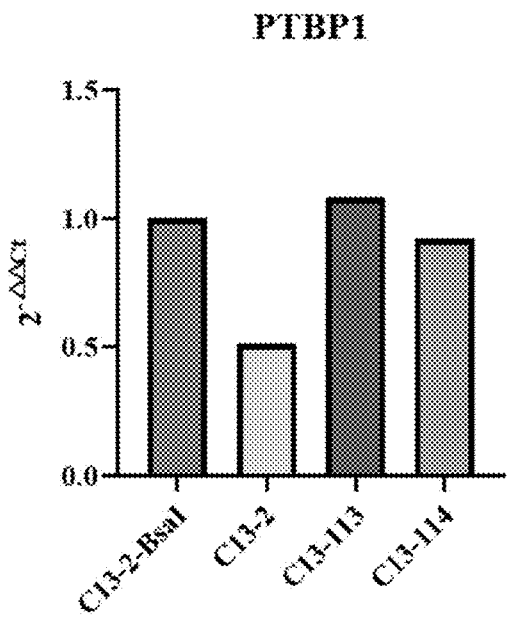
FIG. 6 shows higher activity of C13-2 compared to C13-113 and C13-114 in downregulating PTBP1 RNA in 293T cells.

The experimental results were as shown in Table 6 and FIG. 6.

TABLE 6

Comparison of knockdown test results of PTBP1 RNA

| Group for experiment | PTBP1 RNA level |
|---|---|
| C13-2-BsaI | 1.00 |
| C13-2 | 0.51 |
| C13-113 | 1.08 |
| C13-114 | 0.92 |

The data in the table showed that in combination with the gRNA targeting PTBP1 of the present example, C13-2 was observed to have a relative high editing efficiency, which was better than that of C13-113 and C13-114. No obvious editing was observed in C13-113 group.

Example 6: Off-Target Test of C13-2

Figure 7:
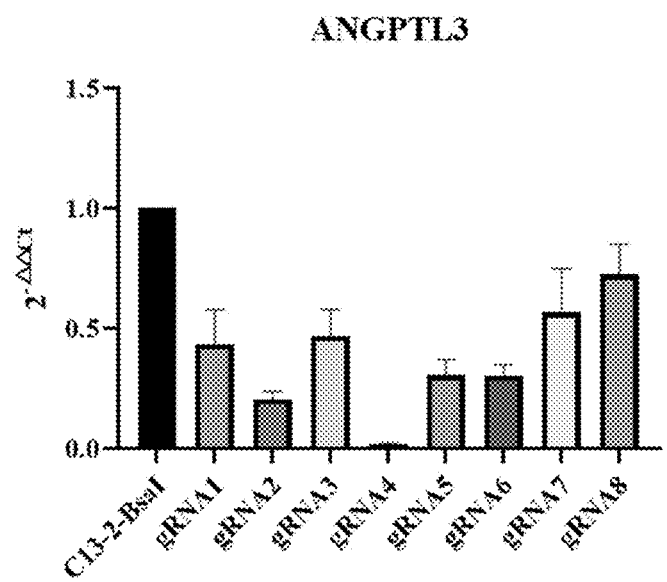
FIG. 7 shows downregulation of ANGPTL3 (Angiopoietin-like 3) RNA in 293T cells by C13-2.

Prediction was performed in the whole genome and whole cDNA sequences of a target species (*Homo sapiens*) with EMBOSS-water program and NCBI-Blast program. Alignment was conducted with the sense and anti-sense strands of the guide sequence of a gRNA. The predicted results were filtered according to the difference of lengths of predicted target and guide sequence of gRNA was no more than four bases and the mismatch+gap was no more than four bases. The potential off-target information obtained was as shown in FIG. 7.

TABLE 7

Predicted number of potential off-target genes

| | guide sequence | Potential Off-Target Gene No. |
|---|---|---|
| C13-2 gRNA/ CasRx gRNA | GUGGUUGGAGAACUG GAUGUAGAUGGGCUG (SEQ ID NO: 6) | 7 |
| shRNA1 | GCCCAUCUACAUCCA GUUCUC (SEQ ID NO: 40) | 6700 |

TABLE 7-continued

Predicted number of potential off-target genes

| guide sequence | Potential Off-Target Gene No. |
|---|---|
| shRNA2 | CAGCCCAUCUACAUC CAGUUC (SEQ ID NO: 41) | 6882 |

The plasmids of C13-2 targeting PTBP1, shRNA-PTBP1 (the shRNA expressed was named "shRNA2" in this example) and CasRx-blank in Example 4 were used.

The sequence of CasRx-PTBP1 plasmid (the positive control vector of CasRx targeting PTBP1) prepared by conventional method was as shown in SEQ ID NO: 8, and the structure of the plasmid was CMV-CasRx-U6-gRNA.

The plasmid expressing shRNA1 was additionally constructed according to the method described in Example 4, and the difference to shRNA-PTBP1 plasmid was only the different guide sequence of encoded shRNA. The plasmid targeted PTBP1, too, and no additional g was added after U6 promoter.

293T cells were transfected with the aforementioned plasmids according to the method described in Example 4, respectively. The cells were subject to transfection in a 24-well plate according to the operation instructions of Lipofectamine™ 2000 (Thermo), and the RNA was extracted with a SteadyPure Universal RNA Extraction Kit AG21017.

RNA samples extracted were sequenced by PE150 bp RNA-Seq, and fastq files obtained by sequencing were aligned with the reference genome of the target species by HISAT2 or STAR software, to obtain BAM files after the alignment. The expression levels of the obtained transcripts and each gene were detected by kallisto, RSEM or HTSeq.

The variation analysis of expression levels among groups (variation relative to CasRx-blank group) was conducted by using DESeq2, limma-voom and edger, and a gene satisfying p.adj<0.05, |log 2FoldChange|≥0.5 and basemean>2.5 was taken as the differential expression gene (DEG). The obtained DEG information was as follows:

TABLE 8

Number of DEGs and intersection with the predicted potential off-target gene

| Group | Up&Sig (number of up-regulated DEG) | Down&Sig (number of down-regulated DEG) | All&Sig (number of up-regulated or down-regulated DEG) | Isec Up | Isec Down | Isec All |
|---|---|---|---|---|---|---|
| CasRx | 4 | 1 | 5 | 0 | 0 | 0 |
| shRNA1 | 182 | 337 | 519 | 45 | 117 | 162 |
| shRNA2 | 171 | 383 | 554 | 23 | 127 | 150 |
| C13-2 | 4 | 68 | 72 | 0 | 0 | 0 |

Note:
Up represents for up-regulation, and Down represents for down-regulation.

Sig represents for the significant difference in gene expression compared to control group (CaxRx-blank group).

Isec represents the number of DEG after taking intersection with the "potential off-target gene" predicted by the program.

It could be seen from the data in the table above that, the number of off-target sites of CasRx and C13-2 by transcriptome sequencing after taking intersection with predicted off-targets was 0, wherein there was hardly any off-target in C13-2, and there was a large number of off-target sites in shRNA1 and shRNA2. In terms of off-target safety, C13-2 had better performance than shRNA1 and shRNA2, and comparable to CasRx. Moreover, the size of C13-2 was only 893 aa, far less than that of CasRx (967 aa), and it was easier to be delivered with gRNA packaged into an AAV.

Example 7: Editing Targeting ANGPTL3

This example was conducted according to the method described in Example 4.

The Lv-ANGPTL3-T2a-GFP vector (SEQ ID NO: 52) overexpressing ANGPTL3 gene and EGFP gene was constructed, wherein ANGPTL3 and EGFP were spaced apart by a 2A peptide. The Lv-ANGPTL3-T2a-GFP plasmid was packaged into a lentivirus and transduced into 293T cells to form a 293T cell line (namely 293T-ANGPTL3 cell) stably overexpressing ANGPTL3 gene.

A target site-targeted fragment was obtained by using a primer annealing manner.

After the Cas13-2-BsaI vector (SEQ ID NO: 15) was digested with a Bsa I endonuclease, the annealed products and the backbones purified and recovered after the digestion were subjected to linkage with a T4 DNA ligase. After the transformation into *Escherichia coli*, the positive clones were selected and the plasmid of C13-2 targeting ANGPTL3 (C13-2 protein expression was driven by CMV, gRNA expression was driven by U6 promoter, the DR sequence of gRNA was as shown in SEQ ID NO: 3, and the guide sequence of gRNA was as shown in Table 9) was extracted and obtained. The plasmid was transfected with 293T-ANGPTL3 cells. The negative control group was transfected with the C13-2-Bsa I plasmid.

TABLE 9

Guide sequence of gRNA targeting ANGPTL3 RNA

| gRNA | gRNA guide sequence |
|---|---|
| ANGPTL3-gRNA1 | CAUGAAAAACUUGAGAGUUGCUGGGUCUGA (SEQ ID NO: 42) |

TABLE 9-continued

Guide sequence of gRNA targeting ANGPTL3 RNA

| gRNA | gRNA guide sequence |
|---|---|
| ANGPTL3-gRNA2 | GAAUUAAGUUAGUUAGUUGCUCUUCUAAAU (SEQ ID NO: 43) |

TABLE 9-continued

Guide sequence of gRNA targeting ANGPTL3 RNA

| gRNA | gRNA guide sequence |
|---|---|
| ANGPTL3-gRNA3 | CGAUGUUGAAUUAAUGUCCAUGGACUACCU (SEQ ID NO: 44) |
| ANGPTL3-gRNA4 | GAUAGAGAAAUUUCUGUGGGUUCUUGAAUA (SEQ ID NO: 45) |
| ANGPTL3-gRNA5 | CUGGAGAAGGUCUUUGAUGCUAUUAUCUUG (SEQ ID NO: 46) |
| ANGPTL3-gRNA6 | CACUAUGGAGUAUAUCUUCUCUAGGCCCAA (SEQ ID NO: 47) |
| ANGPTL3-gRNA7 | CCACACUCAUCAUGCCACCACCAGCCUCCU (SEQ ID NO: 48) |
| ANGPTL3-gRNA8 | GACCAUCUAAAAUUGAUUCCCACAUCACAA (SEQ ID NO: 49) |

The cells were subject to RNA extraction and reverse transcription at 72 h after transfection, and the reverse transcribed product was subject to qPCR detection.

Primers used in qPCR were as follows:

```
Detection of ANGPTL3:
Forward Primer:
                                    (SEQ ID NO: 50)
5'-CCAGAACACCCAGAAGTAACT-3'

Reverse Primer:
                                    (SEQ ID NO: 51)
5'-TCTGTGGGTTCTTGAATACTAGTC-3'

Detection of internal reference GAPDH:
Forward Primer:
                                    (SEQ ID NO: 30)
5'-CCATGGGGAAGGTGAAGGTC-3'

Reverse Primer:
                                    (SEQ ID NO: 31)
5'-GAAGGGGTCATTGATGGCAAC-3'
```

The amount of target RNA was calculated by using a relative quantitative method, i.e., $2^{-\Delta\Delta Ct}$ method.

The transfection of cells with recombinant plasmids, RNA extraction, reverse transcription and qPCR were all conducted independently in triplicate of biological experiments, and the average results of the triplicates were obtained. The results were as shown in Table 10 and FIG. 7.

TABLE 10

Knockdown test results of ANGPTL3 RNA

| Groups for experiments | Experiment 1 | Experiment 2 | Experiment 3 | Average |
|---|---|---|---|---|
| C13-2-BsaI | 1.00 | 1.00 | 1.00 | 1.00 |
| ANGPTL3-gRNA1 | 0.54 | 0.27 | 0.49 | 0.43 |
| ANGPTL3-gRNA2 | 0.17 | 0.24 | 0.20 | 0.20 |
| ANGPTL3-gRNA3 | 0.59 | 0.38 | 0.44 | 0.47 |
| ANGPTL3-gRNA4 | 0.02 | 0.02 | 0.01 | 0.02 |
| ANGPTL3-gRNA5 | 0.26 | 0.28 | 0.38 | 0.31 |
| ANGPTL3-gRNA6 | 0.33 | 0.25 | 0.33 | 0.30 |
| ANGPTL3-gRNA7 | 0.73 | 0.37 | 0.60 | 0.57 |
| ANGPTL3-gRNA8 | 0.64 | 0.67 | 0.87 | 0.73 |

The experimental results showed that C13-2 could achieve effective knockdown against ANGPTL3 RNA, wherein gRNA2, gRNA4, gRNA5 and gRNA6 had significant editing effect.

Example 8: Editing with the Dead Mutant of C13-2 (dC13-2)

C13-2-VEGFA vector (SEQ ID NO: 72) was constructed for expression of C13-2 protein and gRNA targeting VEGFA. The guide sequence of this gRNA was TGGGTGCAGCCTGGGACCACTTGGCATGG (SEQ ID NO: 73).

Then, R4xH mutant verified vectors of C13-2 were constructed from C13-2-VEGFA vector with conventional homologous recombination method, and were as shown in Table 11.

The mutant vector was introduced with the following mutations comparing to the coding sequence of C13-2 in the C13-2-VEGFA vector:

```
R210A + H215A:
AGAAACGCCACCGCCCAC (SEQ ID NO: 74) →
GCAAACGCCACCGCCGCC (SEQ ID NO: 75);

R750A + H755A:
AGAAAGACCAAGAGACAC (SEQ ID NO: 76) →
GCAAAGACCAAGAGAGCC (SEQ ID NO: 77);
and/or R785A + H790A:
AGAAACGACGTGGAGCAC (SEQ ID NO: 78) →
GCAAACGACGTGGAGGCC (SEQ ID NO: 79).
```

TABLE 11

Vectors used for testing dead mutants of C13-2

| Plasmid vector | Notes |
|---|---|
| C13-2-BsaI (SEQ ID NO: 15) | Negative control of C13-2 |
| C13-2-VEGFA (SEQ ID NO: 72) | Expressing wild-type C13-2 |
| R4xH-1-VEGFA | Expressing the C13-2 mutant (R210A/H215A), with the first R4xH of C13-2 mutated |
| R4xH-2-VEGFA | Expressing the C13-2 mutant (R750A/H755A), with the second R4xH of C13-2 mutated |
| R4xH-3-VEGFA | Expressing the C13-2 mutant (R785A/H790A), with the third R4xH of C13-2 mutated |
| R4xH(1,3)-VEGFA | Expressing the C13-2 mutant (R210A/H215A, R785A/H790A), with the first and the third R4xH of C13-2 mutated |
| R4xH(1,2,3)-VEGFA | Expressing the C13-2 mutant (R210A/H215A, R750A/H755A, R785A/H790A), with all the three R4xHs of C13-2 mutated |
| 293T-NC | Untreated 293T cells |

The vectors were transfected with the 293T cell line. The transfection was operated according to the instructions of Lipofectamine™ 2000 (Thermo). The RNA was extracted with SteadyPure Universal RNA Extraction Kit at 72 h after transfection. The extracted RNA of three batches were sent to the sequencing company for RNAseq sequencing, and the detected amount of VEGFA RNA was as shown in Table 12 below:

TABLE 12

The amount of VEGFA RNA determined by RNAseq sequencing

| Group | TPM value (average) | The reduced amount compared to C13-2-BsaI group |
|---|---|---|
| C13-2-BsaI | 67.99067264 | 0 |
| R4xH-1-VEGFA | 61.02221547 | 10.25 |
| R4xH-2-VEGFA | 36.83780119 | 45.82 |
| R4xH-3-VEGFA | 57.89735168 | 14.85 |
| R4xH(1,3)-VEGFA | 52.12446721 | 23.34 |
| R4xH(1,2,3)-VEGFA | 64.72357693 | 4.81 |

The experimental data in Table 12 showed that the editing activity was still high after introduction of R750A+H755A mutation, weak editing activity was retained after introduction of R210A+H215A and/or R785A+H790A mutation, and the editing activity was almost lost completely only after introduction of R210A+H215A, R750A+H755A and R785A+H790A mutations at the same time.

Example 9: Test of C13-2 Truncate

Construction of the Verified Vector of C13-2 Truncate Targeting Endogenous Gene VEGFA The verified vectors of truncates shown in Table 13 were constructed from the C13-2-VEGFA plasmid (SEQ ID NO: 72) by using the three-fragment homologous recombination method, and the only difference from the C13-2-VEGFA vector was that the coding sequence of C13-2 was truncated. The vectors could express each truncated proteins and the gRNA targeting VEGFA.

TABLE 13

Constructed verified vector of C13-2 truncates

| Vector | Expression product/Notes |
|---|---|
| C13-2-BsaI (SEQ ID NO: 15) | Negative control |
| C13-2-VEGFA | Wild-type C13-2 |
| C10 | Truncate with deletion of amino acids at positions 91-120 of C13-2 |
| C16 | Truncate with deletion of amino acids at positions 141-180 of C13-2 |
| C22 | Truncate with deletion of amino acids at positions 211-240 of C13-2 |
| C34 | Truncate with deletion of amino acids at positions 331-360 of C13-2 |
| C38 | Truncate with deletion of amino acids at positions 351-400 of C13-2 |
| C44 | Truncate with deletion of amino acids at positions 431-460 of C13-2 |
| C48 | Truncate with deletion of amino acids at positions 461-500 of C13-2 |
| C54 | Truncate with deletion of amino acids at positions 511-550 of C13-2 |
| C62 | Truncate with deletion of amino acids at positions 611-640 of C13-2 |
| C64 | Truncate with deletion of amino acids at positions 631-660 of C13-2 |
| C67 | Truncate with deletion of amino acids at positions 661-690 of C13-2 |
| C74 | Truncate with deletion of amino acids at positions 691-760 of C13-2 |
| C84 | Truncate with deletion of amino acids at positions 821-860 of C13-2 |
| C87 | Truncate with deletion of amino acids at positions 861-890 of C13-2 |
| 293T-NC | Control group, untransfected 293T cells |

The verified vectors and control vectors were transfected into the 293T cell line according to the operation instructions of Lipofectamine™ 2000 (Thermo). The RNA was extracted with SteadyPure Universal RNA Extraction Kit at 72 h after transfection, and was the subject to reverse transcription by using the Evo M-MLV Mix Kit with gDNA Clean for qPCR reverse transcription kit. A reaction system was configured according to the instructions of the SYBR® Green Premix Pro Taq HS qPCR Kit, and detected by using a QuantStudio™ 5 Real-Time PCR System.

The primers used in the qPCR were as follows:

```
Detection of VEGFA:
                                        (SEQ ID NO: 88)
ACCTCCACCATGCCAAGTGG (SEQ ID NO: 89)
CAGGGTCTCGATTGGATGGC Detection of internal reference GAPDH:
                                        (SEQ ID NO: 30)
CCATGGGGAAGGTGAAGGTC (SEQ ID NO: 31)
GAAGGGGTCATTGATGGCAAC
```

The target RNA was calculated by using a relative quantitative method, i.e., $2^{-\Delta\Delta Ct}$ method. Multiple repeated experiments were conducted, and the average results were taken. The results were as shown in Table 14.

TABLE 14

The relative amount of VEGFA RNA after editing with truncates

| Group | Relative amount of VEGFA RNA |
|---|---|
| C13-2-BsaI | 1.00 |
| C13-2-VEGFA | 0.06 |
| C10 | 0.68 |
| C16 | 0.52 |
| C22 | 0.51 |
| C34 | 0.77 |
| C38 | 0.51 |
| C44 | 0.65 |
| C48 | 0.66 |
| C54 | 0.72 |
| C62 | 0.62 |

TABLE 14-continued

The relative amount of VEGFA RNA after editing with truncates

| Group | Relative amount of VEGFA RNA |
|---|---|
| C64 | 0.69 |
| C67 | 0.69 |
| C74 | 0.65 |
| C84 | 0.81 |
| C87 | 0.90 |
| 293T-NC | 1.05 |

The C13-2 truncates in the present example retained a certain intensity of RNA-editing activity.

Example 10: Test for Different DR (Direct Repeated) Sequences

Verified vectors (as shown in Table 16) targeting endogenous genes VEGFA and PTBP1 were constructed, and encoding different DR sequences (as shown in Table 15).

TABLE 15

Different DR sequences designed

| DR name | DR sequence | Notes |
|---|---|---|
| DRrc | GGAAGATAACTCTACAAACCTGTAGG – GTTCTGAGAC (SEQ ID NO: 3) | |
| DR2 | CCGCACAGTCCCTACAGGTTTGTAGA – GTCATCTTCC (SEQ ID NO: 80) | |
| DR2rc | GGAAGATGACTCTACAAACCTGTAGG GACTGTGCGG (SEQ ID NO: 81) | Reverse complementary to DR2 |
| DR3 | GGTGTACAGGGTGCCTGGATTTGACA – GGGTTACAGC (SEQ ID NO: 82) | |
| DR3rc | GCTGTAACCCTGTCAAATCCAGGCAC CCTGTACACC (SEQ ID NO: 83) | Reverse complementary to DR3 |
| DR4 | GGTGTACAGGGTGCCTAGATTTGACA – GGGTTACAGC (SEQ ID NO: 84) | |
| DR4rc | GCTGTAACCCTGTCAAATCTAGGCAC CCTGTACACC (SEQ ID NO: 85) | Reverse complementary to DR4 |
| DR-hf1 | GGAAGAACTCTACAAACCTGTAGGGT TCTGAGAC (SEQ ID NO: 86) | Unmatched 2 nt in DRrc stem region deleted |
| DR-hf2 | GGAAGATAACTCTACAAACCTGTAGA GTTCTGAGAC (SEQ ID NO: 87) | U-G base pair in DRrc stem region changed to U-A |

TABLE 16

Vector plasmids constructed for expression of various gRNA

| Plasmid Name | Target RNA of the gRNA expressed by each plasmid | Notes |
|---|---|---|
| C13-2-BsaI | Not targeting VEGFA or PTBP1 | Not targeting VEGFA or PTBP1 |
| C13-2-VEGFA | VEGFA | The DR sequence is DRrc. |
| C13-2-DR2-VEGFA | VEGFA | The DR sequence is DR2. |
| C13-2-DR2rc-VEGFA | VEGFA | The DR sequence is DR2rc. |
| C13-2-DR3-VEGFA | VEGFA | The DR sequence is DR3. |
| C13-2-DR3rc-VEGFA | VEGFA | The DR sequence is DR3rc. |
| C13-2-DR4-VEGFA | VEGFA | The DR sequence is DR4. |
| C13-2-DR4rc-VEGFA | VEGFA | The DR sequence is DR4rc. |
| C13-2-DR-hf1-VEGFA | VEGFA | The DR sequence is DR-hf1. |
| C13-2-DR-hf2-VEGFA | VEGFA | The DR sequence is DR-hf2. |
| C13-2-PTBP1 | PTBP1 | The DR sequence is DRrc. |
| C13-2-DR2-PTBP1 | PTBP1 | The DR sequence is DR2. |
| C13-2-DR2rc-PTBP1 | PTBP1 | The DR sequence is DR2rc. |
| C13-2-DR3-PTBP1 | PTBP1 | The DR sequence is DR3. |
| C13-2-DR3rc-PTBP1 | PTBP1 | The DR sequence is DR3rc. |
| C13-2-DR4-PTBP1 | PTBP1 | The DR sequence is DR4. |
| C13-2-DR4rc-PTBP1 | PTBP1 | The DR sequence is DR4rc. |
| C13-2-DR-hf1-PTBP1 | PTBP1 | The DR sequence is DR-hf1. |
| C13-2-DR-hf2-PTBP1 | PTBP1 | The DR sequence is DR-hf2. |
| 293T-NC | N/A | Untreated 293T cells |

The verified vectors expressing various different crRNA sequences (5'-guide-DR-3') in Table 16 were constructed with conventional means (only substitution of the expression frame sequence of crRNA occurred) from the C13-2-VEGFA vectors in Example 8 and the vector plasmid of C13-2 targeting PTBP1 in Example 4.

Figure 9:
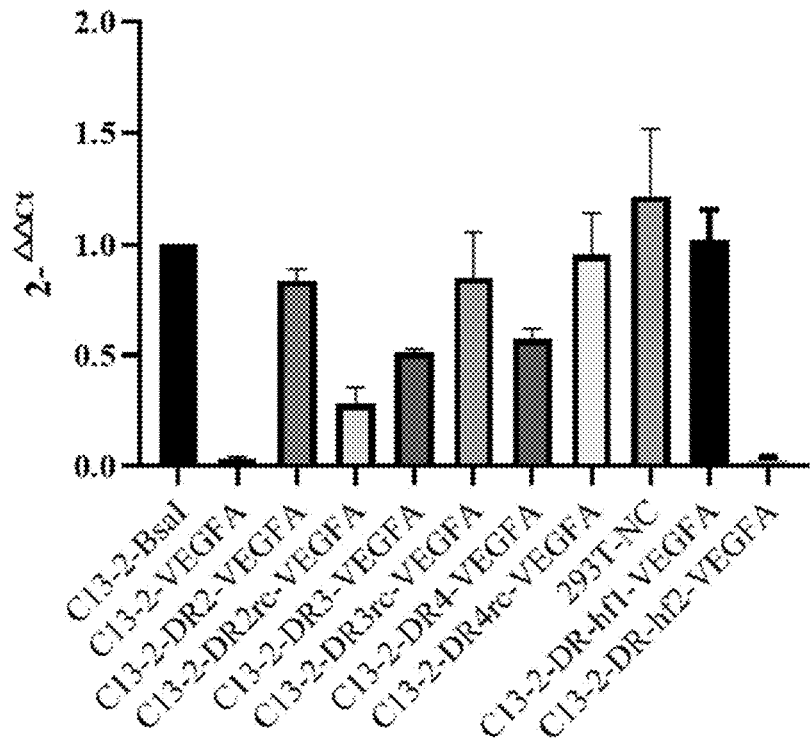
FIG. 9 shows the editing effect targeting VEGFA RNA when using different DRs.
Figure 10:
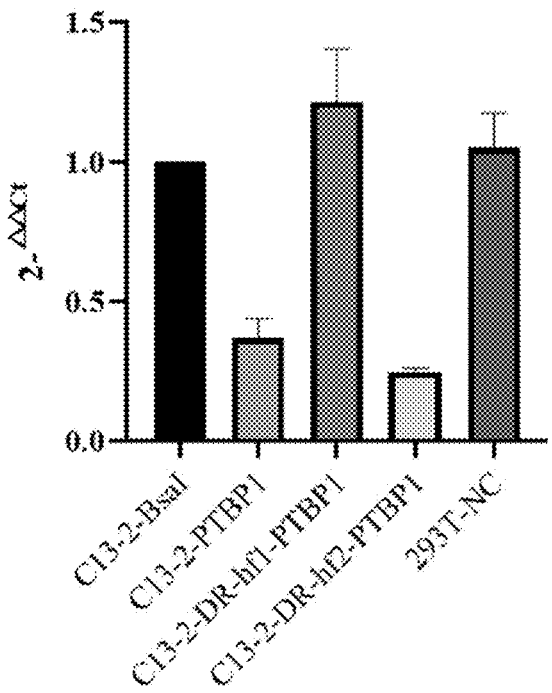
FIG. 10 shows the editing effect targeting PTBP1 RNA when using different DRs.

The 293T cells were transfected with the verified vectors and control vectors according to the method described in the above examples. The cells were subject to RNA extraction, reverse transcription and detection with a qPCR kit after 72 h. Primers used in the qPCR were as follows:

Detection of VEGFA:
(SEQ ID NO: 88)
ACCTCCACCATGCCAAGTGG (SEQ ID NO: 89)
CAGGGTCTCGATTGGATGGC Detection of PTBP1:
(SEQ ID NO: 26)
ATTGTCCCAGATATAGCCGTTG (SEQ ID NO: 27)
GCTGTCATTTCCGTTTGCTG Detection of internal reference GAPDH:
(SEQ ID NO: 30)
CCATGGGGAAGGTGAAGGTC (SEQ ID NO: 31)
GAAGGGGTCATTGATGGCAAC The change of target RNA was calculated by using the $2^{-\Delta\Delta Ct}$ method. Multiple repeated experiments were conducted, and the average results were taken. The results were as shown in Table 17, Table 18, FIG. 9 and FIG. 10.

TABLE 17

Relative amount of VEGFA RNA after editing with different gRNA.

| VEGFA | Relative amount of VEGFA RNA |
|---|---|
| C13-2-BsaI | 1.00 |
| C13-2-VEGFA | 0.03 |

TABLE 17-continued

Relative amount of VEGFA RNA after editing with different gRNA.

| VEGFA | Relative amount of VEGFA RNA |
| --- | --- |
| C13-2-DR2-VEGFA | 0.84 |
| C13-2-DR2rc-VEGFA | 0.28 |
| C13-2-DR3-VEGFA | 0.51 |
| C13-2-DR3rc-VEGFA | 0.85 |
| C13-2-DR4-VEGFA | 0.57 |
| C13-2-DR4rc-VEGFA | 0.95 |
| C13-2-DR-hf1-VEGFA | 1.02 |
| C13-2-DR-hf2-VEGFA | 0.03 |
| 293T-NC | 1.22 |

TABLE 18

Relative amount of PTBP1 RNA after editing with different gRNA

| PTBP1 | Average |
| --- | --- |
| C13-2-BsaI | 1.00 |
| C13-2-PTBP1 | 0.37 |
| C13-2-DR-hf1-PTBP1 | 1.21 |
| C13-2-DR-hf2-PTBP1 | 0.25 |
| 293T-NC | 1.05 |

The experimental results in Table 17 and Table 18 showed that the editing efficiency was the highest when DRrc or DR-hf2 were used, which was better than that with other DR sequences (P<0.05). When DR2rc, DR3 or DR4 was used, a relative high editing efficiency could be achieved, which was better than that with DR2, DR3rc, DR4rc or DR-hf1.

Figures 18, 19:
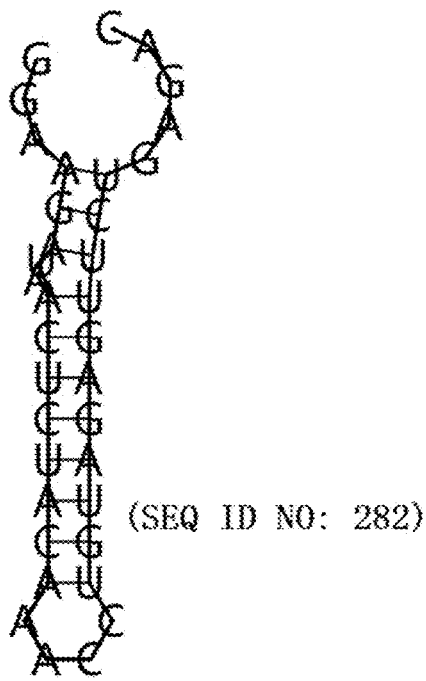
FIG. 18 shows the sequence alignment results of the direct repeat sequences DRrc (SEQ ID NO: 281), DR-hf2 (SEQ ID NO: 87), and DR2rc (SEQ ID NO: 81).
FIG. 19 shows the RNA secondary structure of the direct repeat sequence DR-hf2 (SEQ ID NO: 282) predicted by RNAfold.

The sequence alignment results of direct repeated sequences DRrc, DR-hf2 and DR2rc were as shown in FIG. 18.

The RNA secondary structure of direct repeated sequence DR-hf2 predicted by RNAfold was shown in FIG. 19.

Example 11: Comparison of C13-2 with the Main Stream of Cas 13 Tools

All verified vectors and control vectors (Table 19) in this example utilized the same scaffold sequence with that in C13-2-BsaI (SEQ ID NO: 15), and the only difference was the coding sequence of Cas13 and crRNA.

The NLS sequences and the linking sequences thereof of each vector were the same.

The structure of all vectors was CMV-NLS-Cas13-2×NLS-U6-crRNA, and all Cas13 carried one NLS at N-terminus and two NLSs at C-terminus with the structure of 3×NLS in total.

As EGFP sequence was absent in 293T cells, the vector targeting GFP was used for negative control.

The guide sequence targeting GFP:

(SEQ ID NO: 90)
tgccgttcttctgcttgtcggccatgatat.

The guide sequence targeting PTBP1:

(SEQ ID NO: 6)
GTGGTTGGAGAACTGGATGTAGATGGGCTG

The guide sequence targeting VEGFA:

(SEQ ID NO: 73)
TGGGTGCAGCCTGGGACCACTTGGCATGG.

TABLE 19

Verified vectors and control vectors constructed for comparison with the main stream of Cas13 tools

| Plasmid Name | Structure |
| --- | --- |
| CasRx-3NLS-GFP | CMV-NLS-CasRx-2xNLS-U6-DR-GFP guide |
| CasRx-3NLS-PTBP1 | CMV-NLS-CasRx-2xNLS-U6-DR-PTBP1 guide(SEQ ID NO: 91) |
| PspCas13b-3NLS-GFP | CMV-NLS-PspCas13b-2xNLS-U6-GFP guide-DR |
| PspCas13b-3NLS-PTBP1 | CMV-NLS-PspCas13b-2xNLS-U6-PTBP1 guide-DR(SEQ ID NO: 92) |
| PspCas13b-3NLS-VEGFA | CMV-NLS-PspCas13b-2xNLS-U6-VEGFA guide-DR |
| Cas13X.1-3NLS-GFP | CMV-NLS-Cas13X.1-2xNLS-U6-GFP guide-DR |
| Cas13X.1-3NLS-PTBP1 | CMV-NLS-Cas13X.1-2xNLS-U6-PTBP1 guide-DR(SEQ ID NO: 93) |
| Cas13X.1-3NLS-VEGFA | CMV-NLS-Cas13X.1-2xNLS-U6-VEGFA guide-DR |
| Cas13Y.1-3NLS-GFP | CMV-NLS-Cas13Y.1-2xNLS-U6-GFP guide-DR |
| Cas13Y.1-3NLS-PTBP1 | CMV-NLS-Cas13Y.1-2xNLS-U6-PTBP1 guide-DR(SEQ ID NO: 94) |
| Cas13Y.1-3NLS-VEGFA | CMV-NLS-Cas13Y.1-2xNLS-U6-VEGFA guide-DR |
| C13-2-GFP | CMV-NLS-C13-2-2xNLS-U6-DR-GFP guide |
| C13-2-PTBP1 | CMV-NLS-C13-2-2xNLS-U6-DR-PTBP1 guide |
| C13-2-VEGFA | CMV-NLS-C13-2-2xNLS-U6-DR-VEGFA guide |

To save space, the sequences of four vectors (SEQ ID NOs: 91-94) in Table 19 were shown exemplary.

The 293T cells were transfected with the verified vectors and control vectors. Untransfected plasmids were used as blank control.

The transfection was performed according to the operation instructions of Lipofectamine™ 2000 (Thermo). At 48 h after transfection, the cells were subjected to RNA extraction with a SteadyPure Universal RNA Extraction Kit, and the RNA concentration was detected with an ultramicro spectrophotometer. The RNA product was subject to reverse transcription by using the Evo M-MLV Mix Kit with gDNA Clean for qPCR reverse transcription kit. A reaction system was configured according to the instructions of the SYBR® Green Premix Pro Taq HS qPCR Kit, and detected by using a QuantStudio™ 5 Real-Time PCR System.

Primers used in the qPCR were as follows:

```
Detection of VEGFA:
                                (SEQ ID NO: 88)
ACCTCCACCATGCCAAGTGG (SEQ ID NO: 89)
CAGGGTCTCGATTGGATGGC Detection of PTBP1:
                                (SEQ ID NO: 26)
ATTGTCCCAGATATAGCCGTTG (SEQ ID NO: 27)
GCTGTCATTTCCGTTTGCTG Detection of internal reference GAPDH:
                                (SEQ ID NO: 30)
CCATGGGGAAGGTGAAGGTC (SEQ ID NO: 31)
GAAGGGGTCATTGATGGCAAC
```

Figure 11:
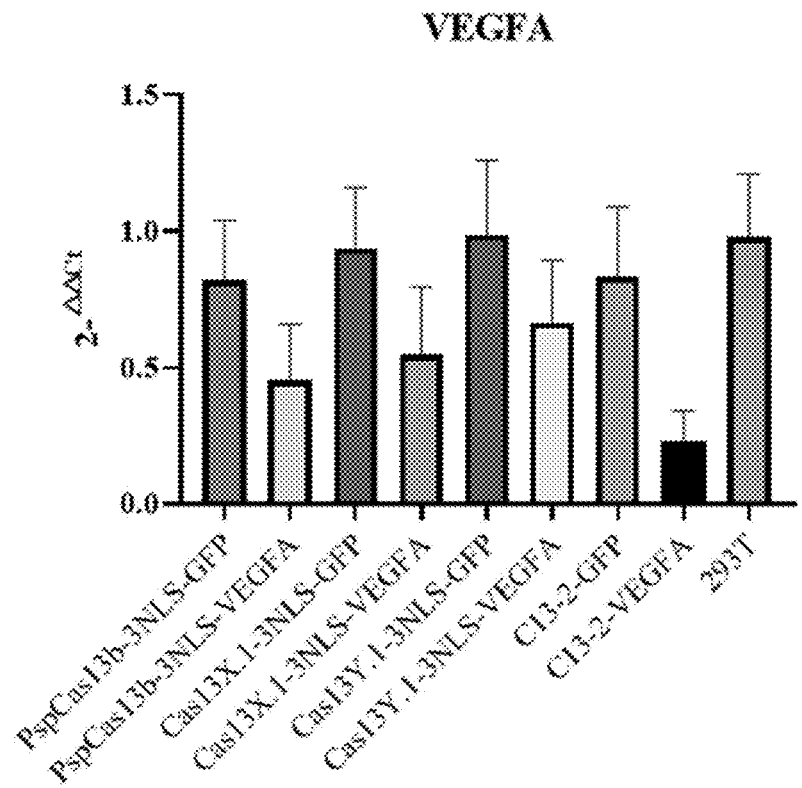
FIG. 11 shows the effect comparison of C13-2 with known Cas13 tools targeting VEGFA RNA.
Figure 12:
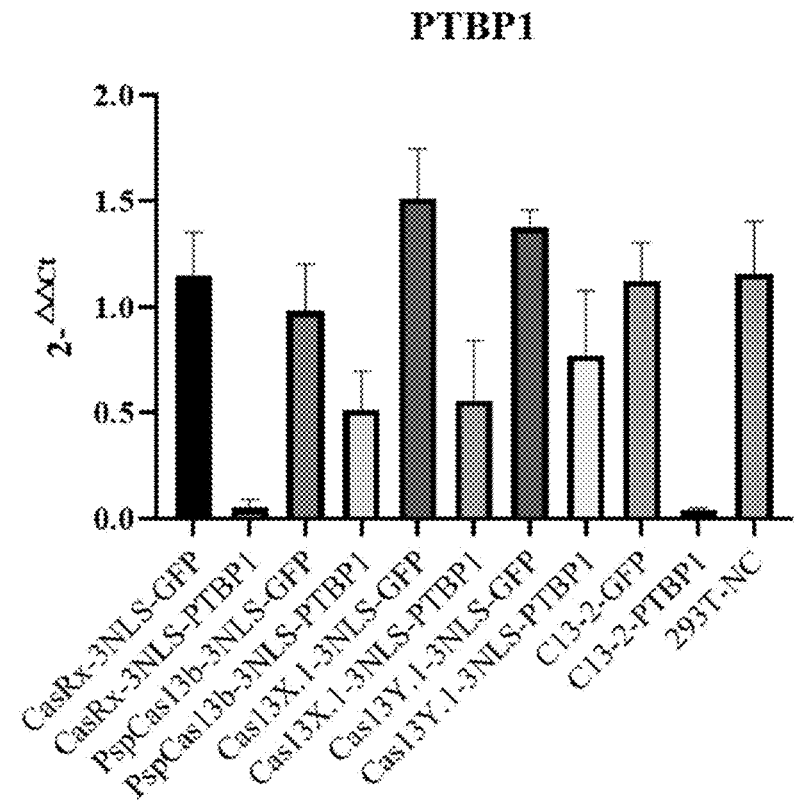
FIG. 12 shows the effect comparison of C13-2 with known Cas13 tools targeting PTBP1 RNA.

The amount of target RNA was calculated by using the $2^{-\Delta\Delta Ct}$ method, and each Cas13 protein took corresponding GFP-targeting group as negative control. Multiple repeated experiments were conducted, and the average results were taken. The results were as shown in Table 20, Table 21, FIG. 11 and FIG. 12.

TABLE 20

C13-2 and known Cas13 tool targeting VEGFA RNA

| Group | Relative amount of VEGFA RNA after editing |
|---|---|
| PspCas13b-3NLS-GFP | 0.82 |
| PspCas13b-3NLS-VEGFA | 0.45 |
| Cas13X.1-3NLS-GFP | 0.94 |
| Cas13X.1-3NLS-VEGFA | 0.55 |
| Cas13Y.1-3NLS-GFP | 0.98 |
| Cas13Y.1-3NLS-VEGFA | 0.67 |
| C13-2-GFP | 0.83 |
| C13-2-VEGFA | 0.23 |
| 293T blank control | 0.98 |

In comparison of editing effects of VEGFA target, C13-2 had excellent editing effect, which was better than the current main stream of Cas13 editing tools. The editing efficiency was C13-2>PspCas13b>Cas13X.1>Cas13Y.1.

TABLE 21

C13-2 and known Cas13 tool targeting PTBP1 RNA

| Group | Relative amount of PTBP1 RNA after editing |
|---|---|
| CasRx-3NLS-GFP | 1.15 |
| CasRx-3NLS-PTBP1 | 0.05 |
| PspCas13b-3NLS-GFP | 0.98 |
| PspCas13b-3NLS-PTBP1 | 0.51 |
| Cas13X.1-3NLS-GFP | 1.51 |
| Cas13X.1-3NLS-PTBP1 | 0.56 |
| Cas13Y.1-3NLS-GFP | 1.37 |
| Cas13Y.1-3NLS-PTBP1 | 0.77 |
| C13-2-GFP | 1.13 |
| C13-2-PTBP1 | 0.03 |
| 293T blank control | 1.16 |

In comparison of editing effects of PTBP1 target, C13-2 had excellent editing effect and the value of editing efficiency was C13-2>CasRx>PspCas13b>Cas13X.1>Cas13Y.1. The editing efficiency of C13-2 was significantly superior to PspCas13b, Cas3X. and Cas13Y.1 ($P<0.05$).

Example 12: Construction of Single-Base Editor from dC13-2

The target used in this example to verify the single-base editing effect was EGFP, and the guide sequence for targeting EGFP was tgccgttcttctgcttgtcggccatgatatagacgttgtggctgttgtagttgtactccagcttgtgccc (SEQ ID NO: 95).

The vectors involving dC3-2 all expressed the dead mutant of C13-2 comprising R210A+H215A, R750A+H755A and R785A+H790A mutations.

TABLE 22

Plasmid vectors and instructions related to single base editing

| Plasmid Name | Notes |
|---|---|
| dC13-2-BsaI(SEQ ID NO: 96) | All three R4XHs of C13-2 were mutated |
| dC13-2-EGFP(SEQ ID NO: 97) | No ADAR was used, as negative control |
| dC13-2-ADAR-EGFP(SEQ ID NO: 98) | ADAR was used, no linking peptide was used |
| dC13-2-A(EAAAK)3A-ADAR-EGFP (SEQ ID NO: 99) | ADAR was used, rigid linking peptide A(EAAAK)3A was used |
| dC13-2-(GGGGS)3-ADAR-EGFP (SEQ ID NO: 100) | ADAR was used, flexible linking peptide (GGGGS)3 was used |
| pAAV-CMV-EGFP(SEQ ID NO: 101) | Plasmid expressing EGFP |
| PLKO-PURO-PspGRNA-EGFP (SEQ ID NO: 102) | Expressing the gRNA used in combination with PspCas13b |
| pC0055-CMV-dPspCas13b-GS-ADAR2DD (addgene) | Commercial plasmid expressing dPspCas13b-ADAR |

Vectors dC13-2-BsaI and dC13-2-EGFP were constructed according to conventional method.

The verified vector of single-base editing dC13-2-ADAR-EGFP, dC13-2-A(EAAAK)3A-ADAR-EGFP and dC13-2-(GGGGS)3-ADAR-EGFP were obtained by homologous recombination from dC13-2-BsaI plasmid, dC13-2-EGFP plasmid and pC0055-CMV-dPspCas13b-GS-ADAR2DD plasmid.

The pC0055-CMV-dPspCas13b-GS-ADAR2DD was taken as positive control. As the plasmid did not comprise a gRNA expression frame, the gRNA expression vector PLKO-PURO-PspGRNA-EGFP was synthesized by an outsourced company.

The transfection was operated according to the instructions of Lipofectamine™ 2000 (Thermo), and the vector to be verified and the EGFP reporter vector pAAV-CMV-EGFP were subject to transfection at 4:1. The transfection protocol was as shown in Table 23 below, wherein pC0055-CMV-dPspCas13b-GS-ADAR2DD and PLKO-PURO-PspGRNA-EGFP-AD were subject to co-transfection with each of 200 ng as they expressed PspCas13b-ADAR protein and gRNA respectively.

TABLE 23

The transfection protocol of the verified vector and reporter vector for single-base editing

| Cell | 293T | |
|---|---|---|
| Vector ratio | Verified vector | Reporter vector |
| Transfected Verified vector: Reporter vector = 4:1(400 g::100 ng) | dC13-2-EGFP dC13-2-ADAR-EGFP dC13-2-A(EAAAK)3A-ADAR-EGFP dC13-2-(GGGGS)3-ADAR-EGFP | pAAV-CMV-EGFP |
| Verified vector: Reporter vector = 2:2:1(200:200:100 ng) | pC0055-CMV-dPspCas13b-GS-ADAR2DD PLKO-PURO-PspGRNA-EGFP | |

At 48 h after transfection, the cells were subjected to RNA extraction with a SteadyPure Universal RNA Extraction Kit, and the RNA concentration was detected with an ultramicro spectrophotometer. The RNA product was subject to reverse transcription by using the Evo M-MLV RT-PCR Universal Transcriptase Kit. The transcription product was subject to PCR with identified primers, and the PCR product was sent to a sequencing company for sequencing.

Sequences of the identified primers were as follows (the length of product was 704 bp):
agggcgaggagctgtt (SEQ ID NO: 103),
gtacagctcgtccatgccg (SEQ ID NO: 104).

Figure 13:
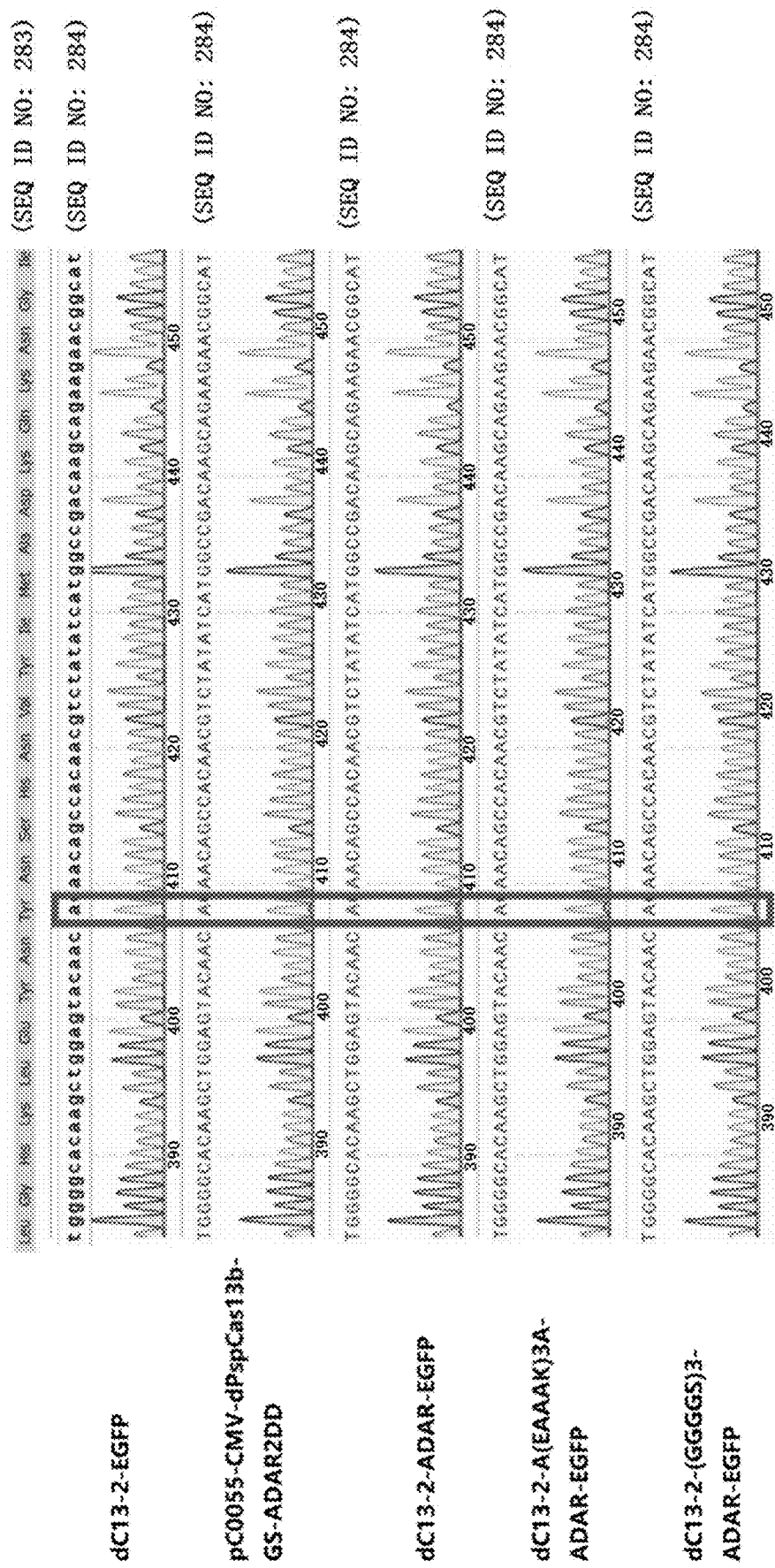
FIG. 13 shows the sequencing peak map of dC13-2 after single-base editing; the sequence shown is SEQ ID NO: 284, and the corresponding amino acid sequence is as shown in SEQ ID NO: 283.

The sequencing results were as shown in FIG. 13, wherein an A→G conversion was occurred at the corresponding position in the target RNA to the base at position 48 of the guide sequence, indicating that the dC13-2 editor constructed by the inventor (s) induced single-base editing successfully.

There was no base conversion occurred in negative control dC13-2-EGFP group, and base conversion was induced to occur in positive control dPspCas13b-ADAR group. The base conversion was induced to occur when no linking peptide, rigid linking peptide A(EAAAK)3A or flexible linking peptide (GGGGS)3 used between dC13-2 and ADAR.

Example 13: First Round of Mutation of C13-2

The principle of the first round of mutation: Using the structure of C13-2 predicted by AlphaFold v2.1, N→A mutation and R→A mutation were made on aa 1-89 and aa 263-417 belonging to REC lobe.

The designed mutants were as shown in Table 24 below.

TABLE 24

The first round of mutation

| Mutant Name | Mutation Site |
|---|---|
| M01 | R11A |
| M02 | N34A |
| M03 | R35A |
| M04 | R47A |
| M05 | R58A |
| M06 | R63A |
| M07 | R64A |
| M08 | N68A |
| M09 | N87A |
| M10 | N265A |
| M11 | N274A |
| M12 | R276A |
| M13 | R290A |
| M14 | R294A |
| M15 | N299A |
| M16 | N303A |
| M17 | R308A |
| M18 | R314A |
| M19 | R320A |
| M20 | R328A |
| M21 | N332A |
| M22 | R341A |
| M23 | N346A |
| M24 | R358A |
| M25 | N372A |
| M26 | N383A |
| M27 | N390A |
| M28 | N394A |

Construction of Verified Vector

The first round of mutation was verified with target VEGFA. Using the C13-2-VEGFA vector in the previous examples as the encoding vector of wild-type C13-2, modification was made with Site Mutation Kit Mut Express II Fast Mutagenesis Kit V2 from Vazyme to obtain the expression constructs (verified vectors) for each mutant, which were used to express the C13-2 mutant and the gRNA targeting VEGFA. Primers used were as shown in Table 25 below.

TABLE 25

Primer sequences for verified vectors

| Mutant | Primer Sequence | SEQ ID NO |
|---|---|---|
| M01 | AACCAAGGCCAAGgcAATGGGCGTGAAGGCCCT | 105 |
| | ATTgcCTTGGCCTTGGTTTTCTTGTCCTTGCTC | 106 |
| M02 | CgcCAGAAGCAAGATCGAGTTCACCGAGGGCTA | 107 |
| | TCGATCTTGCTTCTGgcGCCCTTGCCGAAGGTGGT | 108 |
| M03 | CAACgcAAGCAAGATCGAGTTCACCGAGGGCTA | 109 |
| | TCGATCTTGCTTgcGTTGCCCTTGCCGAAGGTG | 110 |
| M04 | TACCACGGCgcAGCCCTGGAGACACCCAAGCAC | 111 |
| | CAGGGCTgcGCCGTGGTAGCCCTCGGTGAACTC | 112 |
| M05 | AAGCACTTCGGCATCgcAGGCTTCGAGGTGAGAGAATCG | 113 |
| | TgcGATGCCGAAGTGCTTGGGTGTCTCCAGGGC | 114 |

TABLE 25-continued

Primer sequences for verified vectors

| Mutant | Primer Sequence | SEQ ID NO |
|---|---|---|
| M06 | TTCGAGGTGAgcAGAATCGACGAGAACGTGGACC | 115 |
|  | GATTCTgcTCACCTCGAAGCCTCTGATGCCGAA | 116 |
| M07 | AGGTGAGAAgcAATCGACGAGAACGTGGACCTG | 117 |
|  | GTCGATTgcTTCTCACCTCGAAGCCTCTGATGC | 118 |
| M08 | AAGAATCGACGAGgcCGTGGACCTGTGCGGCGA | 119 |
|  | ACGgcCTCGTCGATTCTTCTCACCTCGAAGCCT | 120 |
| M09 | TGGTGgcCCCCAGCGAGAAGGTGGGCGAGGACT | 121 |
|  | TCTCGCTGGGGgcCACCAGCAGGGCCTCGATGG | 122 |
| M10 | AAGAACGCCGTGgcCATGGCCATCCTGTTCGACC | 123 |
|  | CATGgcCACGGCGTTCTTGCTCAGGAAGTCCTT | 124 |
| M11 | TGTTCGACCTGCTGgcCGCCAGAGACGTGGAGCA | 125 |
|  | CGgcCAGCAGGTCGAACAGGATGGCCATGTTCA | 126 |
| M12 | CgcAGACGTGGAGCAGAAGAAGCAGATCACCGA | 127 |
|  | TTCTGCTCCACGTCTgcGGCGTTCAGCAGGTCGAAC | 128 |
| M13 | GAGTTCTACgcATTCACCATCAGAAAGGACGGC | 129 |
|  | GGTGAATgcGTAGAACTCGTCGGTGATCTGCTT | 130 |
| M14 | TTCACCATCgcAAAGGACGGCAAGAACCTGGGC | 131 |
|  | GTCCTTTgcGATGGTGAATCTGTAGAACTCGTCG | 132 |
| M15 | CAAGgcCCTGGGCATGAACCTGGTGAAGATCAG | 133 |
|  | TTCATGCCCAGGgcCTTGCCGTCCTTTCTGATGG | 134 |
| M16 | CATGgcCCTGGTGAAGATCAGAGAGATCATCAT | 135 |
|  | ATCTTCACCAGGgcCATGCCCAGGTTCTTGCCG | 136 |
| M17 | GTGAAGATCgcAGAGATCATCATCGACAGATACGC | 137 |
|  | GATCTCTgcGATCTTCACCAGGTTCATGCCCAG | 138 |
| M18 | TCATCATCGACgcATACGCCAGCGGCCTGAGAG | 139 |
|  | CGTATgcGTCGATGATGATCTCTCTGATCTTCA | 140 |
| M19 | CCTGgcAGACAAGAAGCACGACCCCCACAGACA | 141 |
|  | TGCTTCTTGTCTgcCAGGCCGCTGGCGTATCTG | 142 |
| M20 | CCACgcACAGAAGATCAACGTGATCGCCGACTT | 143 |
|  | TTGATCTTCTGTgcGTGGGGGTCGTGCTTCTTG | 144 |
| M21 | ACAGAAGATCgcCGTGATCGCCGACTTCCTGAT | 145 |
|  | ATCACGgcGATCTTCTGTCTGTGGGGGTCGTGC | 146 |
| M22 | ACTTCCTGATCTTCgcAGCCCTGAGCCAGAACCAGG | 147 |
|  | CTgcGAAGATCAGGAAGTCGGCGATCACGTTG | 148 |
| M23 | CCAGgcCCAGGGCATCATCGACAAGACCGTGAG | 149 |
|  | ATGATGCCCTGGGgcCTGGCTCAGGGCTCTGAAGA | 150 |
| M24 | CAGCCTGgcACTGACCAAGGACGAGGAGGAGAA | 151 |
|  | TTGGTCAGTgcCAGGCTGCTCACGGTCTTGTCG | 152 |
| M25 | ACCACGTGTACCAGgcCGCCGCCGAGCTGGTGTG | 153 |
|  | CGgcCTGGTACACGTGGTCCTTCTCCTCCTCGT | 154 |
| M26 | TGGTGAGCgcCTGCCTGACCCCCTACTTCAACG | 155 |
|  | TCAGGCAGgcGCTCACCATGCCCCACACCAGCT | 156 |
| M27 | CTACTTCgcCGACCCCAAGAACAAGTACATCCT | 157 |
|  | TTGGGGTCGgcGAAGTAGGGGGTCAGGCAGTTG | 158 |
| M28 | CAAGgcCAAGTACATCCTGAAGTACAAGGACGC | 159 |
|  | AGGATGTACTTGgcCTTGGGGTCGTTGAAGTAGGG | 160 |

Transfection

The 293T cells were transfected with verified vectors and control vectors according to the instructions of Lipofectamine™ 2000 (Thermo). The C13-2-BsaI control group was transfected with the C13-2-BsaI vector in previous examples, the WT control group was transfected with the C13-2-VEGFA vector, both of which expressed wild-type C13-2. A 293T cell control group was set additionally, without transfection with any plasmid.

Detection of RNA Level with qPCR

At 48 h after transfection, the cells were subjected to RNA extraction with a SteadyPure Universal RNA Extraction Kit, and the RNA concentration was detected with an ultramicro spectrophotometer. The RNA product was subject to reverse transcription by using the Evo M-MLV Mix Kit with gDNA Clean for qPCR reverse transcription kit. The reverse transcription product was detected with SYBR® Green Premix Pro Taq HS qPCR Kit (Low Rox Plus).

The primers used in qPCR were SEQ ID NOs: 88, 89, 30 and 31.

A reaction system was configured according to the instructions of the SYBR® Green Premix Pro Taq HS qPCR Kit (Rox Plus), and detected by using a QuantStudio™ 5 Real-Time PCR System.

Figure 14:
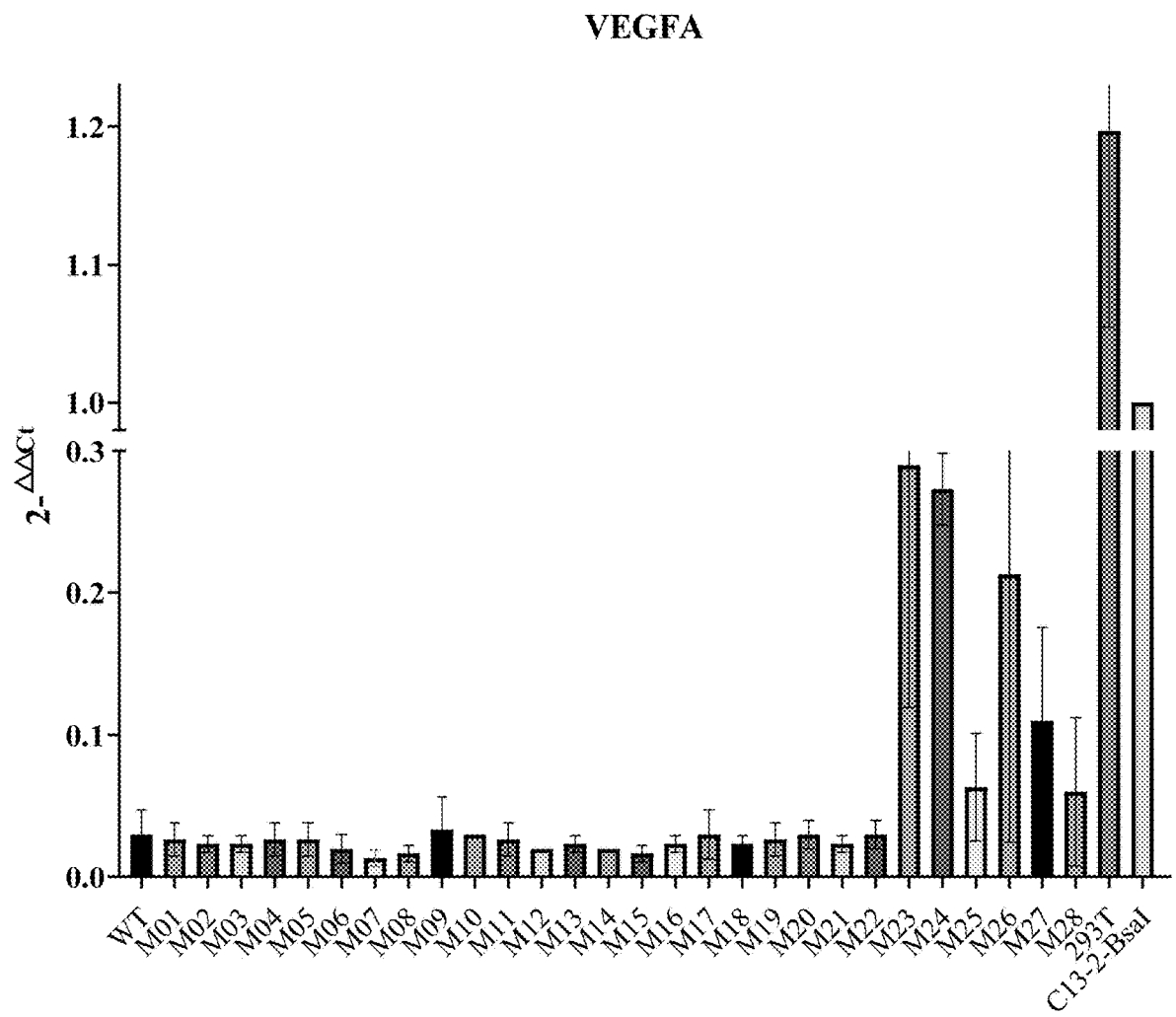
FIG. 14 shows the VEGFA RNA levels tested by qPCR after targeting editing of the mutants.

The target RNA level was calculated by the $2^{-\Delta\Delta Ct}$ method. The experiment was repeated in triplicate, and the average results were taken, as shown in Table 26 and FIG. 14.

TABLE 26

VEGFA RNA level after target editing with the mutant by qPCR test

| Group | Relative amount of VEGFA RNA after editing |
|---|---|
| C13-2-BsaI | 1.00 |
| WT | 0.03 |
| M01 | 0.03 |
| M02 | 0.02 |
| M03 | 0.02 |
| M04 | 0.02 |
| M05 | 0.02 |
| M06 | 0.02 |
| M07 | 0.02 |
| M08 | 0.02 |
| M09 | 0.03 |
| M10 | 0.03 |
| M11 | 0.03 |
| M12 | 0.02 |
| M13 | 0.02 |
| M14 | 0.02 |
| M15 | 0.02 |
| M16 | 0.02 |
| M17 | 0.03 |
| M18 | 0.02 |
| M19 | 0.03 |
| M20 | 0.03 |
| M21 | 0.02 |
| M22 | 0.03 |
| M23 | 0.29 |
| M24 | 0.27 |
| M25 | 0.07 |
| M26 | 0.21 |
| M27 | 0.11 |
| M28 | 0.06 |
| 293T | 1.20 |

It could be seen from the qPCR test results that all site-mutated mutants retained high editing activity.

RNAseq Sequencing

The total RNA sample extracted after editing was subject to RNAseq sequencing, with the type of library was LncRNA strand-specific library, the data amount of sequencing was 16 G, and the sequencing strategy was PE150.

Principle of RNAseq Analysis:

Quality control was performed with fastqc and multiqc, and reads of low-quality were removed y fastp.

Removal was performed by alignment to human rRNA sequences, and the alignment was made by Hisat2 alignment software to hg38 reference genome.

Quantification of genes at expression level was performed by Kallisto software after alignment, and then the variation analysis of expression levels was conducted by sleuth software, wherein a gene with |b|>0.5, qval<0.05 and mean_obs>2 was taken as the differential expression gene; 293T cell control group was taken as the benchmark.

The guide sequence was aligned to reference cDNA by using EMBOSS water software, and the transcript with aligned base no.>=18, mismatched base no.<=6 and the minimum consecutive paired bases no.>=8 was considered as the transcript predicting off-target, and the corresponding gene was considered as potential off-target gene predicted.

The intersection between the differential expression gene significantly down-regulated and potential off-target gene predicted was taken, on-target VEGFA gene was removed, and the off-target gene set was obtained.

Figure 15:
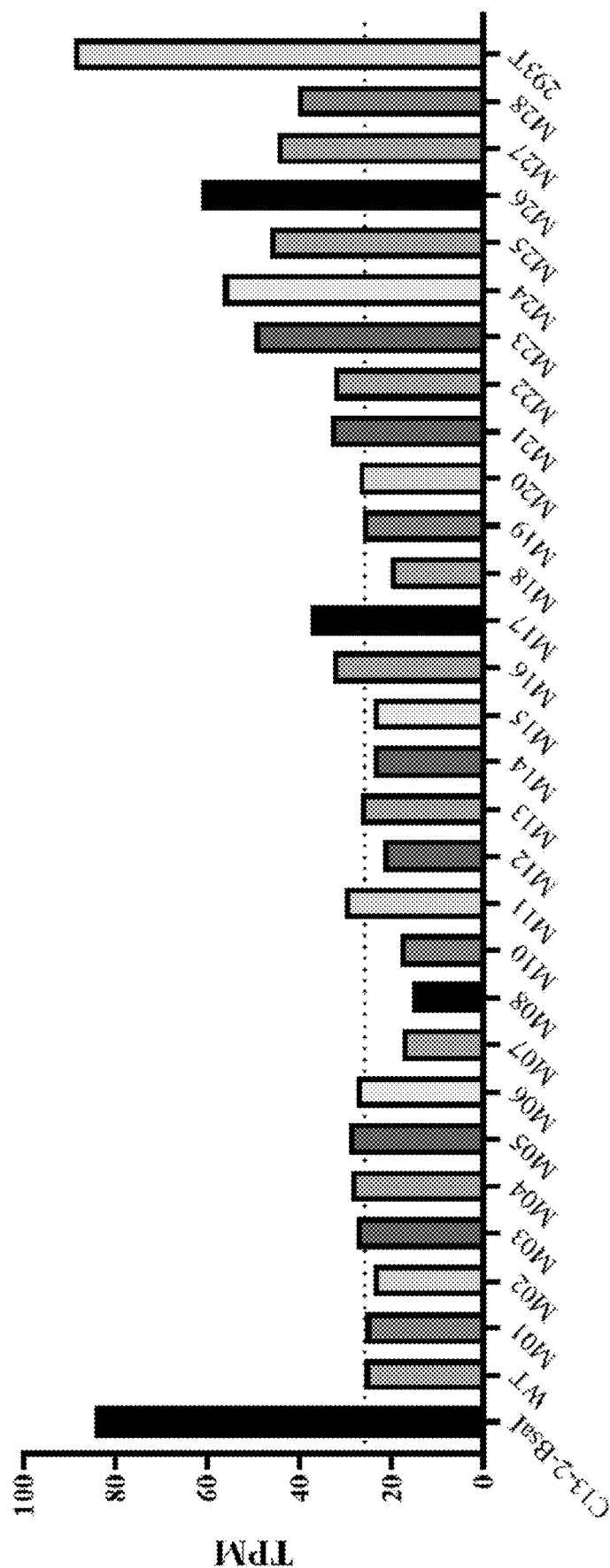
FIG. 15 shows the VEGFA RNA levels tested by RNAseq after editing.

RNAseq Results Analysis 293T cell control group was taken as the benchmark, and the expression level of VEGFA gene of each group was analyzed, and the results were as shown in Table 27 and FIG. 15.

TABLE 27

VEGFA editing efficiency determined by RNAseq

| Groups | TPM value | Editing Efficiency (%) |
|---|---|---|
| C13-2-BsaI | 84.49 | 4.99 |
| 293T | 88.93 | 0 |
| WT | 25.71 | 71.09 |
| M01 | 25.58 | 71.24 |
| M02 | 23.81 | 73.22 |
| M03 | 27.48 | 69.09 |
| M04 | 28.82 | 67.59 |
| M05 | 29.26 | 67.09 |
| M06 | 27.44 | 69.15 |
| M07 | 17.67 | 80.13 |
| M08 | 15.33 | 82.76 |
| M10 | 18.21 | 79.53 |
| M11 | 30.23 | 66.01 |
| M12 | 21.77 | 75.52 |
| M13 | 26.53 | 70.17 |
| M14 | 24.03 | 72.98 |
| M15 | 23.99 | 73.02 |
| M16 | 32.67 | 63.27 |
| M17 | 37.50 | 57.83 |
| M18 | 20.00 | 77.51 |
| M19 | 26.05 | 70.71 |
| M20 | 26.91 | 69.74 |
| M21 | 33.01 | 62.88 |
| M22 | 32.30 | 63.68 |
| M23 | 49.79 | 44.01 |
| M24 | 56.57 | 36.39 |
| M25 | 46.40 | 47.82 |
| M26 | 61.39 | 30.97 |
| M27 | 44.77 | 49.66 |
| M28 | 40.39 | 54.58 |

The result data of RNAseq were substantially consistent with the results of qPCR.

When combined with gRNA in this example, the editing activity of mutants M02, M07, M08, M10, M12, M14, M15 and M18 was slightly increased compared to that of wild-type C13-2.

The number of the differential expression gene and the number of the off-target gene were as shown in Table 28.

In terms of the number of the differential expression gene which was down-regulated in the cell after editing, it is less in M04, M09, M17, M22, M25, M27 and M28 group than that in WT group.

In terms of the number of the off-target gene which was determined after the intersection was taken, it is 0 in M01 group to M28 group, that is, no off-target occurred.

TABLE 28

Differential expression gene and off-target gene targeting VEGFA of different mutants

| Group | Up-regulated differential expression gene | Down-regulated differential expression gene | No. of the off-target gene determined after the intersection was taken (VEGFA gene had already been removed) |
|---|---|---|---|
| WT | 59 | 3 | 0 |
| M01 | 89 | 8 | 0 |
| M02 | 107 | 12 | 0 |
| M03 | 168 | 27 | 0 |
| M04 | 62 | 1 | 0 |
| M05 | 131 | 3 | 0 |
| M06 | 109 | 15 | 0 |
| M07 | 88 | 5 | 0 |
| M08 | 193 | 31 | 0 |
| M09 | 43 | 2 | 0 |
| M10 | 90 | 6 | 0 |
| M11 | 108 | 7 | 0 |
| M12 | 109 | 4 | 0 |
| M13 | 123 | 4 | 0 |
| M14 | 112 | 4 | 0 |
| M15 | 110 | 20 | 0 |
| M16 | 175 | 16 | 0 |
| M17 | 125 | 2 | 0 |
| M18 | 57 | 3 | 0 |
| M19 | 111 | 10 | 0 |
| M20 | 124 | 5 | 0 |
| M21 | 159 | 5 | 0 |
| M22 | 76 | 2 | 0 |
| M23 | 81 | 9 | 0 |
| M24 | 89 | 8 | 0 |
| M26 | 45 | 4 | 0 |
| M28 | 151 | 1 | 0 |

Example 14: Second Round of Mutation of C13-2

Mutants Design

Based on the five mutation sites with low off-target (M09 N87A, M17 R308A, M28 N394A, M04 R47A and M13 R290A) obtained on the basis of the results of Example 1, internal combination or combination with other mutation site among the five sites was designed. In addition, conservative mutations were designed at conservative positions. It was as shown in Table 29.

TABLE 29

Designed mutants in the second round

| Mutant | Mutation |
|---|---|
| M2-1 | R47A + R290A |
| M2-2 | R47A + R314A |
| M2-3 | R290A + R314A |
| M2-4 | R47A + R290A + R314A |
| M2-5 | R308A + N68A |
| M2-6 | N394A + N68A |
| M2-7 | N87A + N68A |
| M2-8 | R308A + N265A |
| M2-9 | N394A + N265A |
| M2-10 | N87A + N265A |
| M2-11 | R308A + N68A + N265A |

TABLE 29-continued

Designed mutants in the second round

| Mutant | Mutation |
|---|---|
| M2-12 | N87A + N68A + N265A |
| M2-13 | T7S |
| M2-14 | A16S |
| M2-15 | S260E |
| M2-16 | A263K |
| M2-17 | M266I |
| M2-18 | N274K |
| M2-19 | F288Y |
| M2-20 | M302F |
| M2-21 | N303S |
| M2-22 | L304I |
| M2-23 | V305K |
| M2-24 | I311M |
| M2-25 | D313E |
| M2-26 | H324Y |
| M2-27 | P326S |
| M2-28 | H327V |
| M2-29 | N332Y |
| M2-30 | N346D |
| M2-31 | T353L |
| M2-32 | T360S |
| M2-33 | E365D |
| M2-34 | A373E |
| M2-35 | M380K |
| M2-36 | S382R |
| M2-37 | K395G |
| M2-38 | Y396D |
| M2-39 | D402L |
| M2-40 | D411E |
| M2-41 | S418K |

Construction of Verified Vectors

The second round of mutation was tested with target human AR (Androgen Receptor), and C13-2-AR-h3 plasmid vector was synthesized (SEQ ID NO: 161, could express wild-type C13-2 and h3 gRNA targeting AR, and the guide sequence was SEQ ID NO: 162, i.e., ATAACATTTCCGAA-GACGACAAGAT).

Site Mutation Kit Mut Express II Fast Mutagenesis Kit V2 from Vazyme was used to modify the C13-2-AR-h3 plasmid vector, and the expression constructs (verified vectors) for each mutant were obtained for expressing the C13-2 mutant and h3 gRNA. Primers used were as shown in Table 30 below.

TABLE 30

Primer used for construction of expression vectors of mutants

| Mutant | Primer Sequence | SEQ ID NO |
|---|---|---|
| M2-1 | TACCACGGCgcAGCCCTGGAGACACCCAAGC | 163 |
|  | GGTGAATgcGTAGAACTCGTCGGTGATCTGCT | 164 |
|  | GAGTTCTACgcATTCACCATCAGAAAGGACGGC | 165 |
|  | CAGGGCTgcGCCGTGGTAGCCCTCGGT | 166 |
| M2-2 | TACCACGGCgcAGCCCTGGAGACACCCAAGC | 167 |
|  | CGTATgcGTCGATGATGATCTCTCTGATCTTCA | 168 |
|  | TCATCATCGACgcATACGCCAGCGGCCTGAG | 169 |
|  | CAGGGCTgcGCCGTGGTAGCCCTCGGT | 170 |
| M2-3 | GAGTTCTACgcATTCACCATCAGAAAGGACGGC | 171 |
|  | CGTATgcGTCGATGATGATCTCTCTGATCTTCA | 172 |
|  | TCATCATCGACgcATACGCCAGCGGCCTGAG | 173 |
|  | GGTGAATgcGTAGAACTCGTCGGTGATCTGCT | 174 |
| M2-4 | TACCACGGCgcAGCCCTGGAGACACCCAAGC | 175 |
|  | GGTGAATgcGTAGAACTCGTCGGTGATCTGCT | 176 |
|  | GAGTTCTACgcATTCACCATCAGAAAGGACGGC | 177 |
|  | CGTATgcGTCGATGATGATCTCTCTGATCTTCA | 178 |
|  | TCATCATCGACgcATACGCCAGCGGCCTGAG | 179 |
|  | CAGGGCTgcGCCGTGGTAGCCCTCGGT | 180 |
| M2-5 | AAGAATCGACGAGgcCGTGGACCTGTGCGGCGA | 181 |
|  | GATCTCTgcGATCTTCACCAGGTTCATGCCC | 182 |
|  | GTGAAGATCgcAGAGATCATCATCGACAGATACGC | 183 |
|  | ACGgcCTCGTCGATTCTTCTCACCTCG | 184 |
| M2-6 | AAGAATCGACGAGgcCGTGGACCTGTGCGGCGA | 185 |
|  | AGGATGTACTTGgcCTTGGGGTCGTTGAAGTAGGG | 186 |
|  | CAAGgcCAAGTACATCCTGAAGTACAAGGACG | 187 |
|  | ACGgcCTCGTCGATTCTTCTCACCTCG | 188 |
| M2-7 | AAGAATCGACGAGgcCGTGGACCTGTGCGGCGA | 189 |
|  | TCTCGCTGGGGgcCACCAGCAGGGCCTCGAT | 190 |
|  | TGGTGgcCCCCAGCGAGAAGGTGGG | 191 |
|  | ACGgcCTCGTCGATTCTTCTCACCTCG | 192 |
| M2-8 | AAGAACGCCGTGgcCATGGCCATCCTGTTCGACC | 193 |
|  | GATCTCTgcGATCTTCACCAGGTTCATGCCC | 194 |
|  | GTGAAGATCgcAGAGATCATCATCGACAGATACGC | 195 |
|  | CATGgcCACGGCGTTCTTGCTCAGG | 196 |
| M2-9 | AAGAACGCCGTGgcCATGGCCATCCTGTTCGACC | 197 |
|  | AGGATGTACTTGgcCTTGGGGTCGTTGAAGTAGGG | 198 |
|  | CAAGgcCAAGTACATCCTGAAGTACAAGGACG | 199 |
|  | CATGgcCACGGCGTTCTTGCTCAGG | 200 |
| M2-10 | TGGTGgcCCCCAGCGAGAAGGTGGG | 201 |
|  | CATGgcCACGGCGTTCTTGCTCAGG | 202 |
|  | AAGAACGCCGTGgcCATGGCCATCCTGTTCGACC | 203 |
|  | TCTCGCTGGGGgcCACCAGCAGGGCCTCGAT | 204 |
| M2-11 | AAGAATCGACGAGgcCGTGGACCTGTGCGGCGA | 205 |
|  | CATGgcCACGGCGTTCTTGCTCAGG | 206 |
|  | AAGAACGCCGTGgcCATGGCCATCCTGTTCGACC | 207 |
|  | GATCTCTgcGATCTTCACCAGGTTCATGCCC | 208 |
|  | GTGAAGATCgcAGAGATCATCATCGACAGATACGC | 209 |
|  | ACGgcCTCGTCGATTCTTCTCACCTCG | 210 |
| M2-12 | AAGAATCGACGAGgcCGTGGACCTGTGCGGCGA | 211 |
|  | TCTCGCTGGGGgcCACCAGCAGGGCCTCGAT | 212 |
|  | TGGTGgcCCCCAGCGAGAAGGTGGG | 213 |
|  | CATGgcCACGGCGTTCTTGCTCAGG | 214 |
|  | AAGAACGCCGTGgcCATGGCCATCCTGTTCGACC | 215 |
|  | ACGgcCTCGTCGATTCTTCTCACCTCG | 216 |
| M2-13 | ACAAGAAAtCCAAGGCCAAGAGAATGGGCGTG | 217 |
|  | GGCCTTGGaTTTCTTGTCCTTGCTCATGTCGA | 218 |
| M2-14 | AGAATGGGCGTGAAGtCCCTGCTGGCCCACGGCG | 219 |
|  | GaCTTCACGCCCATTCTCTTGGCCTTGGTTTT | 220 |
| M2-15 | CTTCCTGgaaAAGAACGCCGTGAACATGGCCA | 221 |
|  | CGTTCTTttcCAGGAAGTCCTTGTTCACCTTCTT | 222 |
| M2-16 | GCAAGAACaagGTGAACATGGCCATCCTGTTCG | 223 |
|  | GTTCACCttGTTCTTGCTCAGGAAGTCCTTGTT | 224 |
| M2-17 | GTGAACATaGCCATCCTGTTCGACCTGCTGAA | 225 |
|  | AGGATGGCtATGTTCACGGCGTTCTTGCTCAG | 226 |
| M2-18 | TGTTCGACCTGCTGAAgGCCAGAGACGTGGAGCAGAA | 227 |
|  | cTTCAGCAGGTCGAACAGGATGGCCATGTTCA | 228 |
| M2-19 | CGACGAGTaCTACAGATTCACCATCAGAAAGGACG | 229 |
|  | ATCTGTAGtACTCGTCGGTGATCTGCTTCTTC | 230 |
| M2-20 | AACCTGGGCttcAACCTGGTGAAGATCAGAGAGATCA | 231 |
|  | AGGTTgaaGCCCAGGTTCTTGCCGTCCTTTCT | 232 |
| M2-21 | CATGAgCCTGGTGAAGATCAGAGATCATCA | 233 |
|  | TCTTCACCAGGcTCATGCCCAGGTTCTTGCCG | 234 |

TABLE 30-continued

Primer used for construction of expression vectors of mutants

| Mutant | Primer Sequence | SEQ ID NO |
|---|---|---|
| M2-22 | GCATGAACatcGTGAAGATCAGAGAGATCATCATCGA<br>CTTCACgatGTTCATGCCCAGGTTCTTGCCGT | 235<br>236 |
| M2-23 | GGCATGAACCTGaaGAAGATCAGAGAGATCATCATCGACA<br>CTTCttCAGGTTCATGCCCAGGTTCTTGCCGTC | 237<br>238 |
| M2-24 | GAGATCATgATCGACAGATACGCCAGCGGCCT<br>CTGTCGATCATGATCTCTCTGATCTTCACCAGGT | 239<br>240 |
| M2-25 | ATCATCGAgAGATACGCCAGCGGCCTGAGAGA<br>GCGTATCTcTCGATGATGATCTCTCTGATCTTCA | 241<br>242 |
| M2-26 | ACAAGAAGtACGACCCCCACAGACAGAAGATC<br>GGGGTCGTaCTTCTTGTCTCTCAGGCCGCTGG | 243<br>244 |
| M2-27 | AAGAAGCACGACtCCCACAGACAGAAGATCAACGTG<br>TGGGaGTCGTGCTTCTTGTCTCTCAGGCCGCT | 245<br>246 |
| M2-28 | CCgtCAGACAGAAGATCAACGTGATCGCCGACT<br>TGATCTTCTGTCTGacGGGGTCGTGCTTCTTGTCTCT | 247<br>248 |
| M2-29 | GAAGATCtACGTGATCGCCGACTTCCTGATCT<br>CGATCACGTaGATCTTCTGTCTGTGGGGGTCG | 249<br>250 |
| M2-30 | CAGgACCAGGGCATCATCGACAAGACCGTGAG<br>ATGATGCCCTGGTcCTGGCTCAGGGCTCTGAAGA | 251<br>252 |
| M2-31 | TCATCGACAAGctCGTGAGCAGCCTGAGACTGAC<br>TCACGagCTTGTCGATGATGCCCTGGTTCTGGC | 253<br>254 |
| M2-32 | TGAGACTGtCCAAGGACGAGGAGGAGAAGGAC<br>GTCCTTGGaCAGTCTCAGGCTGCTCACGGTCT | 255<br>256 |
| M2-33 | AAGGACGAGGAGGAcAAGGACCACGTGTACCAGAACG<br>TTgTCCTCCTCGTCCTTGGTCAGTCTCAGGCT | 257<br>258 |
| M2-34 | ACGTGTACCAGAACGagGCCGAGCTGGTGTGGGGC<br>CctCGTTCTGGTACACGTGGTCCTTCTCCTCCT | 259<br>260 |
| M2-35 | AaGGTGAGCAACTGCCTGACCCCCTACTTCAA<br>AGGCAGTTGCTCACCttGCCCCACACCAGCTCGG | 261<br>262 |
| M2-36 | ATGGTGAGgAACTGCCTGACCCCCTACTTCAA<br>AGGCAGTTcCTCACCATGCCCCACACCAGCTC | 263<br>264 |
| M2-37 | CAAGAACggGTACATCCTGAAGTACAAGGACGC<br>AGGATGTACccGTTCTTGGGGTCGTTGAAGTAGG | 265<br>266 |
| M2-38 | AGAACAAGgACATCCTGAAGTACAAGGACGCC<br>CAGGATGTcCTTGTTCTTGGGGTCGTTGAAGT | 267<br>268 |
| M2-39 | AGTACAAGctCGCCAAGACCCCCGGCGACTTCG<br>TCTTGGCGagCTTGTACTTCAGGATGTACTTGTTCTTG | 269<br>270 |
| M2-40 | TTCGAGGAgTGGATCACCAGCAAGATCAGCGA<br>GTGATCCAcTCCTCGAAGTCGCCGGGGGTCTT | 271<br>272 |
| M2-41 | CAAGATCAagGAGGACGACGGCGAGCCCTTCGT<br>TCGTCCTCctTGATCTTGCTGGTGATCCAGTCC | 273<br>274 |

Transfection

The 293T cells were transfected with verified vectors and control vectors according to the instructions of Lipofectamine™ 2000 (Thermo). The C13-2-BsaI control group was transfected with the C13-2-BsaI vector in previous examples, the WT control group was transfected with the C13-2-AR-h3 vector, both of which expressed wild-type C13-2. A 293T cell control group was set additionally, without transfection with any plasmid.

Detection of RNA Level with qPCR

At 48 h after transfection, the cells were subjected to RNA extraction with a SteadyPure Universal RNA Extraction Kit, and the RNA concentration was detected with an ultramicro spectrophotometer. The RNA product was subject to reverse transcription by using the Evo M-MLV Mix Kit with gDNA Clean for qPCR reverse transcription kit. The reverse transcription product was detected with SYBR® Green Premix Pro Taq HS qPCR Kit (Low Rox Plus).

Primers used in qPCR were as follows:

```
Detection of AR:
                                (SEQ ID NO: 275)
CCAGGGACCATGTTTTGCC (SEQ ID NO: 276)
CGAAGACGACAAGATGGACAA Detection of internal reference GAPDH:
SEQ ID NOs: 30 and 31.
```

A reaction system was configured according to the instructions of the SYBR® Green Premix Pro Taq HS qPCR Kit (Rox Plus), and detected by using a QuantStudio™ 5 Real-Time PCR System.

Figure 16:
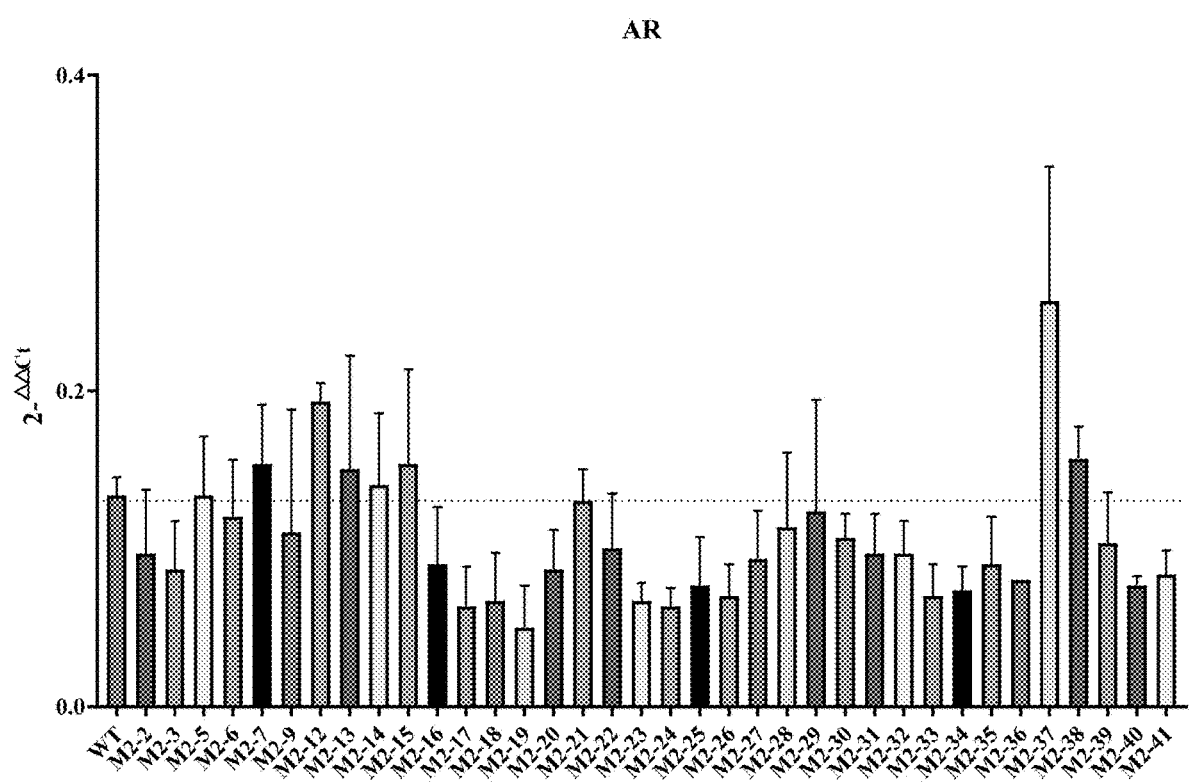
FIG. 16 shows the editing efficiency of the mutants tested by qPCR on AR RNA.

The target RNA level was calculated by the $2^{-\Delta\Delta Ct}$ method. The experiment was repeated in triplicate, and the average results were taken, as shown in Table 31 and FIG. 16.

TABLE 31

AR RNA level after target editing with the mutant by qPCR test

| Group | Relative amount of AR RNA after editing |
|---|---|
| BsaI | 1.00 |
| WT2 | 0.13 |
| M2-2 | 0.09 |
| M2-3 | 0.09 |
| M2-5 | 0.14 |
| M2-6 | 0.12 |
| M2-7 | 0.15 |
| M2-9 | 0.11 |
| M2-12 | 0.19 |
| M2-13 | 0.15 |
| M2-14 | 0.14 |
| M2-15 | 0.15 |
| M2-16 | 0.09 |
| M2-17 | 0.07 |
| M2-18 | 0.07 |
| M2-19 | 0.05 |
| M2-20 | 0.09 |
| M2-21 | 0.13 |
| M2-22 | 0.10 |
| M2-23 | 0.07 |
| M2-24 | 0.06 |
| M2-25 | 0.08 |
| M2-26 | 0.07 |
| M2-27 | 0.10 |
| M2-28 | 0.11 |
| M2-29 | 0.12 |
| M2-30 | 0.10 |
| M2-31 | 0.10 |
| M2-32 | 0.10 |
| M2-33 | 0.07 |
| M2-34 | 0.07 |
| M2-35 | 0.09 |
| M2-36 | 0.08 |
| M2-37 | 0.26 |
| M2-38 | 0.16 |
| M2-39 | 0.10 |
| M2-40 | 0.07 |
| M2-41 | 0.08 |
| 293T | 1.21 |

RNAseq Sequencing

The total RNA sample extracted after editing was subject to RNAseq sequencing, with the type of library to be constructed was LncRNA strand-specific library, the data amount of sequencing was 16 G, and the sequencing strategy was PE150.

Principle of RNAseq Analysis:

Quality control was performed with fastqc and multiqc, and reads of low-quality were removed y fastp.

Removal was performed by alignment to human rRNA sequences, and the alignment was made by Hisat2 alignment software to hg38 reference genome.

Quantification of genes at expression level was performed by Kallisto software after alignment, and then the variation analysis of expression levels was conducted by sleuth software, wherein a gene with |b|>0.5, qval<0.05 and mean_obs>2 was taken as the differential expression gene.

The guide sequence was aligned to reference cDNA by using EMBOSS water software, and the transcript with aligned base no.>=18, mismatched base no.<=6 and the minimum consecutive paired bases no.>=8 was considered as the transcript predicting off-target, and the corresponding gene was considered as potential off-target gene predicted.

The intersection between the differential expression gene significantly down-regulated and potential off-target gene predicted was taken, on-target VEGFA gene was removed, and the off-target gene set was obtained.

Figure 17:
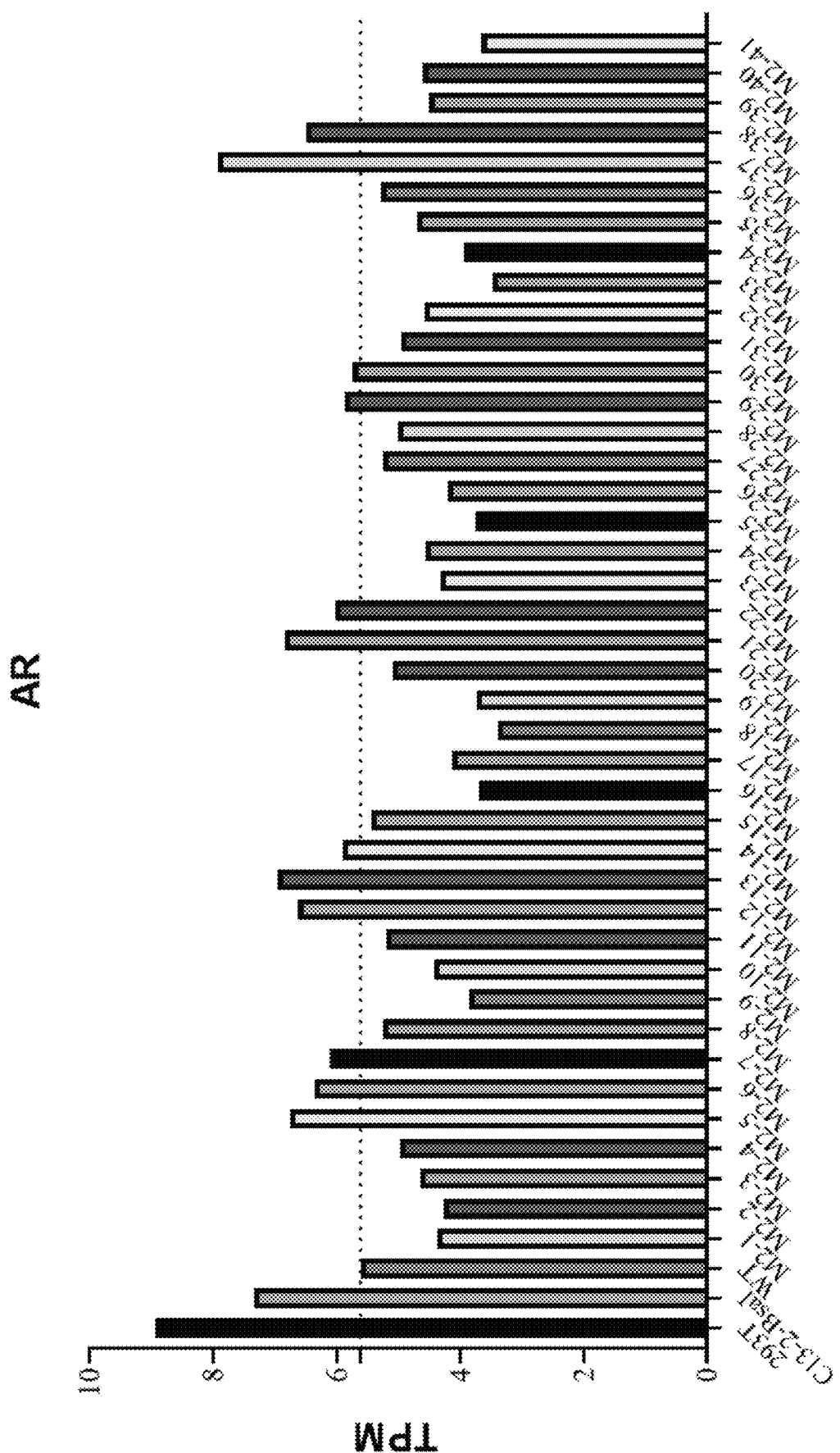
FIG. 17 shows the AR RNA levels tested by RNAseq after editing.

RNAseq Results Analysis 293T cell control group was taken as the benchmark, and the expression level and editing efficiency (average was taken) of AR gene of each group was analyzed, and the results were as shown in Table 32 and FIG. 17.

TABLE 32

AR editing efficiency determined by RNAseq

| Groups | TPM value | Editing Efficiency (%) |
| --- | --- | --- |
| C13-2-BsaI | 7.34 | 17.91 |
| 293T | 8.94 | 0 |
| WT | 5.62 | 37.17 |
| M2-1 | 4.36 | 51.28 |
| M2-2 | 4.27 | 52.2 |
| M2-3 | 4.65 | 47.99 |
| M2-4 | 4.98 | 44.28 |
| M2-5 | 6.75 | 24.54 |
| M2-6 | 6.36 | 28.91 |
| M2-7 | 6.12 | 31.61 |
| M2-8 | 5.24 | 41.38 |
| M2-9 | 3.85 | 56.96 |
| M2-10 | 4.42 | 50.56 |
| M2-11 | 5.20 | 41.82 |
| M2-12 | 6.62 | 25.96 |
| M2-13 | 6.95 | 22.34 |
| M2-14 | 5.90 | 34.01 |
| M2-15 | 5.44 | 39.18 |
| M2-16 | 3.69 | 58.71 |
| M2-17 | 4.13 | 53.8 |
| M2-18 | 3.38 | 62.18 |
| M2-19 | 3.73 | 58.25 |
| M2-20 | 5.10 | 42.96 |
| M2-21 | 6.83 | 23.58 |
| M2-22 | 6.02 | 32.7 |
| M2-23 | 4.32 | 51.74 |
| M2-24 | 4.56 | 49.02 |
| M2-25 | 3.74 | 58.2 |
| M2-26 | 4.19 | 53.18 |
| M2-27 | 5.24 | 41.43 |
| M2-28 | 5.00 | 44.06 |
| M2-29 | 5.87 | 34.42 |
| M2-30 | 5.74 | 35.81 |
| M2-31 | 4.95 | 44.66 |
| M2-32 | 4.58 | 48.76 |
| M2-33 | 3.47 | 61.22 |
| M2-34 | 3.93 | 56.1 |
| M2-35 | 4.69 | 47.52 |
| M2-36 | 5.29 | 40.84 |
| M2-37 | 7.93 | 11.32 |
| M2-38 | 6.49 | 27.47 |
| M2-39 | 4.50 | 49.73 |
| M2-40 | 4.60 | 48.62 |
| M2-41 | 3.65 | 59.17 |

The result data of RNAseq were substantially consistent with the results of qPCR.

When combined with gRNA in this example, the editing activity of mutants M2-1, M2-2, M2-3, M2-4, M2-9, M2-10, M2-16, M2-17, M2-18, M2-19, M2-23, M2-24, M2-25, M2-26, M2-32, M2-33, M2-34, M2-35, M2-39, M2-40 and M2-41 was higher than that of wild-type C13-2.

The number of the differential expression gene and the number of the off-target gene were as shown in Table 33.

In terms of the number of the differential expression gene which was down-regulated in the cell after editing, it is less in M2-1, M2-2, M2-3, M2-4, M2-5, M2-6, M2-7, M2-8, M2-10, M2-13, M2-14, M2-15, M2-16, M2-21, M2-22, M2-23, M2-24, M2-25, M2-26, M2-27, M2-28, M2-29, M2-30, M2-31, M2-32, M2-33, M2-34, M2-35, M2-36, M2-37, M2-38, M2-39, M2-40 and M2-41 groups than that in WT group.

In terms of the number of the off-target gene which was determined after the intersection was taken, it is less in M2-1, M2-2, M2-3, M2-4, M2-5, M2-6, M2-7, M2-8, M2-10, M2-13, M2-14, M2-15, M2-16, M2-21, M2-22, M2-23, M2-24, M2-25, M2-26, M2-27, M2-28, M2-29, M2-30, M2-31, M2-32, M2-33, M2-35, M2-36, M2-37, M2-38, M2-39, M2-40 and M2-41 groups than that in WT group. Among them, no off-target occurred in M2-1, M2-6, M2-7, M2-14, M2-15, M2-22, M2-31, M2-38 and M2-39 groups.

TABLE 33

Differential expression gene and off-target gene targeting AR of mutants

| Group | Up-regulated differential expression gene | Down-regulated differential expression gene | No. of the off-target gene determined after the intersection was taken (AR gene had already been removed) |
| --- | --- | --- | --- |
| C13-2-BsaI | 4 | 42 | N/A |
| WT | 1199 | 1023 | 54 |
| M2-1 | 42 | 4 | 0 |
| M2-2 | 987 | 670 | 40 |
| M2-3 | 55 | 5 | 1 |
| M2-4 | 497 | 114 | 4 |
| M2-5 | 1080 | 923 | 39 |
| M2-6 | 254 | 18 | 0 |
| M2-7 | 55 | 2 | 0 |
| M2-8 | 914 | 633 | 24 |
| M2-9 | 1439 | 1508 | 68 |
| M2-10 | 1195 | 942 | 42 |
| M2-11 | 2344 | 2156 | 102 |
| M2-12 | 1426 | 1366 | 75 |
| M2-13 | 775 | 547 | 24 |
| M2-14 | 41 | 5 | 0 |
| M2-15 | 85 | 3 | 0 |
| M2-16 | 535 | 165 | 9 |

TABLE 33-continued

Differential expression gene and off-target gene targeting AR of mutants

| Group | Up-regulated differential expression gene | Down-regulated differential expression gene | No. of the off-target gene determined after the intersection was taken (AR gene had already been removed) |
|---|---|---|---|
| M2-17 | 1225 | 1055 | 57 |
| M2-18 | 1551 | 1255 | 88 |
| M2-19 | 1481 | 1404 | 81 |
| M2-20 | 1332 | 1264 | 58 |
| M2-21 | 301 | 38 | 2 |
| M2-22 | 39 | 3 | 0 |
| M2-23 | 193 | 14 | 1 |
| M2-24 | 842 | 318 | 21 |
| M2-25 | 908 | 624 | 31 |
| M2-26 | 1221 | 820 | 50 |
| M2-27 | 974 | 457 | 24 |
| M2-28 | 755 | 443 | 20 |
| M2-29 | 473 | 122 | 8 |
| M2-30 | 886 | 490 | 20 |
| M2-31 | 110 | 3 | 0 |
| M2-32 | 694 | 295 | 14 |
| M2-33 | 766 | 417 | 18 |
| M2-34 | 1149 | 959 | 57 |
| M2-35 | 1129 | 861 | 44 |
| M2-36 | 592 | 397 | 20 |
| M2-37 | 306 | 50 | 2 |
| M2-38 | 51 | 4 | 0 |
| M2-39 | 101 | 2 | 0 |
| M2-40 | 828 | 348 | 16 |
| M2-41 | 837 | 385 | 21 |

Example 15: Test at Target Protein Level

The 293T cells were transfected (Lipofectamine™ 2000, Thermo Fisher) with the C13-2-VEGFA vector and the negative control vector C13-2-BsaI in previous examples, cultured at 37° C. for 72h, and the supernatant was collected. The VEGFA protein level was detected with Human VEGF-A (Vascular Endothelial Cell Growth Factor A) ELISA Kit from Elascience, and the results showed that the VEGFA protein expression reduced by 97.4% compared to that of the negative control group.

In 293T cells, after editing by CasRx expressed by the vector and the gRNA comprising the same guide sequence, the VEGFA protein expression reduced by 75.7% compared to that of CasRx negative control group.

What is claimed is:

1. A non-naturally occurring Cas13 protein, wherein the amino acid sequence of the Cas13 protein has at least 90% sequence identity compared to SEQ ID NO: 1, and comprises one or more mutations compared to SEQ ID NO: 1.

2. The Cas13 protein according to claim 1, wherein
   (a) the Cas13 protein comprises at least one mutation at the location corresponding to amino acid residue positions 40-91, 146-153, 158-176, 182-209, 216-253, 271-287, 341-353, 379-424, 456-477, 521-557, 575-588, 609-625, 700-721, 724-783, 796-815, 828-852 or 880-893 of the reference protein as shown in SEQ ID NO: 1;
   (b) the Cas13 protein comprises one or more mutations at the location corresponding to the following amino acid residues of the reference protein as shown in SEQ ID NO: 1: R11, N34, R35, R47, R58, R63, R64, N68, N87, N265, N274, R276, R290, R294, N299, N303, R308, R314, R320, R328, N332, R341, N346, R358, N372, N383, N390, N394, R47+R290, R47+R314, R290+R314, R47+R290+R314, R308+N68, N394+N68, N87+N68, R308+N265, N394+N265, N87+N265, R308+N68+N265, N87+N68+N265, T7, A16, S260, A263, M266, N274, F288, M302, N303, L304, V305, I311, D313, H324, P326, H327, N332, N346, T353, T360, E365, A373, M380, S382, K395, Y396, D402, D411, and S418; and/or,
   (c) the Cas13 protein comprises a mutation at the location corresponding to the RxxxxH motif at positions 210-215, 750-755 and/or 785-790 of the reference protein as shown in SEQ ID NO: 1.

3. The Cas13 protein according to claim 1, wherein the Cas13 protein comprises one or more mutations at the location corresponding to the following amino acid residues of the reference protein as shown in SEQ ID NO: 1: R11A, N34A, R35A, R47A, R58A, R63A, R64A, N68A, N87A, N265A, N274A, R276A, R290A, R294A, N299A, N303A, R308A, R314A, R320A, R328A, N332A, R341A, N346A, R358A, N372A, N383A, N390A, N394A, R47A+R290A, R47A+R314A, R290A+R314A, R47A+R290A+R314A, R308A+N68A, N394A+N68A, N87A+N68A, R308A+N265A, N394A+N265A, N87A+N265A, R308A+N68A+N265A, N87A+N68A+N265A, T7S, A16S, S260E, A263K, M266I, N274K, F288Y, M302F, N303S, L304I, V305K, I311M D313E, H324Y, P326S, H327V, N332Y, N346D, T353L, T360S, E365D, A373E, M380K, S382R, K395G, Y396D, D402L, D411E, and S418K.

4. A CRISPR-Cas13 system comprising (1) a guide polynucleotide or a nucleic acid encoding the guide polynucleotide, wherein the guide polynucleotide comprises (i) a direct repeat sequence having at least 70% sequence identity compared to SEQ ID NO: 3, wherein the direct repeat sequence is linked to (ii) a guide sequence engineered to hybridize with a target RNA, wherein the direct repeat sequence is GGAAGATN$_1$ACTCTACAAACCTGTAGN$_2$GN$_3$N$_4$N$_5$N$_6$N$_7$N$_8$N$_9$N$_{10}$N$_{11}$ (SEQ ID NO: 277); wherein N$_1$ and N$_3$-N$_{11}$ are independently any one selected from A, C, G, and T; and N$_2$ is any one selected from A and G; and (2) the Cas13 protein of claim 1 or a nucleic acid encoding the Cas13 protein of claim 1.

5. A fusion protein comprising a Cas13 protein fused to a heterologous protein domain and/or a polypeptide tag; wherein the amino acid sequence of the Cas13 protein has at least 90% sequence identity compared to SEQ ID NO: 1.

6. The fusion protein according to claim 5, wherein the Cas13 protein is covalently linked to the protein domain; and/or, the Cas13 protein is fused to any one or more of the following protein domains and/or polypeptide tags: a cytosine deaminase domain, an adenosine deaminase domain, a translational activation domain, a translational repression domain, an RNA methylation domain, an RNA demethylation domain, a nuclease domain, a splicing factor domain, a reporter domain, an affinity domain, a subcellular localization signal, a reporter tag, and an affinity tag.

7. The fusion protein according to claim 6, wherein the subcellular localization signal is one or more of a nuclear localization signal (NLS) and a nuclear export signal (NES).

8. The fusion protein according to claim 5, wherein the structure of the fusion protein is NLS-Cas13 protein-SV40 NLS-nucleoplasmin NLS.

9. The fusion protein according to claim 5, wherein the length of the amino acid sequence of the protein domain is ≥40 amino acids; and/or, the length of the amino acid sequence of the polypeptide tag is ≤40 amino acids.

10. A pharmaceutical composition comprising the fusion protein according to claim 5.

11. A non-naturally occurring guide polynucleotide comprising (i) a direct repeat sequence having at least 70% sequence identity compared to SEQ ID NO: 3, wherein the direct repeat sequence is linked to (ii) a guide sequence engineered to hybridize with a target RNA, wherein the guide polynucleotide can form a CRISPR complex with a Cas13 protein and guide the sequence-specific binding of the CRISPR complex to the target RNA; wherein the direct repeat sequence is GGAAGATN$_1$ACTCTACAAACCTGTAGN$_2$GN$_3$N$_4$N$_5$N$_6$N$_7$N$_8$N$_9$N$_{10}$N$_{11}$ (SEQ ID NO: 277); wherein N$_1$ and N$_3$-N$_{11}$ are independently any one selected from A, C, G, and T; and N$_2$ is any one selected from A and G; and wherein the target RNA is a eukaryotic RNA.

12. A method for cleaving one or more target RNA molecules; wherein the method comprises the step of contacting a fusion protein and the guide polynucleotide according to claim 11 with the target RNA; wherein the fusion protein comprises a Cas13 protein fused to a heterologous protein domain and/or a polypeptide tag; and wherein the amino acid sequence of the Cas13 protein has at least 90% sequence identity compared to SEQ ID NO: 1.

13. A method for detecting a target RNA in a nucleic acid sample suspected of comprising the target RNA, wherein the method comprises the step of contacting a fusion protein and the guide polynucleotide according to claim 11 with the nucleic acid sample; wherein the fusion protein comprises a Cas13 protein fused to a heterologous protein domain and/or a polypeptide tag; and wherein the amino acid sequence of the Cas13 protein has at least 90% sequence identity compared to SEQ ID NO: 1.

14. The guide polynucleotide according to claim 11, wherein the direct repeat sequence has at least 80% sequence identity compared to SEQ ID NO: 3;
and/or, the guide sequence is located at the 3' end of the direct repeat sequence;
and/or, the guide sequence comprises 15-35 nucleotides;
and/or, the guide sequence hybridizes with the target RNA with no more than one nucleotide mismatch;
and/or, the guide polynucleotide further comprises an aptamer sequence;
and/or, the guide polynucleotide comprises a nucleotide with modification;
and/or, the Cas13 protein is a non-naturally occurring Cas protein, and the amino acid sequence of the Cas13 protein has at least 90% sequence identity compared to SEQ ID NO: 1.

15. The guide polynucleotide according to claim 14, wherein the aptamer sequence is inserted into a loop of the guide polynucleotide;
and/or, the aptamer sequence comprises an MS2 aptamer sequence, a PP7 aptamer sequence, or a Qβ aptamer sequence;
and/or, wherein the modification comprises 2'-O-methyl, 2'-O-methyl-3'-phosphorothioate, or 2'-O-methyl-3'-thioPACE.

16. The guide polynucleotide according to claim 11, wherein the target RNA is located in the nucleus of a eukaryotic cell; and/or, the target RNA is any one or more selected from TTR RNA, SOD1 RNA, PCSK9 RNA, VEGFA RNA, VEGFR1 RNA, PTBP1 RNA, AQp1 RNA, and ANGPTL3 RNA.

17. The guide polynucleotide according to claim 16, wherein the guide sequence is any one or more selected from the sequences as shown in SEQ ID NOs: 5-6, and SEQ ID NOs: 42-49.

18. A CRISPR-Cas13 system comprising:
(1) a Cas13 protein comprising an amino acid sequence having at least 90% sequence identity compared to SEQ ID NO: 1, or a nucleic acid encoding the Cas13 protein; and
(2) a guide polynucleotide or a nucleic acid encoding the guide polynucleotide; wherein the guide polynucleotide comprises a direct repeat sequence linked to a guide sequence, wherein the direct repeat sequence has at least 70% sequence identity to SEQ ID NO: 3, and has the structure of GGAAGATN$_1$ACTCTACAAACCTGTAGN$_2$GN$_3$N$_4$N$_5$N$_6$N$_7$N$_8$N$_9$N$_{10}$N$_{11}$ (SEQ ID NO: 277); wherein N$_1$ and N$_3$-N$_{11}$ are independently any one selected from A, C, G, and T; and N$_2$ is any one selected from A and G; wherein the guide sequence is engineered to hybridize with a target RNA;
wherein the guide polynucleotide can form a CRISPR complex with the Cas13 protein and guide a sequence-specific binding of the CRISPR complex to the target RNA; wherein the Cas13 protein and the guide polynucleotide do not naturally occur together; and wherein the target RNA is located in a eukaryotic cell.

19. The CRISPR-Cas13 system according to claim 18, wherein the target RNA is any one or more selected from TTR RNA, SOD1 RNA, PCSK9 RNA, VEGFA RNA, VEGFR1 RNA, PTBP1 RNA, AQp1 RNA, and ANGPTL3 RNA; and/or, the guide sequence is any one or more selected from the sequences as shown in SEQ ID NOs: 5-6 and SEQ ID NOs: 42-49.

20. A vector system comprising the CRISPR-Cas13 system according to claim 18, wherein the vector system comprises one or more vectors comprising a polynucleotide sequence encoding the Cas13 protein and a polynucleotide sequence encoding the guide polynucleotide.

21. The vector system according to claim 20, wherein
the vector is an adeno-associated viral vector comprising a DNA encoding the Cas13 protein and the guide polynucleotide;
or, the vector is a lipid nanoparticle comprising the guide polynucleotide and an mRNA encoding the Cas13 protein;
and/or, the vector is a lentiviral vector comprising the guide polynucleotide and an mRNA encoding the Cas13 protein.

22. A ribonucleoprotein complex comprising the CRISPR-Cas13 system according to claim 18, wherein the ribonucleoprotein complex is formed from the guide polynucleotide and the Cas13 protein.

23. A viral-like particle comprising the CRISPR-Cas13 system according to claim 18, wherein the viral-like particle comprises a ribonucleoprotein complex formed from the guide polynucleotide and the Cas13 protein; optionally, the Cas13 protein is fused to a gag protein.

24. A pharmaceutical composition comprising the CRISPR-Cas13 system according to claim 18.

25. An in vitro composition comprising the CRISPR-Cas13 system according to claim 18 and a labeled detector RNA that is not capable of hybridization with the guide polynucleotide.

26. A method for detecting a target RNA in a nucleic acid sample suspected of comprising the target RNA, wherein the method comprises the step of contacting the CRISPR-Cas13 system according to claim 18 with the nucleic acid sample.

27. A method for
cleaving one or more target RNA molecules;
wherein the method comprises the step of contacting the CRISPR-Cas13 system according to claim 18 with the target RNA.

\* \* \* \* \*